United States Patent
Ngai et al.

(10) Patent No.: US 11,760,701 B2
(45) Date of Patent: Sep. 19, 2023

(54) DIFLUOROMETHOXYLATION AND TRIFLUOROMETHOXYLATION COMPOSITIONS AND METHODS FOR SYNTHESIZING SAME

(71) Applicant: The Research Foundation for the State University of New York, Albany, NY (US)

(72) Inventors: Ming-Yu Ngai, Stony Brook, NY (US); Weijia Zheng, Stony Brook, NY (US); Johnny Lee, Stony Brook, NY (US)

(73) Assignee: THE RESEARCH FOUNDATION FOR THE STATE UNIVERSITY OF NEW YROK, Albany, NY (US)

( * ) Notice: Subject to any disclaimer, the term of this patent is extended or adjusted under 35 U.S.C. 154(b) by 91 days.

(21) Appl. No.: 16/975,704

(22) PCT Filed: Feb. 26, 2019

(86) PCT No.: PCT/US2019/019673
§ 371 (c)(1),
(2) Date: Aug. 25, 2020

(87) PCT Pub. No.: WO2019/168874
PCT Pub. Date: Sep. 6, 2019

(65) Prior Publication Data
US 2021/0032181 A1    Feb. 4, 2021

Related U.S. Application Data

(60) Provisional application No. 62/635,711, filed on Feb. 27, 2018, provisional application No. 62/642,668, filed on Mar. 14, 2018, provisional application No. 62/642,917, filed on Mar. 14, 2018, provisional application No. 62/689,315, filed on Jun. 25, 2018, provisional application No. 62/726,885, filed on Sep. 4, 2018, provisional application No. 62/773,510, filed on Nov. 30, 2018.

(51) Int. Cl.
C07B 41/04    (2006.01)
C07D 235/18   (2006.01)
C07D 249/18   (2006.01)

(52) U.S. Cl.
CPC ............ *C07B 41/04* (2013.01); *C07D 235/18* (2013.01); *C07D 249/18* (2013.01)

(58) Field of Classification Search
CPC ...... C07D 235/18; C07D 249/18; C07B 41/04
See application file for complete search history.

(56) References Cited

U.S. PATENT DOCUMENTS

| | | |
|---|---|---|
| 5,869,660 A | 2/1999 | Adams et al. |
| 6,207,835 B1 | 3/2001 | Reiffenrath et al. |
| 6,239,279 B1 | 5/2001 | Sisko |
| 6,255,491 B1 | 7/2001 | Sisko |
| 7,034,043 B2 | 4/2006 | Scott et al. |
| 7,211,666 B2 | 5/2007 | Godfrey, Jr. et al. |
| 7,396,929 B2 | 7/2008 | Kong et al. |
| 7,479,558 B2 | 1/2009 | Callahan et al. |
| 7,501,416 B2 | 3/2009 | Kim et al. |
| 7,544,717 B2 | 6/2009 | Hom et al. |
| 7,638,646 B2 | 12/2009 | Reeder |
| 7,645,780 B2 | 1/2010 | John et al. |
| 7,759,343 B2 | 7/2010 | Dyckman et al. |
| 7,777,048 B2 | 8/2010 | Ansell et al. |
| 7,820,675 B2 | 10/2010 | Johansson et al. |
| 8,329,703 B2 | 12/2012 | Hu et al. |
| 8,598,193 B2 | 12/2013 | Bond et al. |
| 8,927,559 B2 | 1/2015 | Asianian et al. |
| 9,133,215 B2 | 9/2015 | Bailey et al. |
| 9,656,996 B2 | 5/2017 | Xu et al. |
| 9,676,760 B2 | 6/2017 | Corkey et al. |
| 10,087,195 B2 | 10/2018 | Wang et al. |
| 10,183,919 B2 | 1/2019 | Kruegel et al. |
| 10,336,717 B2 | 7/2019 | Cacatian et al. |
| 10,590,094 B2 | 3/2020 | Kleymann et al. |
| 10,633,403 B2 | 4/2020 | Kang et al. |
| 10,676,424 B2 | 6/2020 | Ngai et al. |

(Continued)

FOREIGN PATENT DOCUMENTS

| | | |
|---|---|---|
| CN | 106336349 | 1/2017 |
| CN | 107011127 | 4/2017 |

(Continued)

OTHER PUBLICATIONS

Zheng, Angewandte Chemie, International Edition, 2018, vol. 57(42), 13795-13799. (Year: 2018).*
Zheng, Angewandte Chemie, International Edition, 2018, 57(31), 9645-9649. (Year: 2018).*
Lee, Chem Soc, Feb. 11, 2019, vol. 10, 3217-3222. (Year: 2019).*
Feng P. et al., "Access to a new class of synthetic building blocks via trifluoromethoxylation of pyridines and pyrimidines", Chem. Sci., 2016, vol. 7, pp. 424-429.
PUBCHEM, CID 91686325, Apr. 28, 2015, Retrieved from the Internet <URL: https://pubchem.ncbi.nlm.nih.gov/compound/91686325>.

(Continued)

*Primary Examiner* — D Margaret M Seaman
(74) *Attorney, Agent, or Firm* — Gary J. Gershik

(57) ABSTRACT

The present invention provides a compound having the structure:

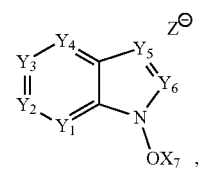

a processing of making the compound; and a process of using the compound as a reagent for the difluoromethoxylation and trifluoromethoxylation of arenes or heteroarenes.

20 Claims, 6 Drawing Sheets

(56) References Cited

U.S. PATENT DOCUMENTS

| | | |
|---|---|---|
| 10,947,237 B2 | 3/2021 | Bhattacharjee et al. |
| 11,066,414 B2 | 7/2021 | Bacon et al. |
| 11,129,813 B2 | 9/2021 | Siddiqui-Jain |
| 11,254,681 B2 | 2/2022 | Schroder et al. |
| 11,278,534 B2 | 3/2022 | Kleymann et al. |
| 2018/0170919 A1 | 6/2018 | Chen et al. |

FOREIGN PATENT DOCUMENTS

| | | |
|---|---|---|
| EP | 1487809 B1 | 1/2008 |
| EP | 2324024 B1 | 9/2012 |
| JP | 7215689 B2 | 1/2023 |
| WO | WO 2014/140704 A1 | 9/2014 |
| WO | WO 2014/154794 | 10/2014 |
| WO | WO 2017/152076 A1 | 9/2018 |

OTHER PUBLICATIONS

PUBCHEM, CID 68637016, Nov. 30, 2012, Retrieved from the Internet <URL: https://pubchem.ncbi.nlm.nih.gov/compound/68637016>.

International Search Report dated May 1, 2019 in connection with PCT International Application No. PCT/US2019/019673.

Written Opinion (form PCT/ISA/237) dated May 1, 2019 in connection with PCT International Application No. PCT/US2019/019673.

International Preliminary Report on Patentability dated Aug. 27, 2020, including Written Opinion of the International Searching Authority dated May 1, 2019, in connection with PCT International Application No. PCT/US2019/019673.

Pitre et al. Metal-Free Photocatalytic Radical Trifluoromethylation Utilizing Methylene Blue and Visible Light Irradiation, *ACS Catal.* 2014, 4, 8, 2530-2535 (Exhibit 2).

Nagib, D., MacMillan, D. Trifluoromethylation of arenes and heteroarenes by means of photoredox catalysis. *Nature* 480, 224-228 (2011) . https://doi.org/10.1038/nature10647 (Exhibit 2).

Beatty, J., Douglas, J., Cole, K. et al. A scalable and operationally simple radical trifluoromethylation. *Nat Commun* 6, 7919 (2015). https://doi.org/10.1038/ncomms8919 (Exhibit 3).

Guo, S., Cong, F., Guo, R. et al. Asymmetric silver-catalysed intermolecular bromotrifluoromethoxylation of alkenes with a new trifluoromethoxylation reagent. *Nature Chem* 9, 546-551 (2017). https://doi.org/10.1038/nchem.2711 (Exhibit 4).

Daniela Federsel, Angelika Herrmann, Dines Christen, Stefan Sander, Helge Willner, Heinz Oberhammer, Structure and conformation of α,α, α-trifluoroanisol, $C_6H_5OCF_3$, Journal of Molecular Structure, vols. 567-568, 2001, pp. 127-136, ISSN 0022-2860 (Exhibit 5).

Martin A. McClinton, Deborah A. McClinton, Trifluoromethylations and related reactions in organic chemistry, Tetrahedron, vol. 48, Issue 32, 1992, pp. 6555-6666, ISSN 0040-4020 (Exhibit 6).

Müller K, Faeh C, Diederich F. Fluorine in pharmaceuticals: looking beyond intuition. Science. Sep. 28, 2007; 317 (5846) :1881-6. doi: 10.1126/science.1131943. PMID: 17901324 (Exhibit 7).

Leroux, F. R. ; Manteau, B.; Vors, J.-P.; Pazenok, S. *Beilstein J. Org. Chem.* 2008, 4, No. 13. doi:10.3762/bjoc.4.13 (Exhibit 8).

Tlili A, Toulgoat F, Billard T. Synthetic Approaches to Trifluoromethoxy-Substituted Compounds. Angew Chem Int Ed Engl. Sep. 19, 2016;55(39) :11726-35. doi: 10.1002/anie,201603697. Epub Jul. 28, 2016. PMID: 27467551 (Exhibit 9).

Lee KN, Lee JW, Ngai MY. Synthesis ot Trifluoromethoxylated (Hetero) Arenes via. $OCF_3$ Migration. Synlett. Feb. 2016;27(3) :313-319. doi: 10.1055/s-0035-1560516. Epub Nov. 16, 2015. PMID: 27872511; PMCID: PMC5115881 (Exhibit 10).

Matoušek, V., Pietrasiak, E., Sigrist, L., Czarniecki, B. and Togni, A. (2014), O-Trifluoromethylation of N,N-Disubstituted Hydroxylamines with Hypervalent Iodine Reagents. Eur. J. Org. Chem., 2014: 3087-3092. https://doi.org/10.1002/ejoc.201402225 (Exhibit 11).

Chen C, Chen P, Liu G. Palladium-Catalyzed Intramolecular Aminotrifluoromethoxylation of Alkenes. J Am Chem Soc. Dec. 23, 2015; 137 (50) :15648-51. doi: 10.1021/jacs.5b10971. Epub Dec. 10, 2015. PMID: 26636720 (Exhibit 12).

Liang A, Han S, Liu Z, Wang L, Li J, Zou D, Wu Y, Wu Y. Regioselective Synthesis of N-Heteroaromatic Trifluoromethoxy Compounds by Direct O-CF3 Bond Formation. Chemistry. Apr. 4, 2016;22(15) :5102-6. doi: 10.1002/chem.201505181. Epub Feb. 25, 2016, 25. PMID: 26791812. (Exhibit 13).

Mejía, Esteban and Antonio Togni. "Rhenium-Catalyzed Trifluoromethylation of Arenes and Heteroarenes by Hypervalent Iodine Reagents." *ACS Catalysis* 2 (2012) : 521-527 (Exhibi t 14).

Tomoya Fujiwara, David O'Hagan, Successful fluorine-containing herbicide agrochemicals, Journal of Fluorine Chemistry, vol. 167, 2014, pp. 16-29, ISSN 0022-1139 (Exhibit 15).

Tlili A, Toulgoat F, Billard T. Synthetic Approaches to Trifluoromethoxy-Substituted Compounds. Angew Chem Int Ed Engl. Sep. 19, 2016;55(39) :11726-35. doi : 10.1002/anie.201603697. Epub Jul. 28, 2016. PMID: 27467551 (Exhibit 16).

Zhou M, Ni C, Zeng Y, Hu J. Trifluoromethyl Benzoate: A Versatile Trifluoromethoxylation Reagent. J Am Chem Soc. Jun. 6, 2018;140(22) :6801-6805. doi: 10.1021/jacs.8b04000. Epub May 25, 2018. PMID: 29787259 (Exhibit 17).

\* cited by examiner a. Design & energies of catalytic & selective formation of the OR$_F$ radical b. Mechanism hypothesis for the polyfluoromethoxylation of arenes

DIFLUOROMETHOXYLATION AND TRIFLUOROMETHOXYLATION COMPOSITIONS AND METHODS FOR SYNTHESIZING SAME

CROSS-REFERENCE TO RELATED APPLICATIONS

This application is a § 371 national stage of PCT International Application No. PCT/US2019/019673, filed Feb. 26, 2019, claiming the benefit of U.S. Provisional Application Nos. 62/773,510, filed Nov. 30, 2018; 62/726,885, filed Sep. 4, 2018; 62/689,315, filed Jun. 25, 2018; 62/642,917, filed Mar. 14, 2018; 62/642,668, filed Mar. 14, 2018; and 62/635,711, filed Feb. 27, 2018, the contents of each of which are hereby incorporated by reference into the application.

GOVERNMENT SUPPORT

This invention was made with government support under GM119652 awarded by the National Institutes of Health. The government has certain rights in the invention.

Throughout this application various publications are referenced. The disclosures of these documents in their entireties are hereby incorporated by reference into this application in order to more fully describe the state of the art to which this invention pertains.

BACKGROUND OF THE INVENTION

Modern drug discovery and development involves extensive fine-tuning of the physicochemical properties of drug candidates. A common approach to control these properties involves incorporation of fluorine-containing functional groups, such as the difluoromethoxy ($OCF_2H$) and trifluoromethoxy ($OCF_3$) groups, into drug candidates (Purser, S. et al. 2008; Ojima, I. 2009; Liang, T. et al. 2013). The $OCF_2H$ and $OCF_3$ groups are privileged functional groups in medicinal chemistry because their introduction into organic molecules often enhances their therapeutic efficacy by increasing metabolic stability, improving cellular membrane permeability, and adjusting pharmacokinetic properties (Muller, K. et al. 2007). More importantly, while molecules bearing the $OCF_2H$ group can adjust their lipophilicity to adapt to the chemical environment via a simple bond rotation (Huchet, Q. A. et al. 2017), both $OCF_2H$- and $OCF_3$-containing aromatic compounds have an orthogonal structural geometry that enriches molecular spatial complexity and provides additional binding affinity to active sites in a target (Muller, K. et al. 2007). Although a number of prescribed pharmaceutical agents have $OCF_2H$ or $OCF_3$ motifs in an aromatic system, access to such analogues often requires the installation of the $OCF_2H$ and $OCF_3$ groups at an early stage of a multi-step synthetic sequence.

The trifluoromethoxy ($OCF_3$) group, which is found in more than 350,000 biologically active compounds according to PubChem database as of October 2017, has a broad spectrum of applications in pharmaceuticals (Jeschke et al. 2007). The prevalence of the $OCF_3$ group in drugs can be attributed to its favorable physicochemical properties such as outstanding electronegativity ($\chi$=3.7) that improves molecular metabolic stability, and excellent lipophilicity (Hansch parameter: $\Pi_x$=1.04) that enhances membrane permeability (Mcclinton, D. A. et al. 1992; Hansch, A. 1979). Notably, arenes bearing the $OCF_3$ group have a distinct three-dimensional scaffold where the plane containing the C—$OCF_3$ group is orthogonal to the plane of the aromatic ring (Federsel, A. et al. 2001). Compounds with such a structural architecture have been shown to provide additional binding affinity to biological targets (Muller, C. et al. 2007).

SUMMARY OF THE INVENTION

The present invention provides a compound having the structure:

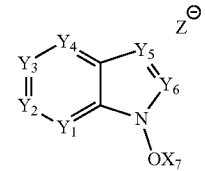

$Y_1$ is N or C—$X_1$, $Y_2$ is N or C—$X_2$, $Y_3$ is N or C—$X_3$, $Y_4$ is N or C—$X_4$ and $Y_6$ is N or C—$X_6$, wherein $X_1$, $X_2$, $X_3$, $X_4$, and $X_6$ are each, independently, —H, halogen, —$CF_3$, —$NO_2$, —$SO_2Me$, —CN, —$OCF_3$, —$OCF_2H$, -(alkyl), -(alkenyl), -(alkynyl), -(aryl), -(heteroaryl), —C(O)—$R_1$, —C(O)—$OR_1$, —C(O)—$SR_1$, —$OR_1$, —$SR_1$, —$NR_1R_2$, or —C(O)—$NR_1R_2$, wherein $R_1$ and $R_2$ are each, independently, —H, -(alkyl), -(alkenyl), -(alkynyl), -(aryl), -(heteroaryl), —C(O)—$R_3$, —C(O)—$OR_3$, —C(O)—$NR_4R_5$, —C(O)—$SR_3$, —C(S)—$R_3$, —C(S)—$OR_3$, —C(S)—$NR_4R_5$, —C(S)—$SR_3$, —C($NR_5$)—$R_3$, —C($NR_5$)—$OR_3$, —C($NR_6$)—$NR_4R_5$ or —C($NR_6$)—$SR_3$, wherein $R_3$, $R_4$, $R_5$ and $R_6$ are each, independently, —H, -(alkyl), -(alkenyl), -(alkynyl), -(aryl) or -(heteroaryl);

$Y_5$ is N or $N^+$—$X_5$, wherein $X_5$ is —H, -alkyl, —C(O)-alkyl, —C(O)-aryl, —C(O)-heteroaryl, —C(O)—O-alkyl or —C(O)—O-aryl;

$X_7$ is $CF_3$, $CF_2H$, $CFH_2$, perfluoroalkyl or polyfluoroalkyl; and

Z is OTf, $BF_4$, B(aryl)$_4$, $SbF_6$, $PF_6$, halogen, —OS(O)$_2OR_7$, —OS(O)$_2$—$R_7$, $ClO_4$ or —OP(O)($OR_8$)($OR_9$), wherein $R_7$, $R_8$, and $R_9$ are each, independently, —H, -(alkyl), -(aryl), -(heteroaryl), wherein when $Y_6$ is N, then $Y_5$ is $N^+$—$X_5$ and $Z^-$ is present, and when $Y_6$ is C—$X_6$, then $Y_5$ is N and $Z^-$ is absent.

BRIEF DESCRIPTION OF THE FIGURES

FIG. 4A. Light on-and-off experiments of difluoromethoxylation reaction of benzene with 1a.

FIG. 6A. Cyclic Voltammetry of reagent 1a.

DETAILED DESCRIPTION OF THE INVENTION

Figure 1:
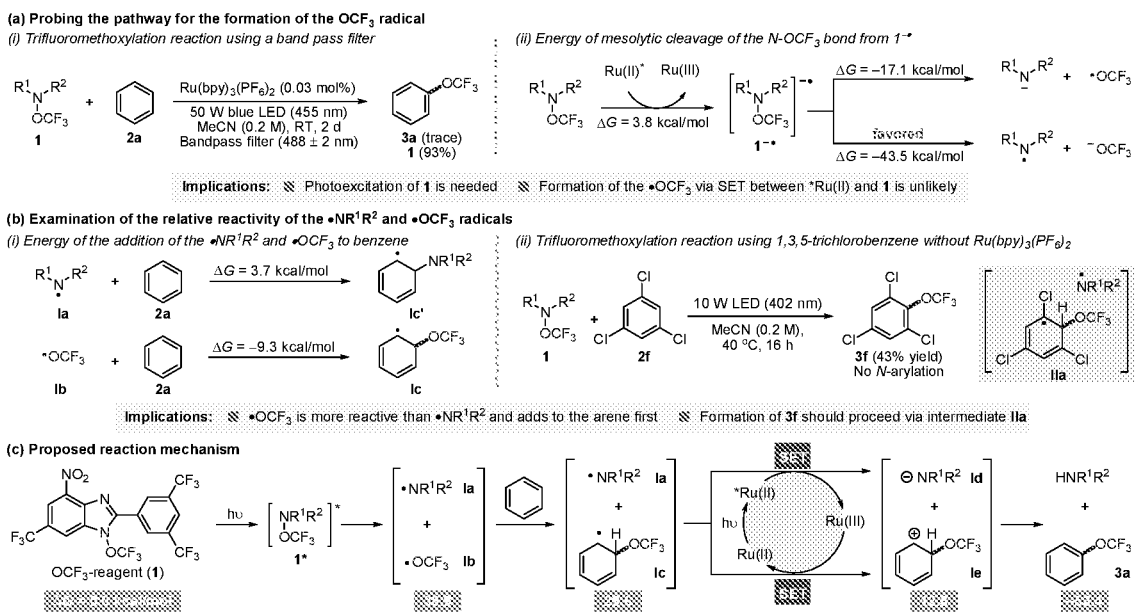
FIG. 1. Mechanistic studies and proposed reaction mechanism. All energies are Gibbs free energies (kcal/mol) with respect to the ground state reagent 1 and benzene calculated at the M06-2X/6-311++G(d,p)/SMD(MeCN)//M06-2X/6-31+G(d,p) level of theory. All the mechanistic study experiments described in a-b used one equivalent of reagent 1 and ten equivalents of arenes.

The present invention provides a compound having the structure:

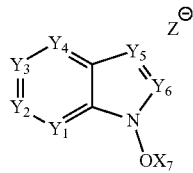

$Y_1$ is N or C—$X_1$, $Y_2$ is N or C—$X_2$, $Y_3$ is N or C—$X_3$, $Y_4$ is N or C—$X_4$ and $Y_6$ is N or C—$X_6$, wherein $X_1$, $X_2$, $X_3$, $X_4$, and $X_6$ are each, independently, —H, halogen, —$CF_3$, —$NO_2$, —$SO_2Me$, —CN, —$OCF_3$, —$OCF_2H$, -(alkyl), -(alkenyl), -(alkynyl), -(aryl), -(heteroaryl), —C(O)—$R_1$, —C(O)—$OR_1$, —C(O)—$SR_1$, —$OR_1$, —$SR_1$, —$NR_1R_2$, or —C(O)—$NR_1R_2$, wherein $R_1$ and $R_2$ are each, independently, —H, -(alkyl), -(alkenyl), -(alkynyl), -(aryl), -(heteroaryl), —C(O)—$R_3$, —C(O)—$OR_3$, —C(O)—$NR_4R_5$, —C(O)—$SR_3$, —C(S)—$R_3$, —C(S)—$OR_3$, —C(S)—$NR_4R_5$, —C(S)—$SR_3$, —C($NR_5$)—$R_3$, —C(NR)—$OR_3$, —C($NR_6$)—$NR_4R_5$ or —C($NR_6$)—$SR_3$, wherein $R_3$, $R_4$, $R_5$ and $R_6$ are each, independently, —H, -(alkyl), -(alkenyl), -(alkynyl), -(aryl) or -(heteroaryl);

$Y_5$ is N or $N^+$—$X_5$, wherein $X_5$ is —H, -alkyl, —C(O)-alkyl, —C(O)-aryl, —C(O)— heteroaryl, —C(O)—O-alkyl or —C(O)—O-aryl;

$X_7$ is $CF_3$, $CF_2H$, $CFH_2$, perfluoroalkyl or polyfluoroalkyl; and

Z is OTf, $BF_4$, $B(aryl)_4$, $SbF_5$, $PF_6$, halogen, —OS(O)$_2OR_7$, —OS(O)—$R_7$, $ClO_4$ or —OP(O)($OR_8$)($OR_9$), wherein $R_7$, $R_8$, and $R_9$ are each, independently, —H, -(alkyl), -(aryl), -(heteroaryl), wherein when $Y_6$ is N, then $Y_5$ is $N^+$—$X_5$ and $Z^-$ is present, and when $Y_6$ is C—$X_6$, then $Y_5$ is N and $Z^-$ is absent.

In some embodiments, the compound wherein $Y_1$ is N or C—$X_1$, $Y_2$ is N or C—$X_2$, $Y_3$ is N or C—$X_3$ and $Y_4$ is N or C—$X_4$, wherein $X_1$, $X_2$, $X_3$ and $X_4$ are each, independently, —H, halogen, —$CF_3$, —$NO_2$, —$SO_2Me$, —CN, —$OCF_3$ or —$OCF_2H$;

$Y_5$ is N or $N^+$—$X_5$, wherein $X_5$ is alkyl;

$Y_6$ is N or C—$X_6$, wherein $X_6$ is substituted aryl or substituted heteroaryl;

$X_7$ is $CF_3$ or $CF_2H$; and

Z is OTf, $BF_4$, $B(aryl)_4$, $SbF_6$, $PF_6$, halogen, —OS(O)$_2OR_7$, —OS(O)$_2$—$R_7$, $ClO_4$ or —OP(O)($OR_8$)($OR_9$), wherein $R_7$, $R_8$, and $R_9$ are each, independently, —H, -(alkyl), -(aryl), -(heteroaryl), wherein when $Y_6$ is N, then $Y_5$ is $N^+$—X and $Z^-$ is present, and when $Y_6$ is C—$X_6$, then $Y_5$ is N and $Z^-$ is absent.

In some embodiments, the compound wherein $Y_1$ is N or C—$X_1$, $Y_2$ is N or C—$X_2$, $Y_3$ is N or C—$X_3$ and $Y_4$ is N or C—$X_4$, wherein $X_1$, $X_2$, $X_3$ and $X_4$ are each, independently, —H, —Cl, —Br, —F, —$CF_3$, —$NO_2$ or —$SO_2Me$ $Y_5$ is N or $N^+$—$X_5$, wherein $X_5$ is alkyl;

$Y_6$ is N or C—$X_6$, wherein $X_6$ is substituted aryl;

$X_7$ is $CF_3$ or $CF_2H$; and

Z is OTf, $BF_4$, $B(aryl)_4$, $SbF_6$, $PF_6$, halogen, —OS(O)$_2OR_7$, —OS(O)$_2$—$R_7$, $ClO_4$ or —OP(O)($OR_8$)($OR_9$), wherein $R_7$, $R_8$, and $R_9$ are each, independently, —H, -(alkyl), -(aryl), -(heteroaryl), wherein when $Y_6$ is N, then $Y_5$ is $N^+$—$X_5$ and $Z^-$ is present, and when $Y_6$ is C—$X_6$, then $Y_5$ is N and $Z^-$ is absent.

In some embodiments, the compound wherein $Y_2$ is C—$X_2$, wherein $X_2$, is halogen, —$CF_3$, —$NO_2$, —$SO_2Me$, —CN, —$OCF_3$ or —$OCF_2H$.

In some embodiments, the compound wherein $Y_2$ is C—$X_2$, and $Y_4$ is C—$X_4$ wherein $X_2$ and $X_4$ are each, independently, halogen, —$CF_3$, —$NO_2$, —$SO_2Me$, —CN, —$OCF_3$ or —$OCF_2H$.

In some embodiments, the compound wherein Z is OTf.

In some embodiments, the compound wherein at least two of $Y_1$, $Y_2$, $Y_3$ and $Y_4$ are other than C—H.

In some embodiments, the compound having the structure:

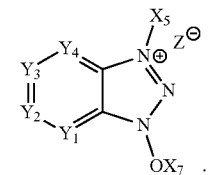

In some embodiments, the compound wherein $X_7$ is —$CF_2H$.

In some embodiments, the compound having the structure:

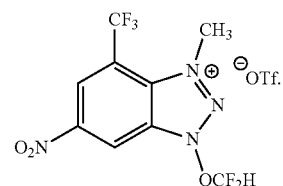

In some embodiments, the compound wherein $X_7$ is —$CF_3$.

In some embodiments, the compound having the structure:

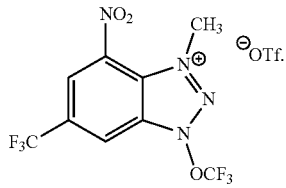 [SMILES: C[n+]1nn(OC(F)(F)F)c2cc(C(F)(F)F)cc([N+](=O)[O-])c21 ; "OTf."]

The present invention provides a process of preparing any one of the above compounds comprising (a) reacting the compound having the structure:

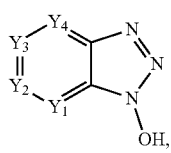

with a fluoromethylating agent in a first suitable solvent under conditions sufficient to produce the compound having the structure:

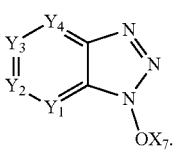

In some embodiments, the process further comprising (b) reacting the product of step (a) with an alkylating agent bearing a Z group in a second suitable solvent.

In some embodiments, the process for preparing the compound having the structure:

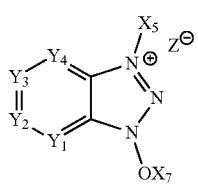

wherein $X_5$ is alkyl and $X_7$ is —$CF_2H$,
comprising
(a) reacting the compound having the structure:

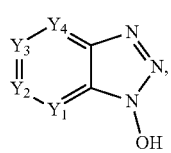

with a difluoromethylating agent in a first suitable solvent under conditions sufficient to produce the compound having the structure:

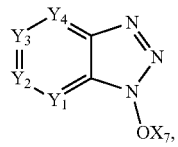

wherein $X_7$ is —$CF_2H$; and
(b) reacting the product of step (a) with an alkylating agent bearing a Z group in a second suitable solvent under conditions sufficient to produce the compound.

In some embodiments, the process for preparing the compound having the structure:

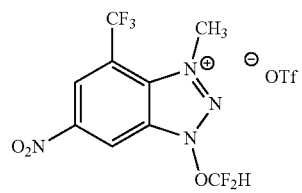

comprising
(a) reacting the compound having the structure:

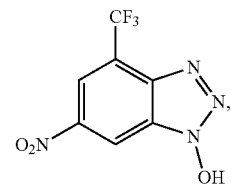

with a difluoromethylating agent in a first suitable solvent under conditions sufficient to produce the compound having the structure:

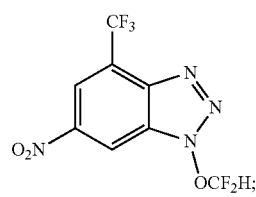

(b) reacting the product of step (a) with a methylating agent bearing a triflate group in a second suitable solvent under conditions sufficient to produce the compound.

In some embodiments, the process wherein the difluormethylating agent is diethyl (bromodifluoromethyl)phosphonate.

In some embodiments, the process, wherein the first suitable solvent is methyltetrahydrofuran/water mixture (1:1).

In some embodiments, the process wherein the second suitable solvent is dichloromethane or dichloroethane.

In some embodiments, the process wherein the alkylating agent is an alkyl triflate.

In some embodiments, the process wherein the alkylating agent is methyl triflate.

In some embodiments, the process for preparing the compound having the structure:

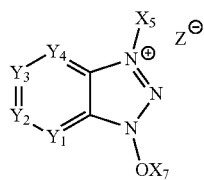

wherein $X_5$ is alkyl and $X_7$ is —$CF_3$,
comprising
(a) reacting the compound having the structure:

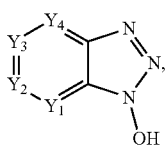

with a trifluoromethylating agent in a first suitable solvent under conditions sufficient to produce the compound having the structure:

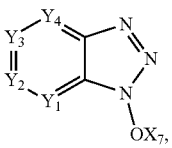

wherein $X_5$ is —$CF_3$;
(b) reacting the product of step (a) with an alkylating agent bearing a triflate group in a second suitable solvent under conditions sufficient to produce the compound.

In some embodiments, the process for preparing the compound having the structure:

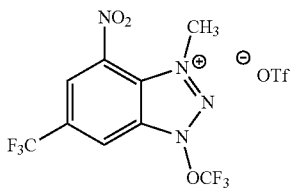

comprising
(a) reacting the compound having the structure:

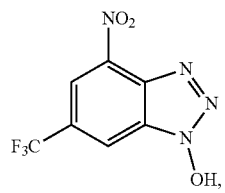

with a trifluoromethylating agent in a first suitable solvent under conditions sufficient to produce the compound having the structure:

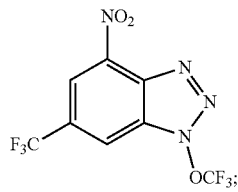 [SMILES: O=[N+]([O-])c1cc(C(F)(F)F)cc2c1nnn2OC(F)(F)F]

(b) reacting the product of step (a) with a methylating agent bearing a triflate group in a second suitable solvent under conditions sufficient to produce the compound.

In some embodiments, the process wherein the trifluormethylating agent is Togni reagent I or Togni reagent II.

In some embodiments, the process wherein the first suitable solvent is hexanes.

In some embodiments, the process wherein the second suitable solvent is hexanes.

In some embodiments, the process wherein the alkylating agent is an alkyl triflate.

In some embodiments, the process wherein the alkylating agent is methyl triflate.

The present invention also provides a process of fluoromethoxylating an arene or heteroarene, wherein at least one carbon of the arene or heteroarene is unsubstituted, comprising reacting the arene or heteroarene with the compound of the present invention under conditions sufficient to thereby produce the fluoromethoxylated arene or heteroarene.

In some embodiments, the process comprising fluoromethoxylating the aryl or heteroaryl group of an aryl or heteroaryl containing compound, wherein at least one carbon of the aryl or heteroaryl is unsubstituted.

In some embodiments, the process comprising difluoromethoxylating an arene or heteroarene, wherein at least one carbon of the arene or heteroarene is unsubstituted.

In some embodiments, the process comprising difluoromethoxylating the aryl or heteroaryl group of an aryl or heteroaryl containing compound, wherein at least one carbon of the aryl or heteroaryl is unsubstituted.

In some embodiments, the process comprising trifluoromethoxylating an arene or heteroarene, wherein at least one carbon of the arene or heteroarene is unsubstituted.

In some embodiments, the process comprising difluoromethoxylating the aryl or heteroaryl group of an aryl or heteroaryl containing compound, wherein at least one carbon of the aryl or heteroaryl is unsubstituted.

In some embodiments, the process wherein the reaction occurs in the presence of a metal catalyst.

In some embodiments, the process wherein the reaction occurs in the presence of a Ruthenium catalyst or Iridium catalyst.

In some embodiments, the process wherein the reaction occurs in the presence of Ru(bpy)$_3$(PF$_6$)$_2$ catalyst.

In some embodiments, the process wherein the reaction occurs under irradiation with visible light.

In some embodiments, the process wherein the reaction occurs under irradiation with 402 nm visible light.

In some embodiments, the process wherein the reaction occurs at room temperature.

In some embodiments, the process wherein the reaction occurs at 20-45° C. In some embodiments, the process wherein the reaction occurs in a suitable solvent.

In some embodiments, the process wherein the suitable solvent is acetonitrile, dichloromethane or nitromethane or mixture thereof.

44 In some embodiments, the process wherein the arene or heteroarene is a phenyl, pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene or quinolone.

In some embodiments, the process for producing a fluoromethoxylated compound having the structure:

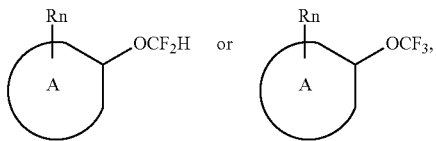

wherein
A is an aryl or heteroaryl; and
R is —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$H, —CO$_2$-(alkyl), —CO$_2$-(alkenyl), —CO$_2$-(alkynyl) —CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —C(O)-(alkyl), —C(O)-(alkenyl), —C(O)-(alkynyl), —C(O)-(aryl), —C(O)-(heteroaryl), —OCO$_2$-(alkyl), —OCO$_2$-(alkenyl), —OCO$_2$-(alkynyl), —OCO$_2$-(aryl), —OCO$_2$-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl) or —S-(heteroaryl); and
n is 0-7,
comprising (a) reacting a compound having the structure:

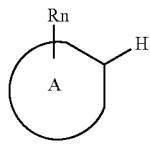

with the compound of the present invention under conditions sufficient to thereby produce the fluoromethoxylated compound.

In some embodiments, the process for producing a difluoromethoxylated compound having the structure:

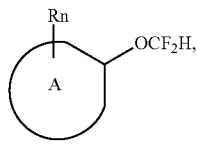

wherein
A is an aryl or heteroaryl; and
R is —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$H, —CO$_2$-(alkyl), —CO$_2$-(alkenyl), —CO$_2$-(alkynyl) —CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —C(O)-(alkyl), —C(O)-(alkenyl), —C(O)-(alkynyl), —C(O)-(aryl), —C(O)-(heteroaryl), —OCO$_2$-(alkyl), —OCO$_2$-(alkenyl), —OCO$_2$-(alkynyl), —OCO$_2$-(aryl), —OCO$_2$-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl) or —S-(heteroaryl); and
n is 0-7,
comprising (a) reacting a compound having the structure:

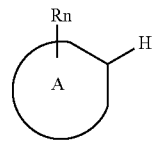

with the compound of the present invention under conditions sufficient to thereby produce the difluoromethoxylated compound.

In some embodiments, the process wherein the aryl or heteroaryl is a phenyl, pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene or quinolone.

In some embodiments, the process for producing a difluoromethoxylated compound having the structure:

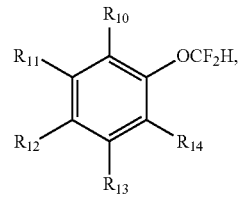

wherein
$R_{10}$, $R_{11}$, $R_{12}$, $R_{13}$ and $R_{14}$ are each, independently, —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$H, —CO$_2$-(alkyl), —CO$_2$-(alkenyl), —CO$_2$-(alkynyl) —CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —C(O)-(alkyl), —C(O)-(alkenyl), —C(O)-(alkynyl), —C(O)-(aryl), —C(O)-(heteroaryl), —OCO$_2$-(alkyl), —OCO$_2$-(alkenyl), —OCO$_2$-(alkynyl), —OCO$_2$-(aryl), —OCO$_2$-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl) or —S-(heteroaryl),
comprising (a) reacting a compound having the structure:

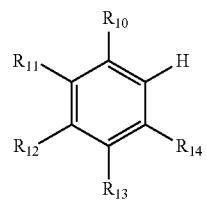

with the compound of the present invention under conditions sufficient to thereby produce the difluoromethoxylated compound.

In some embodiments, the process for producing a difluoromethoxylated compound having the structure:

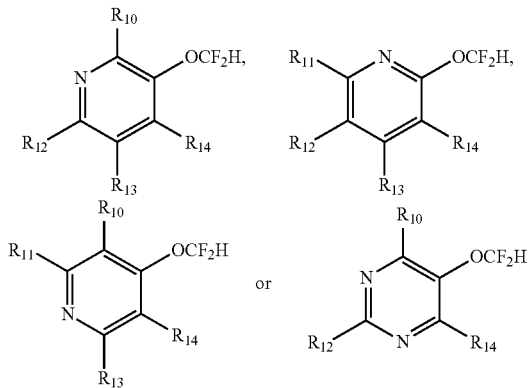

wherein $R_{10}$, $R_{11}$, $R_{12}$, $R_{13}$ and $R_{14}$ are each, independently, —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$H, —CO$_2$-(alkyl), —CO$_2$-(alkenyl), —CO$_2$-(alkynyl) —CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —C(O)-(alkyl), —C(O)-(alkenyl), —C(O)-(alkynyl), —C(O)-(aryl), —C(O)-(heteroaryl), —OCO$_2$-(alkyl), —OCO$_2$-(alkenyl), —OCO$_2$-(alkynyl), —OCO$_2$-(aryl), —OCO$_2$-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl) or —S-(heteroaryl), comprising (a) reacting a compound having the structure:

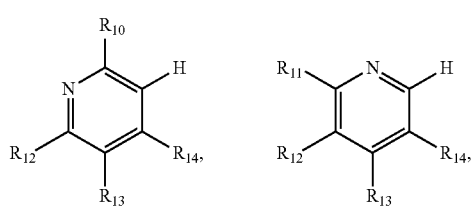

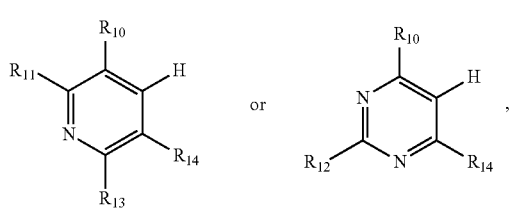

with the compound of the present invention under conditions sufficient to thereby produce the difluoromethoxylated compound.

In some embodiments, the process for producing a difluoromethoxylated compound having the structure:

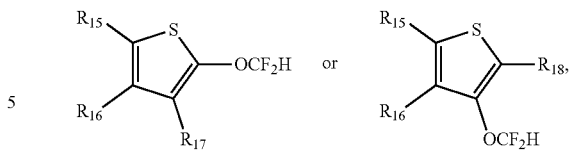

wherein $R_{15}$, $R_{16}$, $R_{17}$ and $R_{18}$ are each, independently, —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$H, —CO$_2$-(alkyl), —CO$_2$-(alkenyl), —CO-(alkynyl) —CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —C(O)-(alkyl), —C(O)-(alkenyl), —C(O)-(alkynyl), —C(O)-(aryl), —C(O)-(heteroaryl), —OCO$_2$-(alkyl), —OCO$_2$-(alkenyl), —OCO$_2$-(alkynyl), —OCO$_2$-(aryl), —OCO$_2$-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl) or —S-(heteroaryl), comprising (a) reacting a compound having the structure:

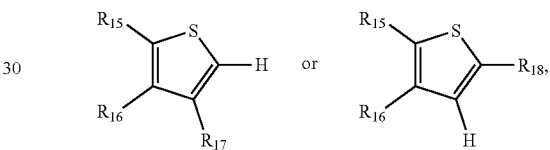

with the compound of the present invention under conditions sufficient to thereby produce the difluoromethoxylated compound.

In some embodiments, the process for producing a trifluoromethoxylated compound having the structure:

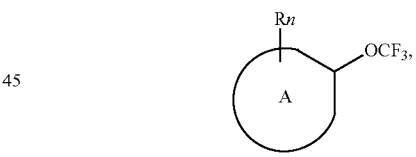

wherein

A is an aryl or heteroaryl; and

R is —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$H, —CO$_2$-(alkyl), —CO$_2$-(alkenyl), —CO$_2$-(alkynyl) —CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —C(O)-(alkyl), —C(O)-(alkenyl), —C(O)-(alkynyl), —C(O)-(aryl), —C(O)-(heteroaryl), —OCO$_2$-(alkyl), —OCO$_2$-(alkenyl), —OCO$_2$-(alkynyl), —OCO$_2$-(aryl), —OCO$_2$-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl) or —S-(heteroaryl); and n is 0-7, comprising (a) reacting a compound having the structure:

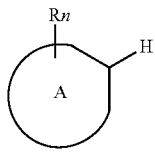

with the compound of the present invention under conditions sufficient to thereby produce the trifluoromethoxylated compound.

In some embodiments, the process wherein the aryl or heteroaryl is a phenyl, pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene or quinolone.

In some embodiments, the process for producing a trifluoromethoxylated compound having the structure:

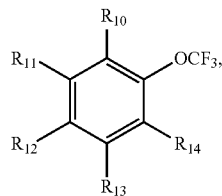

wherein $R_{10}$, $R_{11}$, $R_{12}$, $R_{13}$ and $R_{14}$ are each, independently, —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$H, —CO$_2$-(alkyl), —CO$_2$-(alkenyl), —CO$_2$-(alkynyl) —CO$_2$-(aryl), —C(—CO$_2$-(heteroaryl), —C(O)NH-(alkyl), —C(O) NH-(alkenyl), —C(O)NH-(alkynyl) —C(O)NH-(aryl), —C(O)NH-(heteroaryl), —C(O)N(alkyl)$_2$, —OH, —OAc, —C(O)-(alkyl), —C(O)-(alkenyl), —C(O)-(alkynyl), —C(O)-(aryl), —C(O)-(heteroaryl), —OCO$_2$-(alkyl), —OCO$_2$-(alkenyl), —OCO$_2$-(alkynyl), —OCO$_2$-(aryl), —OCO$_2$-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl) or —S-(heteroaryl), comprising (a) reacting a compound having the structure:

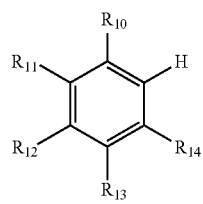

with the compound of the present invention under conditions sufficient to thereby produce the trifluoromethoxylated compound.

In some embodiments, the process for producing a trifluoromethoxylated compound having the structure:

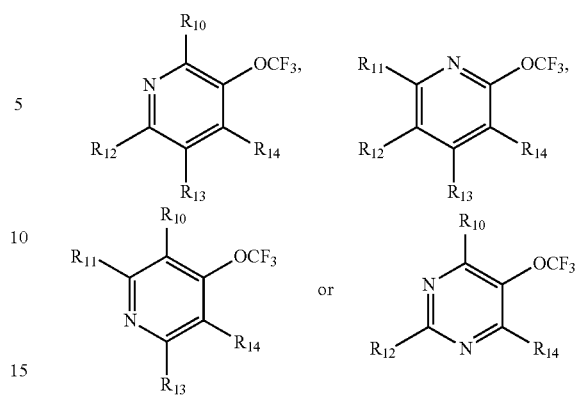

wherein $R_{10}$, $R_{11}$, $R_{12}$, $R_{13}$ and $R_{14}$ are each, independently, —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$H, —CO$_2$-(alkyl), —CO$_2$-(alkenyl), —CO$_2$-(alkynyl) —CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —C(O)-(alkyl), —C(O)-(alkenyl), —C(O)-(alkynyl), —C(O)-(aryl), —C(O)-(heteroaryl), —OCO$_2$-(alkyl), —OCO$_2$-(alkenyl), —OCO$_2$-(alkynyl), —OCO$_2$-(aryl), —OCO$_2$-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl) or —S-(heteroaryl), comprising (a) reacting a compound having the structure:

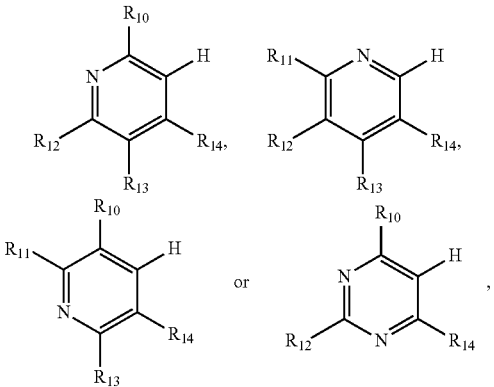

with the compound of the present invention under conditions sufficient to thereby produce the trifluoromethoxylated compound.

In some embodiments, the process for producing a trifluoromethoxylated compound having the structure:

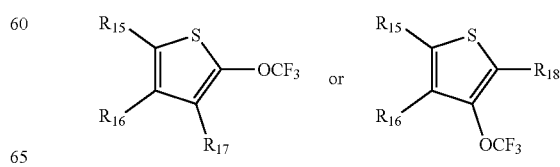

wherein $R_{15}$, $R_{16}$, $R_{17}$ and $R_{18}$ are each, independently, —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$H, —CO$_2$-(alkyl), —CO$_2$-(alkenyl), —CO$_2$-(alkynyl) —CO$_2$-(aryl), —C(—CO$_2$-(heteroaryl), —C(O)NH-(alkyl), —C(O) NH-(alkenyl), —C(O)NH-(alkynyl) —C(O)NH-(aryl), —C(O)NH-(heteroaryl), —C(O)N(alkyl)$_2$, —OH, —OAc, —C(O)-(alkyl), —C(O)-(alkenyl), —C(O)-(alkynyl), —C(O)-(aryl), —C(O)-(heteroaryl), —OCO$_2$-(alkyl), —OCO$_2$-(alkenyl), —OCO$_2$-(alkynyl), —OCO$_2$-(aryl), —OCO$_2$-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl) or —S-(heteroaryl), comprising (a) reacting a compound having the structure:

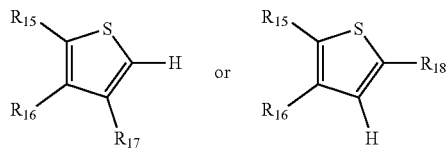

with the compound of the present invention under conditions sufficient to thereby produce the trifluoromethoxylated compound.

In some embodiments, the process wherein the reaction occurs in the presence of a metal catalyst.

In some embodiments, the process wherein the reaction occurs in the presence of a Ruthenium catalyst or Iridium catalyst.

In some embodiments, the process wherein the reaction occurs in the presence of Ru(bpy)$_3$(PF$_6$)$_2$ catalyst.

In some embodiments, the process wherein the reaction occurs under irradiation with visible light.

In some embodiments, the process wherein the reaction occurs under irradiation with 402 nm visible light.

In some embodiments, the process wherein the reaction occurs at room temperature.

In some embodiments, the process wherein the reaction occurs at 20-45° C.

In some embodiments, the process wherein the reaction occurs in a suitable solvent.

In some embodiments, the process wherein the suitable solvent is acetonitrile, dichloromethane or nitromethane or mixture thereof.

In some embodiments, the compound having the structure:

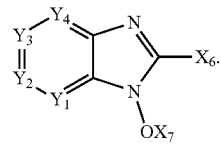

In some embodiments, the compound wherein $X_7$ is —OCF$_3$.

In some embodiments, the compound wherein $X_6$ is

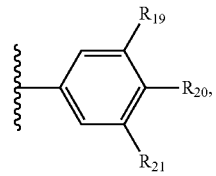

wherein $R_{19}$, $R_{20}$ and $R_{21}$ are each, independently, —H, —Cl, —Br, —F, —CF$_3$, —NO$_2$ or —SO$_2$Me.

In some embodiments, the compound having the structure:

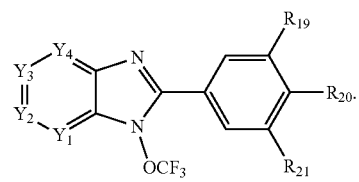

In some embodiments, the compound wherein $Y_2$ is C—X$_2$, wherein $X_2$, is halogen, —CF$_3$, —NO$_2$, —SO$_2$Me, —CN, —OCF$_3$ or —OCF$_2$H.

In some embodiments, the compound wherein wherein $Y_2$ is C—X$_2$, and $Y_4$ is C—X$_4$ wherein $X_2$ and $X_4$ are each, independently, halogen, —CF$_3$, —NO$_2$, —SO$_2$Me, —CN, —OCF$_3$ or —OCF$_2$H.

In some embodiments, the compound wherein wherein $Y_2$ is C—X$_2$, and $Y_4$ is C—X$_4$ wherein $X_2$ and $X_4$ are each, independently, halogen, —CF$_3$ or —NO$_2$.

In some embodiments, the compound having the structure:

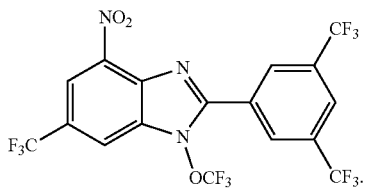 [SMILES: O=[N+]([O-])c1cc(C(F)(F)F)cc2c1nc(-c1cc(C(F)(F)F)cc(C(F)(F)F)c1)n2O]

In some embodiments, a process for preparing the above compound comprising reacting the compound having the structure:

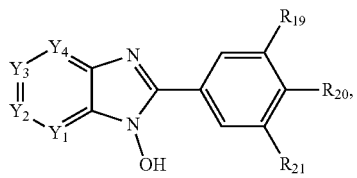

with a trifluoromethylating agent in a suitable solvent under conditions sufficient to thereby produce the compound.

In some embodiments, the process comprising reacting the compound having the structure:

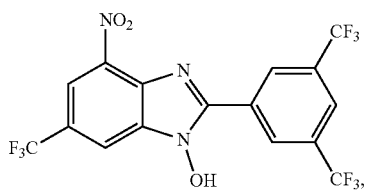

with a trifluoromethylating agent in a suitable solvent under conditions sufficient to thereby produce the compound.

In some embodiments, the process wherein the trifluormethylating agent is Togni reagent I or Togni reagent II.

In some embodiments, the process wherein the suitable solvent is chloroform, dichloromethane, nitromethane, dimethylforamide, diethyl ether, tetrahydrofuran, dioxane, dichloroethane, or hexane.

The present invention provides a process of trifluoromethoxylating an arene or heteroarene, wherein at least one carbon of the arene or heteroarene is unsubstituted, comprising reacting the arene or heteroarene with the compound of the present invention under conditions sufficient to thereby produce the trifluoromethoxylated arene or heteroarene.

In some embodiments, the process comprising trifluoromethoxylating the aryl or heteroaryl group of an aryl or heteroaryl containing compound, wherein at least one carbon of the aryl or heteroaryl is unsubstituted.

In some embodiments, the process wherein the reaction occurs in the presence of a metal catalyst.

In some embodiments, the process wherein the reaction occurs in the presence of a Ruthenium catalyst or Iridium catalyst.

In some embodiments, the process wherein the reaction occurs in the presence of $Ru(bpy)_3(PF_6)_2$ catalyst.

In some embodiments, the process wherein the reaction occurs under irradiation with visible light.

In some embodiments, the process wherein the reaction occurs under irradiation with 402 nm visible light.

In some embodiments, the process wherein the reaction occurs at room temperature.

In some embodiments, the process wherein the reaction occurs at 20-45° C.

In some embodiments, the process wherein the reaction occurs in a suitable solvent.

In some embodiments, the process wherein the suitable solvent is acetonitrile, dichloromethane or nitromethane or mixtures thereof.

In some embodiments, the process wherein the arene or heteroarene is a phenyl, pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene or quinolone.

In some embodiments, the process for producing a trifluoromethoxylated compound having the structure:

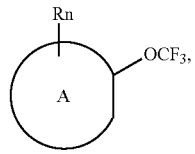

wherein
A is an aryl or heteroaryl; and
R is —H, halogen, —CN, —$CF_3$, —$OCF_3$, -(alkyl), -(alkenyl), -(alkynyl), -(aryl), -(heteroaryl), —$NH_2$, —NH-(alkyl), —NH-(alkenyl), —NH-(alkynyl) —NH-(aryl), —NH-(heteroaryl), —$CO_2H$, —$CO_2$-(alkyl), —$CO_2$-(alkenyl), —$CO_2$-(alkynyl) —$CO_2$-(aryl), —C(—$CO_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —C(O)-(alkyl), —C(O)-(alkenyl), —C(O)-(alkynyl), —C(O)-(aryl), —C(O)-(heteroaryl), —$OCO_2$-(alkyl), —$OCO_2$-(alkenyl), —$OCO_2$-(alkynyl), —$OCO_2$-(aryl), —$OCO_2$-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl) or —S-(heteroaryl); and
n is 0-7,
comprising (a) reacting a compound having the structure:

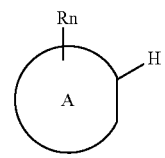

with the compound of the present invention under conditions sufficient to thereby produce the trifluoromethoxylated compound.

In some embodiments, the process wherein the aryl or heteroaryl is a phenyl, pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene or quinolone.

In some embodiments, the process for producing a trifluoromethoxylated compound having the structure:

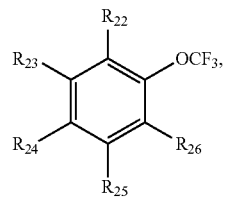

wherein
$R_{22}$, $R_{23}$, $R_{24}$, $R_{25}$ and $R_{26}$ are each, independently, —H, halogen, —CN, —$CF_3$, —$OCF_3$, -(alkyl), -(alkenyl), -(alkynyl), -(aryl), -(heteroaryl), —$NH_2$, —NH-(alkyl), —NH-(alkenyl), —NH-(alkynyl) —NH-(aryl), —NH-(heteroaryl), —$CO_2H$, —$CO_2$-(alkyl), —$CO_2$-(alkenyl), —CO-(alkynyl)

—CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —C(O)-(alkyl), —C(O)-(alkenyl), —C(O)-(alkynyl), —C(O)-(aryl), —C(O)-(heteroaryl), —OCO$_2$-(alkyl), —OCO$_2$-(alkenyl), —OCO$_2$-(alkynyl), —OCO$_2$-(aryl), —OCO$_2$-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl) or —S-(heteroaryl), comprising (a) reacting a compound having the structure:

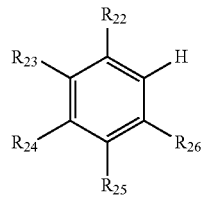

with the compound of the present invention under conditions sufficient to thereby produce the trifluoromethoxylated compound.

In some embodiments, the process for producing a trifluoromethoxylated compound having the structure:

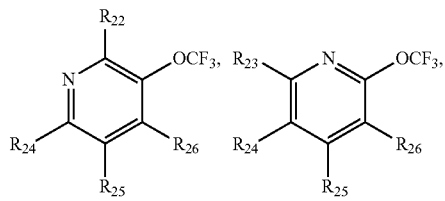

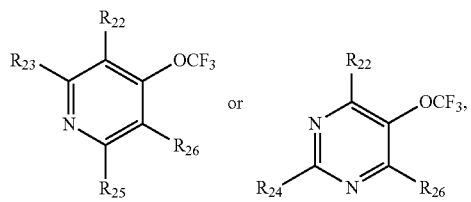

wherein

R$_{22}$, R$_{23}$, R$_{24}$, R$_{25}$ and R$_{26}$ are each, independently, —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$H, —CO$_2$-(alkyl), —CO$_2$-(alkenyl), —CO$_2$-(alkynyl) —CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —C(O)-(alkyl), —C(O)-(alkenyl), —C(O)-(alkynyl), —C(O)-(aryl), —C(O)-(heteroaryl), —OCO$_2$-(alkyl), —OCO$_2$-(alkenyl), —OCO$_2$-(alkynyl), —OCO$_2$-(aryl), —OCO$_2$-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl) or —S-(heteroaryl), comprising (a) reacting a compound having the structure:

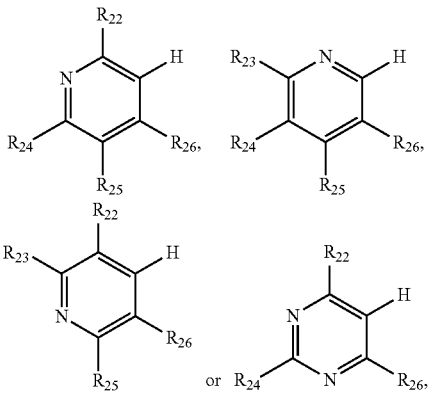

with the compound of the present invention under conditions sufficient to thereby produce the trifluoromethoxylated compound.

In some embodiments, the process for producing a trifluoromethoxylated compound having the structure:

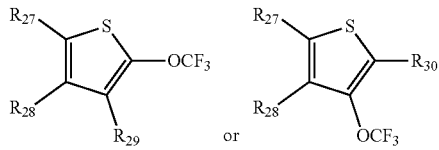

wherein

R$_6$, R$_7$, R$_8$ and R$_9$ is each independently —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$H, —CO$_2$-(alkyl), —CO$_2$-(alkenyl), —CO$_2$-(alkynyl) —CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —C(O)-(alkyl), —C(O)-(alkenyl), —C(O)-(alkynyl), —C(O)-(aryl), —C(O)-(heteroaryl), —OCO$_2$-(alkyl), —OCO$_2$-(alkenyl), —OCO$_2$-(alkynyl), —OCO$_2$-(aryl), —OCO$_2$-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl) or —S-(heteroaryl), comprising (a) reacting a compound having the structure:

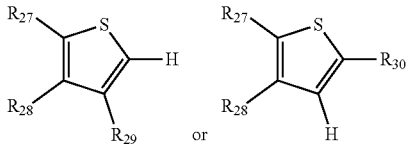

with the compound of the present invention under conditions sufficient to thereby produce the trifluoromethoxylated compound.

In some embodiments, the process wherein the reaction occurs in the presence of a metal catalyst.

In some embodiments, the process wherein the reaction occurs in the presence of a Ruthenium catalyst or Iridium catalyst.

In some embodiments, the process wherein the reaction occurs in the presence of Ru(bpy)$_3$(PF$_6$)$_2$ catalyst.

In some embodiments, the process wherein the reaction occurs under irradiation with visible light.

98. In some embodiments, the process wherein the reaction occurs under irradiation with 402 nm visible light.

In some embodiments, the process wherein the reaction occurs at room temperature.

In some embodiments, the process wherein the reaction occurs at 20-45° C.

In some embodiments, the process wherein the reaction occurs in a suitable solvent.

In some embodiments, the process wherein the suitable solvent is acetonitrile, dichloromethane or nitromethane or mixtures thereof.

A product produced by the process of the present application.

A product produced by the process comprising the process of the present application.

A composition comprising the compound produced by the process of the present application.

A kit comprising the compound of the present application in a container and instructions for use of the compound.

A kit comprising the compound of the present application in a container and instructions for use of the compound to perform the process of the present application.

The kit of the present application further comprising a metal catalyst.

The kit of the present application further comprising an arene or heteroarene substrate.

In some embodiments, a product produced by any process described herein.

In some embodiments, a composition comprising the compound produced by any process described herein.

In some embodiments, a kit comprising the compound of the present invention in a container and instructions for use of the compound.

In some embodiments, a kit comprising the compound of the present invention in a container and instructions for use of the compound to perform the processes described herein.

In some embodiments, the kit further comprising a metal catalyst. In some embodiments, the kit further comprising an arene or heteroarene substrate.

In some embodiments, the container is a vial. In some embodiments, the container is a sealed ampule. In some embodiments, the container contains an inert gas.

In some embodiments, the compound having the structure:

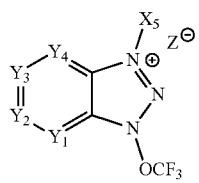

wherein
$Y_2$ is $C-X_2$, wherein $X_2$ is halogen, $-CF_3$, $-NO_2$, $-SO_2Me$, $-CN$, $-OCF_3$, $-OCF_2H$, -(alkyl), -(alkenyl), -(alkynyl), -(aryl), -(heteroaryl), $-NR_1R_2$, $-C(O)-R_1$, $-C(O)-OR_1$, $-C(O)-NR_1R_2$, $-C(O)-SR_1$, $-OR_1$ or $-SR_1$.

In some embodiments, the compound having the structure:

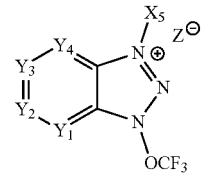

$Y_2$ is $C-X_2$, wherein $X_2$ is halogen, $-CF_3$, $-NO_2$, $-SO_2Me$, $-CN$, $-OCF_3$, $-OCF_2H$, -(alkyl), -(alkenyl), -(alkynyl), -(aryl), -(heteroaryl), $-NR_1R_2$, $-C(O)-R_1$, $-C(O)-OR_1$, $-C(O)-NR_1R_2$, $-C(O)-SR_1$, $-OR_1$ or $-SR_1$; and
$X_5$ is alkyl.

In some embodiments, each of $Y_1$, $Y_2$, $Y_3$ and $Y_4$ are of $X_1$, $X_2$, $X_3$ and $X_4$, respectively.

In some embodiments, at least one of $X_1$, $X_2$, $X_3$ and $X_4$ is other than H.

In some embodiments, at least two of $X_1$, $X_2$, $X_3$ and $X_4$ are other than H.

In some embodiments, at least two of $Y_1$, $Y_2$, $Y_3$ and $Y_4$ is N.

In some embodiments wherein
$X_6$ is

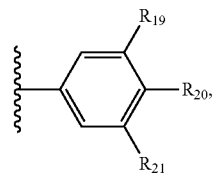

wherein one of $R_{19}$, $R_{20}$ and $R_{21}$ is other than H or two of $R_{19}$, $R_{20}$ and $R_{21}$ are other than H.

In some embodiments, wherein
$X_6$ is

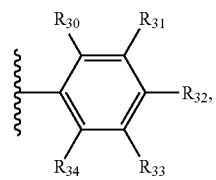

wherein $R_{31}$, $R_{32}$, $R_{33}$, $R_{34}$ and $R_{35}$ are each, independently, $-H$, halogen, $-CF_3$, $-NO_2$, $-SO_2Me$, $-CN$, $-OCF_3$, $-OCF_2H$, -(alkyl), -(alkenyl), -(alkynyl), -(aryl), -(heteroaryl), $-C(O)-R_1$, $-C(O)-OR_1$, $-C(O)-SR_1$, $-OR_1$, $-SR_1$, $-NR_1R_2$, or $-C(O)-NR_1R_2$,
wherein $R_1$ and $R_2$ are each, independently, $-H$, -(alkyl), -(alkenyl), -(alkynyl), -(aryl), -(heteroaryl), $-C(O)-R_3$, $-C(O)-OR_3$, $-C(O)-NR_4R_5$, $-C(O)-SR_3$, $-C(S)-R_3$, $-C(S)-OR_3$, $-C(S)-NR_4R_5$, $-C(S)-SR_3$, $-C(NR_5)-R_3$, $-C(NR_5)-OR_3$, $-C(NR_6)-NR_4R_5$ or $-C(NR_6)-SR_3$,
wherein $R_3$, $R_4$, $R_5$ and $R_6$ are each, independently, $-H$, -(alkyl), -(alkenyl), -(alkynyl), -(aryl) or -(heteroaryl).

In some embodiments, wherein $X_6$ is

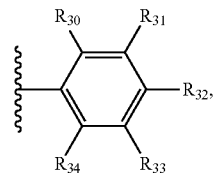

wherein $R_{31}$, $R_{32}$, $R_{33}$, $R_{34}$ and $R_{35}$ are each, independently, —H, halogen, —$CF_3$, —$NO_2$, —$SO_2Me$ or —CN.

The $OCF_3$ group has favorable physicochemical properties and is particularly useful in designing new drugs, agrochemicals, electronic devices, and functional materials. This is because its incorporation into organic molecules would improves their molecular metabolic stability, enhances their membrane permeability, increases their melting point and boiling point difference under ambient pressure, and lowers their surface tension, dielectric constant, and pour point. However, the facile installation of the $OCF_3$ group into organic molecules remains a long-standing and unsolved problem in organic synthesis. The current invention contemplates a new reagent, a method for making that reagent, as well as a method for using that reagent to (i) catalytically and exclusively generate the $OCF_3$ radical and (ii) provide easy access to trifluoromethoxylated compounds. Our new trifluoromethoxylating reagent will allow access to unexplored chemical and patent spaces and find applications in the discovery and development of novel drugs, agrochemicals, materials, and reactions.

Embodiments of the present invention include a new reagent, a method for making that reagent, as well as a method for using that reagent to (i) catalytically and exclusively generate the $OCF_3$ radical and (ii) prepare trifluoromethoxylated compounds.

The trifluoromethoxylating reagent 1 disclosed herein has a novel reaction mode. The new reagent accepts an electron from photoexcited catalysts and catalytically generates only the $OCF_3$ radical at room ambient conditions. In addition, the new trifluoromethoxylating reagent allows direct conversion of aryl C—H bond to the C—$OCF_3$ group. Such an approach is attractive because it precludes the need for the pre-functionalization of aromatic compounds. Moreover, direct disconnection of the $OCF_3$ group could be envisioned anywhere onto the target and at any time of the synthesis, which would allow the late-stage trifluoromethoxylation of complex molecules. Furthermore, our approach is the first example of catalytic generation of the $OCF_3$ radical. It also features operationally simple, proceeds at room temperature, uses easy-to-handle reagents, does not need specialized reaction apparatus, and tolerates a wide variety of functional groups and complex structures.

The most common method available for the construction of the Aryl-$OCF_2H$ is via the O-difluoromethylation of phenols using various sources of difluorocarbene under basic conditions. There are few mild and general synthetic strategies to access these highly valuable compounds. Since Haszeldine and co-workers reported the use of $ClCF_2CO_2Na$ in synthesis in 1960, numerous other difluoro-carbene synthons have been developed and employed in the preparation of aryl difluoromethyl ethers. Most of these reagents, however, are highly toxic, difficult to handle, ozone-depleting, incompatible with common functional groups, and their use often requires elevated temperatures.

Embodiments of the present invention also include a reagent (1a), a method for making that reagent, as well as a method for using that reagent to prepare difluoromethoxylated compounds. This difluoromethoxylating reagent allows direct incorporation of the $OCF_2H$ group into aromatic compounds to afford the products of difluoromethoxylation in excellent yields.

In some embodiments, Z if a Triflate group (OTf). In some embodiments, the compounds is an amine salt.

In some embodiments, the trifluoromethylating reagent is 1-Trifluoromethyl-1,2-benziodoxol-3-(1H)-one (Togni reagent II), which may be purchased from Sigma Aldrich, St. Louis, Mo., USA (Catalog #771147). In some embodiments, the trifluoromethylating reagent is 3,3-Dimethyl-1-(trifluoromethyl)-1,2-benziodoxole (Togni reagent I), which may be purchased from Sigma Aldrich, St. Louis, Mo., USA (Catalog #696641).

In some embodiments, the first or second suitable solvent include, but are not limited to, inert organic solvents or mixtures thereof.

The process described herein is advantageous in that it avoids the need for highly toxic and thermally labile reagents, which is not particularly desirable for industrial implementation due to the hazards associated with such reagents.

The process described herein is also advantageous in that it may be performed in one-pot. The process described herein is further advantageous in that it avoids the need for highly toxic metal containing reagents.

The present reaction occurs under reaction conditions sufficient to produce the desired compound. Such conditions, e.g. temperature, time, molarity, etc., may be varied by one of ordinary skill in the art based on the methods and protocols described herein.

Where a range is given in the specification it is understood that the range includes all integers and 0.1 units within that range, and any sub-range thereof. For example, a range of 77 to 90% is a disclosure of 77, 78, 79, 80, and 81% etc.

As used herein, "alkyl" is intended to include both branched and straight-chain saturated aliphatic hydrocarbon groups having the specified number of carbon atoms. Thus, $C_1$-$C_n$ as in "$C_1$-$C_n$ alkyl" is defined to include groups having 1, 2 ..., n–1 or n carbons in a linear or branched arrangement, and specifically includes methyl, ethyl, propyl, butyl, pentyl, hexyl, heptyl, isopropyl, isobutyl, sec-butyl and so on. An embodiment can be $C_1$-$C_{12}$ alkyl, $C_2$-$C_{12}$ alkyl, $C_3$-$C_{12}$ alkyl, $C_4$-$C_{12}$ alkyl and so on. An embodiment can be $C_1$-$C_8$ alkyl, $C_2$-$C_8$ alkyl, $C_3$-$C_8$ alkyl, $C_4$-$C_8$ alkyl and so on. "Alkoxy" represents an alkyl group as described above attached through an oxygen bridge. The term "alkenyl" refers to a non-aromatic hydrocarbon group, straight or branched, containing at least 1 carbon to carbon double bond, and up to the maximum possible number of non-aromatic carbon-carbon double bonds may be present. Thus, $C_2$-$C_n$ alkenyl is defined to include groups having 1, 2 ..., n–1 or n carbons. For example, "$C_2$-$C_6$ alkenyl" means an alkenyl group having 2, 3, 4, 5, or 6 carbon atoms, and at least 1 carbon-carbon double bond, and up to, for example, 3 carbon-carbon double bonds in the case of a $C_6$ alkenyl, respectively. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated. An embodiment can be $C_2$-$C_{12}$ alkenyl or $C_2$-$C_8$ alkenyl.

The term "alkynyl" refers to a hydrocarbon group straight or branched, containing at least 1 carbon to carbon triple bond, and up to the maximum possible number of non-aromatic carbon-carbon triple bonds may be present. Thus, $C_2$-$C_n$ alkynyl is defined to include groups having 1, 2 . . . , n–1 or n carbons. For example, "$C_2$-$C_6$ alkynyl" means an alkynyl group having 2 or 3 carbon atoms, and 1 carbon-carbon triple bond, or having 4 or 5 carbon atoms, and up to 2 carbon-carbon triple bonds, or having 6 carbon atoms, and up to 3 carbon-carbon triple bonds. Alkynyl groups include ethynyl, propynyl and butynyl. As described above with respect to alkyl, the straight or branched portion of the alkynyl group may contain triple bonds and may be substituted if a substituted alkynyl group is indicated. An embodiment can be a $C_2$-$C_n$ alkynyl. An embodiment can be $C_2$-$C_{12}$ alkynyl or $C_3$-$C_8$ alkynyl.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include but are not limited to: phenyl, p-toluenyl (4-methylphenyl), naphthyl, tetrahydro-naphthyl, indanyl, phenanthryl, anthryl or acenaphthyl. In cases where the aryl substituent is bicyclic and one ring is non-aromatic, it is understood that attachment is via the aromatic ring. The term "heteroaryl", as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include phenyl, pyridine, pyrimidine or pyridazine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "substitution", "substituted" and "substituent" refers to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include the functional groups described above, and halogens (i.e., F, Cl, Br, and I); alkyl groups, such as methyl, ethyl, n-propyl, isopropyl, n-butyl, tert-butyl, and trifluoromethyl; hydroxyl; alkoxy groups, such as methoxy, ethoxy, n-propoxy, and iso-propoxy; aryloxy groups, such as phenoxy; arylalkyloxy, such as benzyloxy (phenylmethoxy) and p-trifluoromethyl-benzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino, protected amino; ester or alkyl ester; and carboxyl. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The starting materials used in the method of the present invention may be prepared by techniques well known in organic synthesis and familiar to a practitioner ordinarily skilled in the art. However, these may not be the only means by which to synthesize or obtain the desired compounds.

The starting materials used in the method of the present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) 5$^{th}$ Edition (1996), March's Advanced Organic Chemistry: Reactions, Mechanisms, and Structure, Michael B. Smith, Jerry March, (Wiley-Interscience) 5$^{th}$ Edition (2007), and references therein, which are incorporated by reference herein. However, these may not be the only means by which to synthesize or obtain the desired compounds.

The reaction conditions used in the present invention may be varied by techniques well known in organic synthesis and familiar to a practitioner ordinarily skilled in the art to provide conditions sufficient to produce the desired product. Such techniques are described in Vogel's Textbook of Practical Organic Chemistry, A. I. Vogel, A. R. Tatchell, B. S. Furnis, A. J. Hannaford, P. W. G. Smith, (Prentice Hall) 5$^{th}$ Edition (1996), March's Advanced Organic Chemistry: Reactions, Mechanisms, and Structure, Michael B. Smith, Jerry March, (Wiley-Interscience) 5$^{th}$ Edition (2007), and references therein, which are incorporated by reference herein.

In the compounds in the process of the present invention, alkyl, alkenyl, alkynyl, aryl, heteroaryl groups can be further substituted by replacing one or more hydrogen atoms with alternative non-hydrogen groups.

The compounds used in the method of the present invention may be in a salt form. As used herein, a "salt" is a salt of the instant compounds which has been modified by making acid or base salts of the compounds.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

Example 1. $OCF_3$-Reagent 1

A key to the success of the proposed transformation is the development of easy-to-handle trifluoromethoxylating reagents that release the $OCF_3$ radical under mild reaction conditions. After exploration of a wide array of reagents bearing the N—$OCF_3$ moiety, we were pleased to identify $OCF_3$-reagent 1 capable of direct trifluoromethoxylation of arenes. Upon exposing 1 (1 equiv) and benzene (10 equiv) in acetonitrile (MeCN) to a 10 W light-emitting diode (LED, $\lambda_{em}$=402 nm) at room temperature for 16 hours, we observed 20% yield of the desired trifluoromethoxybenzene (3a) and 38% yield of N-arylation side product (3a') (Scheme 1, entry 1) (Buzzetti, L. et al. 2017). Interestingly, the addition of 20 mol % of Cu(II) or Cu(I) salts shifted the product distributions and increased the yield of 3a (entries 2-3), which indicated that both Cu(II) and Cu(I) could alter the reaction pathway. Notably, the replacement of the Cu salts with only 0.03 mol of $Ru(bpy)_3(PF_6)_2$ afforded 3a in 70% yield (entry 4). The transformation also worked with one equivalent of benzene, albeit it gave the product with a lower yield (entry 5). Control experiments showed that light and oxygen-free environment are critical for the reaction to proceed with high efficiency (entries 6-7).

Scheme 1

Selected Optimization Experiments[a]

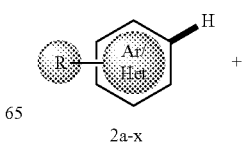

| Entry | Catalyst | Yield[b] | | Selectivity |
|---|---|---|---|---|
| | | 3a | 3a' | 3a:3a' |
| 1 | — | 20% | 38% | 1:2 |
| 2 | $Cu(OTf)_2$ (20 mol %) | 61% | 20% | 3:1 |
| 3 | $Cu(MeCN)_4PF_6$ (20 mol %) | 64% | 10% | 6:1 |
| 4 | $Ru(bpy)_3(PF_6)_2$ (0.03 mol %) | 70% | 3% | 23:1 |
| 5[c] | $Ru(bpy)_3(PF_6)_2$ (0.03 mol %) | 34% | 2% | 17:1 |
| 6[d] | $Ru(bpy)_3(PF_6)_2$ (0.03 mol %) | 0% | 0% | — |
| 7[e] | $Ru(bpy)_3(PF_6)_2$ (0.03 mol %) | 56% | 3% | 19:1 |

Scheme 1

Selected Optimization Experiments[a]

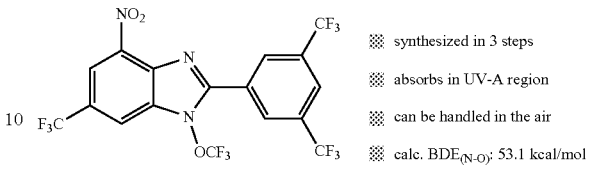

$OCF_3$-reagent (1)

[a]Reactions were performed using 1 equivalent of 1 and 10 equivalents of benzene.
[b]Yields and selectivity were determined by $^{19}$F-NMR using trifluorotoluene as an internal standard.
[c]One equivalent of benzene was used.
[d]Without light.
[e]Air atmosphere. BDE = bond dissociation energy.

With the optimized conditions in hand, we next sought to examine the substrate scope. Gratifyingly, a wide range of different functional groups was tolerated under the C—H trifluoromethoxylation conditions (Scheme 2). Halide substituents (3b-3f, 3q-3r, 3t-3x) remained intact after the reaction, providing an easy handle for further synthetic elaborations. In addition, the mild reaction conditions were compatible with protic functionality such as carboxylic acid (3g) and enolizable ketones (3h, 3x). Other functional groups such as an ester (3j-3k, 3n, 3p, 3s, 3v-3x), nitrile (3l), carbonate (3m-3n), ether (3s), and phosphine oxide (3o) were also viable and afforded the desired products in moderate to good yields. Moreover, substrates with benzylic hydrogens, which are often prone to the hydrogen atom abstraction in the presence of radical species, were tolerated (3p, 3t-3u). Heteroarenes (3q-3x), which are ubiquitous in biologically active molecules, are readily participated in the coupling reaction as well. More importantly, compounds with a more elaborated molecular architecture such as fructose (3v), (−)-menthol (3w), and trans-androsterone (3x) derivatives were successfully trifluoromethoxylated using 1 equivalent of substrates.

The regioselectivity of the reaction is guided by the electronics of the substituent except in the case of the bulky substituent. For example, substrates 3k and 3l, where the tert-butyl group blocks the ortho-position, afforded only one regioisomer. Like other radical-mediated aromatic substitution processes, the $OCF_3$ radical adds to multiple sites of arenes to form various regioisomers. This is beneficial in the context of drug discovery as the isolation of the regioisomers allows rapid biological-activity assays of trifluoromethoxylated analogs (Nagib, D. et al. 2011). Thus, this synthetic method is complementary to the existing site-selective strategies for the synthesis of trifluoromethoxylated (hetero)arenes (Tlili, A. et al. 2016; Huang, C. et al. 2011; Liu, J. B. et al. 2015; Khotavivattana, T. et al. 2015; Zhang, Q. W. et al. 2016).

Scheme 2.
Selected Examples of Trifluoromethoxylation of (Hetero)arenes [a]

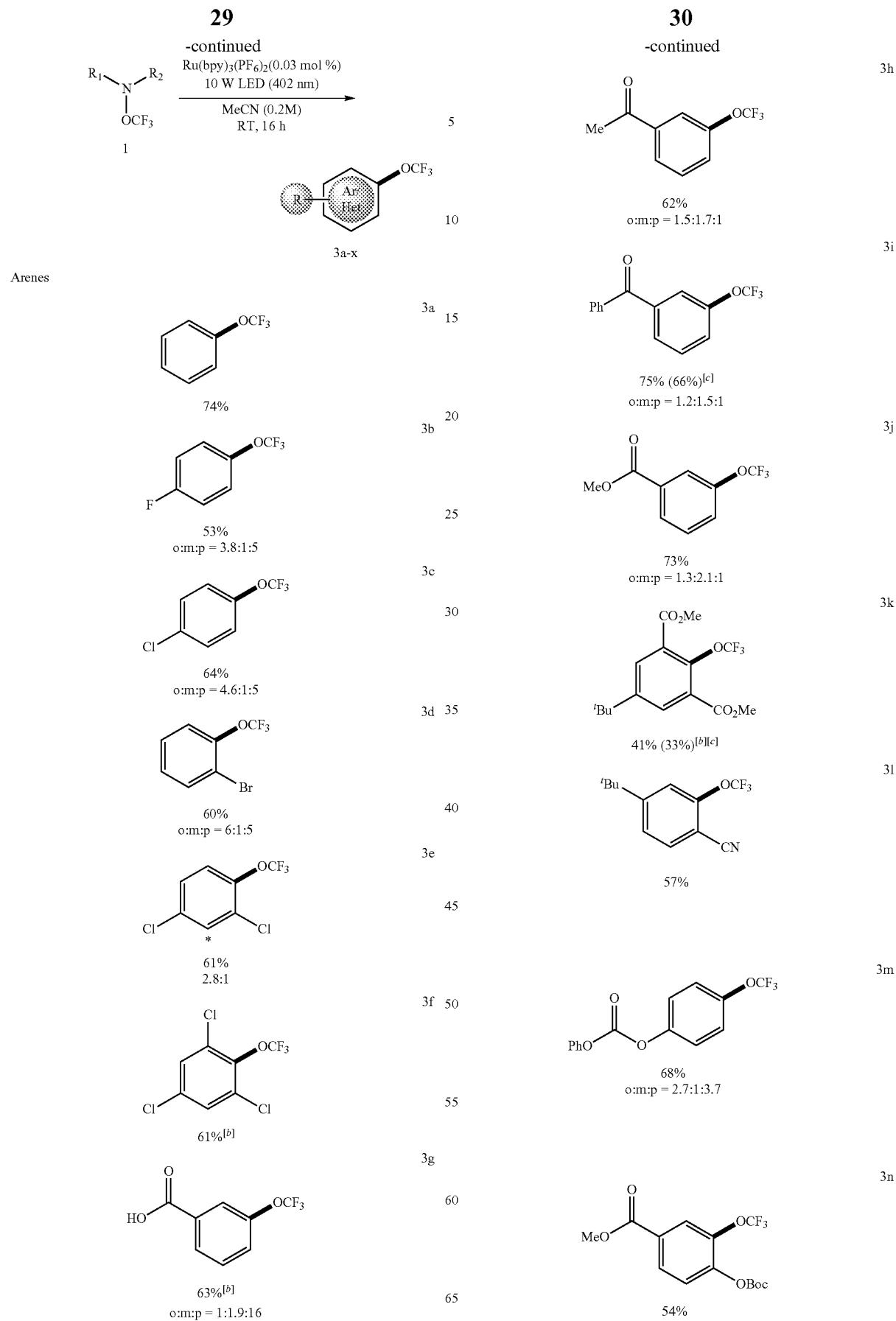

31
-continued

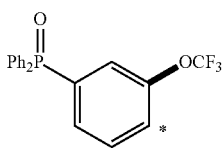

54% (43%)[c]
1.9:1

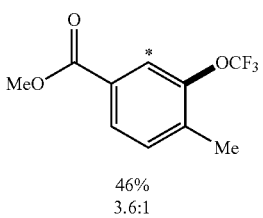

46%
3.6:1

Heteroarenes

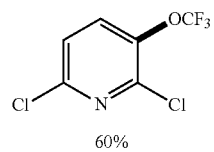

60%

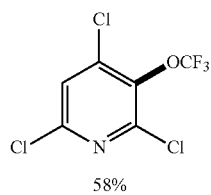

58%

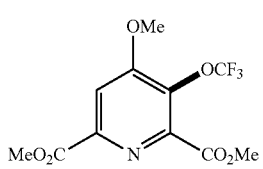

68% (63%)[b][c]

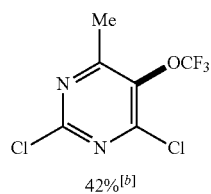

42%[b]

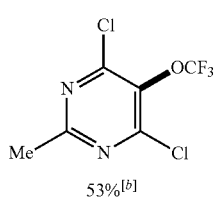

53%[b]

1 equiv of substrate

32
-continued

3o

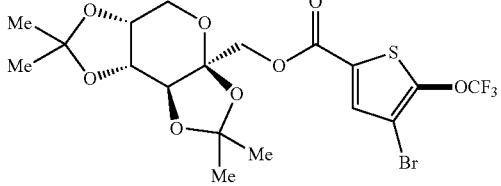

60% BRSM (32%)[b][c][e]

3p

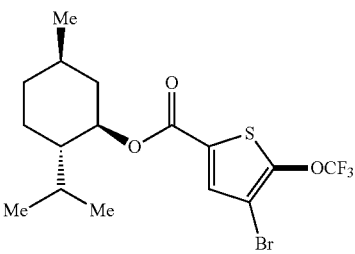

74% BRSM (23%)[c][d][e]

3q

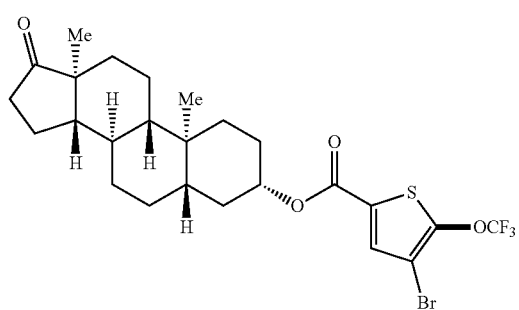

47% BRSM (20%)[c][d][e]

3r

3s

[a]Reactions were performed using 1 equivalent of 1 and 10 equivalents of (hetero)arenes. Yields and regioselectivity were determined by $^{19}$F—NMR using trifluorotoluene as an internal standard. [b]Reaction was performed at 40° C. [c]Yield in parenthesis is of isolated yield. [d]1 equivalent of the substrate was used. [e]Isolated yield based on the recovered starting material (BRSM).

3t

3u

A series of experimental and computational studies were conducted to shed light on the reaction mechanism (FIG. 1). We envisioned that the ·OCF$_3$ could be formed by the homolytic cleavage of the N—O bond through either photoexcited 1 or the anion radical of 1 (1$^{-•}$) generated from SET between 1 and photoredox-catalysts (Cleavage of the N—O bond, see: Jamison, C. R. et al. 2016; Formation of O-centered radical under visible light photoredox conditions, see: Guo, J. J. et al. 2016; Jia, K. F. et al. 2016; Wang, C. Y. et al. 2016; Yayla, H. G. et al. 2016; Zhang, J. et al. 2016; Jia, K. F. et al. 2017).

To distinguish these two possible reaction pathways, we performed the trifluoromethoxylation reaction using a band-pass filter (488±2 nm), where the photoexcitation of the reagent 1 is not feasible but that of Ru(bpy)$_3$(PF$_6$)$_2$ is possible (FIG. 1(a)(i)). We recovered 93% of the starting material 1, which implicates that the formation of the ·OCF$_3$ requires the photoexcitation of reagent 1. In addition, DFT calculations showed that if the anion radical of 1 was formed, the mesolytic cleavage of the N—O bond favors the formation of the ·NR$^1$R$^2$ instead of the ·OCF$_3$ (Allen, L. J. et al. 2014). Thus, these collective results suggest that the formation of the ·OCF$_3$ via the reduction of reagent 1 by excited Ru(bpy)$_3$(PF$_6$)$_2$ is unlikely.

We then examined the relative reactivity of the ·OCF$_3$ and ·NR$^1$R$^2$ towards an arene. DFT calculations showed the addition of the ·OCF$_3$ to benzene is energetically more favorable than that of the ·NR$^1$R$^2$ (FIG. 1(b)). This result corroborates the experimental outcome where irradiation of a mixture of reagent 1 and 1,3,5-trichlorobenzene in the absence of a redox-active catalyst gave only the product of trifluoromethoxylation. Finally, redox-active catalysts play a critical role in the final product distribution (3a vs. 3a'). In the absence of a redox-active catalyst, a significant amount of N-arylation side-product (3a') was obtained (Scheme 1, entry 1). We speculate that once Ic and ·NR$^3$R$^2$ are formed, they can undergo either the hydrogen atom abstraction to give the desired product 3a or the radical coupling reaction to produce cyclohexadiene If (Scheme 3). The elimination of H—NR$_1$R$^2$ or H—OCF$_3$ from If would afford 3a or 3a', respectively. Computational studies showed that the formation of 3a' through the elimination of H—OCF$_3$ is both kinetically ($\Delta\Delta G^\ddagger$=−8.7 kcal/mol) and thermodynamically ($\Delta\Delta G$=−5.3 kcal/mol, more favorable than that of H—NR$^1$R$^2$. These data indicate that once If is formed, it will be exclusively converted to N-arylation product 3a'. Thus, the low selectivity between N- and O-arylation in the absence of a redox-active catalyst is likely due to the competing pathways of radical coupling and H-atom abstraction, which would form N- and O-arylation products (3a' and 3a), respectively. However, in the presence of redox-active catalysts, the reaction favors the formation of the desired product 3a. Presumably, redox-active catalysts intervene in the reactions between If and Ic through single electron transfer (SET) processes. Our experimental and computational data (Zheng, W. et al. 2018) demonstrate that ground state redox-active catalysts are effective to promote the SET processes. With the photoexcited redox-active catalyst, [Ru(bpy)$_3$(PF$_6$)$_2$$^+$], such processes should be more efficient (Prier, C. K. et al. 2013), and thus only 0.03 mol % of Ru(bpy)$_3$(PF$_6$)$_2$ is needed.

(FIG. 1(c)). Once the ·OCF$_3$ is formed, it adds to an arene to afford the cyclohexadienyl radical Ic. Redox-active catalysts then mediate sequential single electron transfer (SET) processes between ·NR$^1$R$^2$ and Ic to form ionic species Id and Is, respectively. Deprotonation of Is restores the aromaticity and gives the desired product of trifluoromethoxylation (3a).

Materials and Methods

All air- and moisture-insensitive reactions were carried out under an ambient atmosphere, magnetically stirred, and monitored by thin layer chromatography (TLC) using Agela Technologies TLC plates pre-coated with 250 μm thickness silica gel 60 F254 plates and visualized by fluorescence quenching under UV light. Flash chromatography was performed on SiliaFlash® Silica Gel 40-63 μm 60 Å particle size using a forced flow of eluent at 0.3-0.5 bar pressure (Still, W. C. et al. 1978).

All air and moisture-sensitive manipulations were performed using oven-dried glassware, including standard Schlenk and glovebox techniques under an atmosphere of nitrogen. All reaction vials were capped using green caps with F-217 PTFE liners. Dimethylformamide, hexanes and ethyl acetate were directly used upon purchase. Acetonitrile and dichloromethane were dried over CaH$_2$ and distilled. Acetonitrile was degassed via three freeze-pump-thaw cycles.

All deuterated solvents were purchased from Cambridge Isotope Laboratories. NMR spectra were recorded on (i) a Bruker Ascend 700 spectrometer operating at 700 MHz for H acquisitions and 175 MHz for $^{13}$C acquisitions, (ii) a Bruker 500 Advance spectrometer operating at 500 MHz, 125 MHz, and 470 MHz for $^1$H, $^{13}$C, and $^{19}$F acquisitions, or (iii) a Bruker 400 Nanobay spectrometer operating at 400 MHz, 100 MHz, and 376 MHz for $^1$H, $^{13}$C, and $^{19}$F acquisitions. Chemical shifts were referenced to the residual proton solvent peaks ($^1$H: CDCl$_3$, δ 7.26; (CD$_3$)$_2$SO, δ 2.50), solvent $^{13}$C signals (CDCl$_3$, δ 77.16; (CD$_3$)$_2$SO, δ 39.52), Scheme 3.

without a redox-active catalyst

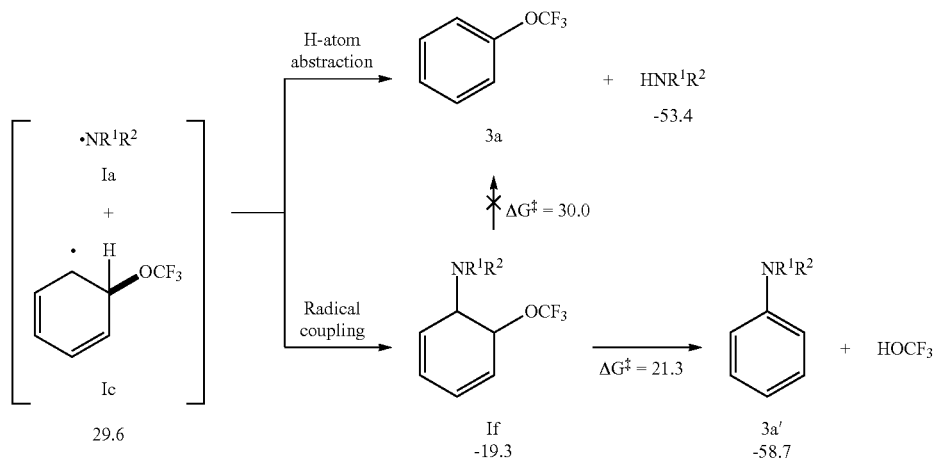

On the basis of these mechanistic studies, we envisage that the photoexcitation of reagent 1 under the irradiation of 10 W violet LED light ($\Delta_{em}$=402 nm) forms excited 1, which undergoes homolytic N—O bond cleavage to generate the N-centered radical (·NR$^1$R$^2$) and the OCF$_3$ radical (·OCF$_3$) dissolved or external neat PhCF$_3$ ($^{19}$F, δ −63.3 relative to CFCl$_3$) (Fulmer, G. R. et al. 2010, Huang, C. et al. 2011). Signals are listed in ppm, and multiplicity identified as s=singlet, br=broad, d=doublet, t=triplet, q=quartet, m=multiplet; coupling constants in Hz; integration.

HPLC separation were performed on Shimazu HPLC system (Pump model: LC-20AP, detector model: SPD-20A). HPLC columns including: Luna® PFP(2) 100 Å (size: 250×21.2 mm, AXIA™ Packs) and Gemini® 5 μm NX-C18 110 Å (size: 250×10 mm) were purchased from Phenomenex®. Absorptions were measured on a Cary 100 UV-Vis spectrophotometer from Agilent Technologies. Emission of LED was measured on a broad range spectrometer LR1-B from ASEQ instruments.

Reagents were purchased at highest quality. Liquid reagents were distilled and degassed before use. Solid reagents were used without further purification unless otherwise stated. Compounds 82a was prepared according to the literature procedure (Hojczyk, K. N. et al. 2016). Yields of trifluoromethoxylated products were calculated by $^{19}F$ NMR using PhCF$_3$ as an internal standard, other yields refer to purified and spectroscopically pure compounds unless otherwise noted. Violet LED light (400 nm-410 nm; 10 W, chip size=45×45 mm).

In a glovebox, to an oven-dried 4 mL screw cap vial was added a trifluoromethoxylating reagent (0.0200 mmol, 1.00 equiv), benzene, and photoredox catalyst. Then solvent and a magnetic stir bar were added. The vial was capped and taken out of the glovebox. The reaction mixture was then stirred and irradiated with LEDs at room temperature. Upon completion of the reaction, an internal standard PhCF$_3$ (2.95 mg, 2.47 μL, 0.0200 mmol, 1.00 eqiv) was added to the reaction vial, 0.100 mL of the resulting mixture was transferred to a 2 mL vial containing 0.500 mL of CDCl$_3$ and the yield was determined using $^{19}F$ NMR.

With the required criteria for the reagent development in mind (vide supra), we first explored the reactivity of a range of N—OCF$_3$ containing molecules (S2a-S2e, and 1) in the presence of benzene (5 equiv) and Ru(bpy)$_3$(PF$_6$)$_2$ (0.03 mol) under irradiation of blue LED light for 16 h (Scheme 4). We were please to identify that compound 1 gave the desired product of trifluoromethoxylation with the best yield of 46%. After we identified the best trifluoromethoxylating reagent, we then optimized solvents (Scheme 5), redox-active catalysts (Scheme 6), substrate stoichiometry (Scheme 7), and light sources (Scheme 8).

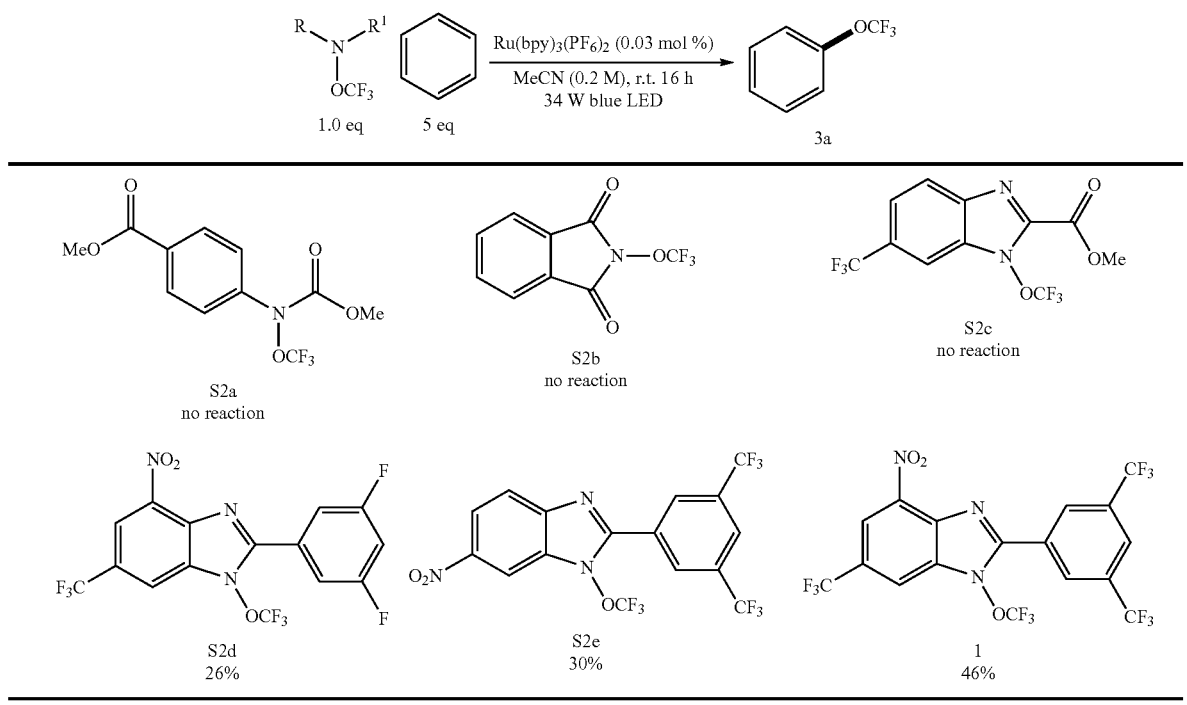

Yields were determined by $^{19}F$-NMR using trifluorotoluene as an internal standard.

Synthetic Methods

General Procedure A: Optimization

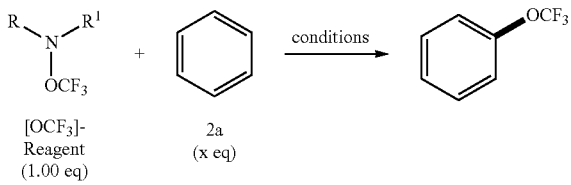

Scheme 5. Solvent Screening

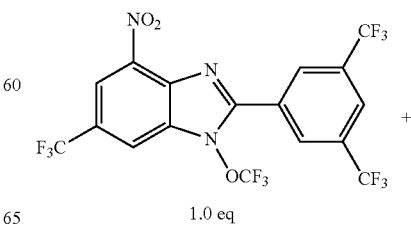

37

| Entry | Solvent | Yield$^b$ 3a |
|---|---|---|
| 1 | MeCN | 29% |
| 2 | DCM | 22% |
| 3 | DMF | 0% |
| 4 | THF | 0% |
| 5 | Acetone | 0% |
| 6 | MeNO$_2$ | 26% |
| 7 | MeOH | 0% |
| 8 | H$_2$O | 0% |

Yields were determined by $^{19}$F-NMR using trifluorotoluene as an internal standard.

Scheme 6. Redox-Active Catalyst Screening

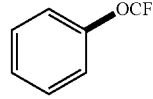

| Entry | Catalyst (0.5 mol %) | Yield$^b$ 3a |
|---|---|---|
| 1 | Ru(bpz)$_3$(PF$_6$)$_2$ | 28% |
| 2 | fac-Ir(ppy)$_3$ | 33% |
| 3 | Ir(ppy)$_2$(dtbbpy)PF$_6$ | 38% |
| 4 | fac-Ir(Fppy)$_3$ | 45% |
| 5 | Ir(dF(CF$_3$)ppy)$_2$(dtbbpy)PF$_6$ | 29% |
| 6 | Ru(phen)$_3$(PF$_6$)$_2$ | 43% |
| 7 | Ru(bpy)$_3$(PF$_6$)$_2$ | 34% |
| 8 | Ru(bpy)$_3$(PF$_6$)$_2$(0.03 mol %) | 46% |

Yields were determined by $^{19}$F-NMR using trifluorotoluene as an internal standard.

Scheme 7. Reactant Stoichiometry Screening

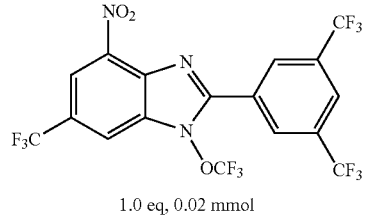

38

| Entry | Stoichiometry (equiv) | Yield$^b$ 3a |
|---|---|---|
| 1 | 1 | 36% |
| 2 | 5 | 62% |
| 3 | 10 | 71% |

Yields were determined by $^{19}$F-NMR using trifluorotoluene as an internal standard.

Scheme 8. Light Source Screening

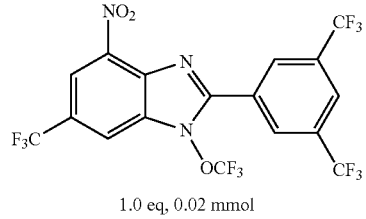

| Entry | Light Source | Yield$^b$ 3a |
|---|---|---|
| 1 | 26 W CFL | — |
| 2 | 3 W green | — |
| 3 | 3 W white | trace |
| 4 | 3 W blue | trace |
| 5 | 3 W purple | 42% |
| 6 | 34 W blue | 66% |
| 7 | 10 W purple (402 nm) | 71% |

Yields were determined by $^{19}$F-NMR using trifluorotoluene as an internal standard.

Although most of the optimizations were done using 0.5 mol %. Ru(phen)$_3$(PF$_6$)$_2$, we found that using 0.03 mol % of Ru(bpy)$_3$(PF$_6$) gave comparable yield. We decided to use Ru(bpy)$_3$(PF$_6$)$_2$ for the exploration of substrate scope because it is cheaper than Ru(phen)$_3$(PF$_6$)$_2$ and only 0.03 mol % of the catalyst is needed.

2-(3,5-Bis(trifluoromethyl)phenyl)-4-nitro-6-(trifluoromethyl)-1H-benzo[d]imidazol-1-ol (S1)

-continued

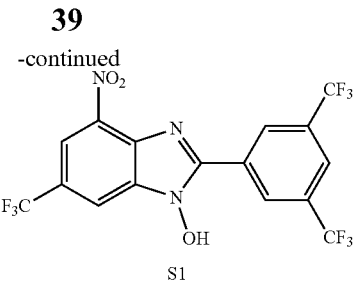

S1

To an oven-dried 100 mL round bottom flask charged with a magnetic stir bar, 2-chloro-1,3-dinitro-5-(trifluoromethyl)benzene (1.08 g, 4.00 mmol, 1.00 equiv), and (3,5-bis(trifluoromethyl)phenyl)methanamine (1.16 g, 4.80 mmol, 1.20 equiv) was added DMF (40.0 mL, 0.100 M). After the reaction mixture was stirred for 10 min, potassium carbonate (0.330 g, 2.40 mmol, 0.600 equiv) was added. The resulting mixture was heated at 50° C. for 2 h and then cooled to room temperature and quenched with 100 mL 1 M HCl aqueous solution. The mixture was transferred to a 500 mL separatory funnel and extracted with ethyl acetate (3×100 mL). The combined organic layers were sequentially washed with 1 M HCl aqueous solution (2×50 mL), water (2×50 mL), and brine (2×50 mL). The organic layer was then dried with magnesium sulfate, filtered, and concentrated in vacuo. The dry residue was dissolved in dry methanol (30 mL) under nitrogen atmosphere followed by the addition of freshly made 0.8 M sodium methoxide solution (10 mL, 8.00 mmol, 2.00 equiv). The reaction mixture was stirred under nitrogen at room temperature for 2 h and then poured into 100 mL of 1 M HCl aqueous solution. The aqueous layer was transferred to a 500 mL separatory funnel and extracted with ethyl acetate (3×100 mL). The combined organic layers were sequentially washed with 1 M HCl aqueous solution (3×50 mL), water (3×50 mL), and brine (3×50 mL). The organic layer was collected, dried with magnesium sulfate, and filtered. The filtrate was concentrated in vacuo and the solid residue was sonicated with 100 mL dichloromethane and solid was collected by filtration to afford the title compound as a white solid (1.30 g, 2.84 mmol, 71% yield over 2 steps). $^1$H NMR (400 MHz, (CD$_3$)$_2$SO, 25° C.), δ 13.52 (br, 1H), 8.86 (s, 2H), 8.43 (s, 1H), 8.38 (s, 1H); $^{13}$C NMR (175 MHz, (CD$_3$)$_2$SO, ° C.), δ 149.4, 138.3, 136.1, 132.9, 131.0 (q, J=33.5 Hz), 129.5, 128.9, 124.9, 123.5 (q, J=271.4 Hz), 123.1 (q, J=33.8 Hz), 123.0 (q, J=273.0 Hz), 116.3 (d, J=3.5 Hz), 113.8 (d, J=3.7 Hz); $^{19}$F NMR (376 MHz, (CD$_3$)$_2$SO, 25° C.) δ −59.5 (s, 3F), −61.5 (s, 6F). HRMS (ESI): Calcd for: $C_{16}H_7F_9N_3O_3^+$ ([M+H]$^+$) 460.0344, found: 460.0354.

2-(3,5-Bis(trifluoromethyl)phenyl)-4-nitro-1-(trifluoromethoxy)-6-(trifluoromethyl)-1H-benzo[d]imidazole (1)

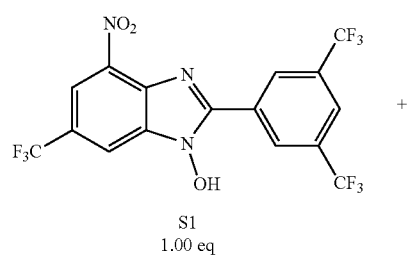

S1
1.00 eq

+

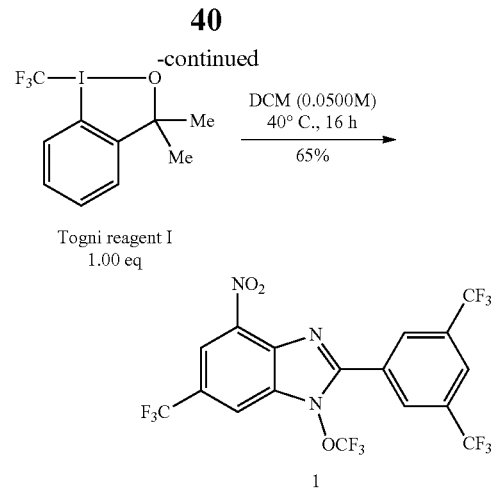

Togni reagent I
1.00 eq

Under nitrogen atmosphere, to an oven-dried 250 mL round bottom flask charged with a magnetic stir bar was added 2-(3,5-bis(trifluoromethyl)phenyl)-4-nitro-6-(trifluoromethyl)-1H-benzo[d]imidazol-1-ol (S1) (1.30 g, 2.84 mmol) and Togni reagent I (0.937 g, 2.84 mmol, 1.00 equiv). Then, freshly distilled dichloromethane (80.0 mL, 0.0500 M) was added. After the reaction mixture was reflux at 40° C. for 16 h, it was cooled to room temperature, concentrated in vacuo, and purified by flash column chromatography using 10-20 dichloromethane in hexanes to afford the title compound 1 as a white or off-white solid (0.970 g, 1.84 mmol, 65% yield). $R_f$=0.56 (ethyl acetate:hexanes v/v=1:10); $^1$H NMR (400 MHz, CDCl$_3$, 25° C.), δ 8.65 (s, 2H), 8.52 (s, 1H), 8.15 (s, 1H), 8.14 (s, 1H); $^{13}$C NMR (175 MHz, CDCl$_3$, 25° C.), δ 150.0, 139.9, 134.1, 133.3 (q, J=34.5 Hz), 133.2, 129.2 (d, J=4.2 Hz), 128.1 (q, J=35.2 Hz), 128.0, 126.0 (m), 122.9 (q, J=273.0 Hz), 122.8 (q, J=273.0 Hz), 122.3 (q, J=275.1 Hz), 118.7 (q, J=3.9 Hz), 112.8 (d, J=3.2 Hz); $^{19}$F NMR (376 MHz, CDCl$_3$, 25° C.) δ −62.3 (s, 3F), −63.8 (s, 6F), −64.3 (s, 3F). HRMS (ESI): Calcd for: $C_{17}H_6F_{12}N_3O_3^+$ ([M+H]$^+$) 528.0218, found: 528.0199.

2-(Trifluoromethoxy)isoindoline-1,3-dione (S2b)

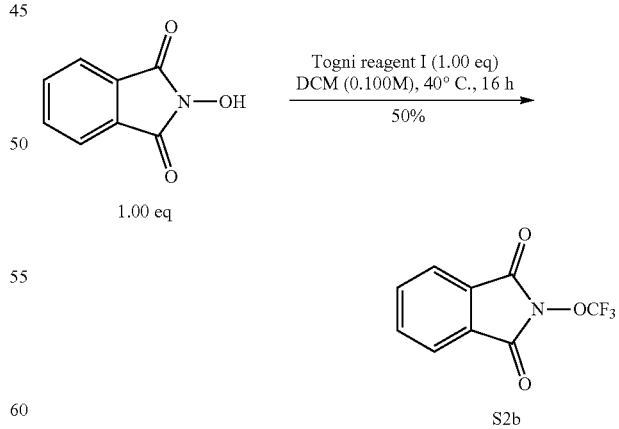

In a glovebox, to an oven-dried 20 mL screw cap vial was added 2-hydroxyisoindoline-1,3-dione (0.163 g, 1.00 mmol, 1.00 equiv), Togni reagent I (0.330 g, 1.00 mmol, 1.00 eq). Then 10 mL DCM (0.100 M) was added with a magnetic stir bar. The vial was capped and taken out of the glovebox. The reaction mixture was then stirred at 40° C. for 16 h. Then the reaction mixture was concentrated in vacuo and purified by flash column chromatography using 5% ethyl acetate in hexanes. The solid was further purified by recrystallization using DCM and hexanes to afford 0.115 g, 0.498 mmol of the title compound as a white solid (50% yield). $R_f$=0.23 (ethyl acetate:hexanes=1:10); $^1$H NMR (400 MHz, CDCl$_3$, 25° C.), δ 7.95 (dd, J=5.6, 3.2 Hz), 7.86 (dd, J=5.6, 3.2 Hz); $^{13}$C NMR (175 MHz, CDCl$_3$, 25° C.), δ 161.7, 135.6, 128.7, 124.7, 122.2 (q, J=268.3 Hz); $^{19}$F NMR (376 MHz, CDCl$_3$, 25° C.) δ −65.2 (s, 3F). The spectroscopic data is in agreement with the literature.[8]

Methyl 1-(trifluoromethoxy)-6-(trifluoromethyl)-1H-benzo[d]imidazole-2-carboxylate (S2c)

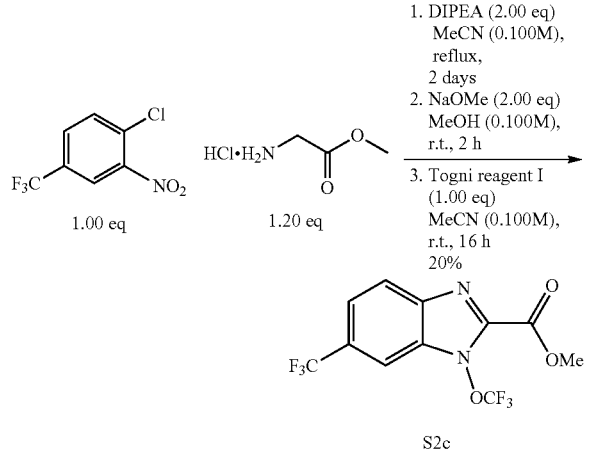

S2c

To an oven-dried 100 mL round bottom flask was added 1-chloro-2-nitro-4-(trifluoromethyl)benzene (0.900 g, 4.00 mmol, 1.00 equiv) and methyl 2-aminoacetate hydrochloride (0.600 g, 4.80 mmol, 1.20 equiv). Then 40 mL MeCN (0.100 M) was added with a magnetic stir bar. The reaction mixture was stirred for 10 min and then DIPEA (1.03 g, 8.00 mmol, 2.00 equiv) was added. The reaction mixture was then heated to reflux and stirred for 2 days. After cooling to room temperature, the reaction mixture was quenched with 1M HCl aqueous solution. The mixture was extracted with ethyl acetate (3×100 mL), washed with 1M HCl aqueous solution (2×50 mL) and water (2×50 mL). The organic layer was then concentrated in vacuo, and the residue was taken up by methanol (30 mL), and freshly made sodium methoxide solution (10 mL, 8 mmol, 2.00 equiv) was added. The reaction mixture was stirred at room temperature for 2 h and then poured into 100 mL 1M HCl aqueous solution. The aqueous layer was extracted with ethyl acetate (3×100 mL) and the organic layer was washed with 1M HCl aqueous solution (3×50 mL) and water (3×50 mL) and brine (3×50 mL). Solvent was removed in vacuo and the solid residue was washed with dichloromethane (3×100 mL). Without further purification the residue was dissolved in 40 mL acetonitrile and Togni reagent I (1.31 g, 4.00 mmol, 1.00 equiv) was added. The reaction mixture stirred at room temperature for 16 h then concentrated in vacuo and purified by flash column chromatography using 3-5% ethyl acetate in hexanes to afford 0.262 g (0.799 mmol) of the title compound as a white or off-white solid (20% yield). $R_f$=0.29 (ethyl acetate:hexanes=1:10); $^1$H NMR (500 MHz, CDCl$_3$, 25° C.), δ 7.79 (d, J=8.3 Hz, 1H), 7.65 (s, 1H), 7.63 (d, J=8.3 Hz, 1H); $^{13}$C NMR (175 MHz, CDCl$_3$, 25° C.), δ 156.3, 147.2, 129.8 (q, J=33.5 Hz), 128.3, 123.5 (q, J=272.5 Hz), 122.7 (q, J=273.0 Hz), 122.5 (q, J=3.9 Hz), 109.3 (d, J=6.3 Hz); $^{19}$F NMR (470 MHz, CDCl$_3$, 25° C.) δ −62.3 (s, 3F), −62.9 (s, 3F). HRMS (ESI): Calcd for: $C_{11}H_7N_2O_3F_6^+$ ([M+H]$^+$) 329.0361, found: 329.0346.

2-(3,5-Difluorophenyl)-4-nitro-1-(trifluoromethoxy)-6-(trifluoromethyl)-1H-benzo[d]imidazole (S2d)

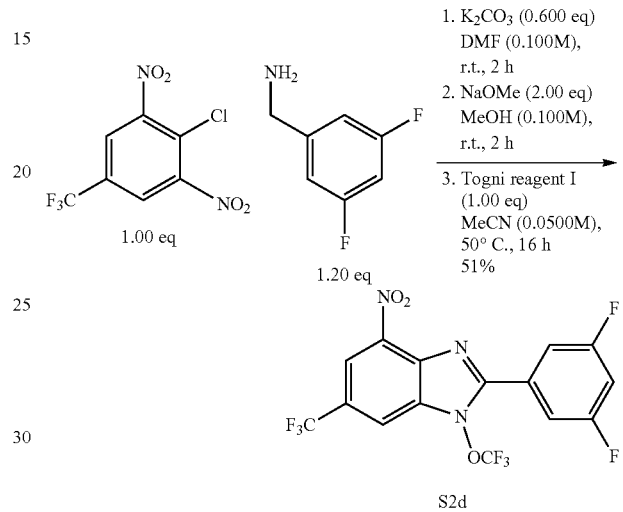

S2d

To an oven-dried 100 mL round bottom flask was added 2-chloro-1,3-dinitro-5-(trifluoromethyl)benzene (1.08 g, 4.00 mmol, 1.00 equiv) and (3,5-difluorophenyl)methanamine (0.686 g, 4.80 mmol, 1.20 equiv). Then 40 mL DMF was added with a magnetic stir bar. The reaction mixture was stirred for 10 min and then potassium carbonate (0.330 g, 2.40 mmol, 0.600 equiv) was added. The reaction mixture was then stirred at room temperature for 2 h and quenched with 1M HCl aqueous solution. The mixture was transferred to a 500 mL separatory funnel and extracted with ethyl acetate (3×100 mL). The combined organic layers were sequentially washed with 1 M HCl aqueous solution (2×50 mL), water (2×50 mL), and brine (2×50 mL). The organic layer was then dried with magnesium sulfate, filtered, and concentrated in vacuo. The dry residue was dissolved in dried methanol (30 mL) under nitrogen atmosphere followed by the addition of freshly made 0.8 M sodium methoxide solution (10 mL, 8.00 mmol, 2.00 equiv). The reaction mixture was stirred under nitrogen at room temperature for 2 h and then poured into 100 mL of 1 M HCl aqueous solution. The aqueous layer was transferred to a 500 mL separatory funnel and extracted with ethyl acetate (3×100 mL). The combined organic layers were sequentially washed with 1 M HCl aqueous solution (3×50 mL), water (3×50 mL), and brine (3×50 mL). The organic layer was collected, dried with magnesium sulfate, and filtered. The filtrate was concentrated in vacuo and the solid residue was sonicated with 100 mL dichloromethane. Without further purification the residue was dissolved in 80 mL acetonitrile and Togni reagent I (1.31 g, 4.00 mmol, 1.00 equiv) was added. The reaction mixture was heated to 50° C. and stirred for 16 h. After cooling down. The reaction mixture was concentrated in vacuo and purified by flash column chromatography using 0-2% ethyl acetate in hexanes to afford 0.871 g (2.03 mmol) of the title compound as a white or off-white solid (51% yield). $R_f$=0.55 (ethyl acetate:hexanes=1:10); $^1$H NMR (400 MHz, CDCl$_3$, 25° C.), δ 8.49 (d, J=0.90 Hz, 1H), 8.10 (s, 1H), 7.76-7.71 (m, 2H), 7.11 (tt, 8.5, 2.2 Hz, 1H); $^{13}$C NMR (175 MHz, CDCl$_3$, 25° C.), δ 163.2 (dd, J=251.2, 12.2 Hz), 150.7 (t, J=3.8), 139.6, 134.0, 133.1, 128.3 (t, J=10.2), 127.5, 127.3, 122.8 (q, J=273.0), 122.4 (q, J=249.2), 118.3 (t, J=3.8 Hz), 112.4 (dd, J=22.9, 6.4 Hz), 108.2 (t, J=24.9 Hz); $^{19}$F NMR (470 MHz, CDCl$_3$, 25° C.) δ −61.5 (s, 3F), −63.6 (s, 3F), −106.3 (t, J=7.6 Hz, 2F). HRMS (ESI): Calcd for: $C_{15}H_6N_3O_3F_8^+$ ([M+H]$^+$) 428.0281, found: 428.0282.

2-(3,5-Bis(trifluoromethyl)phenyl)-6-nitro-1-(trifluoromethoxy)-1H-benzo[d]imidazole (S2e)

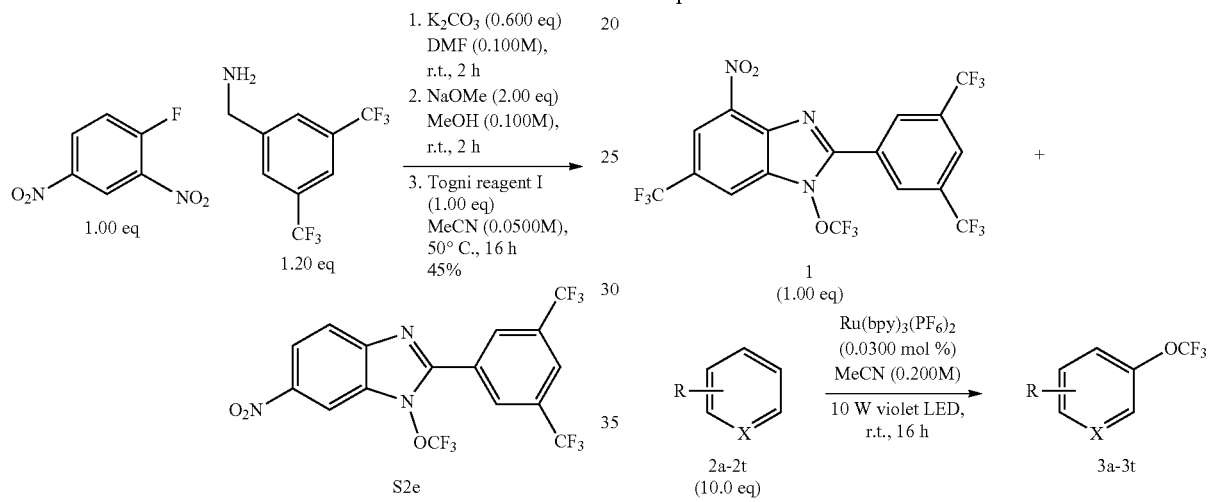

To an oven-dried 100 mL round bottom flask was added 1-fluoro-2,4-dinitrobenzene (0.744 g, 4.00 mmol, 1.00 equiv) and (3,5-bis(trifluoromethyl)phenyl)methanamine (1.16 g, 4.80 mmol, 1.20 equiv). Then 40 mL DMF was added with a magnetic stir bar. The reaction mixture was stirred for 10 min and then potassium carbonate (0.330 g, 2.40 mmol, 0.600 equiv) was added. The reaction mixture was then stirred at room temperature for 2 h and quenched with 1M HCl aqueous solution. The mixture was transferred to a 500 mL separatory funnel and extracted with ethyl acetate (3×100 mL). The combined organic layers were sequentially washed with 1 M HCl aqueous solution (2×50 mL), water (2×50 mL), and brine (2×50 mL). The organic layer was then dried with magnesium sulfate, filtered, and concentrated in vacuo. The dry residue was dissolved in dried methanol (30 mL) under nitrogen atmosphere followed by the addition of freshly made 0.8 M sodium methoxide solution (10 mL, 8.00 mmol, 2.00 equiv). The reaction mixture was stirred under nitrogen at room temperature for 2 h and then poured into 100 mL of 1 M HCl aqueous solution. The aqueous layer was transferred to a 500 mL separatory funnel and extracted with ethyl acetate (3×100 mL). The combined organic layers were sequentially washed with 1 M HCl aqueous solution (3×50 mL), water (3×50 mL), and brine (3×50 mL). The organic layer was collected, dried with magnesium sulfate, and filtered. The filtrate was concentrated in vacuo and the solid residue was sonicated with 100 mL dichloromethane. Without further purification the residue was dissolved in 80 mL acetonitrile and Togni reagent I (1.31 g, 4.00 mmol, 1.00 equiv) was added. The reaction mixture was heated to 50° C. and stirred for 16 h. After cooling down. The reaction mixture was concentrated in vacuo and purified by flash column chromatography using 0-2% ethyl acetate in hexanes to afford 0.905 g (97 mmol) of the title compound as a white or off-white solid (49% yield). $R_f$=0.50 (ethyl acetate:hexanes=1:10); $^1$H NMR (400 MHz, CDCl$_3$, 25° C.), δ 8.61 (s, 2H), 8.50 (s, 1H), 8.36 (dd, J=8.9, 2.2 Hz, 1H), 8.11 (s, 1H), 7.96 (d, J=8.9 Hz); $^{13}$C NMR (175 MHz, CDCl$_3$, 25° C.), δ 149.0, 145.8, 141.6, 133.1 (q, J=34.3 Hz), 131.4, 128.84 (m), 128.81, 125.4 (q, J=3.7 Hz), 122.8 (q, J=273.3 Hz), 122.4 (q, J=274.2 Hz), 121.6, 120.5, 106.5; $^{19}$F NMR (376 MHz, CDCl$_3$, 25° C.) δ −63.2 (s, 6F), 63.7 (s, 3F). HRMS (ESI): Calcd for: $C_{16}H_7N_3O_3F_9^+$ ([M+H]$^+$) 460.0344, found: 460.0339.

General Procedure B: Trifluoromethoxylation at Room Temperature

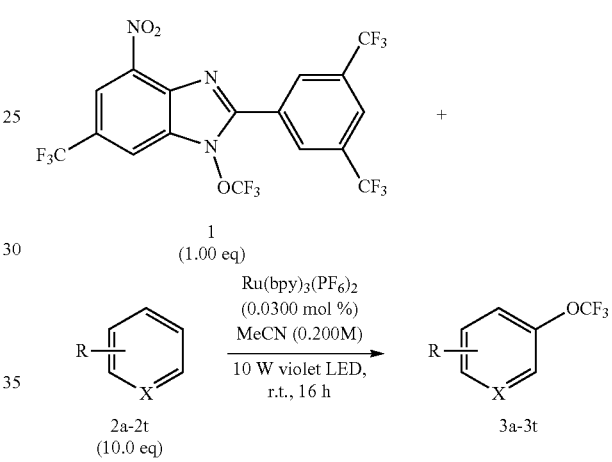

In a glovebox, to an oven-dried 20 mL screw cap vial was added 2-(3,5-bis(trifluoromethyl)phenyl)-4-nitro-1-(trifluoromethoxy)-6-(trifluoromethyl)-1H-benzo[d]imidazole (1) (105 mg, 0.200 mmol, 1.00 equiv), arene (2.00 mmol, 10.0 equiv) and Ru(bpy)$_3$(PF$_6$)$_2$, (0.0516 mg, 0.0600 μmol, 0.0300 mol %). Then MeCN (1.00 mL, 0.200 M) and a magnetic stir bar were added. The vial was capped and taken out of the glovebox. The reaction mixture was then stirred and irradiated with a 10 W LED (402 nm) at room temperature. After 16 h, an internal standard PhCF$_3$ (5.84 mg, 4.95 μL, 0.04 mmol, 0.200 equiv) was added to the reaction vial, 0.200 mL of the resulting mixture was transferred to a 2 mL vial containing 0.500 mL of CDCl$_3$. After the yield was determined using $^{19}$F NMR, the NMR sample was combined with the rest of the reaction mixture and the solvent was removed in vacuo. The crude material was purified by HPLC under noted conditions. The fractions containing the desired product were combined and extracted with CDCl$_3$ (3×1 mL), dried with magnesium sulfate, and filtered. The filtrate was concentrated in vacuo to furnish the desired product of trifluoromethoxylation. For volatile compounds, after purification by HPLC, the desired product was extracted with 1 mL CDCl$_3$ and then directly characterized. The NMR peaks are referring to CH$_3$CN residue signal ($^1$H-NMR: δ 1.94, $^{13}$C-NMR: δ 118.26, 1.32).[2]

General Procedure C: Trifluoromethoxylation at 40° C.

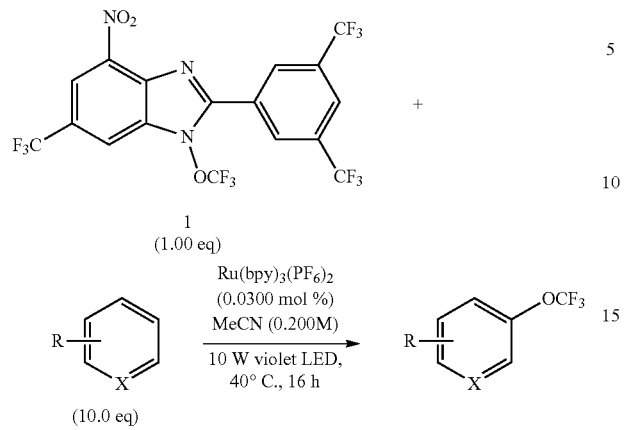

This procedure is identical to the General Procedure B except that the reaction mixture was stirred and irradiated with LED (402 nm) light at 40° C.

(Trifluoromethoxy)benzene (3a)

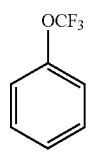

The reaction was performed according to the general procedure B using benzene (0.156 g, 2.00 mmol) as the substrate. After 16 h, the reaction mixture (74% yield by $^{19}$F NMR) was purified by HPLC on the Luna® PFP(2) preparative column (250×21.2 mm) using 65% acetonitrile in water (12.0 mL/min flow rate, retention time 16.5 min) to provide the title compound. $^{1}$H NMR (400 MHz, CDCl$_3$/CH$_3$CN, 25° C.) δ 7.41 (t, J=7.8 Hz, 2H), 7.29 (dd, J=7.8, 7.8 Hz), 7.22 (d, J=7.8 Hz); 13C NMR (175 MHz, CDCl$_3$/CH$_3$CN, 25° C.) δ 149.4, 129.9, 126.9, 121.1, 120.6 (q, J=256.7 Hz); $^{19}$F NMR (376 MHz, CDCl$_3$/CH$_3$CN, 25° C.) δ −58.5 (s, 3F). The spectroscopic data is in agreement with the literature.[9]

Fluoro(trifluoromethoxy)benzene (3b)

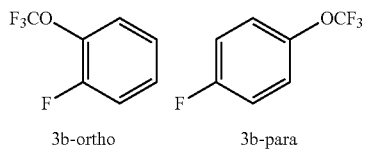

The reaction was performed according to the general procedure B using flourobenzene (0.192 g, 2.00 mmol) as the substrate. After 16 h, the reaction mixture (53% yield with o:m:p=3.8:1:5 by $^{19}$F NMR) was purified by HPLC on the Luna® PFP(2) preparative column (250×21.2 mm) using 65 acetonitrile in water (12 mL/min flow rate, retention time 16.5 min) to provide a mixture of p- and o-regioisomers. $^{1}$H NMR (700 MHz, CH$_3$CN, 25° C.), δ 7.16-7.12 (m), 7.06-7.00 (m), 6.94-6.91 (m); $^{13}$C NMR (175 MHz, CH$_3$CN, 25° C.), δ 160.7 (d, J=245.4 Hz), 154.2 (d, J=250.5 Hz), 144.7, 136.0, 135.9, 128.70, 128.66, 124.9, 124.8, 122.9 (d, J=8.9 Hz), 120.3 (q, J=256.2 Hz), 120.2 (q, J=256.2 Hz); $^{19}$F NMR (470 MHz, CH$_3$CN, 25° C.) δ −59.1 (s, 3F), −59.5 (d, J=4.9 Hz), −116.1 (m, 1F), −130.8 (m, 1F).

Chloro(trifluoromethoxy)benzene (3c)

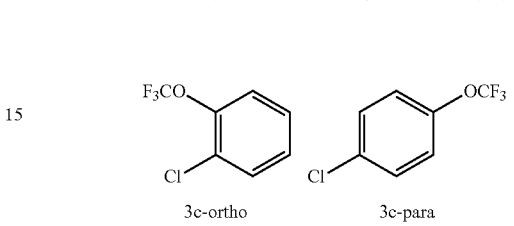

The reaction was performed according to the general procedure B using chlorobenzene (0.224 g, 2.00 mmol) as the substrate. After 16 h, the reaction mixture (64% yield with o:m:p=4.6:1:5 by $^{19}$F NMR) was purified by HPLC on the Luna® PFP(2) preparative column (250×21.2 mm) using 55% acetonitrile in water (12 mL/min flow rate, retention time 40 min) to provide a mixture of m- and p-regioisomers.

1-Chloro-4-(trifluoromethoxy)benzene (3c-para): $^{1}$H NMR (400 MHz, CDCl$_3$/CH$_3$CN, 25° C.) δ 7.40-7.36 (m, 2H), 7.18-7.16 (m, 2H). $^{19}$F NMR (376 MHz, CDCl$_3$/CH$_3$CN, 25° C.) δ −58.5. The spectroscopic data is in agreement with the literature.[9]

1-Chloro-2-(trifluoromethoxy)benzene (3c-ortho): Retention time 36 min. $^{1}$H NMR (400 MHz, CDCl$_3$/CH$_3$CN, 25° C.), δ 7.46 (d, J=7.4, 1H), 7.31-7.23 (m, 3H); $^{13}$C NMR (175 MHz, CDCl$_3$/CH$_3$CN, 25° C.), δ 144.7, 130.8, 128.1, 128.0, 126.8, 122.5, 120.2 (q, J=256.6 Hz); $^{19}$F NMR (376 MHz, CDCl$_3$/CH$_3$CN, 25° C.) δ −58.2 (s, 3F). HRMS (EI): Calcd for: C$_7$H$_4$OClF$_3$$^+$ (M$^+$) 195.9903, found: 195.9895.

Bromo(trifluoromethoxy)benzene (3d)

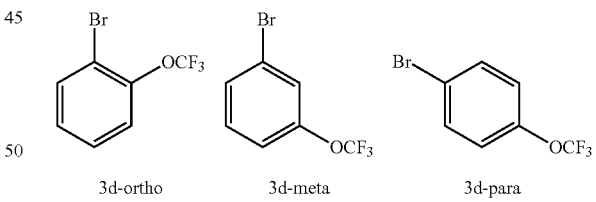

The reaction was performed according to the general procedure B using bromobenzene (0.312 g, 2.00 mmol) as the substrate. After 16 h, the reaction mixture (60% yield with o:m:p=6:1:5 by $^{19}$F NMR) was purified by HPLC on the Luna® PFP(2) preparative column (250×21.2 mm) using 552 acetonitrile in water (12 mL/min flow rate, retention time 38 min) to provide a mixture of m- and p-regioisomers.

Bromo-4-(trifluoromethoxy)benzene (3d-para): $^{1}$H NMR (500 MHz, CDCl$_3$/CH$_3$CN, 25° C.), δ 7.47 (m, 2H), 7.07 (m, 2H); $^{19}$F NMR (470 MHz, CDCl$_3$/CH$_3$CN, 25° C.) δ −58.5 (s, 3F). The spectroscopic data is in agreement with the literature.[9]

Bromo-3-(trifluoromethoxy)benzene (3d-meta): $^{1}$H NMR (500 MHz, CDCl$_3$/CH$_3$CN, 25° C.) δ 7.43-7.38 (m, 2H), 7.27-7.23 (m, 1H), 7.16-7.13 (m, 1H). $^{19}$F NMR (470 MHz, CDCl$_3$/CH$_3$CN, 25° C.) δ −58.3. The spectroscopic data is in agreement with the literature.[9]

Bromo-4-(trifluoromethoxy)benzene (3d-ortho): Retention time: 34 min. $^1$H NMR (400 MHz, CDCl$_3$, 25° C.), δ 7.59 (dd, J=8.0, 1.5, 1H), 7.32-7.26 (m, 2H), 7.13 (ddd, J=9.0, 8.9, 1.5 Hz, 1H); $^{13}$C NMR (175 MHz, CDCl$_3$, 25° C.), δ 145.9, 133.7, 128.6, 122.3, 120.1 (q, J=256.5 Hz), 115.5; $^{19}$F NMR (470 MHz, CDCl$_3$, 25° C.) δ −58.2 (s, 3F). HRMS (EI): Calcd for: C$_7$H$_4$OF$_3$Br$^+$ (M$^+$) 239.9398, found: 239.9406.

1,3-Dichloro(trifluoromethoxy)benzene (3e)

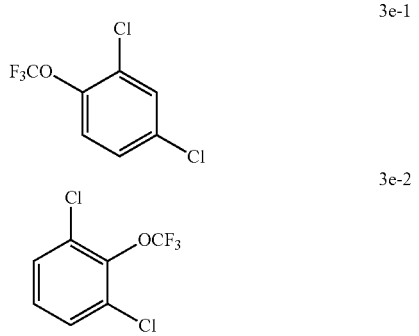

The reaction was performed according to the general procedure B using 1,3-dichlorobenzene (0.362 g, 2.00 mmol) as the substrate. After 16 h, the reaction mixture (68% yield with 2-:4-=1:2.8 by $^{19}$F NMR) was purified by HPLC on the Luna® PFP(2) preparative column (250×21.2 mm) using 55% acetonitrile in water (12.0 mL/min flow rate, retention time 33 min) to provide 1,3-Dichloro-2-(trifluoromethoxy)benzene (3e-1): $^1$H NMR (400 MHz, CDCl$_3$/CH$_3$CN, 25° C.) δ 7.52-7.51 (m, 1H), 7.32-7.32 (m, 2H). $^{19}$F NMR (376 MHz, CDCl$_3$/CH$_3$CN, 25° C.) δ −58.4. The spectroscopic data is in agreement with the literature.[9]

1,3-Dichloro-2-(trifluoromethoxy)benzene (3e-2): Retention time 36 min. $^1$H NMR (400 MHz, CDCl$_3$/CH$_3$CN, 25° C.) δ 7.28-7.27 (m, 2H), 7.10 (m, 1H); $^{13}$C NMR (175 MHz, CDCl$_3$/CH$_3$CN, 25° C.) δ 142.2, 130.3, 129.4, 128.5, 120.6 (q, J=259.8 Hz); $^{19}$F NMR (376 MHz, CDCl$_3$/CH$_3$CN, 25° C.) δ −56.8 (s, 3F). HRMS (EI): Calcd for: C$_7$H$_3$OF$_3$Cl$_2$$^+$ (M$^+$) 229.9513, found: 229.9517.

1,3,5-trichloro-2-(trifluoromethoxy)benzene (3f)

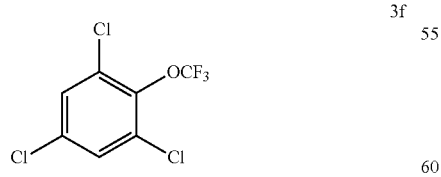

The reaction was performed according to the general procedure C using 1,3,5-trichloro-benzene (0.360 g, 2.00 mmol) as the substrate. After 16 h, the reaction mixture (61% yield by $^{19}$F NMR) was purified by HPLC on the Luna® PFP(2) preparative column (250×21.2 mm) using 65% acetonitrile in water (10 mL/min flow rate, retention time 35 min) to provide the title compound. $^1$H NMR (400 MHz, CDCl$_3$, 25° C.) 7.4 (s, 2H); $^{13}$C NMR (175 MHz, CDCl$_3$, 25° C.) δ 141.3, 133.6, 131.2, 129.4, 120.7 (q, J=262.6 Hz); $^{19}$F NMR (376 MHz, CDCl$_3$, 25° C.) δ −56.9 (s, 3F). HRMS (EI): Calcd for: C$_7$H$_2$OF$_3$Cl$_3$$^+$ (M$^+$) 263.9124, found: 263.9125.

(Trifluoromethoxy)benzoic acid (3g)

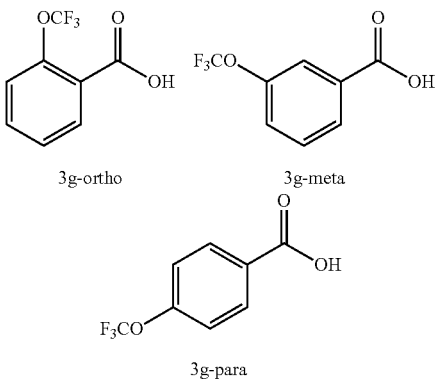

The reaction was performed according to the general procedure C using benzoic acid (0.412 g, 2.00 mmol) as the substrate. After 16 h, the reaction mixture (63% yield with o:m:p=1:1.9:1.6 by $^{19}$F NMR) was purified by HPLC on the Luna® PFP(2) preparative column (250×21.2 mm) using 50% acetonitrile in water (contains 0.1z trifluoroacetic acid) (12 mL/min flow rate, retention time 52 min) to provide 3-(trifluoromethoxy)benzoic acid (3g-meta): $^1$H NMR (400 MHz, CDCl$_3$, 25° C.) δ 8.06 (d, J=7.9 Hz, 1H), 7.97 (s, 1H), 7.54 (dd, J=7.9 Hz, 7.9 Hz, 1H), 7.48 (d, J=7.9 Hz, 1H); $^{13}$C NMR (176 MHz, CDCl$_3$, 25° C.) δ 170.2, 149.4, 131.3, 130.3, 128.7, 126.5, 122.8, 120.5 (q, J=258.3 Hz); $^{19}$F NMR (376 MHz, CDCl$_3$, 25° C.) δ −58.3 (s, 3F). HRMS (ESI): Calcd for: C$_8$H$_4$O$_3$F$_3$$^-$ ([M−H]$^-$) 205.0113, found: 205.0114.

2-(Trifluoromethoxy)benzoic acid (3g-ortho): Retention time 34 min. $^1$H NMR (500 MHz, CDCl$_3$, 25° C.) δ 8.11 (dd, J=7.8, 1.3 Hz, 1H), 7.63 (ddd, J=7.8, 7.8, 1.3 Hz, 1H), 7.43 (dd, J=7.8 Hz, 1H), 7.38 (d, J=7.8 Hz, 1H); $^{13}$C NMR (176 MHz, CDCl$_3$, 25° C.) δ 169.4, 148.7, 134.8, 133.1, 127.3, 123.9, 123.0, 120.5 (q, J=257.9 Hz); $^{19}$F NMR (376 MHz, CDCl$_3$, 25° C.) δ −58.1 (s, 3F). The spectroscopic data is in agreement with the literature.[10]

4-(Trifluoromethoxy)benzoic acid (3g-para): Retention time 55 min. $^1$H NMR (500 MHz, CDCl$_3$, 25° C.) δ $^1$H NMR: 5=8.17 (dd, J=8.8, 3.1 Hz, 2H), 7.31 (d, J=8.8 Hz, 2H); $^{19}$F NMR (376 MHz, CDCl$_3$, 25° C.) δ −58.7 (s, 3F). The spectroscopic data is in agreement with the literature.[10]

(Trifluoromethoxy)phenylethanone (3h)

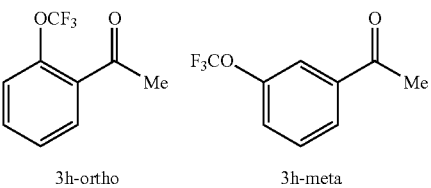

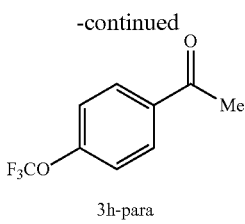

3h-para

The reaction was performed according to the general procedure B using acetophenone (0.240 g, 2.00 mmol) as the substrate. After 16 h, the reaction mixture (62% yield with o:m:p=1.5:1.7:1 by $^{19}$F NMR) was purified by HPLC on the Luna® PFP(2) preparative column (250×21.2 mm) using 50% acetonitrile in water (12 mL/min flow rate, retention time 43 min) to provide a mixture of o-, m-, and p-regioisomers.

1-(3-(Trifluoromethoxy)phenyl)ethanone (3h-meta): $^{1}$H NMR (500 MHz, CDCl$_3$/CH$_3$CN, 25° C.) δ 7.91 (d, J=7.7 Hz, 1H), 7.76 (s, 1H), 7.59 (t, J=7.9 Hz, 1H), 7.43 (d, J=8.2 Hz, 1H), 2.60 (s, 3H). $^{19}$F NMR (376 MHz, CDCl$_3$/CH$_3$CN, 25° C.) δ −57.9 (s, 3F). The spectroscopic data is in agreement with the literature.[11]

1-(4-(Trifluoromethoxy)phenyl)ethanone (3h-para): $^{1}$H NMR (500 MHz, CDCl$_3$/CH$_3$CN, 25° C.) δ 8.02-7.95 (m, 2H), 7.27 (d, J=8.0 Hz, 2H), 2.59 (s, 3H). $^{19}$F NMR (376 MHz, CDCl$_3$/CH$_3$CN, 25° C.) δ −57.7 (s, 3F). The spectroscopic data is in agreement with the literature.[11]

1-(2-(Trifluoromethoxy)phenyl)ethanone (3h-ortho): Retention time 40 min. $^{1}$H NMR (700 MHz, CDCl$_3$/CH$_3$CN, 25° C.) δ 7.70 (dd, J=7.7, 1.7 Hz, 1H), 7.56 (ddd, J=8.3, 7.7, 1.7 Hz 1H), 7.49 (ddd, J=7.7, 7.7, 1.1 Hz, 1H), 7.41 (ddd, J=8.3, 1.7, 1.1 Hz, 1H), 2.53 (s, 3H); $^{13}$C NMR (175 MHz, CDCl$_3$/CH$_3$CN, 25° C.) δ 199.2, 147.7, 134.8, 133.9, 131.6, 128.8, 122.9, 121.6 (q, J=257.3 Hz), 31.5; =$^{19}$F NMR (376 MHz, CDCl$_3$/CH$_3$CN, 25° C.) δ −57.7 (s, 3F). HRMS (EI): Calcd for: C$_9$H$_7$O$_2$F$_3^-$ (M$^+$) 204.0398, found: 204.0400.

Phenyl(trifluoromethoxy)phenylmethanone (3i)

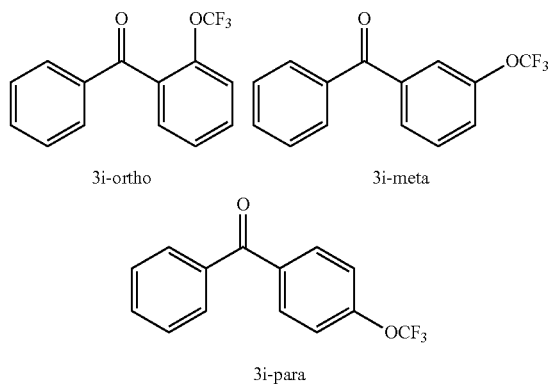

The reaction was performed according to the general procedure B using benzophenone (0.364 g, 2.00 mmol) as the substrate. After 16 h, the reaction mixture (75% yield with o:m:p=1.2:1.5:1 by $^{19}$F NMR) was purified by HPLC on the Luna® PFP(2) preparative column (250×21.2 mm) using 60 acetonitrile in water (10 mL/min flow rate, retention time 50 min) to provide a mixture of m-, and p-regioisomers.

Phenyl(3-(trifluoromethoxy)phenyl)methanone (3i-meta): $^{1}$H NMR (400 MHz, CDCl$_3$, 25° C.), 7.81-7.78 (m, 2H), 7.73 (dt, J=7.6, 1.3 Hz, 1H), 7.67 (dd, J=2.4, 1.2 Hz, 1H), 7.65-7.59 (m, 1H), 7.57-7.48 (m, 3H), 7.45 (ddt, J=8.2, 2.3, 1.1 Hz, 1H). $^{13}$C NMR (175 MHz, CDCl$_3$, ° C.): δ 195.2, 149.4, 139.7, 137.0, 133.2, 130.3, 130.1, 128.72, 128.67, 125.0, 122.6, 120.7 (q, J=258.2 Hz). $^{19}$F NMR (376 MHz, CDCl$_3$, 25° C.) δ −57.9 (s, 3F). The spectroscopic data is in agreement with the literature.[12]

Phenyl(4-(trifluoromethoxy)phenyl)methanone (3i-para): $^{1}$H NMR (400 MHz, CDCl$_3$, 25° C.), δ=7.88 (dt, J=2.4 Hz, 8.8 Hz, 2H), 7.81-7.79 (m, 2H), 7.62 (tt, J=1.9 Hz, 7.5 Hz, 1H), 7.53-7.49 (m, 2H), 7.33-7.31 (m, 2H); $^{13}$C NMR (175 MHz, CDCl$_3$, 25° C.): δ 195.4, 152.4, 137.4, 136.1, 132.9, 132.2, 130.2, 128.6, 120.6 (t, J=259.6 Hz), 120.2; $^{19}$F NMR, 376 MHz, CDCl$_3$, 25° C.): δ −57.6 (s, 3F). The spectroscopic data is in agreement with the literature.[13]

Phenyl(2-(trifluoromethoxy)phenyl)methanone (3i-ortho): Retention time 37 min. $^{1}$H NMR (500 MHz, CDCl$_3$, 25° C.), δ 7.79 (d, J=7.2 Hz, 2H), 7.60 (t, J=7.6 Hz, 1H), 7.57 (ddd, J=8.3 Hz, 7.6 Hz, 1.45 Hz, 1H), 7.51 (dd, J=7.6, 1.45 Hz, 1H), 7.47 (t, J=7.2 Hz, 2H), 7.41 (t, J=7.2 Hz, 1H), 7.37 (d, J=8.3 Hz, 1H); $^{13}$C NMR (175 MHz, CDCl$_3$, 25° C.), δ 194.1, 146.5, 137.1, 133.8, 133.1, 132.2, 130.4, 130.1, 128.7, 127.0, 121.4, 120.4 (q, J=256.5 Hz); $^{19}$F NMR (470 MHz, CDCl$_3$, 25° C.) δ −58.1 (s, 3F). HRMS (ESI): Calcd for: C$_{14}$H$_{10}$O$_2$F$_3^+$ ([M+H]$^+$) 267.0633, found: 267.0632.

Methyl 3-(trifluoromethoxy)benzoate (3j)

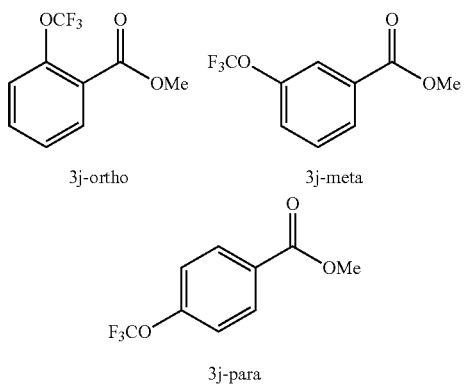

The reaction was performed according to the general procedure B using methyl benzoate (0.272 g, 2.00 mmol) as the substrate. After 16 h, the reaction mixture (73% yield with o:m:p=1.3:2.1:1 by $^{19}$F NMR) was purified by HPLC on the Luna® PFP (2) preparative column (250×21.2 mm) using 50% acetonitrile in water (10 mL/min flow rate, retention time 42 min) to provide a mixture of m-, p-regioisomers.

Methyl 3-(trifluoromethoxy)benzoate (3j-meta): $^{1}$H NMR (500 MHz, CDCl$_3$, 25° C.), δ 7.98 (d, J=8.0 Hz, 1H), 7.89 (s, 1H), 7.48 (dd, J=8.0 Hz), 7.41 (d, J=8.0 Hz, 1H), 3.94 (s, 3H); $^{13}$C NMR (175 MHz, CDCl$_3$, ° C.), δ 165.9, 149.4, 132.4, 130.1, 128.1, 125.6, 122.3, 120.6 (q, J=258.0 Hz), 52.7; $^{19}$F NMR (376 MHz, CDCl$_3$, 25° C.) δ −58.5 (s, 3F). The spectroscopic data is in agreement with the literature.[14]

Methyl 4-(trifluoromethoxy)benzoate (3j-para): $^{1}$H NMR (500 MHz, CDCl$_3$, 25° C.) δ 8.10-8.08 (m, 2H), 7.26 (d, J=8.7 Hz, 2H), 3.92 (s, 3H). $^{13}$C NMR (175 MHz, CDCl$_3$, 25° C.) δ 166.1, 152.8, 131.8, 128.7, 120.5 (q, J=258.7 Hz), 120.6, 52.6. $^{19}$F NMR (376 MHz, CDCl$_3$, 25° C.) δ −58.2 (s, 3F). The spectroscopic data is in agreement with the literature.[11]

Methyl 2-(trifluoromethoxy)benzoate (3j-ortho): Retention time 32 min. $^1$H NMR (400 MHz, CDCl$_3$, 25° C.), δ 7.98 (d, J=7.6 Hz, 1H), 7.56 (ddd, J=8.2, 7.6, 1.6 Hz, 1H), 7.38 (ddd, J=7.6 Hz, 7.6 Hz, 0.8 Hz, 1H), 7.33 (d, 8.2 Hz, 1H), 3.93 (s, 3H); $^{13}$C NMR (175 MHz, CDCl$_3$, ° C.), δ 165.2, 147.8, 133.7, 132.2, 127.1, 125.1, 122.8, 120.5 (q, J=255.8 Hz), 52.6; $^{19}$F NMR (376 MHz, CDCl$_3$, 25° C.) δ −58.0 (s, 3F). HRMS (EI): Calcd for: C$_9$H$_7$O$_3$F$_3{}^+$ (M$^+$) 220.0347, found: 220.0348.

Dimethyl 5-(tert-butyl)-2-(trifluoromethoxy)isophthalate (3k)

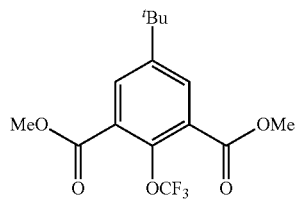

3k

Dimethyl 5-(tert-butyl)isophthalate was prepared according to a reported procedure (Murai, K. et al. 2011). The reaction was performed according to the general procedure C using dimethyl 5-(tert-butyl)isophthalate (0.500 g, 2.00 mmol) as the substrate. After 16 h, the reaction mixture (41% yield by $^{19}$F NMR) was purified by HPLC on the Luna® PFP(2) preparative column (250×21.2 mm) using 65% acetonitrile in water (10.0 mL/min flow rate, retention time 33 min) to provide the title compound. $^1$H NMR (400 MHz, CDCl$_3$, 25° C.) δ 8.03 (s, 2H), 3.94 (s, 6H), 1.36 (s, 9H); $^{13}$C NMR (175 MHz, CDCl$_3$, 25° C.) δ 165.6, 151.0, 143.1, 132.3, 127.2, 120.3 (q, J=258.5 Hz), 52.8, 36.1, 31.2; $^{19}$F NMR (376 MHz, CDCl$_3$, 25° C.) δ −58.8 (s, 3F). HRMS (ESI): Calcd for: C$_{15}$H$_{17}$O$_5$F$_3$Na$^+$ ([M+Na]$^+$) 357.0926, found: 357.0926.

4-(tert-Butyl)-2-(trifluoromethoxy)benzonitrile (3l)

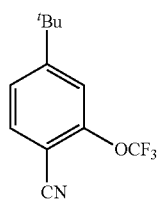

3l

The reaction was performed according to the general procedure B using 4-(tert-butyl)benzonitrile (0.320 g, 2.00 mmol) as the substrate. After 16 h, the reaction mixture (57% yield by $^{19}$F NMR) was purified by HPLC on the Luna® PFP(2) preparative column (250×21.2 mm) using 60% acetonitrile in water (10 mL/min flow rate, retention time 61 min) to provide the title compound. $^1$H NMR (400 MHz, CDCl$_3$, 25° C.) δ 7.63 (d, J=8.2 Hz, 1H), 7.43 (dd, J=8.2, 1.5 Hz, 1H), 7.38 (dd, J=1.5 Hz, 1.5 Hz, 1H), 1.34 (s, 9H); $^{13}$C NMR (175 MHz, CDCl$_3$, 25° C.), δ 159.6, 150.0, 133.7, 124.6, 120.4 (q, J=260.3 Hz), 119.0, 114.7, 104.4, 35.7, 30.9; $^{19}$F NMR (376 MHz, CDCl$_3$, 25° C.) δ −58.5 (s, 3F). HRMS (EI): Calcd for: C$_{12}$H$_{12}$OF$_3$N$^+$ (M$^+$) 243.0871, found: 243.0866.

Phenyl (trifluoromethoxy)phenyl carbonate (3m)

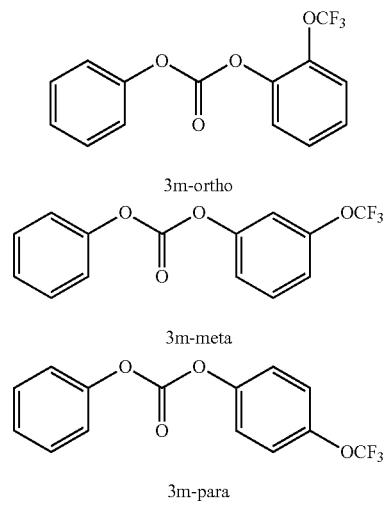

The reaction was performed according to the general procedure B using diphenyl carbonate (0.428 g, 2.00 mmol) as the substrate. After 16 h, the reaction mixture (68% yield with o:m:p=2.7:1:3.7 by $^{19}$F NMR) was purified by HPLC on the Luna® PFP(2) preparative column (250×21.2 mm) using 70% acetonitrile in water (10.0 mL/min flow rate, retention time 27 min) to provide a mixture of m- and p-regioisomers.

Phenyl (3-(trifluoromethoxy)phenyl) carbonate (3m- by HPLC on the Luna® PFP(2) preparative column (250×21.2 mm) using 70% acetonitrile in water (10.0 mL/min flow rate, retention time 27 min) to provide a mixture of m- and p-regioisomers.meta): $^1$H NMR (700 MHz, CDCl$_3$, 25° C.) δ 7.46-7.42 (m, 2H), 7.34-7.25 (m, 5H), 7.22 (s, 1H), 7.16 (ddd, J=8.3, 1.0, 1.0 Hz, 1H); $^{19}$F NMR (376 MHz, CDCl$_3$, 25° C.) δ −58.0 (s, 3F).

Phenyl (4-(trifluoromethoxy)phenyl) carbonate (3m-para): $^1$H NMR (700 MHz, CDCl$_3$, 25° C.) δ 7.46-7.42 (m, 2H), 7.34-7.25 (m, 7H); $^{19}$F NMR (376 MHz, CDCl$_3$, 25° C.) δ −58.1 (s, 3F). $^{13}$C NMR (175 MHz, CDCl$_3$, 25° C.) (a mixture of 3-,4-regioisomers) δ 151.8, 151.6, 151.5, 150.9, 150.8, 149.6, 149.1, 146.9, 130.4, 129.7, 126.54, 126.50, 122.32, 122.25, 120.8, 120.41 (q, J=258.5 Hz), 120.36 (q, J=258.7 Hz), 119.4, 118.7, 114.4.

Phenyl (2-(trifluoromethoxy)phenyl) carbonate (3m-ortho): Retention time: 25 min. $^1$H NMR (400 MHz, CDCl$_3$, 25° C.) δ 7.33-7.41 (m, 2H), 7.40-7.37 (m, 2H), 7.36 (td, J=7.7, 1.8 Hz, 1H), 7.34-7.31 (m, 1H), 7.29 (dd, J=7.7 Hz, 7.7 Hz, 1H), 7.27-7.25 (m, 2H); $^{13}$C NMR (175 MHz, CDCl$_3$, 25° C.) δ 151.4, 151.1, 142.9, 140.8 (d, J=2.9 Hz), 129.8, 127.9, 127.6, 126.6, 123.7, 122.5, 120.9, 120.6 (q, J=259.4 Hz); $^{19}$F NMR (376 MHz, CDCl$_3$, 25° C.) δ −58.6 (s, 3F). HRMS (EI): Calcd for: C$_{14}$H$_9$O$_4$F$_3{}^+$ (M$^+$) 298.0453, found: 298.0458.

Methyl 4-((tert-butoxycarbonyl)oxy)-3-(trifluoromethoxy)benzoate (3n)

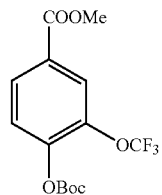

Methyl 4-((tert-butoxycarbonyl)oxy)benzoate was prepared according to a reported procedure (Leowanawat, P. et al. 2012). The reaction was performed according to the general procedure B using methyl 4-((tert-butoxycarbonyl)oxy)benzoate (0.504 g, 2.00 mmol) as the substrate. After 16 h, the reaction mixture (54% yield by $^{19}$F NMR) was purified by HPLC on the Luna® PFP (2) preparative column (250×21.2 mm) using 65% acetonitrile in water (10.0 mL/min flow rate, retention time 18 min) to provide the title compound. $^1$H NMR (700 MHz, CDCl$_3$, 25° C.) δ 8.00-7.99 (m, 2H), 7.34 (d, J=8.9 Hz, 1H), 3.93 (s, 3H), 1.55 (s, 9H); $^{13}$C NMR (175 MHz, CDCl$_3$, 25° C.) δ 165.3, 150.3, 146.7, 140.9, 129.1, 129.1, 124.0, 123.5, 120.5 (q, J=254.0 Hz), 85.1, 82.7, 27.6; $^{19}$F NMR (376 MHz, CDCl$_3$, 25° C.) δ −58.5 (s, 3F). HRMS (ESI): Calcd for: C$_{14}$H$_{15}$O$_6$F$_3$Na$^+$ ([M+Na]$^+$) 359.0734, found: 35.0713.

Diphenyl(3-(trifluoromethoxy)phenyl)phosphine oxide (3o)

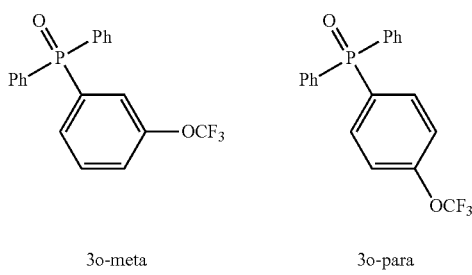 [SMILES: O=P(c1ccccc1)(c1ccccc1)c1cccc(OC(F)(F)F)c1 ; O=P(c1ccccc1)(c1ccccc1)c1ccc(OC(F)(F)F)cc1]

The reaction was performed according to the general procedure C using triphenylphosphine oxide (0.556 g, 2.00 mmol) as the substrate. After 16 h, the reaction mixture (52% yield, m:p=2:1 by $^{19}$F NMR) was purified by HPLC on Luna® PFP(2) preparative column (250×21.2 mm) using 50 acetonitrile in water (10.0 mL/min flow rate, retention time 26 min) to provide the a mixture of m-, p-regioisomers.

Diphenyl(3-(trifluoromethoxy)phenyl)phosphine oxide (3o-meta): $^1$H NMR (700 MHz, CDCl$_3$, 25° C.) δ 7.71 (dd, J=11.3, 8.7 Hz, 1H), 7.66 (dd, J=12.1, 7.1 Hz, 4H), 7.62-7.45 (m, 9H); $^{19}$F NMR (376 MHz, CDCl$_3$, 25° C.) δ −58.3 (s, 3F). $^{31}$P NMR (202 MHz, CDCl$_3$, 25° C.) δ −27.8 (s, 1P). The spectroscopic data is in agreement with the literature (Zhang, D. Y. et al. 2012).

Diphenyl(4-(trifluoromethoxy)phenyl)phosphine oxide (3o-para): $^1$H NMR (700 MHz, CDCl$_3$, 25° C.) δ 7.73-7.65 (m, 6H), 7.49-7.47 (m, 4H), 7.39 (d, J=8.4 Hz, 2H) 7.30 (d, J=8.4 Hz, 2H); $^{13}$C NMR (175 MHz, CDCl$_3$, 25° C.): δ 152.1, 134.3 (d, J=11.3 Hz), 132.4 (d, J=2.5 Hz), 132.3 (d, J=10.2 Hz), 132.2 (d, J=99.2 Hz), 130.6, 128.8 (d, J=12.7 Hz), 120.7 (d, J=12.8 Hz), 120.5 (q, J=258.6 Hz) $^{19}$F NMR (376 MHz, CDCl$_3$, 25° C.) δ −58.1 (s, 3F). $^{31}$P NMR (202 MHz, CDCl$_3$, 25° C.) δ −28.0 (s, 1P). The spectroscopic data is in agreement with the literature (Xu, J. et al. 2013).

Methyl 4-methyl-3-(trifluoromethoxy)benzoate (3p)

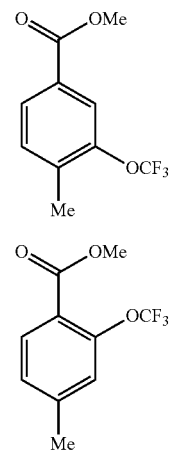

The reaction was performed according to the general procedure B using methyl 4-methylbenzoate (0.300 g, 2.00 mmol) as the substrate. After 16 h, the reaction mixture (46% yield, 1-:2-=3.6:1 by $^{19}$F NMR) was purified by HPLC on the Luna® PFP(2) preparative column (250×21.2 mm) using 50% acetonitrile in water (10.0 mL/min flow rate, retention time 44 min) to provide Methyl 4-methyl-3-(trifluoromethoxy)benzoate (3p-1): $^1$H NMR (400 MHz, CDCl$_3$, 25° C.) δ 7.81-7.78 (m, 2H), 7.28 (d, J=7.8 Hz, 1H), 3.84 (s, 3H), 2.30 (s, 3H). $^{13}$C NMR (175 MHz, CDCl$_3$, 25° C.) δ 165.7, 147.4, 136.5, 131.6, 129.9, 127.8, 121.7, 120.5 (q, J=257.4), 52.2, 16.2. $^{19}$F NMR (376 MHz, CDCl$_3$/CH$_3$CN, 25° C.) δ −58.4.

Methyl 4-methyl-2-(trifluoromethoxy)benzoate (3p-2): Retention time: 53 min. $^1$H NMR (400 MHz, CDCl$_3$, 25° C.) δ 7.80 (d, J=8.0 Hz, 1H), 7.14 (d, J=8.0 Hz, 1H), 7.08 (s, 1H), 3.85 (s, 3H), 2.37 (s, 3H). $^{13}$C NMR (175 MHz, CDCl$_3$, 25° C.) δ 164.8, 147.6, 145.0, 131.9, 127.8, 123.2, 122.4, 120.2 (q, J=257.4 Hz), 52.2, 21.3. $^{19}$F NMR (376 MHz, CDCl$_3$, 25° C.) δ −58.0. HRMS (ESI): Calcd for: C$_{10}$H$_9$O$_3$F$_3$Na$^+$ ([M+Na]$^+$) 257.0401, found: 257.0410.

2,6-Dichloro-3-(trifluoromethoxy)pyridine (3q)

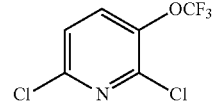

The reaction was performed according to the general procedure B using 2,6-dichloropyridine (0.362 g, 2.00 mmol) as the substrate. After 16 h, the reaction mixture (60% yield by $^{19}$F NMR) was purified by HPLC on the Gemini® 5 μm NX-C18 semi-preparative column (250×10 mm) using 50% acetonitrile in water (3.5 mL/min flow rate, retention time 26 min) to provide the title compound. $^1$H NMR (400 MHz, CDCl$_3$, 25° C.) δ 7.6 (dd, J=8.4, 1.2 Hz, 1H), 7.3 (d, J=8.4 Hz, 1H); $^{13}$C NMR (175 MHz, CDCl$_3$, 25° C.) δ 148.0, 144.3, 141.5, 133.0, 124.1, 120.5 (q, J=261.6 Hz); $^{19}$F NMR (376 MHz, CDCl$_3$, 25° C.) δ −58.9 (s, 3F). HRMS (EI): Calcd for: C$_6$H$_2$ONF$_3$Cl$_2$$^+$ (M$^+$) 230.9456, found: 230.9462.

2,4,6-Trichloro-3-(trifluoromethoxy)pyridine (3r)

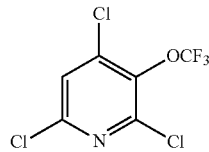

The reaction was performed according to the general procedure B using 2,4,6-trichloropyridine (0.362 g, 2.00 mmol) as the substrate. After 16 h, the reaction mixture (58% yield by $^{19}$F NMR) was purified by HPLC on the Gemini® 5 μm NX-C18 semi-preparative column (250×10 mm) using 60% acetonitrile in water (3.5 mL/min flow rate, retention time 23 min) to provide the title compound. $^1$H NMR (400 MHz, CDCl$_3$, 25° C.) 7.4 (s, 1H); $^{13}$C NMR (175 MHz, CDCl$_3$, 25° C.) δ 148.4, 146.6, 142.3, 139.1, 125.3, 120.7 (q, J=264.1 Hz); $^{19}$F NMR (376 MHz, CDCl$_3$, 25° C.) δ −56.9 (s, 3F). HRMS (EI): Calcd for: C$_6$HONF$_3$Cl$_3$$^+$ (M$^+$) 264.9076, found: 264.9070.

Dimethyl 4-methoxy-3-(trifluoromethoxy)pyridine-2,6-dicarboxylate (3s)

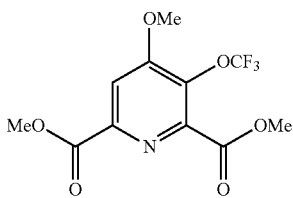

Dimethyl 4-methoxypyridine-2,6-dicarboxylate was prepared according to reported procedures (Pellegatti, L. et al. 2008; Zeng, T. et al. 2011). The reaction was performed according to the general procedure C using dimethyl 4-methoxypyridine-2,6-dicarboxylate (0.550 g, 2.00 mmol) as the substrate. After 16 h, the reaction mixture (68% yield by $^{19}$F NMR) was purified by HPLC on the Gemini® 5 μm NX-C18 semi-preparative column (250×10 mm) using 40% acetonitrile in water (3.5 mL/min flow rate, retention time 19 min) to provide the title compound. $^1$H NMR (400 MHz, CDCl$_3$, 25° C.) δ 7.91 (s, 1H), 4.06 (s, 3H), 4.02 (s, 3H), 3.99 (s, 3H); $^{13}$C NMR (175 MHz, CDCl$_3$, 25° C.) δ 164.4, 163.4, 160.6, 147.8, 145.3, 136.5, 120.5 (q, J=260.6 Hz), 111.8, 57.2, 53.7, 53.4; $^{19}$F NMR (376 MHz, CDCl$_3$, 25° C.) δ −58.2 (s, 3F). HRMS (ESI): Calcd for: C$_{11}$H$_{11}$NO$_6$F$_3$$^+$ ([M+H]$^+$) 310.0538, found: 310.0530.

2,4-dichloro-6-methyl-5-(trifluoromethoxy)pyrimidine (3t)

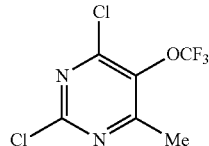

The reaction was performed according to the general procedure C using 2,4-dichloro-6-methylpyrimidine (0.324 g, 2.00 mmol) as the substrate. After 16 h, the reaction mixture (42% yield by $^{19}$F NMR) was purified by HPLC on the Gemini® 5 μm NX-C18 semi-preparative column (250× 10 mm) using 652 acetonitrile in water (3.5 mL/min flow rate, retention time 25 min) to provide the title compound. $^1$H NMR (400 MHz, CDCl$_3$) δ 2.60 (s, 3H); $^{13}$C NMR (175 MHz, CDCl$_3$, 25° C.) δ 166.6, 157.1, 157.0, 139.3, 120.8 (q, J=264.3 Hz), 20.1; $^{19}$F NMR (376 MHz, CDCl$_3$, 25° C.) δ −57.5 (s, 3F). HRMS (EI): Calcd for: C$_6$H$_3$ON$_2$F$_3$Cl$_2$$^-$ (M$^-$) 245.9575, found: 245.9577.

4,6-Dichloro-2-methyl-5-(trifluoromethoxy)pyrimidine (3u)

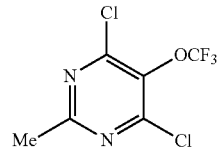

The reaction was performed according to the general procedure C using 4,6-dichloro-2-methylpyrimidine (0.324 g, 2.00 mmol) as the substrate. After 16 h, the reaction mixture (68% yield by $^{19}$F NMR) was purified by HPLC on the Gemini® 5 μm NX-C18 semi-preparative column (250× 10 mm) using 40 acetonitrile in water (3.5 mL/min flow rate, retention time 19 min) to provide the title compound. $^1$H NMR (400 MHz, CDCl$_3$, 25° C.) δ 2.72 (s, 3H); $^{13}$C NMR (175 MHz, CDCl$_3$, 25° C.) δ 166.9, 156.1, 136.2, 120.7 (q, J=264.5 Hz), 25.4; $^{19}$F NMR (376 MHz, CDCl$_3$, 25° C.) δ −57.1 (s, 3F). HRMS (EI): Calcd for: C$_6$H$_3$ON$_2$F$_3$Cl$_2$$^+$ (M$^+$) 245.9575, found: 245.9576.

((3aS,5aR,8aR,8bS)-2,2,7,7-tetramethyltetrahydro-3aH-bis([1,3]dioxolo)[4,5-b:4',5'-d]pyran-3a-yl)methyl 4-bromothiophene-2-carboxylate (2v)

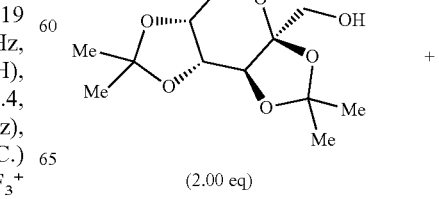

(2.00 eq)

-continued

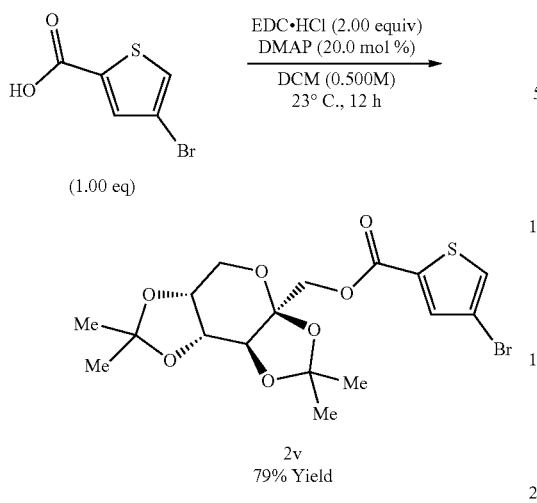

(1.00 eq)

2v
79% Yield

-continued

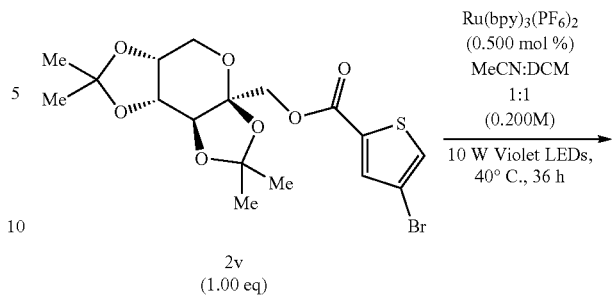

2v
(1.00 eq)

An oven-dried 20 mL screw cap vial equipped with a magnetic stir bar was charged with 4-bromothiophene-2-carboxylic acid (1.04 g, 5.00 mmol, 1.00 equiv), ((3aS,5aR,8aR,8bS)-2,2,7,7-tetramethyltetrahydro-3aH-bis([1,3]di-oxolo)[4,5-b:4',5'-d]pyran-3a-yl)methanol (2.60 g, 10.0 mmol), N-(3-dimethylaminopropyl)-N'-ethylcarbodiimide hydrochloride (EDC.HCl) (1.92 g, 10.0 mmol, 2.00 equiv), 4-dimethylaminopyridine (DMAP) (122 mg, 1.00 mmol, 20.0 mol %) and 10 mL anhydrous DCM (0.500 M). The mixture was stirred at room temperature for overnight. After the reaction was complete, the mixture was diluted with EtOAc (20 mL) and washed with brine (20 mL×3). The organic layer was collected, dried with $Mg_2SO_4$, filtered, and concentrated in vacuo. The residue was purification by flash column chromatography (eluting with 20 G EtOAc in hexanes) to afford the title compound (1.77 g, 79f) as a clear oil. $^1$H NMR (400 MHz, $CDCl_3$, 25° C.) δ 7.72 (d, J=1.5 Hz, 1H), 7.46 (d, J=1.5 Hz, 1H), 4.64-4.61 (m, 2H), 4.41 (d, J=2.7 Hz, 1H), 4.28-4.24 (m, 2H), 3.94 (dd, J=13.0 Hz, 2.6 Hz, 1H), 3.78 (d, J=13.0 Hz, 1H), 1.54 (s, 3H), 1.46 (s, 3H), 1.40 (s, 3H), 1.34 (s, 3H); $^{13}$C NMR (175 MHz, $CDCl_3$, ° C.) δ 160.2, 135.9, 134.1, 129.8, 110.7, 109.2, 109.0, 101.3, 70.7, 70.4, 70.0, 65.5, 61.4, 26.5, 25.9, 25.6, 24.0. HRMS (ESI): Calcd for: $C_{17}H_{22}O_7SBr^+$ ([M+H]$^+$) 449.0270, found: 449.0257.

((3aS,5aR,8aR,8bS)-2,2,7,7-tetramethyltetrahydro-3aH-bis([1,3]dioxolo)[4,5-b:4',5'-d]pyran-3a-yl) methyl 4-bromo-5-(trifluoromethoxy) thiophene-2-carboxylate (3v)

3v
32% Yield
(60% Yield BRSM)

In a glovebox, to an oven-dried 20 mL screw cap vial was added 2-(3,5-bis(trifluoromethyl)phenyl)-4-nitro-1-(trifluoromethoxy)-6-(trifluoromethyl)-1H-benzo[d]imidazole (1) (158 mg, 0.300 mmol, 1.50 equiv), ((3aS,5aR,8aR,8bS)-2,2,7,7-tetramethyltetrahydro-3aH-bis([1,3]dioxolo)[4,5-b:4',5'-d]pyran-3a-yl)methyl 4-bromothiophene-2-carboxylate (2v) (89.6 mg. 0.200 mmol, 1.00 equiv) and Ru(bpy)$_3$(PF$_6$)$_2$, (0.860 mg, 0.100 μmol, 0.500 mol %). Then MeCN (0.500 mL) and DCM (0.500 mL, 0.200 M) and a magnetic stir bar were added. The vial was capped and taken out of the glovebox. The reaction mixture was then stirred and irradiated with a 10 W LED (402 nm) at 40° C. After 36 h, the crude material was purified by HPLC on the Luna® PFP(2) preparative column (250×21.2 mm) using 55% acetonitrile in water (10.0 mL/min flow rate, retention time 83.2 min) to provide 33.0 mg (32% yield) of the title compound (3v). 42.0 mg unreacted substrate (2v) was recovered (retention time 34.6 min, 47% recovery) from the reaction mixture. $^1$H NMR (400 MHz, $CDCl_3$, 25° C.) δ 7.63 (s, 1H), 4.65-4.61 (m, 2H), 4.38 (d, J=2.6 Hz, 1H), 4.29-4.24 (m, 2H), 3.94 (dd, J=13.0 Hz, 2.6 Hz, 1H), 3.77 (d, J—13.0 Hz, 1H), 1.55 (s, 3H), 1.47 (s, 3H), 1.39 (s, 3H), 1.35 (s, 3H); $^{13}$C NMR (175 MHz, $CDCl_3$, 25° C.) δ 160.0, 149.3, 134.0, 127.0 120.1 (q, J=263.5 Hz), 109.3, 109.2, 104.1, 101.4, 70.8, 70.6, 70.1, 66.1, 61.5, 26.6, 26.0, 25.6, 24.1; $^{19}$F NMR (376 MHz, $CDCl_3$, 25° C.) δ −60.1 (s, 3F). HRMS (ESI): Calcd for: $C_{16}H_{21}O_8SBrF_3^+$ ([M+H]$^+$) 533.0093, found: 533.0081.

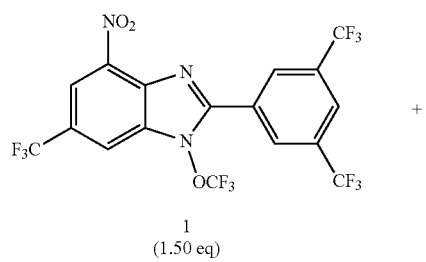

1
(1.50 eq)

+

59

(1R,2S,5R)-2-isopropyl-5-methylcyclohexyl 4-bromothiophene-2-carboxylate (2w)

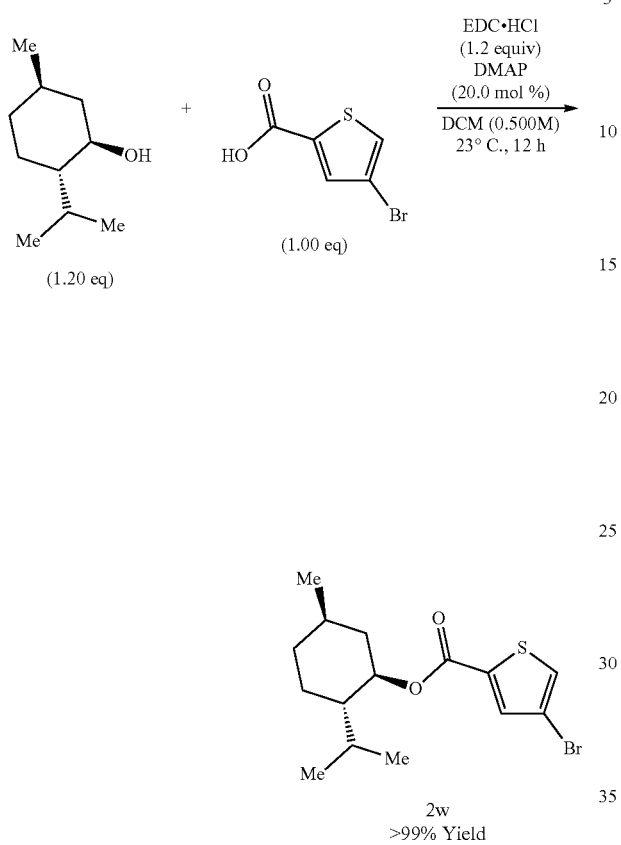

An oven-dried 20 mL screw cap vial equipped with a magnetic stir bar was charged with 4-bromothiophene-2-carboxylic acid (0.994 g, 4.80 mmol, 1.20 equiv), (1R,2S,5R)-2-isopropyl-5-methylcyclohexan-1-ol (0.623 g, 4.00 mmol, 1.00 equiv), N-(3-dimethylaminopropyl)-N'-ethyl-carbodiimide hydrochloride (EDC.HCl) (0.920 g, 4.80 mmol, 1.20 equiv), 4-4-dimethylaminopyridine (DMAP) (97.7 mg, 0.080 mmol, 20.0 mol %) and 8 mL anhydrous DCM (0.500 M). The mixture was stirred at room temperature for overnight. After the reaction was complete, the mixture was diluted with EtOAc (20 mL) and washed with brine (20 mL×3). The organic layer was separated, dried with Mg$_2$SO$_4$, filtered, and concentrated in vacuo. The residue was purification by flash column chromatography (eluting with 20% EtOAc in hexanes) to afford the title compound (1.38 g, >99%) as a light-yellow oil. $^1$H NMR (700 MHz, CDCl$_3$) δ 7.66 (s, 1H), 7.43 (s, 1H), 4.87 (m, 1H), 2.10 (d, J=12.0 Hz, 1H), 1.91 (m, 2H), 1.72 (d, J=12.7 Hz, 2H), 1.52 (m, 2H), 1.10 (s, 3H), 0.92 (d, J=7.7 Hz, 3H), 0.91 (d, J=7.7, 1H), 0.79 (d, J=7.0 Hz, 3H); $^{13}$C NMR (176 MHz, CDCl$_3$) δ 160.76, 135.63, 135.14, 129.39, 110.59, 75.96, 47.24, 40.96, 34.32, 31.55, 26.66, 23.77, 22.13, 20.83, 16.68. HRMS (ESI): Calcd for: C$_{15}$H$_{21}$O$_2$SBr$^+$ ([M+H]$^+$) 344.0446, found: 344.0435.

60

(1R,2S,5R)-2-isopropyl-5-methylcyclohexyl 4-bromo-5-(trifluoromethoxy) thiophene-2-carboxylate (3w)

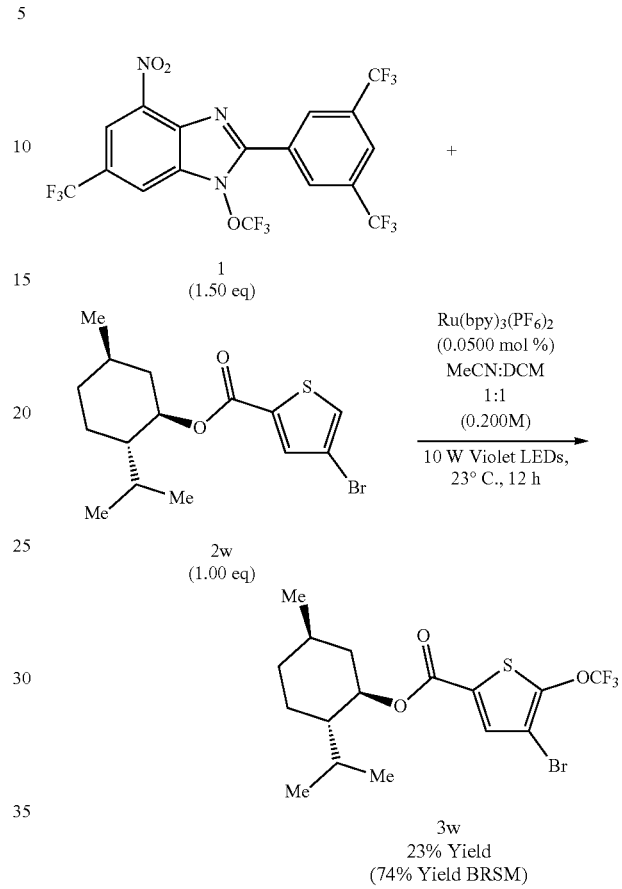

In a glovebox, to an oven-dried 20 mL screw cap vial was added 2-(3,5-bis(trifluoromethyl)phenyl)-4-nitro-1-(trifluoromethoxy)-6-(trifluoromethyl)-1H-benzo[d]imidazole (1) (158 mg, 0.300 mmol, 1.50 equiv), (1R,2S,5R)-2-isopropyl-5-methylcyclohexyl 4-bromothiophene-2-carboxylate (2w) (69.1 mg, 0.200 mmol, 1.00 equiv) and Ru(bpy)$_3$(PF$_6$)$_2$, (0.860 mg, 0.100 µmol, 0.500 mol %). Then MeCN (0.500 mL), DCM (0.500 mL, 0.200 M) and a magnetic stir bar were added. The vial was capped and taken out of the glovebox. The reaction mixture was then stirred and irradiated with a 10 W LEDs (402 nm) at 23° C. for 12 h. After that period, the reaction mixture was directly concentrated in vacuo and the residue was purified by preparative TLC, developing with DCM:Hexanes [1:1 (v/v)] to afford a mixture of 2w and 3w (R$_f$=0.61 DCM:Hexanes [1:1 (v/v)]). The crude material was then purified by HPLC on the Luna® PFP(2) preparative column (250×21.2 mm) using 70% acetonitrile in water (10.6 mL/min flow rate, retention time 59.4 min) to afford 19.6 mg (23% yield) of the title compound. 47.6 mg unreacted substrate (2w) was recovered (retention time 41.1 min, 69% recovery) from the reaction mixture. $^1$H NMR (700 MHz, CDCl$_3$) δ 7.56 (s, 1H), 4.88 (m, 1H), 2.08 (d, J=12.0 Hz, 1H), 1.89 (m, 1H), 1.72 (m, 2H), 1.52 (m, 2H), 1.09 (m, 2H), 0.93 (d, J=7.7 Hz, 3H), 0.91 (d, J=7.7 Hz, 3H), 0.79 (d, J=7.0 Hz, 3H); $^{13}$C NMR (176 MHz, CDCl$_3$) δ 160.34, 148.88 (d, J=2.3 Hz), 133.12, 128.32, 120.14 (q, J=263.2 Hz), 103.95, 76.51, 47.22, 40.93, 34.27, 31.58, 26.67, 23.72, 22.12, 20.84, 16.63; $^{19}$F NMR (376 MHz, CDCl$_3$, 25° C.) δ −60.3 (s, 3F). HRMS (ESI): Calcd for: C$_{16}$H$_{20}$O$_3$F$_3$SBr$^+$ ([M+H]$^+$) 428.0269, found: 428.0265.

(3S,5S,8R,9S,10S,13S,14S)-10,13-dimethyl-17-oxo-hexadecahydro-1E-cyclopenta[□]phenanthren-3-yl 4-bromothiophene-2-carboxylate (2x)

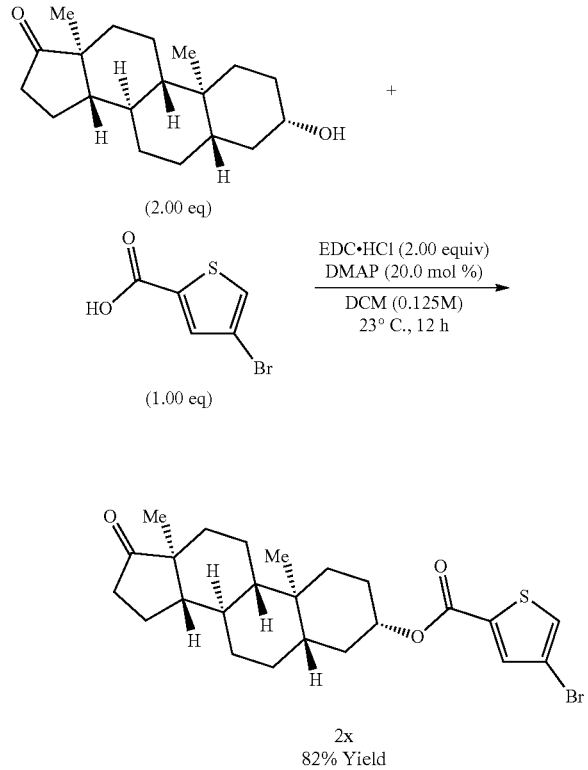

An oven-dried 20 mL screw cap vial equipped with a magnetic stir bar was charged with 4-bromothiophene-2-carboxylic acid (0.828 g, 4.00 mmol, 1.00 equiv), (3S,5S, 8R,9S,10S,13S,14S)-3-hydroxy-10,13-dimethylhexadecahydro-17H-cyclopenta[α]phenanthren-17-one (2.32 g, 8.00 mmol, 2.00 equiv), N-(3-dimethylaminopropyl)-N'-ethylcarbodiimide hydrochloride (EDC.HCl) (1.53 g, 8.00 mmol, 2.00 equiv), 4-dimethylaminopyridine (DMAP) (97.7 mg, 0.080 mmol, 20.0 mol %) and 32 mL anhydrous DCM (0.125 M). The mixture was stirred at room temperature for overnight. After the reaction was complete, the mixture was concentrated in vacuo. The residue was purification by flash column chromatography eluting with DCM:Hexanes [1:1 (v/v)] (R$_f$=0.68 DCM:Hexanes [1:1 (v/v)]) to afford the title compound (1.38 g, 82) as a white solid. $^1$H NMR (700 MHz, CDCl$_3$) δ 7.66 (s, 1H), 7.42 (s, 1H), 4.89 (m, 1H), 2.44 (m, 1H), 2.07 (m, 1H), 1.93 (m, 2H), 1.79 (m, 4H), 1.52 (m, 5H), 1.32 (m, 6H), 1.09 (m, 1H), 1.00 (m, 1H), 0.89 (s, 3H), 0.86 (s, 3H), 0.74 (m, 1H); $^{13}$C NMR (176 MHz, CDCl$_3$) δ 221.36, 160.68, 135.59, 135.21, 129.41, 110.54, 75.16, 54.38, 51.45, 47.90, 44.77, 36.78, 35.96, 35.77, 35.13, 34.03, 31.63, 30.91, 28.37, 27.53, 21.89, 20.59, 13.94, 12.38; HRMS (ESI): Calcd for: C$_{24}$H$_{32}$O$_3$SBr$^+$ ([M+H]$^+$) 479.1256, found: 479.1262.

(3S,5S,8R,9S,10S,13S,14S)-10,13-dimethyl-17-oxo-hexadecahydro-1B-cyclopenta[a]phenanthren-3-yl 4-bromo-5-(trifluoromethoxy)thiophene-2-carboxylate (3x)

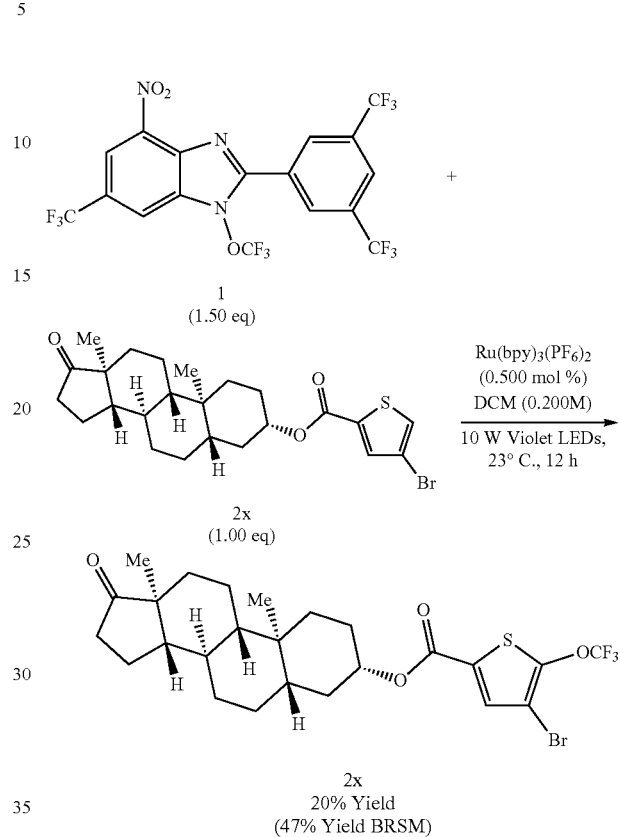

In a glovebox, to an oven-dried 20 mL screw cap vial was added 2-(3,5-bis(trifluoromethyl)phenyl)-4-nitro-1-(trifluoromethoxy)-6-(trifluoromethyl)-1H-benzo[d]imidazole (1) (158 mg, 0.300 mmol, 1.50 equiv), (3S,5S,8R,9S,10S,13S, 14S)-10,13-dimethyl-17-oxohexadecahydro-1H-cyclopenta[α]phenanthren-3-yl-4-bromothiophene-2-carboxylate (2x) (95.9 mg. 0.200 mmol, 1.00 equiv) and Ru(bpy)$_3$(PF$_6$)$_2$, (0.860 mg, 0.100 µmol, 0.500 mol %). Then DCM (1.00 mL, 0.200 M) and a magnetic stir bar were added. The vial was capped and taken out of the glovebox. The reaction mixture was then stirred and irradiated with a 10 W LEDs (402 nm) at 23° C. for 12 h. After that period, the reaction mixture was directly concentrated in vacuo and the residue was purified by preparative TLC, developing with DCM:DCE [1:1 (v/v)] to afford 3x (R$_f$=0.69 DCM:Hexanes [1:1 (v/v)]) 22.8 mg (204% yield) of the title compound. 54.2 mg unreacted substrate (2x) was recovered (R$_f$=0.59 in DCM:DCE [1:1 (v/v)]) from the reaction mixture. $^1$H NMR (700 MHz, CDCl$_3$) δ 7.66 (s, 1H), 7.42 (s, 1H), 4.89 (m, 1H), 2.44 (m, 1H), 2.07 (m, 1H), 1.93 (m, 2H), 1.79 (m, 4H), 1.52 (m, 5H), 1.32 (m, 6H), 1.09 (m, 1H), 1.00 (m, 1H), 0.89 (s, 3H), 0.86 (s, 3H), 0.74 (m, 1H); $^{13}$C NMR (176 MHz, CDCl$_3$) δ 221.33, 160.23, 148.82, 133.17, 128.26, 120.10 (q, J=263.3 Hz), 103.85, 75.65, 54.37, 51.45, 47.89, 44.76, 36.75, 35.96, 35.76, 35.13, 33.98, 31.62, 30.89, 28.35, 27.49, 21.89, 20.60, 13.93, 12.37; $^{19}$F NMR (376 MHz, CDCl$_3$, 25° C.) δ −60.4 (s, 3F); HRMS (ESI): Calcd for: C$_{25}$H$_{30}$O$_4$NaSBr$^+$ ([M+Na]) 585.0898, found: 585.0883.

Example 2. OCF$_2$H-Reagent 1a and OCF$_3$-Reagent 1b

As shown in Scheme 9, a broad array of arenes and heteroarenes with diverse electronic properties and substitution patterns underwent photocatalytic (hetero)aryl C—H difluoromethoxylation under optimised reaction conditions using reagent 1a at room temperature. The reaction tolerated halide substituents such as fluorine (3r), chloride (3b-3d), and bromide (3e-3f, 3ab-3ad), which is important from a synthetic perspective since these substituents provide useful handles for further structural elaboration through metal-catalysed coupling reactions. The weak benzylic C—H bond (BDE≈88 kcal/mol, 3f-3i) (Ellison, G. B. et al. 1996), which is often a site for undesired reactivity in radical processes, proved compatible. More remarkably, unprotected alcohols (3i) and phenols (3k-3n) remained intact during the reaction. Carbonyl derivatives such as aldehydes (3n), ketones with or without enolizable protons (3o-3p), carboxylic acids (3r-3s, 3ad), esters (3q), amides (3x), and carbonates (3z) reacted smoothly to afford the desired products in good yields. Other functional groups such as trifluoromethyl (3d), methoxy (3q), trifluoromethoxy (3x), cyano (3j-3k, 3ac), nitro (3l-3m), sulfonyl (3y), and pyridinium (3v) were all well tolerated under the reaction conditions. Moreover, no competing radical addition to electron deficient olefins (3m) or alkynes (3t) was observed during the aryl difluoromethoxylation reaction. Heteroarenes such as pyridine (3aa) and thiophene (3ab-3ad) derivatives were also viable substrates.

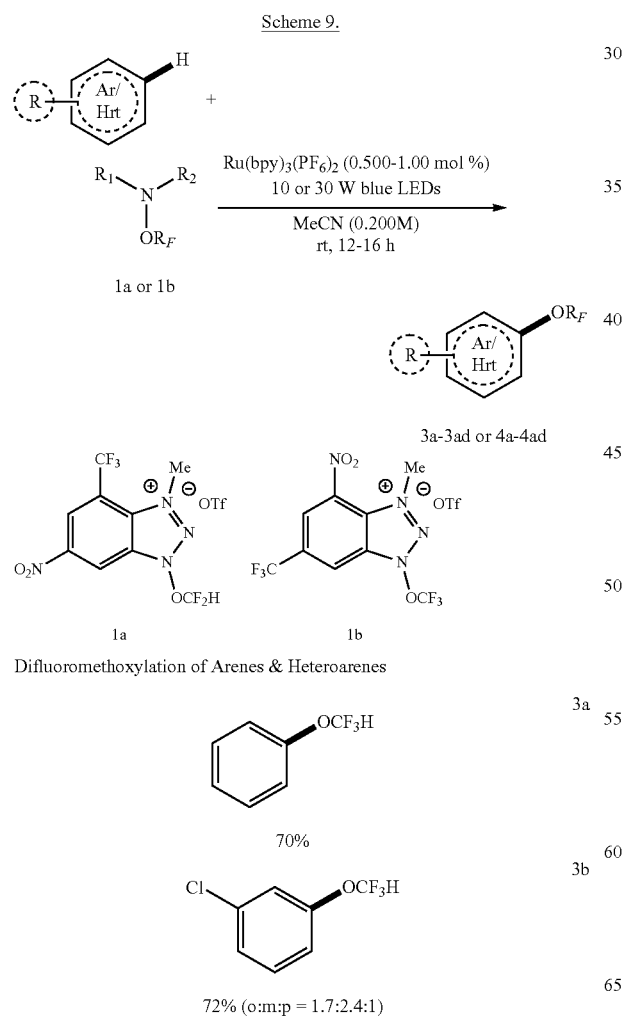

Scheme 9.

Difluoromethoxylation of Arenes & Heteroarenes

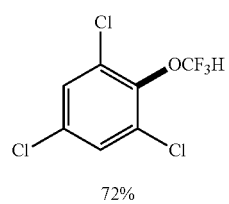

3c

72%

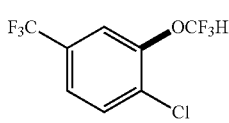

3d

59%

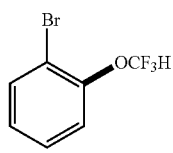

3e

72% (o:m:p = 2.3:1.9:1)

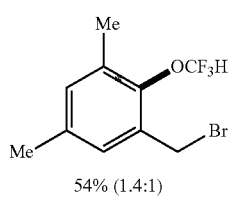

3f

54% (1.4:1)

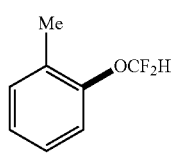

3g

66% (o:m:p = 2:1:1)

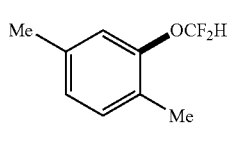

3h

45%

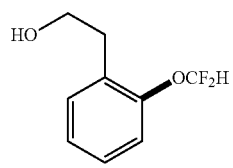

3i

58% (o:m:p = 3.4:1:1.1)

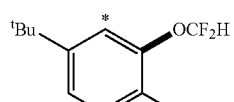

3j

63% (9.5:1)

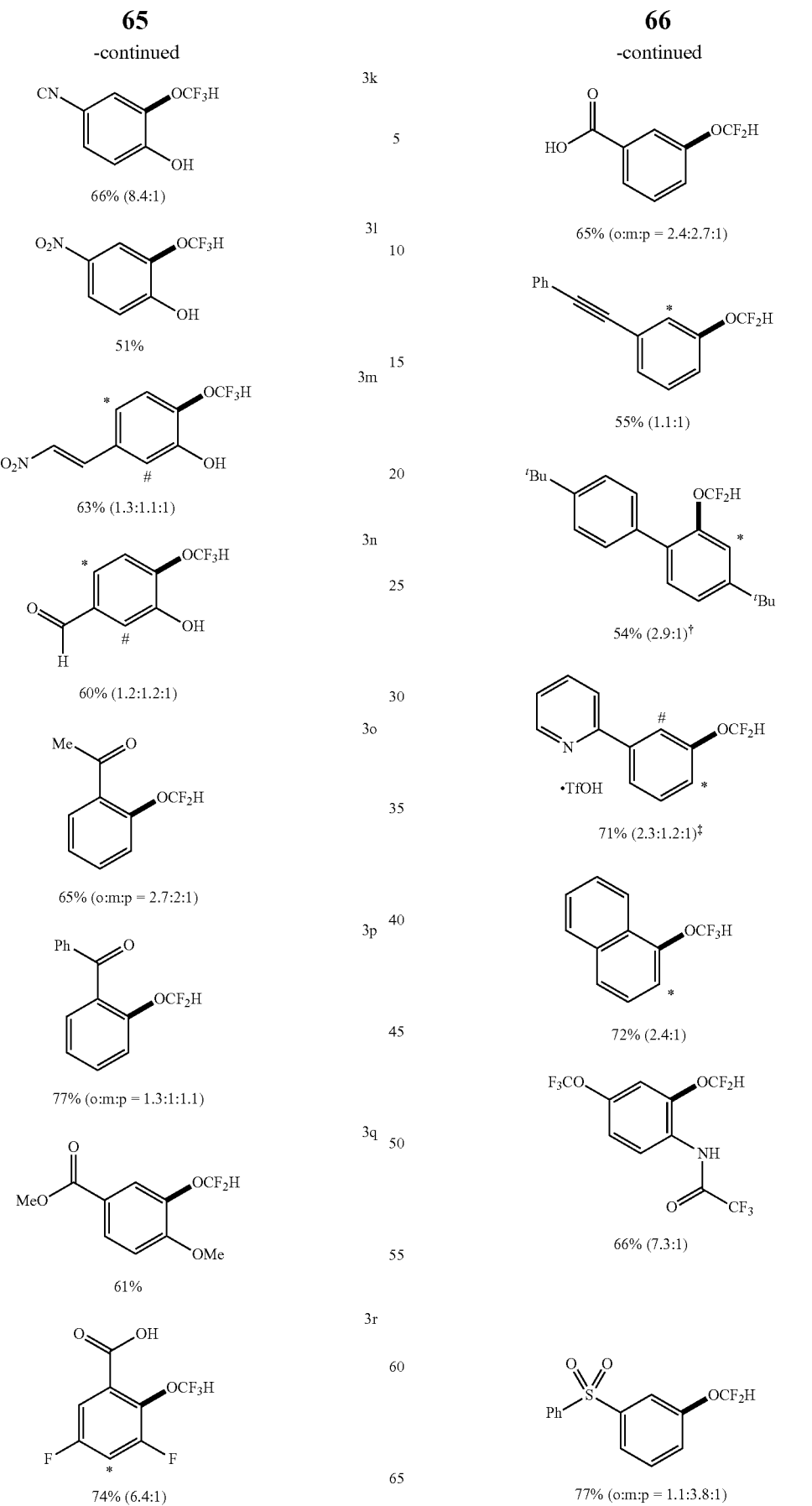

3z
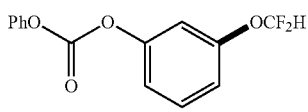
74% (o:m:p = 1.4:1.5:1)
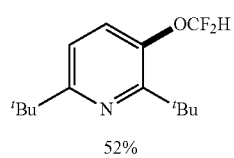
52%
3aa
3ab
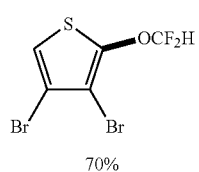
70%
3ac
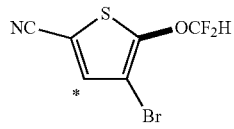
61% (3.8:1)
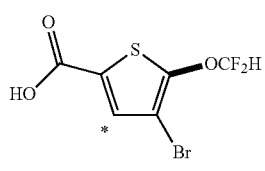
53% (3.5:1)
3ad
Trifluoromethoxylation of Arenes & Heteroarenes
4a
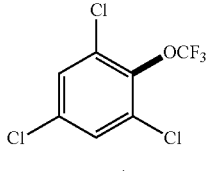
80%[†]
4b
66% (o:m:p = 1.8:1:1.4)
4c
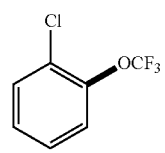
73% (o:m:p = 1.7:1:1.3)
4d
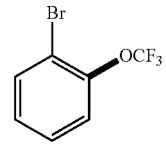
54% (o:m:p = 2.9:1:2.1)
4e
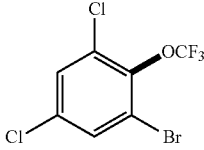
68% (1.8:1)[†]
4f
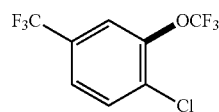
58%
4g
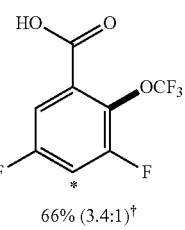
66% (3.4:1)[†]
4h
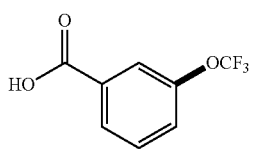
63% (o:m:p = 1.8:2.4:1)[†]
4i
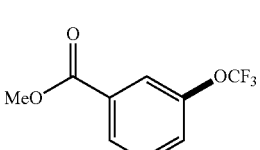
73% (o:m:p = 1.6:1.9:1)
4j
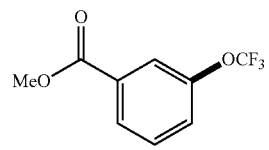
75% (o:m:p = 1.8:2.2:1)
4k
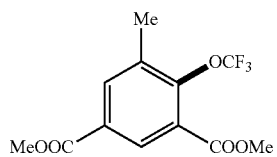
63% (2.2:1)[†]

-continued
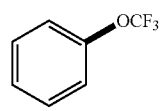
63%
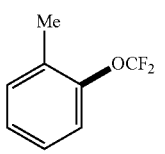
54% (o:m:p = 1.7:1:1.3)
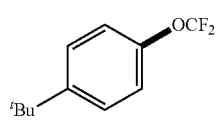
61% (o:m:p = 1:2.5:3.2)
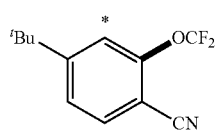
56% (13:1)
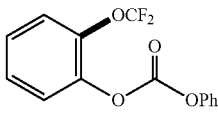
84% (o:m:p = 1.3:1:1.1)
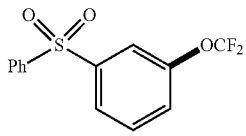
71% (o:m:p = 1:4.1:1.4)†
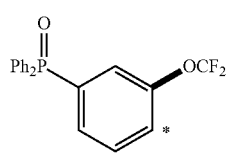
68% (2.4:1)
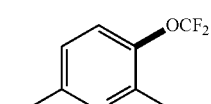
73%†
4l
4m
4n
4o
4p
4q
4r
4s
-continued
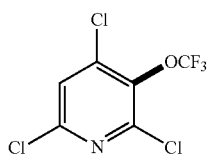
82%†
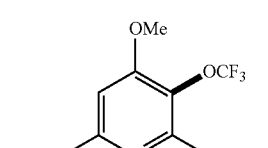
78%†
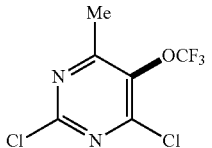
72%†
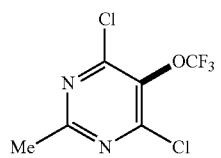
74%†
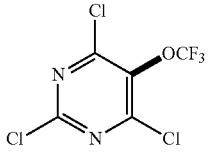
62%†
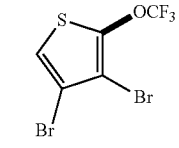
53%
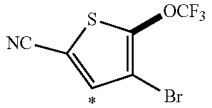
48% (7.7:1)
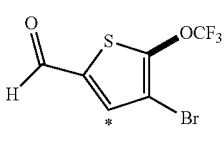
48% (11:1)
4t
4u
4v
4w
4x
4y
4z
4aa

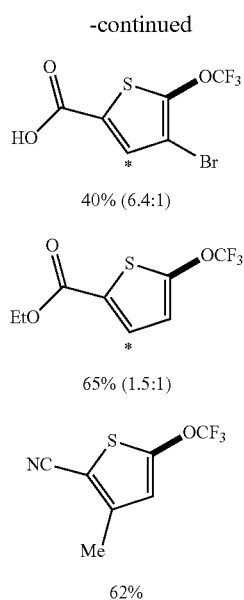

4ab

40% (6.4:1)

4ac

65% (1.5:1)

4ad

62%

Photocatalytic radical (hetero)aryl C—H difluoromethoxylation and trifluoromethoxylation using redox-active reagents 1a and 1b. Aromatic and heteroaromatic systems with varying stereoelectronics are efficiently di- and trifluoromethoxylated under these standard conditions (top, generalized reaction) using 1 equivalent of reagent and 10 equivalents of (hetero)arenes. The asterisk (*) and hastag (#) denote functionalization of minor regioisomeric products. Isolated yields ($^{19}$F NMR yields for volatile compounds) are indiciated below each entry. †Reaction performed using a mixed solvent of MeCN/CH$_2$Cl$_2$ (1:1 v/v, 0.200M). ‡Reaction performed with 10.0 equivalents of TfOH.

Having established the scope of the difluoromethoxylation reaction, we then explored the generality of the catalytic (hetero)aryl C—H trifluoromethoxylation reaction (Scheme 9) using reagent 1b. A wide range of mono-, di-, and tri-substituted (hetero)arenes were found to react well, affording the desired C—H trifluoromethoxylation products. Functional groups such as halides (F, Cl, Br, 4a-4g, 4s-4t, 4v-4ab) carboxylic acids (4g-4h), enolizable ketones (4i), esters (4j-4k, 4u, 4ac), aldehyde (4aa), and substrates with benzylic hydrogen atoms (4k, 4m, 4v-4w, 4ad] were compatible under the optimized reaction conditions. Unlike Ngai's photoactive reagents, our redox-active reagent 1b could be used to functionalize electron rich arenes such as toluene (4m) and tert-butylbenzene (4n), affording the desired products in synthetically useful yields. A striking feature of this reaction is that substrates bearing electron withdrawing groups such as nitrile (4o, 4z, and 4ad), sulfonyl (4q), phosphine oxide (4r), and trifluoromethyl (4f) groups reacted smoothly. Notably, the ever-present pyridine and pyrimidine motifs (4s-4x), found in thousands of medicinally important structures, could also be used in this reaction. Moreover, five-membered thiophenes with various substitution patterns (4y-4ad) could be trifluoromethoxylated to give the desired products in good yields. Although ten equivalents of arenes were used, we could recover 7.9-9.2 equivalents of the aromatic substrates at the end of the reaction, which is critical for valuable aromatic compounds.

A major advantage of our approach is its ability to form multiple regioisomers in a single synthetic operation. The regioselectivity of the reaction resembles that of radical-mediated aromatic substitution processes and is guided by the electronics of the substituent except in the case of bulky substituents (e.g., 3j and 4o), in which cases the OR$_F$ radical adds preferably to the position distal from the tert-butyl group. If an aromatic substrate has multiple reaction sites, the OR$_F$ radical will add to these sites to form regioisomeric products. Such reactivity is particularly attractive from a drug discovery point of view because it allows rapid access to various OR$_F$ derivatives without labour-intensive, parallel multi-step analogue synthesis. More importantly, it will increase the efficiency of structure-activity relationship studies of OR$_F$ analogues and can conveniently produce promising new candidates that might have never been evaluated otherwise.

Late-stage modifications of biologically active molecules are often a key to identification of medicinal agents (Cernak, T. et al. 2016). To demonstrate the amenability of the photocatalytic polyfluoromethoxylation processes to late-stage synthetic applications, bio-relevant molecules were subjected to our standard reaction conditions using arenes as limiting reactants (Scheme 10). Notably, approved drug molecules such as Baclofen® (muscle relaxant), Febuxostat® (anti-hyperuricemic), Mexlietine® (anti-arrhythmic), Efavirenz® (antiretroviral drug for treating HIV), as well as Metronidazole® (antiparasitic) and L-menthol (decongestants and analgesics) analogues were successfully difluoromethoxylated using reagent 1a to afford the desired products (5a-5f) in synthetically useful 42-76% yields, based on the recovery of the starting materials (BRSM). Similarly, photocatalytic aryl C—H trifluoromethoxylation reaction could be used for direct trifluoromethoxylation of Chlorpropamide® (anti-diabetic), Baclofen®, Metronidazole® derivatives, L-menthol, trans-Androsterone, and diacetonefructose to give the corresponding OCF$_3$-analogues (6a-6f) in 40-62% yields (BRSM).

Our polyfluoromethoxylation strategy is applicable to a wide range of drug molecules and tolerates a number of sensitive functionalities and this clearly shows its potential applicability to modern drug discovery programs.

Scheme 10. Photocatalytic difluoromethoxylation and trifluoromethoxylation of bio-relevant molecules.

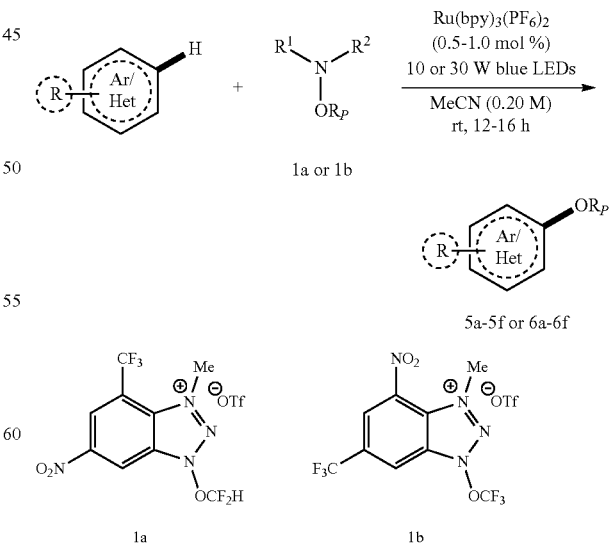

Difluoromethoxylation of Bio-relevant Molecules

73
-continued
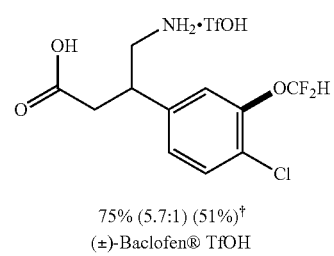
75% (5.7:1) (51%)†
(±)-Baclofen® TfOH
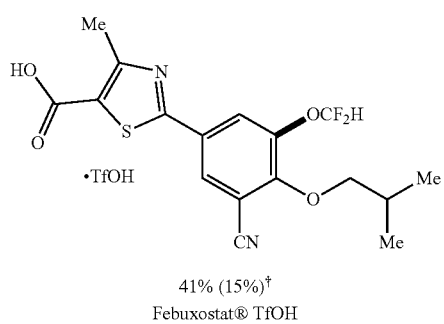
41% (15%)†
Febuxostat® TfOH
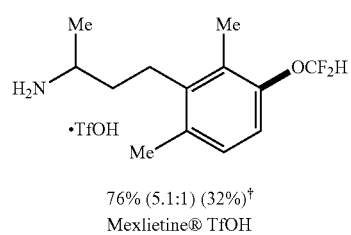
76% (5.1:1) (32%)†
Mexlietine® TfOH
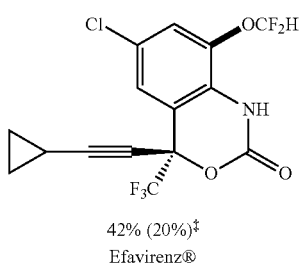
42% (20%)‡
Efavirenz®
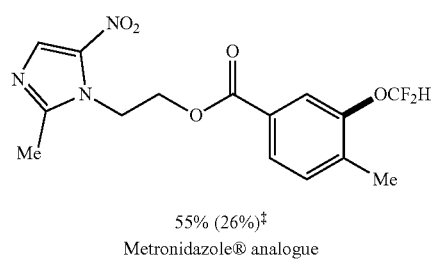
55% (26%)‡
Metronidazole® analogue
74
-continued
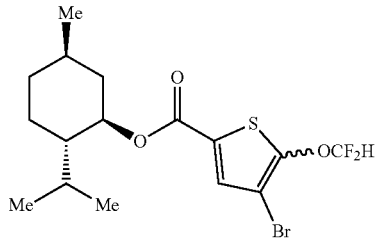
42% (20%)‡
L-Menthol analogue
Trifluoromethyoxylation of Bio-relevant Molecules
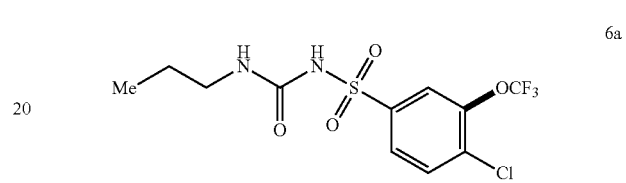
40% (27%)
Chlorpropamide®
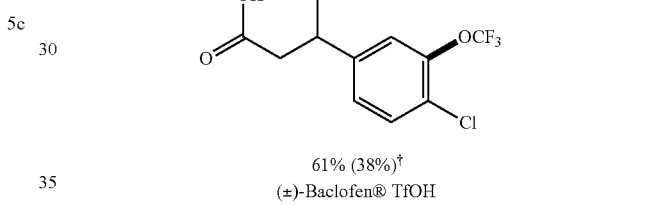
61% (38%)†
(±)-Baclofen® TfOH
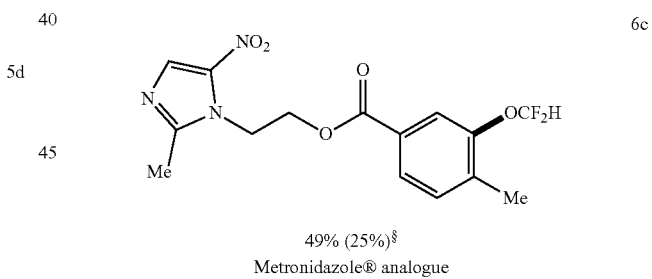
49% (25%)§
Metronidazole® analogue
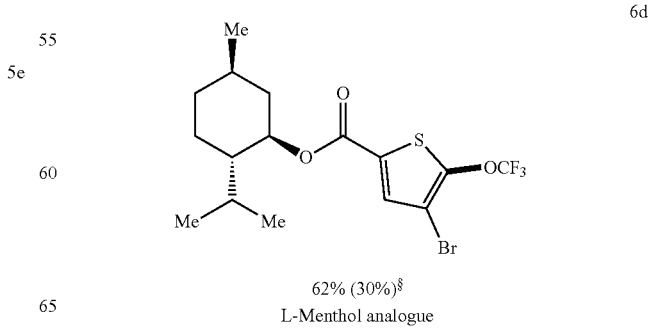
62% (30%)§
L-Menthol analogue

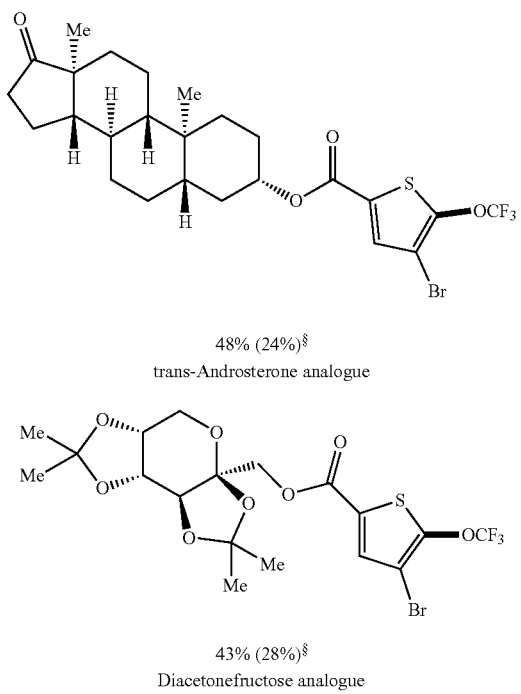

48% (24%)§
trans-Androsterone analogue

43% (28%)§
Diacetonefructose analogue

Reactions were performed using 1.00 equivalent of (hetero)arene and 2.00 equivalents of reagent 1a or 1b. The asterisk (*) denotes functionalization of a minor regioisomeric product. Yields were determined based on the recovered starting material. The yield in parentheses is the isolated yield. †Reaction performed with 1.00 equivalent of TfOH. ‡1.00 equivalent K$_2$CO$_3$. §Reaction performed using MeCN/CH$_2$Cl$_2$ (1:1 v/v, 0.200 M) as solvent.

Materials and Methods

All air- and moisture-insensitive reactions were carried out under an ambient atmosphere, magnetically stirred, and monitored by thin layer chromatography (TLC) using Agela Technologies TLC plates pre-coated with 250 μm thickness silica gel 60 F254 plates and visualized by fluorescence quenching under UV light. Flash chromatography was performed on SiliaFlash® Silica Gel 40-63 μm 60 Å particle size using a forced flow of eluent at 0.3-0.5 bar pressure (Still, W. C. et al. 1978). Preparative TLC was performed on Uniplate® UV254 (20×20 cm) with 1000 μm thickness and visualized fluorescence quenching under UV light.

All air and moisture-sensitive manipulations were performed using oven-dried glassware, including standard Schlenk and glovebox techniques under an atmosphere of nitrogen. All reaction vials were capped using green caps with F-217 PTFE liners. Diethyl ether and THF were distilled from deep purple sodium benzophenone ketyl. Acetonitrile were dried over CaH$_2$ and distilled. Acetonitrile was degassed via three freeze-pump-thaw cycles.

All deuterated solvents were purchased from Cambridge Isotope Laboratories. NMR spectra were recorded on (i) a Bruker Ascend 700 spectrometer operating at 700 MHz for $^1$H acquisitions and 175 MHz for $^{13}$C acquisitions, (ii) a Bruker 500 Advance spectrometer operating at 500 MHz, 125 MHz, and 470 MHz for $^1$H, $^{13}$C, and $^{19}$F acquisitions, or (iii) a Bruker 400 Nanobay spectrometer operating at 400 MHz, 100 MHz, and 376 MHz for $^1$H, $^{13}$C, and $^{19}$F acquisitions. Chemical shifts were referenced to the residual proton solvent peaks ($^1$H: CDCl$_3$, δ 7.26; (CD$_3$)$_2$SO, δ 2.50), solvent $^{13}$C signals (CDCl$_3$, δ 77.16; (CD$_3$)$_2$SO, δ 39.52), dissolved or external neat PhCF$_3$ ($^{19}$F, δ −63.3 relative to CFCl$_3$) (Fulmer, G. R. et al. 2010, Huang, C. et al. 2011). Signals are listed in ppm, and multiplicity identified as s=singlet, br=broad, d=doublet, t=triplet, q=quartet, m=multiplet; coupling constants in Hz; integration.

Absorptions were measured on a Cary 100 UV-Vis spectrophotometer from Agilent Technologies. Emission of LED was measured on a broad range spectrometer LR1-B from ASEQ instruments. Cyclic voltammetry was performed using BioLogic VSP-300 potentiostat. High-resolution mass spectra were performed at Mass Spectrometry Services at the Univ. of Illinois at Urbana-Champaign and were obtained using Waters Q-TOF Ultima ESI mass spectrometer. Concentration under reduced pressure was performed by rotary evaporation at 25-30° C. at appropriate pressure.

Reagents were purchased at highest quality. Liquid reagents were distilled and degassed before use. Solid reagents were used without further purification unless otherwise stated. Compounds 82a was prepared according to the literature procedure (Hojczyk, K. N. et al. 2016). Yields of trifluoromethoxylated products were calculated by $^{19}$F NMR using PhCF$_3$ as an internal standard, other yields refer to purified and spectroscopically pure compounds unless otherwise noted. Bluelight emitting diodes (LEDs, 10 W Royal Blue 455 nm, chip size=45×45 mm); the heat sink (diameter: 90 mm); and DC12V power plug adapter male female connector for 5050 3528 SMD LED strip light were used.

All HPLC chromatograms were generated on a Shimadzu LC-20AP system equipped with an auto injector, a fraction collector, and a UV detector (model: SPD-20A). Analytical injections were performed on a Luna® PFP(2) analytic column (size: 250×4.60 mm, AXIA™ Packs) with a flow rate of 0.500 mL/min. Preparative isolation were performed on a Luna® PFP(2) preparative column 100 Å (size: 250× 21.2 mm, AXIA™ Packs) or Gemini® 5 μm NX-C18 110 Å (size: 250×10 mm) with a flow rate of 10.6 mL/min. The column was fitted with a column guard. Chromatograms were obtained with a solvent composition of acetonitrile in water. Chromatograms of compounds containing acid functional groups were obtained with a solvent composition of 0.100V trifluoroacetic acid in water and 0.1004 trifluoroacetic acid acetonitrile.

Synthetic Methods

Difluoromethoxylation Reaction Optimization

Scheme 11

Photoredox Catalyst Screening

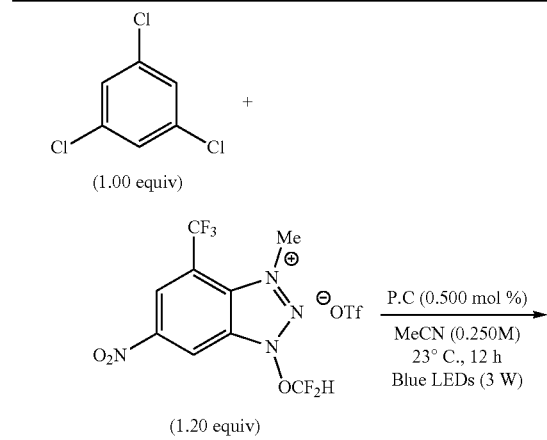

Scheme 11

Photoredox Catalyst Screening

| Entry | P.C | Yield (%) |
|---|---|---|
| 1 | — | 8 |
| 2 | Ru(bpy)$_3$(PF$_6$)$_2$ | 53 (5:1) |
| 3 | Ru(dmb)$_3$(PF$_6$)$_2$ | 53 (5:1) |
| 4 | Ru(dtbbpy)$_3$(PF$_6$)$_2$ | 52 (5.5:1) |
| 5 | Ru(phen)$_3$(PF$_6$)$_2$ | 49 (6:1) |
| 6 | Ru(bpz)$_3$(PF$_6$)$_2$ | 7 |
| 7 | Ir(ppy)$_2$(dtbbpy)PF$_6$ | 40 (9:1) |
| 8 | fac-Ir(ppy)$_3$ | 45 (8:1) |
| 9 | fac-Ir(Fppy)$_3$ | 43 (7.6:1) |
| 10 | fac-Ir(dmppy)$_2$(dtbbpy) | 45 (8:1) |
| 11 | Ir(dtbppy)$_2$(dtbbpy)PF$_6$ | 56 (4.6:1) |
| 12 | Ir[(dF(CF$_3$)ppy)$_2$(dtbbpy)](PF$_6$) | 50 (7.3:1) |

Position of the bis product.

Scheme 12

Photoredox Catalyst Loading Screening

| Entry | X | Yield (%) |
|---|---|---|
| 1 | 1.00 | 52 (4.8:1) |
| 2 | 0.50 | 54 (5.0:1) |
| 3 | 0.25 | 52 (4.8:1) |
| 4 | 0.10 | 56 (5.2:1) |
| 5 | 0.05 | 50 (4.9:1) |
| 6 | 0.01 | 47 (15:1) |

Position of the bis product.

Scheme 13

Substrate Stoichiometry Screening

| Entry | X | Yield (%) |
|---|---|---|
| 1 | 1.00 | 48 (7:1) |
| 2 | 1.20 | 50 (7.3:1) |
| 3 | 1.50 | 50 (12:1) |
| 4 | 2.00 | 53 (17:1) |
| 5 | 3.00 | 59 (19:1) |
| 6 | 5.00 | 61 (19:1) |
| 7 | 10.0 | 70 |

Position of the bis product.

Scheme 14

Reagent Screening

| Entry | Reagent | Yield (%)[b] |
|---|---|---|
| 1 | 1a | 68 |
| 2 | DR1 | 16 |
| 3 | DR2 | 50 |
| 4 | DR3 | 47 |
| 5 | DR4 | 35 |
| 6 | DR5 | 80 |
| 7 | 1a | 40[c] |
| 8 | 1a | 5[d] |
| 9 | 1a | N.R.[e] |
| 10 | 1a | 63[f] |

Scheme 14

Reagent Screening

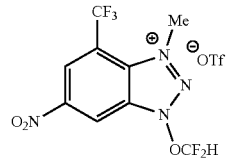
1a

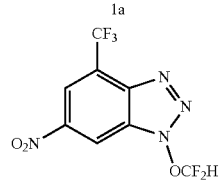
DR1

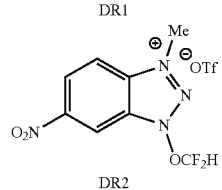
DR2

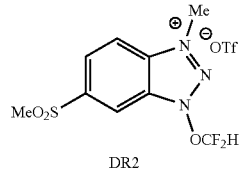
DR2

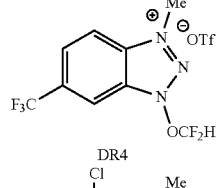
DR4

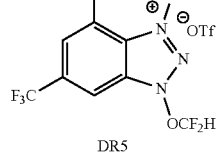
DR5

[a] Reactions were performed using 1 equivalent of reagent and 10 equivalents of benzene.
[b] Yields were determined by $^{19}$F NMR spectroscopy using trifluorotoluene as an internal standard.
[c] 1 equivalent of benzene.
[d] Without Ru(bpy)$_3$(PF$_6$)$_2$.
[e] Without light.
[f] The reaction was set-up under air atomsphere.

6-Nitro-4-(trifluoromethyl)-1H-benzo[d][1,2,3]triazol-1-ol (S1a)

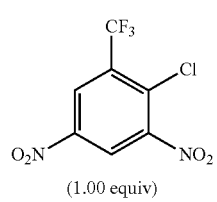

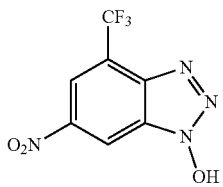

Under ambient atmosphere, to an 200 mL round bottom flask equipped a stir bar was added 2-chloro-1,5-dinitro-3-(trifluoromethyl) benzene (43.3 g, 160 mmol, 1.00 equiv and EtOH (80.0 mL, 2.00 M, with respect to the arene). The suspension was cooled to −20° C. in a cryogenic ethanol bath and hydrazine monohydrate (40.0 g, 38.8 mL, 800 mmol, 5.00 equiv) was added dropwise with an addition funnel with pressure-equalization arm. Afterwards, the funnel was replaced with a reflux condenser and heated to 85° C. for 12 h. The reaction mixture was then cooled to cooled to ambient temperature (23° C.) and concentrated in vacuo. To the reside was added 37% HCl (aq) (80 mL) and the reaction mixture was stirred for 10 min, at which point a pale brown suspension was observed. The solids were collected by filtration and washed with 1.00 M HCl (3×☐100 mL) and then DCM (3×100 mL). The combined solids were then dried under vacuum to afford the title compound as a pale brown solid (32.7 g, 132 mmol, 82% yield).

$^1$H NMR (700 MHz, (CD$_3$)$_2$SO, 25° C.): δ 9.01 (d, J=1.6 Hz, 1H), 8.47 (d, J=1.6 Hz, 1H). $^{13}$C NMR (175 MHz, (CD$_3$)$_2$SO, 25° C.): δ 145.36, 140.16, 128.20, 122.26 (q, J=269.7 Hz), 119.64 (q, J=31.9 Hz), 117.58 (q, J=5.4 Hz), 112.68. $^{19}$F NMR (376 MHz, (CD$_3$)$_2$SO, 25° C.): δ −60.3 (s, 3F). HRMS (ESI) m/z calcd for C$_7$H$_4$N$_4$O$_3$F$_3$ [(M+H)$^+$], 249.0235, found, 249.0237.

1-(Difluoromethoxy)-6-nitro-4-(trifluoromethyl)-1H-benzo[d][1,2,3]triazole (DR1)

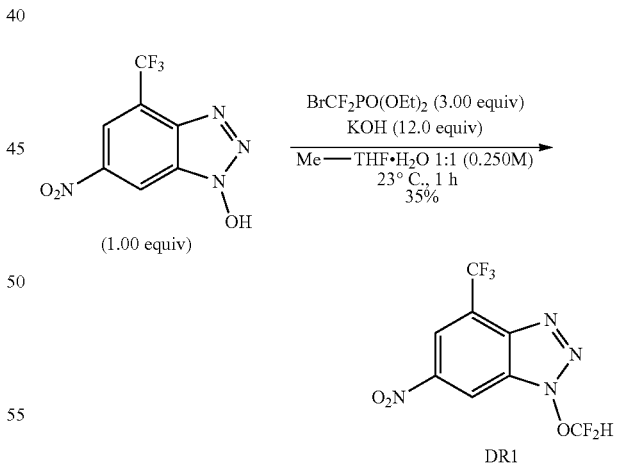

Under nitrogen atmosphere, to an oven-dried 100 mL round bottom flask equipped a stir bar was added 6-nitro-4-(trifluoromethyl)-1H-benzo[d][1,2,3]triazol-1-ol (S1a) (2.98 g, 12.0 mmol, 1.00 equiv), 85% potassium hydroxide (9.50 g, 144 mmol, 12.0 equiv), Me-THF (24.0 mL, 0.500 M, with respect to S1a) and H$_2$O (24.0 mL, 0.500 M, with respect to S1a). To this solution was added diethyl (bromodifluoromethyl)phosphonate (9.61 g, 6.40 mL, 36.0 mmol, 3.00 equiv) and the reaction vial was stirred at 23° C.

for 1 h. Afterwards, the reaction mixture was diluted with DCM (50 mL) and the organic layer was separated, and the aqueous layer was extracted twice with DCM (50 mL). The combined organics were dried over anhydrous $Mg_2SO_4$ and concentrated in vacuo. The residue was purified by column chromatography (eluting from 1 to 5% (v/v) EtOAc in Hexanes) to afford the title compound as a white solid (1.24 g, 4.16 mmol, 35% yield).

$^1$H NMR (700 MHz, $CDCl_3$, 25° C.): δ 8.79 (s, 1H), 8.63 (s, 1H), 7.07 (t, $^2J_{HF}$=66.8 Hz, 1H). $^{13}$C NMR (175 MHz, $CDCl_3$, 25° C.): δ 147.47, 141.04, 129.91, 123.89 (q, J=36.4 Hz), 121.69 (q, $^1J_{CF}$=273.7 Hz), 118.51 (q, J=4.8 Hz), 117.15 (t, $^1J_{CF}$=279.8 Hz), 110.24. $^{19}$F NMR (376 MHz, $CDCl_3$, 25° C.): δ 61.05 (s, 3F), −87.32 (d, $^1J_{FH}$=67.0 Hz, 2F). HRMS (ESI) m/z calcd for $C_8H_4N_4O_3F_5$ [(M+H)$^+$], 249.0235, found, 249.0237.

1-(Difluoromethoxy)-3-methyl-6-nitro-4-(trifluoromethyl)-1H-benzo[d][1,2,3]triazol-3-ium trifluoromethanesulfonate (1a)

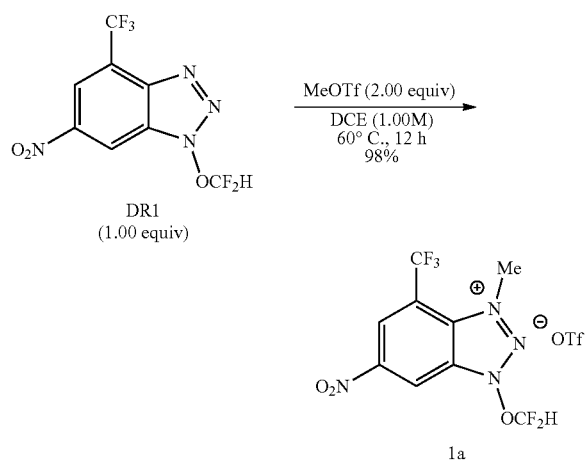

Under nitrogen atmosphere, to an oven-dried 20 mL screw cap vial equipped a stir bar was added 1-(difluoromethoxy)-6-nitro-4-(trifluoromethyl)-1H-benzo[d][1,2,3]triazole (DR1) (2.15 g, 7.20 mmol, 1.00 equiv) and DCE (7.20 mL, 1.00 M, with respect to 1b). To this solution was added methyl trifluoromethanesulfonate (2.36 g, 1.63 mL, 0.200 mmol, 1.00 equiv) and the reaction vial was stirred at 60° C. for 12h. Afterwards the reaction vial was cooled to ambient temperature (23° C.) and a white suspension was observed. Hexanes (7.2 mL) was added the reaction vial and the solids were collected by filtration and washed with hexanes (3×10 mL). The combined solids were then dried in vacuo to afford the title compound as a white solid (3.27 g, 7.07 mmol, 98% yield).

$^1$H NMR (700 MHz, $(CD_3)_2SO$, 25° C.): δ 9.92 (d, J=1.6 Hz, 1H), 9.06 (d, J=1.6 Hz, 1H), 8.05 (t, $^2J_{HF}$=64.5 Hz, 1H), 4.77 (s, 3H). $^{13}$C NMR (175 MHz, $(CD_3)_2SO$, 25° C.): δ 148.91, 133.48, 133.45, 126.33 (q, J=6.1 Hz), 120.65 (q, $^1J_{CF}$=322.1 Hz), 120.64 (q, $^1J_{CF}$=272.8 Hz), 118.18 (t, $^1J_{CF}$=285.4 Hz), 116.04 (q, J=37.2 Hz), 115.10, 42.84 (q, J=4.6 Hz). $^{19}$F NMR (376 MHz, $(CD_3)_2SO$, 25° C.): δ −56.10 (s, 3F), −77.91 (s, 3F), −87.11 (d, $^2J_{FH}$=64.6 Hz, 2F). HRMS (ESI) m/z calcd for $C_9H_6N_4O_3F_5$ [M$^+$], 313.0360, found, 313.0359.

1-(Difluoromethoxy)-3-methyl-6-nitro-1H-benzo[d][1,2,3]triazol-3-ium trifluoromethanesulfonate (DR2)

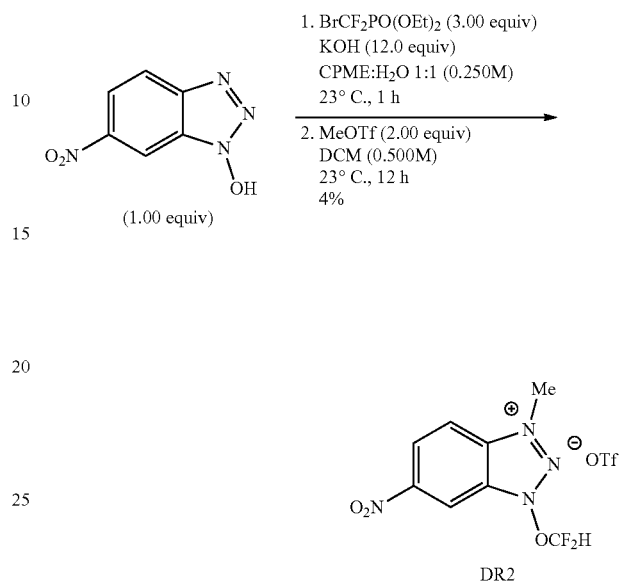

Under nitrogen atmosphere, to an oven-dried 100 mL 100 mL round bottom flask equipped a stir bar was added 6-nitro-1H-benzo[d][1,2,3]triazol-1-ol (1.17 g, 6.50 mmol, 1.00 equiv), 85% potassium hydroxide (5.15 g, 78.0 mmol, 12.0 equiv), CPME (13.00 mL, 0.500 M, with respect to 1-hydroxy-benzotriazole) and $H_2O$ (13.00 mL, 0.500 M, with respect to 1-hydroxy-benzotriazole). To this solution was added diethyl (bromodifluoromethyl)phosphonate (5.21 g, 3.46 mL, 19.5 mmol, 3.00 equiv) and the reaction mixture was stirred at 23° C. for 1 h. Afterwards, the reaction mixture was diluted with DCM (20 mL) and the organic layer was separated, and the aqueous layer was extracted twice with DCM (20 mL). The combined organics were dried over anhydrous Mg $SO_4$ and concentrated in vacuo. The residue was purified by column chromatography ($R_f$=0.34 10% (v/v) EtOAc in Hexanes, eluting from 5 to 10% (v/v) EtOAc in Hexanes) to afford the an off-white solid. Next, the solid was dissolved in DCM (13.0 mL, 0.500 M, with respect to 1-hydroxy-benzotriazole) and to this solution was added methyl trifluoromethanesulfonate (1.28 g, 0.883 mL, 7.80 mmol, 1.20 equiv) and the reaction vial was stirred at 23° C. for 12h. Afterwards a white suspension was observed. Hexanes (5 mL) was added the reaction vial and the solids were collected by filtration and washed with Hexanes (3×5 mL). The combined solids were then dried in vacuo to afford the title compound as a white solid (112 mg, 0.284 mmol, 4% yield).

$^1$H NMR (700 MHz, $(CD_3)_2SO$, 25° C.): δ 9.43 (d, J=1.7 Hz, 1H), 8.83 (d, J=9.5 Hz, 1H), 8.73 (dd, J=1.7, 9.5 Hz, 1H), 7.99 (t, $^2J_{HF}$=65.0 Hz, 1H), 4.76 (s, 3H). $^{13}$C NMR (175 MHz, $(CD_3)_2SO$, 25° C.): δ 150.58, 138.04, 131.59, 127.13, 121.25 (q, $^1J_{CF}$=323.9 Hz), 118.73 (t, $^1J_{CF}$=285.2 Hz), 117.39, 110.44, 40.60. $^{19}$F NMR (376 MHz, $(CD_3)_2SO$, 25° C.): δ −77.86 (s, 3F), −$^+$87.39 (d, $^2J_{FH}$=65.8 Hz, 2F). HRMS (ESI) m/z calcd for $C_8H_7N_4O_3F_2$ [M$^+$], 245.0486, found, 245.0489.

1-(Difluoromethoxy)-3-methyl-6-(methylsulfonyl)-1H-benzo[d][1,2,3]triazol-3-ium trifluoromethanesulfonate (DR3)

1-(Difluoromethoxy)-3-methyl-6-(trifluoromethyl)-1-benzo[d][1,2,3]triazol-3-ium trifluoromethanesulfonate (DR4)

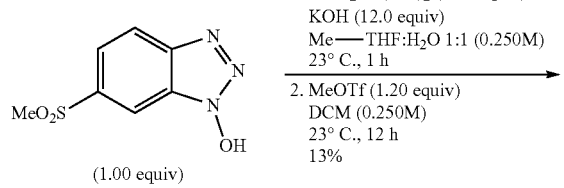

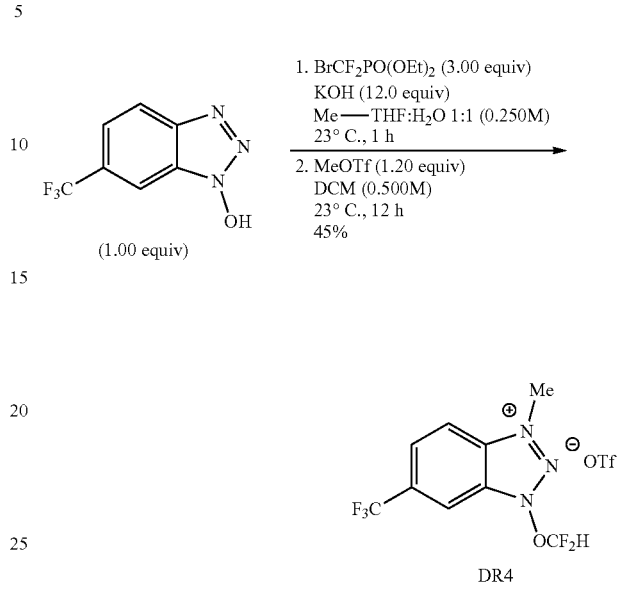

Under nitrogen atmosphere, to an oven-dried 20 mL screw cap vial equipped a stir bar was added 6-nitro-1H-benzo[d][1,2,3]triazol-1-ol (0.640 g, 3.20 mmol, 1.00 equiv), 85 potassium hydroxide (2.38 g, 36.0 mmol, 12.0 equiv), Me-THF (6.00 mL, 0.500 M, with respect to 1-hydroxy-benzotriazole) and H$_2$O (6.00 mL, 0.500 M, with respect to 1-hydroxy-benzotriazole). To this suspension was added diethyl (bromodifluoromethyl)phosphonate (2.40 g, 1.60 mL, 9.00 mmol, 3.00 equiv) and the reaction vial was stirred at 23° C. for 1 h. Afterwards, the reaction mixture was diluted with DCM (10 mL) and the organic layer was separated, and the aqueous layer was extracted twice with DCM (10 mL). The combined organics were dried over anhydrous Mg$_2$SO$_4$ and concentrated in vacuo. The residue was purified by column chromatography (R$_f$=0.11 60% (v/v) EtOAc in Hexanes, eluting from 30 to 80% (v/v) EtOAc in Hexanes) to afford the a white solid. Next, the solid was dissolved in DCM (12.0 mL, 0.250 M, with respect to 1-hydroxy-benzotriazole) and to this solution was added methyl trifluoromethanesulfonate (0.591 g, 0.407 mL, 3.60 mmol, 1.20 equiv) and the reaction vial was stirred at 23° C. for 12h. Afterwards a white suspension was observed. Hexanes (5 mL) was added the reaction vial and the solids were collected by filtration and washed with Hexanes (3×5 mL). The combined solids were then dried in vacuo to afford the title compound as a white solid (165 mg, 0.386 mmol, 13% yield).

$^1$H NMR (700 MHz, (CD$_3$)$_2$SO, 25° C.): δ 9.03 (s, 1H), 8.79 (dd, J=1.5, 9.0 Hz, 1H), 8.62 (dd, J=1.5, 9.0 Hz, 1H), 8.01 (t, $^2J_{HF}$=65.3 Hz, 1H), 4.77 (s, 3H), 3.51 (s, 3H). $^{13}$C NMR (175 MHz, (CD$_3$)$_2$SO, 25° C.): δ 144.95, 137.23, 130.75, 129.31, 120.68 (q, $^1J_{CF}$=321.9 Hz), 118.21 (t, $^1J_{CF}$=283.4 Hz), 116.96, 113.09, 42.92. $^{19}$F NMR (376 MHz, (CD$_3$)$_2$SO, 25° C.): −77.86 (s, 3F), −87.31 (d, $^2J_{FH}$=65.3 Hz, 2F). HRMS (ESI) m/z calcd for C$_9$H$_{10}$N$_3$O$_3$F$_2$S [M$^+$], 278.0411, found, 278.0409.

Under nitrogen atmosphere, to an oven-dried 100 mL 100 mL round bottom flask equipped a stir bar was added 6-(trifluoromethyl)-1H-benzo[d][1,2,3]triazol-1-ol (1.63 g, 8.00 mmol, 1.00 equiv), 85% potassium hydroxide (6.34 g, 96.0 mmol, 12.0 equiv), Me-THF (16.00 mL, 0.500 M, with respect to S1e) and H$_2$O (16.00 mL, 0.500 M, with respect to 1-hydroxy-benzotriazole). To this solution was added diethyl (bromodifluoromethyl)phosphonate (6.40 g, 4.26 mL, 24.0 mmol, 3.00 equiv) and the reaction mixture was stirred at 23° C. for 1 h. Afterwards, the reaction mixture was diluted with DCM (30 mL) and the organic layer was separated, and the aqueous layer was extracted twice with DCM (30 mL). The combined organics were dried over anhydrous Mg$_2$SO$_4$ and concentrated in vacuo. The residue was purified by column chromatography (R$_f$=0.31 5% (v/v) EtOAc in Hexanes, eluting from 1 to 5% (v/v) EtOAc in Hexanes) to afford a white solid. Next, the solid was dissolved in DCM (16.0 mL, 0.500 M, with respect to 1-hydroxy-benzotriazole) and to this solution was added methyl trifluoromethanesulfonate (1.58 g, 1.09 mL, 9.60 mmol, 1.20 equiv) and the reaction vial was stirred at 23° C. for 12h. Afterwards a white suspension was observed. Hexanes (10 mL) was added the reaction vial and the solids were collected by filtration and washed with Hexanes (3×10 mL). The combined solids were then dried in vacuo to afford the title compound as a white solid (1.51 g, 3.61 mmol, 45% yield).

$^1$H NMR (700 MHz, (CD$_3$)$_2$SO, 25° C.): δ 9.09 (s, 1H), 8.77 (dd, J=1.3, 9.0 Hz, 1H), 8.51 (dd, J=1.3, 9.0 Hz, 1H), 8.00 (t, $^2J_{HF}$=65.3 Hz, 1H), 4.77 (s, 3H). $^{13}$C NMR (175 MHz, (CD$_3$)$_2$SO, 25° C.): δ 137.01, 132.77 (q, $^1J_{CF}$=33.7 Hz), 130.84, 128.26, 122.09 (q, $^1J_{CF}$=273.2 Hz), 120.67 (q, $^1J_{CF}$=321.9 Hz), 118.18 (t, $^1J_{CF}$=283.1 Hz), 117.09, 111.77, 40.01. $^{19}$F NMR (376 MHz, (CD$_3$)$_2$SO, 25° C.): −60.98 (s, 3F), −77.88 (s, 3F), −87.42 (d, $^2J_{FH}$=65.3 Hz, 2F). HRMS (ESI) m/z calcd for C$_9$H$_7$N$_3$OF$_5$ [M$^+$], 268.0509, found, 268.0509.

4-Chloro-1-(difluoromethoxy)-3-methyl-6-(trifluoromethyl)-1H-benzo[d][1,2,3]triazol-3-ium trifluoromethanesulfonate (DR5)

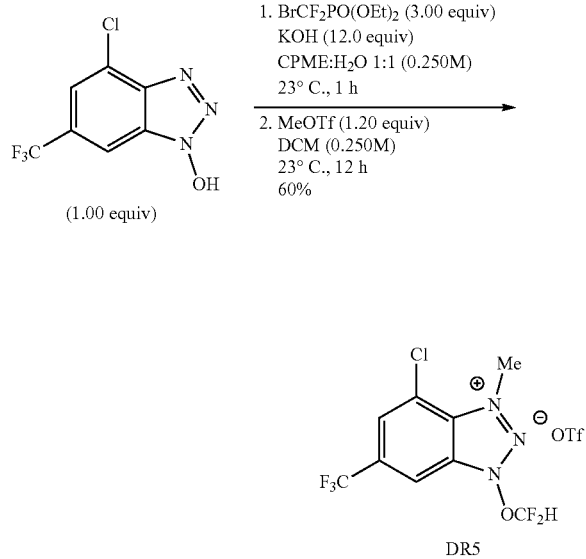

Under nitrogen atmosphere, to an oven-dried 100 mL 100 mL round bottom flask equipped a stir bar was added 4-chloro-6-(trifluoromethyl)-1H-benzo[d][1,2,3]triazol-1-ol (0.594 g, 2.50 mmol, 1.00 equiv), 85% potassium hydroxide (1.98 g, 30.0 mmol, 12.0 equiv), CPME (5.00 mL, 0.500 M, with respect to 1-hydroxy-benzotriazole) and H$_2$O (5.00 mL, 0.500 M, with respect to 1-hydroxy-benzotriazole). To this solution was added diethyl (bromodifluoromethyl)phosphonate (2.00 g, 1.33 mL, 7.50 mmol, 3.00 equiv) and the reaction mixture was stirred at 23° C. for 1 h. Afterwards, the reaction mixture was diluted with DCM (15 mL) and the organic layer was separated, and the aqueous layer was extracted twice with DCM (15 mL). The combined organics were dried over anhydrous Mg$_2$SO$_4$ and concentrated in vacuo. The residue was purified by column chromatography (R$_f$=0.44 5% (v/v) EtOAc in Hexanes, eluting from 1 to 5% (v/v) EtOAc in Hexanes) to afford the a white solid. Next, the solid was dissolved in DCM (10.0 mL, 0.250 M, with respect to 1-hydroxy-benzotriazole) and to this solution was added methyl trifluoromethanesulfonate (0.492 g, 0.340 mL, 3.00 mmol, 1.20 equiv) and the reaction vial was stirred at 23° C. for 12h. Afterwards a white suspension was observed. Hexanes (5 mL) was added the reaction vial and the solids were collected by filtration and washed with Hexanes (3×5 mL). The combined solids were then dried in vacuo to afford the title compound as a white solid (0.630 g, 1.51 mmol, 60% yield).

$^1$H NMR (700 MHz, (CD$_3$)$_2$SO, 25° C.): δ 9.13 (s, 1H), 8.76 (s, 1H), 8.04 (t, $^2J_{HF}$=64.7 Hz, 1H), 4.91 (s, 3H). $^{13}$C NMR (175 MHz, (CD$_3$)$_2$SO, 25° C.): δ 134.20, 133.43 (q, J=34.5 Hz), 132.83, 128.92, 122.09 (q, $^1J_{CF}$=274.8 Hz), 121.97, 119.75 (q, $^1J_{CF}$=321.3 Hz), 118.10 (t, $^1J_{CF}$=284.6 Hz), 111.04 (q, J=8.5 Hz), 42.31. $^{19}$F NMR (376 MHz, (CD$_3$)$_2$SO, 25° C.): −61.03 (s, 3F), −77.88 (s, 3F), −87.44 (d, $^2J_{FH}$=64.8 Hz, 2F). HRMS (ESI) m/z calcd for C$_9$H$_6$N$_3$OF$_5$Cl [M$^+$], 302.0120, found, 302.0120.

General Procedure A: Drifluoromethoxylation of (Hetero)Arenes

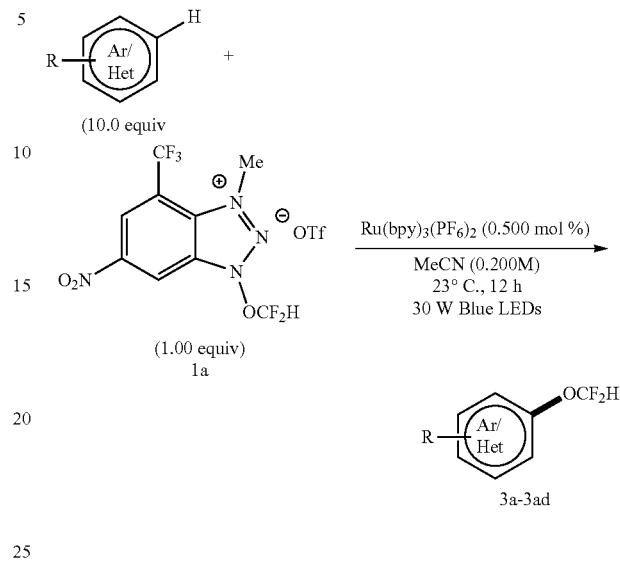

In a glovebox, to an oven-dried 20 mL screw cap vial was added 1-(difluoromethoxy)-3-methyl-6-nitro-4-(trifluoromethyl)-1H-benzo[d][1,2,3]triazol-3-ium trifluoromethanesulfonate (1a) (92.4 mg, 0.200 mmol, 1.00 equiv), (hetero)arene (2.00 mmol, 10.0 equiv), Ru(bpy)$_3$(PF$_6$)$_2$, (0.860 mg, 1.00 μmol, 0.500 mol), and MeCN (1.00 mL, 0.200 M, with respect to 1a). To this suspension or solution was added a magnetic stir bar. Next, the reaction vial was capped and taken out of the glovebox. The reaction mixture was stirred at ambient temperature (23° C.) and irradiated with blue LEDs (30 W, λ$_{max}$=450 nm) which was placed 20.0 mm from the vial for 12 h. To determine the yield of the products, an internal standard, trifluorotoluene (PhCF$_3$) (14.6 mg, 12.3 μL, 0.100 mmol, 0.500 equiv) was added to the vial. Then, a 100 μL of the reaction mixture was taken and then dilute with 500 μL CD$_3$CN followed by $^{19}$F NMR (the NMR sample was recombined with the rest of the reaction mixture afterward). The combined reaction mixture was then purified by HPLC on the Luna® PFP(2) preparative column (250×21.2 mm) column eluting with MeCN:H$_2$O (v/v) with a flow rate of 10.6 mL/min to provide the purified products. In cases of closely-eluting peaks, products were isolated as a mixture of isomers. Afterwards, the products were extracted with CDCl$_3$ (3×1 mL), dried with magnesium sulfate, and filtered. The filtrate was concentrated in vacuo to afford the desired product(s). For very volatile compounds, the products were extracted immediately with CDCl$_3$ (1×1 mL) and then directly characterized. $^1$H and $^{13}$C NMR of these compound(s) contains MeCN residue signal ($^1$H NMR: □ 1.94, $^{13}$C NMR: □ 118.26, 1.32 in CDCl$_3$).

General Procedure B: Difluoromethoxylation of Complex Substrates

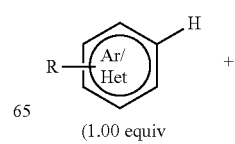

-continued

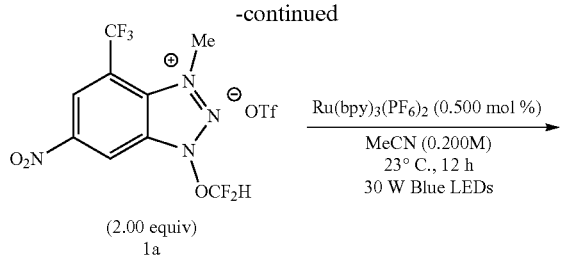

(2.00 equiv)
1a

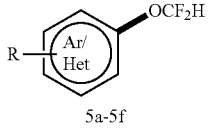

5a-5f

In a glovebox, to an oven-dried 20 mL screw cap vial was added 1-(difluoromethoxy)-3-methyl-6-nitro-4-(trifluoromethyl)-1H-benzo[d][1,2,3]triazol-3-ium trifluoromethanesulfonate (1a) (185 mg, 0.400 mmol, 2.00 equiv), (hetero)arene (0.200 mmol, 1.00 equiv), Ru(bpy)$_3$(PF$_6$)$_2$, (0.860 mg, 1.00 μmol, 0.500 mol %), and MeCN (1.00 mL, 0.200 M, with respect to (hetero)arene). To this suspension or solution was added a magnetic stir bar. Next, the reaction vial was capped and taken out of the glovebox. The reaction mixture was stirred at ambient temperature (23° C.) and irradiated with blue LEDs (30 W, $\lambda_{max}$=450 nm) which was placed 20.0 mm from the vial for 12 h. The combined reaction mixture was then purified by HPLC on the Luna® PFP(2) preparative column (250×21.2 mm) column eluting with MeCN:H$_2$O (v/v) with a flow rate of 10.6 mL/min to provide the purified products. In cases of closely-eluting peaks, products were isolated as a mixture of isomers. Afterwards, the product(s) was concentrated in vacuo to afford the desired product(s).

(Difluoromethoxy)benzene (3a)

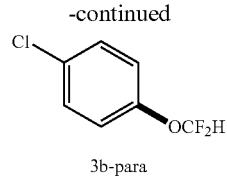

Prepared according to the General Procedure A using benzene (156 mg, 178 μL, 2.00 mmol, 10.0 equiv) as the substrate. After 12 h, the yield was determined to be 70% by $^{19}$F NMR and afterwards the samples was spiked with an authentic sample of (difluoromethoxy)benzene to confirm the product.

$^{19}$F NMR (376 MHz, CDCl$_3$, 25° C.): δ −82.7 (d, 2J$_{FH}$=74.5 Hz, 2F). Spectral data match those previously reported.[6]

1-Chloro-3-(difluoromethoxy)benzene (3b)

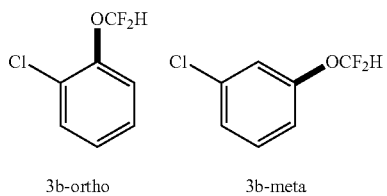

3b-ortho 3b-meta

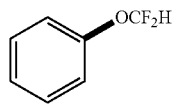

3b-para

Prepared according to the General Procedure A using chlorobenzene (225 mg, 204 μL, 2.00 mmol, 10.0 equiv) as the substrate. After 12 h, the reaction mixture (72% yield, 3b-ortho:3b-meta:3b-para=2.4:1.7:1 by $^{19}$F NMR) was purified by HPLC to provide the title compound(s).

1-Chloro-2-(difluoromethoxy)benzene (3b-ortho) $t_R$=119 min, 352 (v/v) acetonitrile in water. $^1$H NMR (700 MHz, CDCl$_3$, 25° C.): δ 7.37 (dd, J=1.5, 8.0 Hz, 1H), 7.21 (m, 1H), 7.14 (d, J=8.0 Hz, 1H), 7.12 (dd, J=1.5, 8.0 Hz, 1H), 6.49 (t, $^2$J$_{HF}$=73.6 Hz, 1H). $^{13}$C NMR (175 MHz, CDCl$_3$, 25° C.): δ 146.65, 130.57, 127.88, 126.50, 125.79, 121.36, 115.72 (t, $^1$J$_{CF}$=261.3 Hz). $^{19}$F NMR (376 MHz, CDCl$_3$, 25° C.): δ −83.1 (d, $^2$J$_{FH}$=73.6 Hz, 2F).

1-Chloro-3-(difluoromethoxy)benzene (3b-meta) and 1-chloro-4-(difluoromethoxy)benzene (3b-para) $t_R$=133 min, 35% (v/v) acetonitrile in water. $^1$H NMR (700 MHz, CDCl$_3$, 25° C.): δ 7.23 (m, 2.56H), 7.11 (d, J=8.1 Hz, 0.56H), 7.04 (m, 0.52H), 6.97 (d, J=9.0 Hz, 2H), 6.93 (m, 0.55H), 6.48 (t, $^2$J$_{HF}$=73.4 Hz, 0.57H), 6.45 (t, 2J$_{HF}$=73.6 Hz, 1H). $^{13}$C NMR (175 MHz, CDCl$_3$, 25° C.): δ 151.32, 149.30, 134.64, 130.51, 130.37, 129.54, 125.33, 120.75, 119.62, 117.40, 115.51 (t, $^1$J$_{CF}$=260.1 Hz), 115.42 (t, $^1$J$_{CF}$=260.3 Hz). $^{19}$F NMR (376 MHz, CDCl$_3$, 25° C.): δ −83.3 (d, $^2$J$_{FH}$=73.6 Hz, 2F), −83.5 (d, $^2$J$_{FH}$=73.4 Hz, 1.12F). HRMS (EI) m/z calcd for C$_7$H$_5$OF$_2$Cl [M$^+$], 177.9997, found, 177.9994.

1,3,5-Trichloro-2-(difluoromethoxy)benzene (3c)

Prepared according to the General Procedure A using 1,3,5-trichlorobenzene (363 mg, 2.00 mmol, 10.0 equiv) as the substrate. After 12 h, the reaction mixture (72% yield by $^{19}$F NMR) was purified by HPLC to provide the title compound(s).

$t_R$=108 min, 50% (v/v) acetonitrile in water. $^1$H NMR (700 MHz, CDCl$_3$, 25° C.): δ 7.40 (s, 2H), 6.56 (t, $^2$J$_{HF}$=73.7 Hz, 1H). $^{13}$C NMR (175 MHz, CDCl$_3$, 25° C.): δ 142.87, 132.65, 130.71, 129.32, 116.24 (t, $^1$J$_{CF}$=265.4 Hz). $^{19}$F NMR (376 MHz, CDCl$_3$, 25° C.): δ −81.3 (d, $^2$J$_{FH}$=73.7 Hz, 2F). HRMS (EI) m/z calcd for C$_7$H$_3$OF$_2$Cl$_3$ [M$^+$], 245.9218, found, 245.9214.

1-Bromo-2-(difluoromethoxy)benzene (3e)

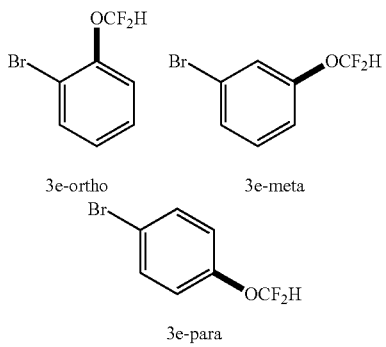

Prepared according to the General Procedure A using bromobenzene (314 mg, 211 μL, 2.00 mmol, 10.0 equiv) as the substrate. After 12 h, the reaction mixture (72% yield, 3e-ortho:3e-meta:3e-para=2.3:1.9:1 by $^{19}$F NMR) was purified by HPLC to provide the title compound (s).

1-Bromo-2-(difluoromethoxy)benzene (3e-ortho) $t_R$=83.9 min, 40% (v/v) acetonitrile in water. $^1$H NMR (700 MHz, CDCl$_3$, 25° C.): δ 7.62 (dd, J=1.4, 8.0 Hz, 1H), 7.31 (m, 1H), 7.22 (d, J=8.0 Hz, 1H), 7.11 (dt, J=1.4, 7.7 Hz, 1H), 6.53 (t, 2J$_{HF}$=73.6 Hz, 1H). $^{13}$C NMR (175 MHz, CDCl$_3$, 25° C.): δ 148.09, 133.93, 128.69, 126.99, 121.67, 115.86 (t, $^1J_{CF}$=262.3 Hz), 115.38. $^{19}$F NMR (376 MHz, CDCl$_3$, 25° C.): δ −83.0 (d, $^2J_{FH}$=73.6 Hz, 2F).

1-Bromo-3-(difluoromethoxy)benzene (3e-meta) and 1-bromo-4-(difluoromethoxy)benzene (3e-para) $t_R$=99.5 min, 40% (v/v) acetonitrile in water. $^1$H NMR (700 MHz, CDCl$_3$, 25° C.): δ 7.36 (d, J=8.8 Hz, 2H), 7.22 (m, 0.53H), 7.15 (m, 1.27H), 6.95 (m, 0.53H), 6.89 (d, J=8.8 Hz, 1H), 6.50 (t, $^2J_{HF}$=73.8 Hz, 0.46H), 6.42 (t, $^2J_{HF}$=73.9 Hz, 1H). $^{13}$C NMR (175 MHz, CDCl$_3$, 25° C.): δ 151.25, 149.78, 132.42, 130.76, 129.79, 128.13, 122.32, 122.19, 120.96, 117.77, 115.39 (t, $^1J_{CF}$=259.9 Hz), 115.36 (t, $^1J_{CF}$=260.1 Hz). $^{19}$F NMR (376 MHz, CDCl$_3$, 25° C.): δ −83.3 (d, $^2J_{FH}$=73.9 Hz, 2F), −83.5 (d, $^2J_{FH}$=73.8 Hz, 2F). HRMS (EI) m/z calcd for C$_2$H$_5$OF$_2$Br [M$^+$], 221.9492, found, 221.9493.

1-Chloro-2-(difluoromethoxy)-4-(trifluoromethyl)benzene (3d)

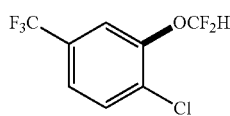

Prepared according to the General Procedure A using 1-chloro-4-(trifluoromethyl)benzene (361 mg, 2.00 mmol, 10.0 equiv) as the substrate. After 12 h, the reaction mixture (59% yield by $^{19}$F NMR) was purified by HPLC to provide the title compound(s).

$t_R$=66.7 min, 50S (v/v) acetonitrile in water. $^1$H NMR (700 MHz, CDCl$_3$, ° C.): δ 7.50 (d, J=8.3 Hz, 1H), 7.36 (s, 1H), 7.35 (d, J=8.3 Hz, 1H), 6.57 (t, $^2J_{HF}$=72.9 Hz, 1H). $^{13}$C NMR (175 MHz, CDCl$_3$, 25° C.): δ 146.93, 131.54, 130.19, 130.00, 123.34 (q, J=6.2 Hz), 122.24 (q, $^1J_{CF}$=273.4 Hz), 118.31 (q, J=3.5 Hz), 115.59 (t, $^1J_{CF}$=263.3 Hz). $^{19}$F NMR (376 MHz, CDCl$_3$, 25° C.): δ −64.7 (s, 3F), −83.8 (d, $^2J$=72.9 Hz, 2F). HRMS (EI) m/z calcd for C$_8$H$_4$OF$_5$Cl [M$^+$], 245.9871, found, 245.9871.

1-(Bromomethyl)-2-(difluoromethoxy)-3,5-dimethylbenzene (3f)

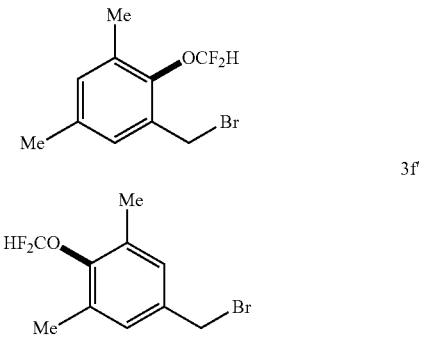

Prepared according to the General Procedure A using 1-(bromomethyl)-3,5-dimethylbenzene (398 mg, 2.00 mmol, 10.0 equiv) as the substrate. After 12 h, the reaction mixture (64% 3f:3f'=1.4:1 yield by $^{19}$F NMR) was purified by HPLC to provide the title compound(s).

1-(Bromomethyl)-2-(difluoromethoxy)-3,5-dimethylbenzene (3f) and 5-(bromomethyl)-2-(difluoromethoxy)-1,3-dimethylbenzene (3f'): to =62.8 min, 50% (v/v) acetonitrile in water. $^1$H NMR (700 MHz, CDCl$_3$, 25° C.): δ 2.5 (s, 2.5H), 7.00 (s, 1H), 6.47 (t, $^2J_{HF}$=74.6 Hz, 1H), 6.32 (t, $^2J_{HF}$=74.5 Hz, 0.75H), 4.53 (s, 2H), 4.41 (s, 1.5H), 2.29 (s, 3H), 2.29 (s, 2.25H), 2.28 (s, 3H). $^{13}$C NMR (175 MHz, CDCl$_3$, 25° C.): δ 148.67, 145.83, 136.77, 135.79, 133.09, 132.40, 132.23, 131.53, 130.00, 129.95, 117.49 (t, $^1J_{CF}$=259.5 Hz), 117.30 (t, $^1J_{CF}$=259.3 Hz), 32.88, 27.94, 20.84, 16.79, 16.77. $^{19}$F NMR (376 MHz, CDCl$_3$, 25° C.): δ −79.9 (d, $^2J$=74.5 Hz, 1.5F), −80.1 (d, $^2J_{HF}$=74.6 Hz, 2F). HRMS (ESI) m/z calcd for C$_{10}$H$_{11}$OF$_2$Br [M$^+$], 263.9961, found, 263.9960.

1-(Difluoromethoxy)-2-methylbenzene (3g)

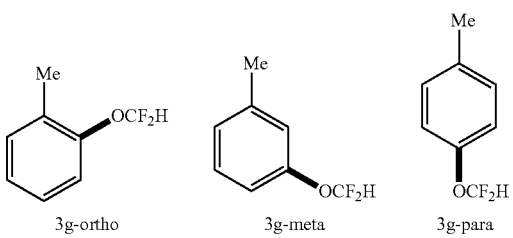

Prepared according to the General Procedure A using toluene (184 mg, 212 μL 2.00 mmol, 10.0 equiv) as the substrate. After 12 h, the reaction mixture (66% yield, 3g-ortho:3g-meta:3g-para=2:1:1 by $^{19}$F NMR) was purified by HPLC to provide the title compound(s).

1-(Difluoromethoxy)-2-methylbenzene (3g-ortho), 1-(difluoromethoxy)-3-methylbenzene (3g-meta), and 1-(difluoromethoxy)-4-methylbenzene (3g-para): $t_R$=85.4 min, (v/v)

acetonitrile in water. $^1$H NMR (700 MHz, CDCl$_3$, 25° C.): δ 7.26 (m, 1.10H), 7.21 (m, 1H), 7.18 (m, 1H), 7.14 (m, 1H), 7.09 (m, 1H), 7.04 (m, 1.48H), 6.95 (m, 0.82H), 6.52 (t, $^2J_{HF}$=74.8 Hz, 1H), 6.52 (t, $^2J_{HF}$=74.6 Hz, 1H), 6.49 (t, $^2J_{HF}$=74.8 Hz, 1H), 2.39 (s, 1.28H), 2.36 (s, 1.64H), 2.32 (s, 3H). $^{13}$C NMR (175 MHz, CDCl$_3$, 25° C.): δ 151.30, 149.79, 149.02, 140.15, 135.16, 131.51, 130.27, 129.98, 129.52, 127.05, 126.14, 125.40, 120.11, 119.54, 119.03, 116.38 (t, $^1J_{CF}$=258.8 Hz), 116.34, 116.13 (t, $^1J_{CF}$=259.2 Hz), 116.06 (t, $^1J_{CF}$=258.8 Hz), 21.35, 20.74, 16.17. $^{19}$F NMR (376 MHz, CDCl$_3$, 25° C.): δ −81.8.6 (d, $^2J_{FH}$=74.8 Hz, 2F), −82.4 (d, 2J$_{FH}$=74.6 Hz, 2F), −82.5 (d, $^2J_{FH}$=74.8 Hz, 2F). HRMS (EI) m/z calcd for C$_8$H$_8$OF$_2$[M$^+$], 158.0543, found, 158.0544.

2-(Difluoromethoxy)-1,4-dimethylbenzene (3h)

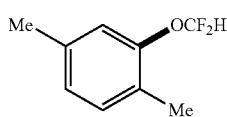

Prepared according to the General Procedure A using p-xylene (212 mg, 246 μL, 2.00 mmol, 10.0 equiv) as the substrate. After 12 h, the reaction mixture (45% yield by $^{19}$F NMR) was purified by HPLC to provide the title compound(s).

t$_R$=49.2 min, 50% (v/v) acetonitrile in water. $^1$H NMR (700 MHz, CDCl$_3$, ° C.): δ 7.10 (d, J=7.6 Hz, 1H), 6.92 (d, J=7.6 Hz, 1H), 6.88 (s, 1H), 6.47 (t, $^2J_{HF}$=74.5 Hz, 1H), 2.32 (s, 3H), 2.24 (s, 3H). $^{13}$C NMR (175 MHz, CDCl$_3$, 25° C.): δ 149.74, 137.21, 131.28, 126.74, 126.19, 119.82, 116.56 (t, $^1J_{CF}$=258.5 Hz), 21.14, 15.89. $^{19}$F NMR (376 MHz, CDCl$_3$, 25° C.): δ −81.6 (d, $^2J_{FH}$=74.5 Hz, 2F). HRMS (EI) m/z calcd for C$_9$H$_{10}$OF$_2$ [M$^+$], 172.0700, found, 172.0701.

2-(2-(Difluoromethoxy)phenyl)ethan-1-ol (3i)

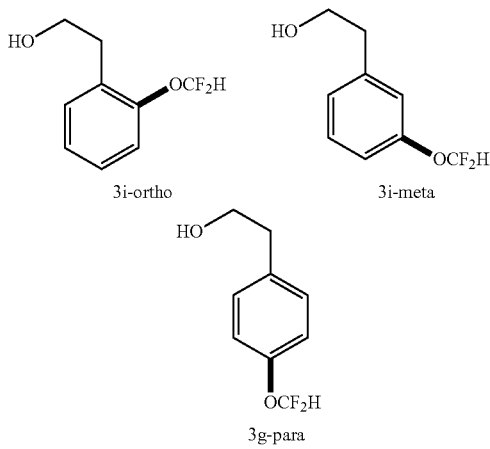

Prepared according to the General Procedure A using 2-phenylethan-1-ol (244 mg, 240 μL, 2.00 mmol, 10.0 equiv) as the substrate. After 12 h, the reaction mixture (58% yield, 3i-ortho:3i-meta:3i-para=3.4:1:1.1 by $^{19}$F NMR) was purified by HPLC to provide the title compound(s).

2-(2-(Difluoromethoxy)phenyl)ethan-1-ol (3i-ortho), 2-(3-(difluoromethoxy)phenyl)ethan-1-ol (3i-meta), and 2-(4-(difluoromethoxy)phenyl)ethan-1-ol (3i-para): t$_R$=66.4 min, 50% (v/v) acetonitrile in water. $^1$H NMR (700 MHz, CDCl$_3$, 25° C.): δ 7.30 (m, 1.50H), 7.23 (m, 1.88H), 7.17 (m, 1H), 7.09 (m, 2.52H), 7.00 (m, 1H), 6.53 (t, $^2J_{HF}$=74.1 Hz, 1H), 6.51 (t, $^2J_{HF}$=74.1 Hz, 1H), 6.48 (t, $^2J_{HF}$=74.1 Hz, 1H), 3.86 (s, 1H), 2.94 (s, 1H), 2.87 (s, 1H). $^{13}$C NMR (175 MHz, CDCl$_3$, 25° C.): δ 151.57, 150.10, 149.93, 141.06, 135.98, 131.65, 130.47, 130.26, 130.02, 128.13, 126.19, 125.65, 120.25, 119.95, 118.91, 117.53, 116.54 (t, $^1J_{CF}$=258.8 Hz), 116.12 (t, $^1J_{CF}$=259.5 Hz), 115.34 (d, $^1J_{CF}$=259.3 Hz), 63.69, 63.49, 62.67, 39.05, 38.52, 33.60. $^{19}$F NMR (376 MHz, CDCl$_3$, 25° C.): δ −79.9 (d, $^2J_{FH}$=74.1 Hz, 2F), −80.6 (d, $^2J_{FH}$=74.1 Hz, 1.14F), −80.6 (d, $^2J_{FH}$=74.1 Hz, 1.30F). HRMS (EI) m/z calcd for C$_9$H$_{10}$O$_2$F$_2$ [M$^+$], 188.0649, found, 188.0649.

4-(tert-Butyl)-2-(difluoromethoxy)benzonitrile (3j)

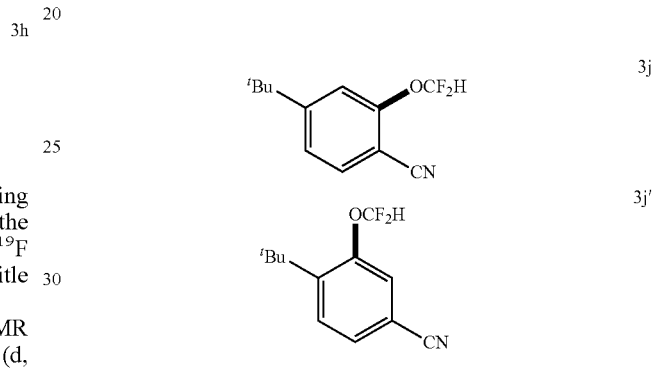

Prepared according to the General Procedure A using 4-(tert-butyl)benzonitrile (319 mg, 2.00 mmol, 10.0 equiv) as the substrate. After 12 h, the reaction mixture (63% yield, 3j:3j'=9.5:1 by $^{19}$F NMR) was purified by HPLC to provide the title compound(s).

4-(tert-Butyl)-2-(difluoromethoxy)benzonitrile (3j): t$_R$=103 min, 45% (v/v) acetonitrile in water. $^1$H NMR (700 MHz, CDCl$_3$, 25° C.): δ 7.60 (d, J=8.2 Hz, 1H), 7.34 (s, 1H), 7.33 (d, J=8.2 Hz, 1H), 7.30 (s, 1H), 6.64 (t, $^2J_{HF}$=72.1 Hz, 1H), 1.33 (s, 9H). $^{13}$C NMR (175 MHz, CDCl$_3$, 25° C.): δ 159.37, 151.85, 133.56, 123.30, 117.92, 115.43, 115.31 (t, $^1J_{CF}$=265.5 Hz), 103.45, 35.71, 30.99. $^{19}$F NMR (376 MHz, CDCl$_3$, 25° C.): δ −81.8 (d, $^2J_{FH}$=72.1 Hz, 2F).

4-(tert-Butyl)-3-(difluoromethoxy)benzonitrile (3j'): t$_R$=116 min, 45% (v/v) acetonitrile in water. 1H NMR (700 MHz, CDCl$_3$, 25° C.): δ 7.49 (d, J=8.2 Hz, 1H), 7.44 (d, J=8.2 Hz, 1H), 7.33 (s, 1H), 6.54 (t, $^2J_{HF}$=72.9 Hz, 1H), 1.40 (s, 9H). $^{13}$C NMR (175 MHz, CDCl$_3$, 25° C.): δ 151.00, 146.43, 128.90, 128.88, 120.98, 118.01, 116.07 (t, $^1J_{CF}$=259.8 Hz), 111.28, 35.67, 29.76. $^{19}$F NMR (376 MHz, CDCl$_3$, 25° C.): δ −83.8 (d, $^2J_{FH}$=72.9 Hz, 2F). HRMS (EI) m/z calcd for C$_{12}$H$_{13}$NOF$_2$ [M$^+$], 225.0965, found, 225.0965.

3-(Difluoromethoxy)-4-hydroxybenzonitrile (3k)

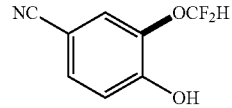

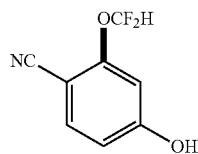

3k'

Prepared according to the General Procedure A using 4-hydroxybenzonitrile (238 mg, 2.00 mmol, 10.0 equiv) as the substrate. After 12 h, the reaction mixture (66% yield, 3k:3k'=8.4:1 by $^{19}$F NMR) was purified by HPLC to provide the title compound(s). Afterwards, the product(s) was concentrated in vacuo to afford the desired product(s).

3-(Difluoromethoxy)-4-hydroxybenzonitrile (3k): $t_R$=30.8 min, 40% (v/v) acetonitrile in water. $^1$H NMR (700 MHz, CDCl$_3$, 25° C.): δ 7.47 (s, 1H), 7.46 (d, J=8.1 Hz, 1H), 7.10 (d, J=8.1 Hz, 1H), 6.60 (t, $^2J_{HF}$=73.8 Hz, 1H), 6.27 (br. s, 1H). $^{13}$C NMR (175 MHz, CDCl$_3$, 25° C.): δ 153.72, 137.83, 131.67, 124.33, 118.14, 118.02, 115.57 (t, $^1J_{CF}$=265.7 Hz), 104.07. $^{19}$F NMR (376 MHz, CDCl$_3$, 25° C.): δ −83.6 (d, $^2J_{CF}$=73.8 Hz, 2F). HRMS (ESI-TOF) m/z calcd for C$_8$H$_4$F$_2$NO$_2$ [(M−H)$^-$], 184.0216, found, 184.0215.

2-(Difluoromethoxy)-4-hydroxybenzonitrile (3k'): $t_R$=76.9 min, 40% (v/v) acetonitrile in water. $^1$H NMR (700 MHz, CDCl$_3$, 25° C.): δ 7.53 (d, J=8.4 Hz, 1H), 6.81 (s, 1H), 6.77 (d, J=8.4 Hz) 6.61 (t, $^2J_{HF}$=74.7 Hz, 1H), 6.27 (br. s, 1H). $^{13}$C NMR (175 MHz, CDCl$_3$, 25° C.): δ 161.36, 153.18, 135.24, 115.57, 115.17 (t, $^1J_{CF}$=266.2 Hz), 113.30, 107.59, 97.13. $^{19}$F NMR (376 MHz, CDCl$_3$, 25° C.): δ −84.1 (d, $^2J_{FH}$=74.7 Hz, 2F).

2-(Difluoromethoxy)-4-nitrophenol (3l)

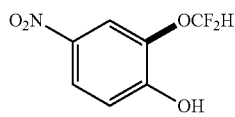

3l

Prepared according to the General Procedure A using 4-nitrophenol (278 mg, 2.00 mmol, 10.0 equiv) as the substrate. After 12 h, the reaction mixture (60% yield by $^{19}$F NMR) was concentrated and added 1.00 M NaOH (aq) (5 mL), dichloromethane (10 mL), and extracted with dichloromethane (3×10 mL). Then to the aqueous layer was added 1.00 M HCl (aq) (20 mL) and extracted with ethyl acetate (5×20 mL), dried with MgSO$_4$ and concentrated. Then the mixture was purified by HPLC to provide the title compound (s). Afterwards, the product(s) was concentrated in vacuo to afford 21.0 mg (51S yield) of the desired product(s). And 248 mg, 892% of 4-nitrophenol was recovered. ($t_R$=16.6 min, 40% (v/v) acetonitrile in water).

$t_R$=31.3 min, 40% (v/v) acetonitrile in water. $^1$H NMR (700 MHz, CDCl$_3$, 25° C.): δ 8.11 (d, J=2.5 Hz, 1H), 8.10 (d, J=8.9 Hz, 1H), 8.10 (d, J=2.5 Hz, 1H), 7.14 (d, J=8.9 Hz, 1H), 6.65 (t, $^2J_{HF}$=73.5 Hz, 1H), 6.17 (s, 1H). $^{13}$C NMR (175 MHz, CDCl$_3$, 25° C.): δ 153.33, 141.09, 137.19, 123.22, 116.80, 116.17, 115.71 (t, $^1J_{CF}$=265.8 Hz). $^{19}$F NMR (376 MHz, CDCl$_3$, 25° C.): δ −83.9 (d, $^2$J, =73.5 Hz, 2F). HRMS (ESI-TOF) m/z calcd for C$_7$H$_4$F$_2$NO$_4$ [(M−H)$^-$], 204.0114, found, 204.0109.

(E)-2-(Difluoromethoxy)-5-(2-nitrovinyl)phenol (3m)

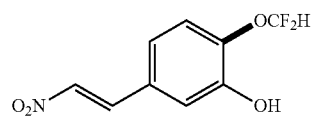

3m

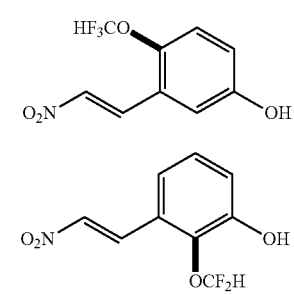

3m'

3m"

Prepared according to the General Procedure A using (E)-3-(2-nitrovinyl)phenol (330 mg, 2.00 mmol, 10.0 equiv) as the substrate. After 12 h, the reaction mixture (63% yield, 3m:3m':3m"=1.3:1.1:1 by $^{19}$F NMR) was purified by HPLC to provide the title compound(s). Afterwards, the product(s) was concentrated in vacuo to afford the desired product(s).

(E)-2-(Difluoromethoxy)-5-(2-nitrovinyl) phenol (3m) and (Z)-4-(difluoromethoxy)-3-(2-nitrovinyl)phenol (3m') and (Z)-2-(difluoromethoxy)-3-(2-nitrovinyl)phenol (3m"): $t_R$=70.6 min, 35?(v/v) acetonitrile in water. $^1$H NMR (700 MHz, CDCl$_3$, 25° C.): δ 8.16 (d, J=13.7 Hz, 0.42H), 8.13 (d, J=13.8 Hz, 0.42H), 7.92 (d, J=13.6 Hz, 1H), 7.63 (d, J=13.7 Hz, 0.42H), 7.62 (d, J=13.8 Hz, 0.42H), 7.51 (d, J=13.6 Hz, 1H), 7.22 (m, 1.21H), 7.19 (m, 0.89H), 7.16 (m, 1.24H), 7.10 (dd, J=1.8, 8.4 Hz, 1H), 7.03 (d, J=2.9 Hz, 0.42H), 6.97 (dd, J=2.9, 8.9 Hz, 0.42H), 6.62 (t, $^2J_{HF}$=73.6 Hz, 1H), 6.61 (t, $^2J_{CF}$=73.4 Hz, 0.42H), 6.53 (t, $^2J_{HF}$=74.9 Hz, 0.42H), 5.52 (br. s, 1.78H). $^{13}$C NMR (175 MHz, CDCl$_3$, 25° C.): δ 153.41, 149.58, 147.92, 143.99, 140.91, 139.35, 139.25, 138.03, 137.58, 137.09, 133.15, 133.10, 128.64, 128.16, 125.81, 124.02, 122.52, 122.23, 120.95, 120.94, 120.24, 120.00, 116.69, 116.66 (t, $^1J_{CF}$=265.3 Hz), 115.87 (t, $^1J_{CF}$=263.3 Hz), 115.80 (t, $^1J_{CF}$=264.3 Hz), 115.68. $^{19}$F NMR (376 MHz, CDCl$_3$, 25° C.): δ −83.6.5 (d, $^2J_{FH}$=73.4 Hz, 1F), −83.0 (d, $^2J_{FH}$=74.9 Hz, 2F), −83.3 (d, $^2J_{FH}$=73.6 Hz, 2F). HRMS (ESI-TOF) m/z calcd for C$_9$H$_6$F$_2$NO$_4$ [(M−H)$^-$], 230.0270, found, 230.0274.

4-(Difluoromethoxy)-3-hydroxybenzaldehyde (3n)

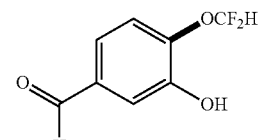

3n

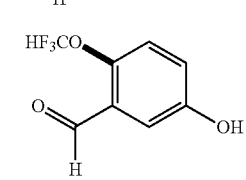

3n'

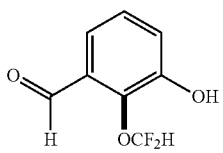

3n″

Prepared according to the General Procedure A using 3-hydroxybenzaldehyde (244 mg, 2.00 mmol, 10.0 equiv) as the substrate. After 12 h, the reaction mixture (60% yield, 3n:3n′:3n″=1.2:1.2:1 by $^{19}$F NMR) was purified by HPLC to provide the title compound(s).

4-(Difluoromethoxy)-3-hydroxybenzaldehyde (3n) and 2-(difluoromethoxy)-5-hydroxybenzaldehyde (3n′): $t_R$=57.8 min, 25 (v/v) acetonitrile in water. $^1$H NMR (700 MHz, CDCl$_3$, 25° C.): δ 10.30 (s, 1H), 9.92 (s, 0.50H), 7.56 (d, J=1.8 Hz, 0.50H), 7.46 (m, 1H), 7.40 (m, 0.50H), 7.27 (m, 1H), 7.17 (m, 1H), 7.14 (m, 1H), 6.66 (t, $^2J_{HF}$=73.8 Hz, 0.50H), 6.58 (t, $^2J_{HF}$=74.9 Hz, 1H), 5.95 (br. s, 1.50H). $^{13}$C NMR (175 MHz, CDCl$_3$, 25° C.): δ 191.25, 189.08, 153.96, 147.86, 146.44, 143.11, 134.65, 129.09, 123.40, 123.17, 122.88, 119.31, 117.19, 115.86 (t, $^1J_{CF}$=263.3 Hz), 115.73 (t, $^1J_{CF}$=263.8 Hz), 114.10. $^{19}$F NMR (376 MHz, CDCl$_3$, 25° C.): δ −83.5 (d, $^2J_{FH}$=73.8 Hz, 1F), −84.1 (d, $^2J_{FH}$=74.9 Hz, 2F). HRMS (ESI-TOF) m/z calcd for C$_8$H$_5$F$_2$O$_3$ [(M−H)$^-$], 187.0212, found, 187.0213.

2-(Difluoromethoxy)-3-hydroxybenzaldehyde (3n″): $t_R$=55.4 min, 25% (v/v) acetonitrile in water. $^1$H NMR (700 MHz, CDCl$_3$, 25° C.): δ 10.17 (s, 1H), 7.45 (dd, J=1.3, 7.5 Hz, 1H), 7.34 (t, J=7.5 Hz, 1H), 7.31 (d, J=1.3 Hz, 1H), 7.30 (d, J=1.3 Hz, 1H), 6.70 (t, $^2J_{HF}$=73.9 Hz, 1H), 5.73 (s, 1H). $^{13}$C NMR (175 MHz, CDCl$_3$, 25° C.): δ 189.24, 149.71, 137.86, 130.24, 127.96, 123.27, 123.13, 116.89 (t, $^1J_C$=264.6 Hz). $^{19}$F NMR (376 MHz, CDCl$_3$, 25° C.): δ −83.1 (d, $^2J_{FH}$=73.9 Hz, 2F).

1-(2-(Difluoromethoxy)phenyl)ethan-1-one (3o)

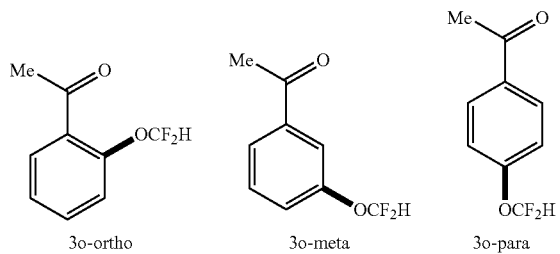

3o-ortho  3o-meta  3o-para

Prepared according to the General Procedure A using acetophenone (240 mg, 233 μL, 2.00 mmol, 10.0 equiv) as the substrate. After 12 h, the reaction mixture (65% yield, 3o-ortho:3o-meta:3o-para=2.7:2:1 by $^{19}$F NMR) was purified by HPLC to provide the title compound (s).

1-(2-(Difluoromethoxy)phenyl)ethan-1-one (3o-ortho) and 1-(3-(difluoromethoxy)phenyl)ethan-1-one (3o-para): $t_R$=101 min, 25% (v/v) acetonitrile in water. $^1$H NMR (700 MHz, CDCl$_3$, 25° C.): δ 7.99 (m, 0.60H), 7.76 (m, 1H), 7.53 (m, 1H), 7.52 (m, 1H), 7.30 (m, 1H), 7.18 (m, 1.60H), 6.60 (t, $^2J_{HF}$=73.5 Hz, 1H), 6.60 (t, $^2J_{HF}$=73.0 Hz, 0.30H), 2.63 (s, 3H), 2.60 (s, 0.90H). $^{13}$C NMR (175 MHz, CDCl$_3$, 25° C.): δ 198.56, 196.61, 154.73, 149.54, 134.11, 133.42, 131.58, 130.51, 130.48, 125.68, 119.75, 118.76, 116.11 (t, $^1J_{CF}$=260.6 Hz), 115.33 (t, $^1J_{CF}$=261.5 Hz), 31.25, 26.58. $^{19}$F NMR (376 MHz, CDCl$_3$, 25° C.): δ −82.8 (d, $^2J_{FH}$=73.5 Hz, 2F), −84.0 (d, $^2J_{FH}$=73.0 Hz, 2F). Spectral data match those previously reported.[6]

1-(4-(Difluoromethoxy)phenyl)ethan-1-one (3o-meta) $t_R$=111 min, 25% (v/v) acetonitrile in water. $^1$H NMR (700 MHz, CDCl$_3$, 25° C.): δ 7.80 (m, 1H), 7.70 (t, J=1.7 Hz, 1H), 7.48 (t, J=7.9 Hz, 1H), 7.34 (dd, J=7.9, 1.7 Hz, 1H), 6.57 (t, $^2J_{HF}$=73.3 Hz, 1H), 2.61 (s, 3H) $^{13}$C NMR (175 MHz, CDCl$_3$, 25° C.): δ 197.01, 151.43, 138.97, 130.26, 125.52, 124.52, 119.17, 115.75 (t, $^1J_{CF}$=261.2 Hz), 26.85. $^{19}$F NMR (376 MHz, CDCl$_3$, 25° C.): δ −83.3 (d, $^2J_{FH}$=73.3 Hz, 2F).

(2-(Difluoromethoxy)phenyl) (phenyl)methanone (3p)

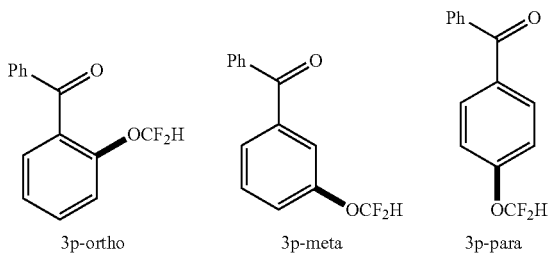

3p-ortho  3p-meta  3p-para

Prepared according to the General Procedure A using benzophenone (364 mg, 2.00 mmol, 10.0 equiv) as the substrate. After 12 h, the reaction mixture (77% yield, 3p-ortho:3p-meta:3p-para=1.3:1:1.4 by $^{19}$F NMR) was purified by HPLC to provide the title compound(s).

(2-(Difluoromethoxy)phenyl) (phenyl)methanone (3p-ortho) to =57.6 min, 45% (v/v) acetonitrile in water. $^1$H NMR (700 MHz, CDCl$_3$, 25° C.): δ 7.81 (m, 2H), 7.60 (m, 1H), 7.54 (m, 1H), 7.46 (m, 3H), 7.34 (m, 1H), 7.30 (m, 1H), 6.45 (t, $J_{HF}$=73.8 Hz, 1H). $^{13}$C NMR (175 MHz, CDCl$_3$, 25° C.): δ 194.72, 148.27, 137.04, 133.53, 132.46, 131.90, 130.01, 129.94, 128.48, 125.58, 121.18, 115.98 (t, $^1J_{CF}$=262.4 Hz). $^{19}$F NMR (376 MHz, CDCl$_3$, 25° C.): δ −82.8 (d, $^2J_{FH}$=73.8 Hz, 2F). Spectral data match those previously reported.[6]

(3-(Difluoromethoxy)phenyl)(phenyl)methanone (3p-meta) and (4-(difluoromethoxy)phenyl)(phenyl)methanone (3p-para) to =73.2 min, 50% (v/v) acetonitrile in water. $^1$H NMR (700 MHz, CDCl$_3$, 25° C.): δ 7.86 (d, J=8.7 Hz, 2H), 7.79 (m, 3.71H), 7.62 (m, 2.56H), 7.57 (s, 0.82H), 7.51 (m, 4.37H), 7.36 (m, 0.84H), 7.21 (d, J=8.7 Hz, 2H), 6.62 (t, $^2J_{HF}$=73.1 Hz, 1H), 6.57 (t, $^2J_{HF}$=73.3 Hz, 0.87H). $^{13}$C NMR (175 MHz, CDCl$_3$, 25° C.): δ 153.72, 137.83, 131.67, 124.33, 118.14, 118.02, 115.57 (t, $^1J_{CF}$=265.7 Hz), 104.07. $^{19}$F NMR (376 MHz, CDCl$_3$, 25° C.): δ −83.3 (d, $^2J_{FH}$=73.7 Hz, 2F), −83.9 (d, $^2J_{FH}$=73.6 Hz, 2F). Spectral data match those previously reported.[6]

1-(Difluoromethoxy)-3-(phenylethyl)benzene (3t)

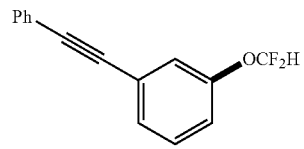

-continued

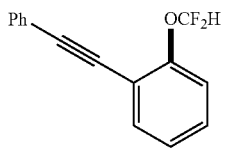
3t'

Prepared according to the General Procedure A using 1,2-diphenylethyne (357 mg, 2.00 mmol, 10.0 equiv) as the substrate. After 12 h, the reaction mixture (55% yield, 3t:3t'=1.1:1 by $^{19}$F NMR) was purified by HPLC to provide the title compound(s).

1-(Difluoromethoxy)-3-(phenylethynyl)benzene (3t): $t_R$=220 min, 45?(v/v) acetonitrile in water. $^1$H NMR (700 MHz, CDCl$_3$, 25° C.): δ 7.53 (m, 4H), 7.35 (m, 3H), 7.10 (m, 2H), 6.53 (t, $^2J_{HF}$=73.9 Hz, 1H). $^{13}$C NMR (175 MHz, CDCl$_3$, 25° C.): δ 151.03, 133.31, 131.73, 128.56, 128.53, 128.49, 128.40, 123.13, 120.67, 119.54, 115.82 (t, $^1J_{CF}$=260.6 Hz), 89.78, 88.34. $^{19}$F NMR (376 MHz, CDCl$_3$, 25° C.): δ −83.3 (d, $^2J_{FH}$=73.9 Hz, 2F).

1-(Difluoromethoxy)-2-(phenylethynyl)benzene (3t'): $t_R$=244 min, 50% (v/v) acetonitrile in water. $^1$H NMR (700 MHz, CDCl$_3$, 25° C.): δ 7.56 (m, 3H), 7.36 (m, 4H), 7.22 (m, 2H), 6.65 (t, $^2J_{HF}$=74.1 Hz, 1H). $^{13}$C NMR (175 MHz, CDCl$_3$, 25° C.): δ 151.58, 133.65, 131.83, 129.81, 128.84, 128.55, 125.86, 122.93, 120.98, 116.91, 116.47 (t, $^1J_{CF}$=260.2 Hz), 94.95, 83.98. $^{19}$F NMR (376 MHz, CDCl$_3$, 25° C.): δ −82.7 (d, $^2J_{FH}$=74.1 Hz, 2F). HRMS (EI) m/z calcd for C$_{15}$H$_{10}$OF$_2$ [M$^+$], 244.0700, found, 244.0700.

Methyl 3-(difluoromethoxy)-4-methoxybenzoate (3q)

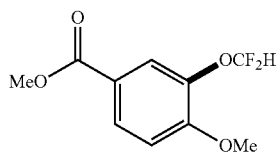
3q

Prepared according to the General Procedure A using methyl 4-methoxybenzoate (332 mg, 2.00 mmol, 10.0 equiv) as the substrate. After 12 h, the reaction mixture (61% yield by $^{19}$F NMR) was purified by HPLC to provide the title compound(s).

$t_R$=157 min, 30% (v/v) acetonitrile in water. $^1$H NMR (700 MHz, CDCl$_3$, 25° C.): δ 7.93 (dd, J=8.6, 1.8 Hz, 1H), 7.83 (d, J=1.8 Hz, 1H), 7.00 (d, J=8.6 Hz, 1H), 6.56 (t, $^2J_{FH}$=74.6 Hz, 1H), 3.94 (s, 3H), 3.90 (s, 3H). $^{13}$C NMR (175 MHz, CDCl$_3$, 25° C.): δ 165.98, 154.98, 139.43, 128.81, 123.39, 123.02, 115.93 (t, $^1J_{CF}$=260.7 Hz), 111.80, 56.20, 52.21. $^{19}$F NMR (376 MHz, CDCl$_3$, 25° C.): δ −83.2 (d, $^2J$; =74.6 Hz, 2F). HRMS (ESI-TOF) m/z calcd for C$_{10}$H$_{11}$F$_3$O$_4$ [(M+H)$^+$], 233.0620, found, 233.0621.

2-(Difluoromethoxy)-3,5-difluorobenzoic acid (3r)

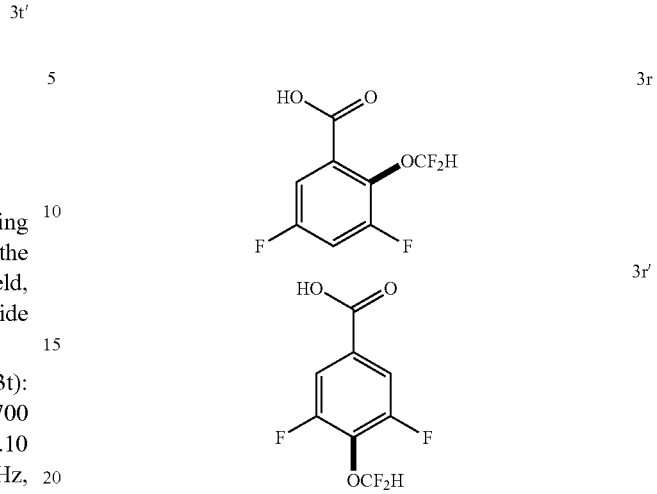

Prepared according to the General Procedure A using 3,5-difluorobenzoic acid (316 mg, 2.00 mmol, 10.0 equiv) as the substrate. After 12 h, the reaction mixture (74% yield, 3r:3r'=6.4:1 by $^{19}$F NMR) was purified by HPLC to provide the title compound(s).

2-(Difluoromethoxy)-3,5-difluorobenzoic acid (3r): $t_R$=59.2 min, 30 (v/v) acetonitrile in water. $^1$H NMR (700 MHz, CDCl$_3$, 25° C.): δ 7.53 (m, 1H), 7.52 (m, 1H), 7.18 (s, 1H), 6.63 (t, $^2J_{HF}$=74.2 Hz, 1H). $^{19}$F NMR (376 MHz, CDCl$_3$, 25° C.): δ −83.00 (dd, J=74.2, 9.0 Hz, 2F), −109.62 (m, 1F), −120.51 (m, 1F). HRMS (ESI-TOF) m/z calcd for C$_8$H$_3$F$_4$O$_3$ [(M−H)$^−$], 233.0024, found, 223.0024.

4-(Difluoromethoxy)-3,5-difluorobenzoic acid (3r'): $t_R$=82.9 min, 30% (v/v) acetonitrile in water. $^1$H NMR (700 MHz, CDCl$_3$, 25° C.): δ 7.73 (m, 1H), 6.68 (t, $^2J_{HF}$=72.6 Hz, 1H). $^{19}$F NMR (376 MHz, CDCl$_3$, 25° C.): δ −82.35 (dt, J=72.6, 7.4 Hz, 2F), −123.17 (m, 2F).

3-(Difluoromethoxy)benzoic acid (3s)

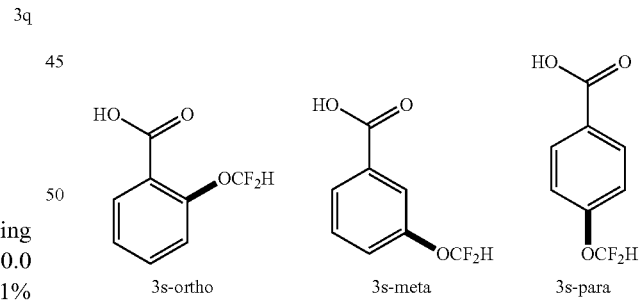

Prepared according to the General Procedure A using benzoic acid (244 mg, 2.00 mmol, 10.0 equiv) as the substrate. After 12 h, the reaction mixture (65% yield, 3s-ortho:3s-meta:3s-para=2.4:2.7:1 by $^{19}$F NMR) was purified by HPLC to provide the title compound(s).

2-(Difluoromethoxy)benzoic acid (3s-ortho) to =56.7 min, 20% (v/v) acetonitrile in water. $^1$H NMR (700 MHz, CDCl$_3$, 25° C.): δ 8.07 (d, J=7.9 Hz, 1H), 7.61 (t, J=7.9 Hz, 1H), 7.35 (t, J=8.5 Hz, 1H), 7.29 (d, J=8.5 Hz, 1H), 6.62 (t, $^2J_{HF}$=73.8 Hz, 1H). $^{13}$C NMR (175 MHz, CDCl$_3$, 25° C.): δ 166.35, 150.44, 134.77, 133.02, 126.25, 122.46, 122.25, 116.23 (t, $^1J_{CF}$=262.1 Hz). $^{19}$F NMR (376 MHz, CDCl$_3$, 25°

C.): δ −83.3 (d, $^2J_{CF}$=73.8 Hz, 2F). HRMS (ESI-TOF) m/z calcd for $C_8H_5F_2O_3$ [(M−H)$^−$], 187.0212. found, 187.0214.

3-(Difluoromethoxy)benzoic acid (3s-meta) and 4-(difluoromethoxy)benzoic acid (3s-para) to =88.7 min, 20% (v/v) acetonitrile in water. $^1$H NMR (700 MHz, CDCl$_3$, 25° C.): δ 8.13 (d, J=8.6 Hz, 0.75H), 7.97 (d, J=7.8 Hz, 1H), 7.85 (s, 1H), 7.50 (t, J=7.9 Hz, 1H), 7.39 (d, J=6.5 Hz, 1H), 7.20 (d, J=8.5 Hz, 0.75H), 6.63 (t, J=73.9 Hz, 0.38H), 6.56 (t, J=73.6 Hz, 1H). $^{13}$C NMR (175 MHz, CDCl$_3$, 25° C.): δ 168.81, 168.77, 155.46, 151.19, 132.54, 131.02, 130.22, 127.32, 125.98, 125.29, 121.21, 118.85, 115.44 (t, $^1J_{CF}$=261.6 Hz), 114.98 (t, $^1J_{CF}$=392.2 Hz). $^{19}$F NMR (376 MHz, CDCl$_3$, 25° C.): δ −83.4 (d, $^2J_{FH}$=73.9 Hz, 2F), −84.0 (d, $^2J_{FH}$=73.6 Hz, 0.75F).

4,4'-Di-tert-butyl-2-(difluoromethoxy)-1,1'-biphenyl (3u)

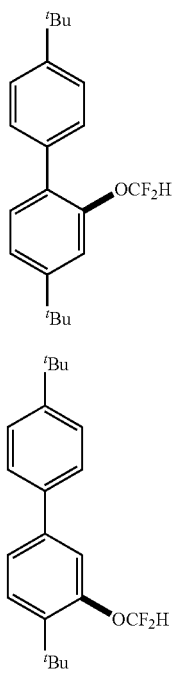

Prepared according to the General Procedure A using 4,4'-di-tert-butyl-1,1'-biphenyl (533 mg, 2.00 mmol, 10.0 equiv) as the substrate with MeCN:DCM 1:1 (1.00 mL, 0.200 M, with respect to 1a). After 12 h, the reaction mixture (54% yield, 3u:3u'=2.9:1 by $^{19}$F NMR) was purified by HPLC to provide the title compound(s).

4,4'-Di-tert-butyl-2-(difluoromethoxy)-1,1'-biphenyl (3u): $t_R$=149 min, 60% (v/v) acetonitrile in water. $^1$H NMR (700 MHz, CDCl$_3$, 25° C.): δ 7.44 (m, 4H), 7.35 (d, J=8.1 Hz, 1H), 7.30 (dd, J=1.8, 8.1 Hz, 1H), 7.22 (d, J=1.8, 1H), 6.30 (t, $^2J_{HF}$=74.3 Hz, 1H), 1.36 (s, 9H), 1.36 (s, 9H). $^{13}$C NMR (175 MHz, CDCl$_3$, 25° C.): δ 152.44, 150.42, 148.20, 134.02, 131.02, 130.98, 129.08, 125.37, 123.10, 117.92, 116.56 (t, $^1J_{CF}$=258.8 Hz), 34.85, 34.71, 31.50, 31.38. $^{19}$F NMR (376 MHz, CDCl$_3$, 25° C.): δ −82.8 (d, $^2J_{FH}$=74.3 Hz, 2F). HRMS (EI) m/z calcd for $C_{21}H_{26}OF_2$ [M$^+$], 332.1952, found, 332.1953.

4,4'-Di-tert-butyl-3-(difluoromethoxy)-1,1'-biphenyl (3u'): $t_R$=163 min, 60% (v/v) acetonitrile in water. $^1$H NMR (700 MHz, CDCl$_3$, 25° C.): 7.48 (m, 4H), 7.43 (d, J=8.2 Hz, 1H), 7.34 (dd, J=1.8, 8.2 Hz, 1H), 7.23 (d, J=1.8, 1H), 6.57 (t, $^2J_{HF}$=74.8 Hz, 1H), 1.43 (s, 9H), 1.36 (s, 9H). $^{13}$C NMR (175 MHz, CDCl$_3$, 25° C.): δ 151.64, 150.88, 140.68, 139.03, 137.05, 128.08, 126.76, 125.97, 123.34, 116.95 (t, $^1J_{CF}$=255.6 Hz), 116.62, 34.79, 34.72, 31.48, 30.23. $^{19}$F NMR (376 MHz, CDCl$_3$, 25° C.): δ −81.8 (d, $^2J_{FH}$=74.8 Hz, 2F).

2-(3-(Difluoromethoxy)phenyl)pyridine (3v)

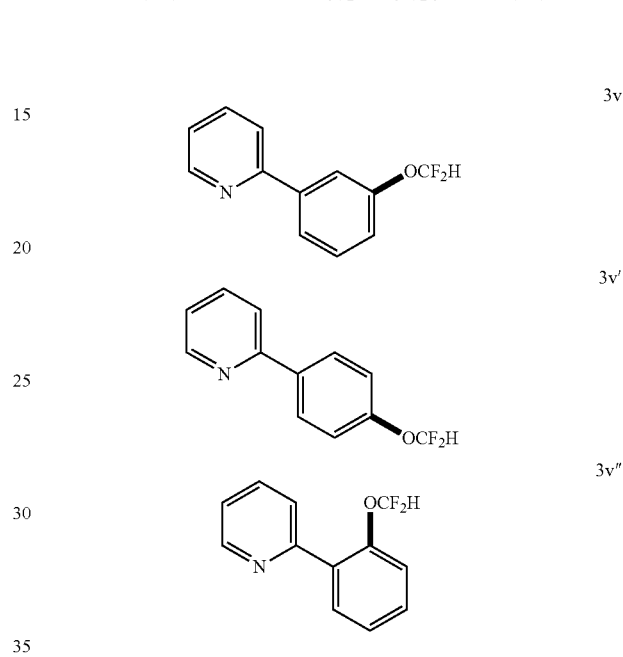

Prepared according to the General Procedure A using 2-phenylpyridine (244 mg, 2.00 mmol, 10.0 equiv) as the substrate with trifluoromethanesulfonic acid (300 mg, 177 µL, 2.00 mmol, 10.0 equiv). After 12 h, the reaction mixture (71% yield, 3v:3v':3v"=2.3:1.2:1 by $^{19}$F NMR) was quenched with 10% NaHCO$_3$ in water (2 mL), extracted with DCM (3×2 mL), and concentrated in vacuo. The residue was purified by HPLC to provide the title compound(s).

2-(3-(Difluoromethoxy)phenyl)pyridine (3v) $t_R$=132 min, 50% (v/v) acetonitrile in water. $^1$H NMR (700 MHz, CDCl$_3$, 25° C.): 8.72 (d, J=4.7 Hz, 1H), 7.79 (dd, J=1.4, 7.7 Hz, 1H), 7.76 (td, J=7.7, 1.4 Hz, 1H), 7.71 (d, J=7.8 Hz, 1H), 7.42 (m, 1H), 7.35 (t, J=7.5 Hz, 1H), 7.28 (d, J=7.3 Hz, 1H), 7.24 (d, J=8.1 Hz, 1H), 6.49 (t, $^2J_{HF}$=74.5 Hz, 1H). $^{13}$C NMR (175 MHz, CDCl$_3$, 25° C.): δ 155.00, 149.78, 148.78, 136.26, 133.00, 131.77, 130.14, 126.23, 125.02, 122.50, 120.53, 116.76 (t, $^1J_{CF}$=259.2 Hz). $^{19}$F NMR (376 MHz, CDCl$_3$, 25° C.): δ −83.5 (d, $^2J$, =73.5 Hz, 2F). HRMS (ESI-TOF) m/z calcd for $C_{12}H_{10}F_2NO$ [(M+H)$^+$], 222.0725, found, 222.0724.

2-(4-(Difluoromethoxy)phenyl)pyridine (3v') and 2-(2-(difluoromethoxy)phenyl)pyridine (3v") $t_R$=118 min, 50's (v/v) acetonitrile in water. $^1$H NMR (700 MHz, CDCl$_3$, 25° C.): δ 8.70 (d, J=4.7 Hz, 0.74H), 8.69 (d, J=4.8 Hz, 1H), 8.01 (d, J=8.7 Hz, 2H), 7.76 (m, 5.13H), 7.47 (t, J=7.8 Hz, 0.77H), 7.24 (m, 2H), 6.60 (t, $^2J_{HF}$=73.3 Hz, 0.80H), 6.57 (t, $^2J_{HF}$=73.5 Hz, 1H). $^{13}$C NMR (175 MHz, CDCl$_3$, 25° C.): δ 156.43, 156.22, 152.05, 151.96, 149.94, 149.89, 141.59, 137.06, 137.01, 136.78, 130.27, 128.58, 123.92, 122.83, 122.37, 120.78, 120.45, 120.11, 119.68, 118.10, 116.18 (t, $^1J_{CF}$=259.5 Hz), 115.99 (t, $^1J_{CF}$=259.5 Hz). $^{19}$F NMR (376 MHz, CDCl$_3$, 25° C.): δ −83.5 (d, $^2J_{FH}$=73.3 Hz, 1.56F), −84.3 (d, $^2J_{FH}$=73.5 Hz, 2F).

1-(Difluoromethoxy)naphthalene (3w)

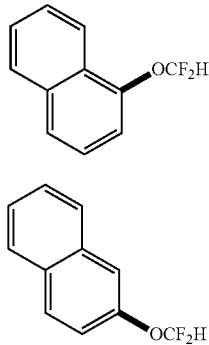

Prepared according to the General Procedure A using naphthalene (256 mg, 2.00 mmol, 10.0 equiv) as the substrate. After 12 h, the reaction mixture (72% yield, 3w:3w'=2.4:1 by $^{19}$F NMR) was purified by HPLC to provide the title compound(s).

1-(Difluoromethoxy)naphthalene (3w) and 2-(difluoromethoxy)naphthalene (3w') $t_R$=23.8 min, 50% (v/v) acetonitrile in water. $^1$H NMR (700 MHz, CDCl$_3$, 25° C.): δ 8.19 (m, 1H), 7.86 (m, 1.75H), 7.80 (m, 0.37H), 7.71 (m, 1.92H), 7.56 (m, 0.70H), 7.52 (m, 0.36H), 7.42 (t, J=7.9 Hz, 1H), 7.29 (m, 0.34H), 7.20 (m, 1H), 6.67 (t, $^2J_{HF}$=74.1 Hz, 1H), 6.63 (t, $^2J_{HF}$=73.9 Hz, 0.40H). $^{13}$C NMR (175 MHz, CDCl$_3$, 25° C.): δ 149.09, 147.57, 134.83, 133.91, 131.17, 130.22, 127.91, 127.89, 127.63, 127.10, 127.09, 127.09, 126.75, 126.58, 125.83, 125.52, 125.47, 121.75, 119.83, 116.70 (t, $^1J_{CF}$=259.1 Hz), 116.20 (t, J$_{CF}$=259.1 Hz), 115.48, 113.83. $^{19}$F NMR (376 MHz, CDCl$_3$, 25° C.): δ −80.0 (d, $^2J_{FH}$=74.1 Hz, 2F), −80.7 (d, $^2J_{FH}$=74.0 Hz, 0.80F). HRMS (EI) m/z calcd for C$_{11}$H$_8$OF$_2$ [M$^+$], 194.0543, found, 194.0542. Spectral data match those previously reported.

N-(2-(Difluoromethoxy)-4-(trifluoromethoxy)phenyl)-2,2,2-trifluoroacetamide (3x)

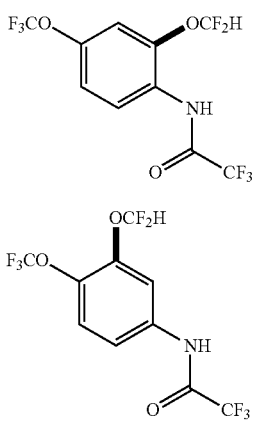

Prepared according to the General Procedure A using 2,2,2-trifluoro-N-(4-(trifluoromethoxy)phenyl)acetamide (546 mg, 2.00 mmol, 10.0 equiv) as the substrate. After 12 h, the reaction mixture (66% yield, 3x:3x'=7.3:1 by $^{19}$F NMR) was purified by HPLC to provide the title compound (s).

N-(2-(Difluoromethoxy)-4-(trifluoromethoxy)phenyl)-2,2,2-trifluoroacetamide (3x): $t_R$=151 min. 40% (v/v) acetonitrile in water. $^1$H NMR (700 MHz, CDCl$_3$, 25° C.): 8.41 (d, J=9.0 Hz, 1H), 8.26 (br. s, 1H), 7.19 (d, J=9.0 Hz, 1H), 7.13 (s, 1H), 6.63 (t, $^2J_{HF}$=72.7 Hz, 1H). $^{13}$C NMR (175 MHz, CDCl$_3$, 25° C.): δ 154.74 (q, $^2J_{CF}$=38.1 Hz), 146.15, 140.55, 126.12, 122.49, 120.28 (q, $^1J_{CF}$=258.6 Hz), 118.76, 115.52 (t, $^1J_{CF}$=265.6 Hz), 115.41 (q, $^1J_{CF}$=288.4 Hz), 112.74. $^{19}$F NMR (376 MHz, CDCl$_3$, 25° C.): δ −63.7 (s, 3F), −81.3 (s, 3F), −86.9. (d, $^2J_{FH}$=72.7 Hz, 2F). HRMS (ESI-TOF) m/z calcd for C$_{10}$H$_6$F$_8$NO$_3$ [(M+H)$^+$], 340.0214, found, 340.0217.

N-(3-(Difluoromethoxy)-4-(trifluoromethoxy)phenyl)-2,2,2-trifluoroacetamide (3x'): $t_R$=168 min, 40% (v/v) acetonitrile in water. $^1$H NMR (700 MHz, CDCl$_3$, 25° C.): 7.89 (br. s, 1H), 7.67 (d, J=2.4 Hz, 1H), 7.46 (dd, J=2.4, 8.9 Hz, 1H), 7.38 (d, J=8.9 Hz, 1H), 6.56 (t, $^2J_{HF}$=72.9 Hz, 1H). $^{13}$C NMR (175 MHz, CDCl$_3$, 25° C.): δ 154.88 (q, $^2J_{CF}$=38.2 Hz), 143.33, 138.04, 134.43, 123.91, 120.35 (q, $^1J_{CF}$=259.1 Hz), 117.92, 115.43 (q, $^1J_{CF}$=288.1 Hz), 115.37 (t, $^1J_{CF}$=265.0 Hz), 114.40. $^{19}$F NMR (376 MHz, CDCl$_3$, 25° C.): δ −63.8 (s, 3F), −81.1 (s, 3F), −87.2. (d, $^2J_{FH}$=72.9 Hz, 2F).

1-(Difluoromethoxy)-3-(phenylsulfonyl)benzene (3y)

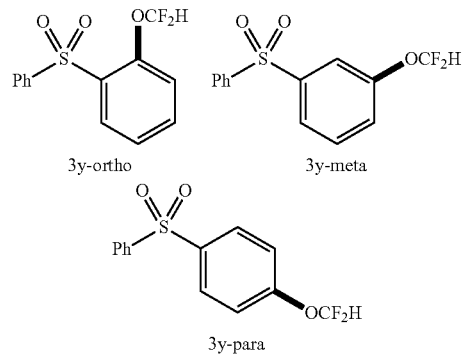

Prepared according to the General Procedure A using sulfonyldibenzene (437 mg, 2.00 mmol, 10.0 equiv) as the substrate. After 12 h, the reaction mixture (77% yield, 3y-ortho:3y-meta:3y-para=1.1:3.8:1 by $^{19}$F NMR) was purified by HPLC to provide the title compound(s).

1-(Difluoromethoxy)-2-(phenylsulfonyl)benzene (3y-ortho) $t_R$=70.8 min, 40V (v/v) acetonitrile in water. $^1$H NMR (700 MHz, CDCl$_3$, 25° C.): δ 8.25 (m, 1H), 7.98 (d, J=7.4 Hz, 2H), 7.61 (t, J=7.4 Hz, 2H), 7.52 (t, J=7.8 Hz, 2H), 7.43 (t, J=7.8 Hz, 1H), 7.21 (d, J=7.5 Hz, 1H), 6.50 (t, $^2J_{HF}$=74.2 Hz, 1H). $^{13}$C NMR (175 MHz, CDCl$_3$, 25° C.): δ 148.58, 140.73, 135.56, 133.73, 133.59, 130.31, 129.07, 128.61, 126.22, 121.98, 116.18 (t, $^2J_{HF}$=262.3 Hz). $^{19}$F NMR (376 MHz, CDCl$_3$, 25° C.): δ −83.6 (d, $^2J_{HF}$=74.2 Hz, 2F).

1-(Difluoromethoxy)-3-(phenylsulfonyl)benzene (3y-meta) and 1-(difluoromethoxy)-4-(phenylsulfonyl)benzene (3y-para)) $t_R$=90.6 min. 40% (v/v) acetonitrile in water. $^1$H NMR (700 MHz, CDCl$_3$, 25° C.): δ 7.96 (m, 3.44H), 7.79 (m, 1H), 7.70 (m, 1H), 7.59 (m, 1.31H), 7.52 (m, 3.79H), 7.32 (m, 1H), 7.22 (m, 0.67H), 6.57 (t, $^2J_{HF}$=73.2 Hz, 0.38H), 6.55 (t, $^2J_{HF}$=73.4 Hz, 1H). $^{13}$C NMR (175 MHz, CDCl$_3$, 25° C.): δ 154.66, 151.34, 143.67, 141.53, 141.06, 138.42, 133.71, 133.50, 131.04, 130.07, 129.60, 129.54, 127.94, 127.76, 124.66, 124.53, 119.74, 118.93, 116.20 (t, $^1J_{CF}$=394.8 Hz), 115.98 (t, $^1J_{CF}$=394.2 Hz). $^{19}$F NMR (376 MHz, CDCl$_3$, 25° C.): δ −83.9 (d, $^1J_{CF}$=73.4 Hz, 2F), −84.5 (d, $^2J_{FH}$=73.2 Hz, 2F). HRMS (EI) m/z calcd for C$_{13}$H$_{10}$O$_3$F$_2$S [M$^+$], 284.0319, found, 284.0318.

3-(Difluoromethoxy)phenyl phenyl carbonate (3z)

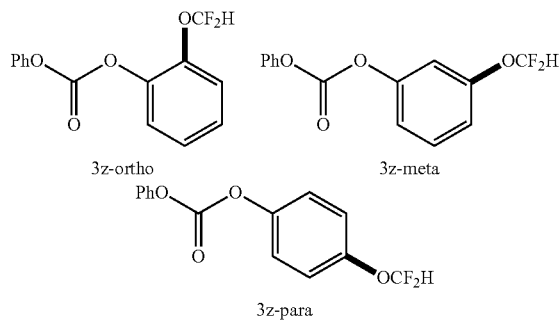

Prepared according to the General Procedure A using diphenyl carbonate (428 mg, 2.00 mmol, 10.0 equiv) as the substrate. After 12 h, the reaction mixture (74% yield, 3z-ortho:3z-meta:3z-para=1.4:1.5:1 by $^{19}$F NMR) was purified by HPLC to provide the title compound(s).

2-(Difluoromethoxy)phenyl phenyl carbonate (3z-ortho)) to =88.9 min, 45% (v/v) acetonitrile in water. $^1$H NMR (700 MHz, CDCl$_3$, 25° C.): δ 7.42 (m, 2H), 7.34 (m, 1H), 7.28 (m, 6H), 6.49 (t, $^2J_{HF}$=73.4 Hz, 1H). $^{13}$C NMR (175 MHz, CDCl$_3$, 25° C.): δ 151.74, 151.13, 143.15, 142.44, 129.79, 127.74, 126.70, 126.64, 123.32, 121.63, 120.99, 116.41 (t, $^1J_{CF}$=261.3 Hz). $^{19}$F NMR (376 MHz, CDCl$_3$, 25° C.): δ −82.3 (d, $^2J_{FH}$=73.4 Hz, 2F).

3-(Difluoromethoxy)phenyl phenyl carbonate (3z-meta) and 4-(difluoromethoxy)phenyl phenyl carbonate (3z-para)) t$_R$=100 min, 4% (v/v) acetonitrile in water. $^1$H NMR (700 MHz, CDCl$_3$, 25° C.): δ 7.43 (m, 4.54H), 7.28 (m, 7.38H), 7.18 (m, 2.76H), 7.11 (m, 0.60H), 7.06 (m, 0.62H), 6.53 (t, $^2J_{HF}$=73.8 Hz, 0.55H), 6.50 (t, $^2J_{HF}$=74.0 Hz, 1H). $^{13}$C NMR (175 MHz, CDCl$_3$, 25° C.): δ 152.13, 151.83, 151.78, 151.72, 151.02, 150.98, 148.90, 148.25, 130.54, 129.77, 129.71, 126.62, 126.58, 126.45, 122.42, 121.03, 120.98, 118.10, 117.41, 115.90 (t, $^1J_{CF}$=260.9 Hz), 115.80 (t, $^1J_{CF}$=260.8 Hz), 113.04. $^{19}$F NMR (376 MHz, CDCl$_3$, 25° C.): δ −83.1 (d, $^2J_{FH}$=74.0 Hz, 2F), −83.5 (d, $^2J_{FH}$=73.8 Hz, 1.55F). HRMS (EI) m/z calcd for C$_{14}$H$_{10}$O$_4$F$_2$ [M$^+$], 280.0547, found, 280.0549.

2,6-Di-tert-butyl-3-(difluoromethoxy)pyridine (3aa)

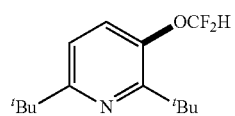

Prepared according to the General Procedure A using 2,6-di-tert-butylpyridine (383 mg, 2.00 mmol, 10.0 equiv) as the substrate. After 12 h, the reaction mixture (52% yield by $^{19}$F NMR) was purified by HPLC to provide the title compound(s).

t$_R$=154 min, 55% (v/v) acetonitrile in water. $^1$H NMR (700 MHz, CDCl$_3$, 25° C.): 7.26 (d, J=8.4 Hz, 1H), 7.14 (d, J=8.4 Hz, 1H), 6.48 (t, $^2J_{HF}$=73.9 Hz, 1H), 1.41 (s, 9H), 1.33 (s, 9H). $^{13}$C NMR (175 MHz, CDCl$_3$, 25° C.): δ 163.69, 156.98, 144.57, 125.74, 116.87, 116.61 (t, $^1J_{CF}$=258.3 Hz), 38.39, 37.55, 30.25, 29.17. $^{19}$F NMR (376 MHz, CDCl$_3$, 25° C.): δ −81.3 (d, $^2J_{FH}$=73.9 Hz, 2F). HRMS (ESI-TOF) m/z calcd for C$_{14}$H$_{22}$F$_2$NO [(M+H)$^+$], 258.1664, found, 258.1661.

3,4-Dibromo-2-(difluoromethoxy)thiophene (3ab)

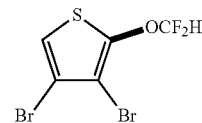

Prepared according to the General Procedure A using 3,4-dibromothiophene (484 mg, 2.00 mmol, 10.0 equiv) as the substrate. After 12 h, the reaction mixture (70% yield by $^{19}$F NMR) was purified by HPLC to provide the title compound(s).

t$_R$=111 min, 50% (v/v) acetonitrile in water. $^1$H NMR (700 MHz, CDCl$_3$, 25° C.): 7.08 (s, 1H), 6.48 (t, $^2J_{HF}$=72.1 Hz, 1H). $^{13}$C NMR (175 MHz, CDCl$_3$, 25° C.): δ 146.51, 116.31, 115.55 (t, $^1J_{CF}$=269.2 Hz), 111.43, 105.59. $^{19}$F NMR (376 MHz, CDCl$_3$, 25° C.): δ −84.7 (d, $^2J_{FH}$=72.1 Hz, 2F). HRMS (EI) m/z calcd for C$_5$H$_2$OSBr$_2$F$_2$ [M$^+$], 305.8161, found, 305.8161.

4-Bromo-5-(difluoromethoxy)thiophene-2-carbonitrile (3ac)

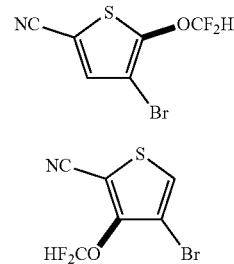

Prepared according to the General Procedure A using 4-bromothiophene-2-carbonitrile (376 mg, 2.00 mmol, 10.0 equiv) as the substrate. After 12 h, the reaction mixture (67% yield, 3ac:3ac'=3.8:1 by $^{19}$F NMR) was purified by HPLC to provide the title compound(s). 342 mg, 91% 4-bromothiophene-2-carbonitrile was recovered (t$_R$=33 min, 35% (v/v) acetonitrile in water).

4-Bromo-5-(difluoromethoxy)thiophene-2-carbonitrile (3ac): 24.5 mg, 48% yield, t$_R$=118 min, 35% (v/v) acetonitrile in water. $^1$H NMR (700 MHz, CDCl$_3$, 25° C.): 7.41 (s, 1H), 6.58 (t, $^2J_{HF}$=71.4 Hz, 1H). $^{13}$C NMR (175 MHz, CDCl$_3$, 25° C.): δ 150.25, 137.61, 114.79 (t, $^1J_{CF}$=271.8 Hz), 112.53, 104.12, 102.20. $^{19}$F NMR (376 MHz, CDCl$_3$, 25° C.): δ −85.4 (d, $^2J_{FH}$=71.4 Hz, 2F).

4-Bromo-3-(difluoromethoxy)thiophene-2-carbonitrile (3ac'): 6.8 mg, 13% yield. $t_R$=139 min, 35% (v/v) acetonitrile in water. $^1$H NMR (700 MHz, CDCl$_3$, 25° C.): 7.54 (s, 1H), 6.71 (t, $J_{HF}$=71.8 Hz, 1H). $^{13}$C NMR (175 MHz, CDCl$_3$, 25° C.): δ 150.76, 128.82, 115.15 (t, $^2J_{CF}$=269.7 Hz), 110.67, 107.60, 100.70. $^{19}$F NMR (376 MHz, CDCl$_3$, 25° C.): δ −82.2 (d, $^2J_{FH}$=71.8 Hz, 2F). HRMS (EI) m/z calcd for C$_6$H$_2$NOSF$_2$Br [M$^+$], 252.9009, found, 252.9008.

4-Bromo-5-(difluoromethoxy)thiophene-2-carboxylic acid (3ad)

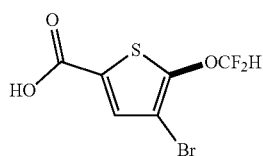

Prepared according to the General Procedure A using 4-bromothiophene-2-carboxylic acid (414 mg, 2.00 mmol, 10.0 equiv) as the substrate. After 12 h, the reaction mixture (59% yield, 3ad:3ad'=3.5:1 by $^{19}$F NMR) was concentrated and added 1.00 M NaOH (aq) (5 mL), dichloromethane (10.0 mL), and extracted with dichloromethane (3×10 mL). Then to the aqueous layer was added 1.00 M HCl (aq) (20 mL), extracted with diethyl ether (5×20 mL), dried with MgSO$_4$, and concentrated. Then the mixture was purified by HPLC to provide the title compound(s). 342 mg, 83% of 4-bromothiophene-2-carboxylic acid was recovered. ($t_R$=33.2 min, 30% (v/v) acetonitrile in water with 0.100% TFA).

4-Bromo-5-(difluoromethoxy)thiophene-2-carboxylic acid (3ad): 23.1 mg, 42% yield, $t_R$=85.8 min, 30% (v/v) acetonitrile in water. $^1$H NMR (700 MHz, CDCl$_3$, 25° C.): 7.68 (s, 1H), 6.58 (t, $^2J_{HF}$=71.5 Hz, 1H). $^{13}$C NMR (175 MHz, CDCl$_3$, 25° C.): δ 166.06, 152.43, 135.43, 125.14, 115.17 (t, $^1J_{CF}$=270.1 Hz), 102.35. $^{19}$F NMR (376 MHz, CDCl$_3$, 25° C.): δ −85.2 (d, $^2J_{FH}$=71.5 Hz, 2F). HRMS (ESI-TOF) m/z calcd for C$_6$H$_2$BrF$_2$O$_3$S [(M−H)$^−$], 270.8882, found, 270.8893.

4-Bromo-3-(difluoromethoxy)thiophene-2-carboxylic acid (3ad'): 6.2 mg, 11% yield, $t_R$=73.9 min, 30% (v/v) acetonitrile in water. $^1$H NMR (700 MHz, CDCl$_3$, 25° C.): 7.58 (s, 1H), 6.80 (t, $^2J_{HF}$=74.6 Hz, 1H). $^{13}$C NMR (175 MHz, CDCl$_3$, 25° C.): δ 163.23, 149.07, 129.39, 119.77, 116.46 (t, $^1J_{CF}$=265.3 Hz), 109.33. $^{19}$F NMR (376 MHz, CDCl$_3$, 25° C.): δ −83.2 (d, $^2J_{FH}$=74.6 Hz, 2F).

4-Amino-3-(4-chloro-2-(difluoromethoxy)phenyl)butanoic acid di-trifluoroacetic acid (5a)

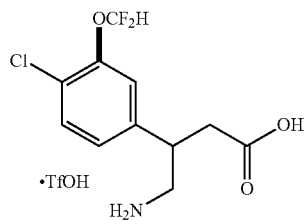

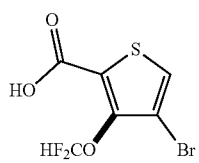

Prepared according to the General Procedure B using (±)-Baclofen® (42.7 mg, 0.200 mmol, 1.00 equiv) as the substrate with trifluoromethanesulfonic acid (30.0 mg, 17.8 μL, 0.200 mmol, 1.0 equiv). After 12 h, the reaction mixture (51.7 mg, 51% yield, 5a:5a' =5.7:1) was purified by HPLC to provide the title compound(s). Substrate (±) -Baclofen® was also recovered ($t_R$=22.2 min, 28.2 mg, 32% yield) as the di-trifluoroacetic acid salt.

4-Amino-3-(4-chloro-3-(difluoromethoxy)phenyl)butanoic acid di-trifluoroacetic acid (5a") and 4-amino-3-(4-chloro-2-(difluoromethoxy)phenyl)butanoic acid di-trifluoroacetic acid (5a'"): t, =62.0 min, 15% (v/v) acetonitrile in water with 0.1004 TFA. $^1$H NMR (700 MHz, CD$_3$CN, 25° C.): δ 10.82 (br. s, 2.1H), 7.52 (d, J=8.3 Hz, 1H), 7.37 (d, J=8.4 Hz, 0.39H), 7.29 (dd, J=1.9, 8.4 Hz, 0.32H), 7.26 (m, 0.85H), 7.25 (m, 0.31H), 7.21 (m, 1H), 7.21 (br. s, 2.74), 6.86 (t, $^2J_{HF}$=73.2 Hz, 0.45H), 6.86 (t, $^2J_{HF}$=73.4 Hz, 1H), 3.79 (m, 0.43H), 3.49 (m, 1H), 3.37 (m, 1.43H), 3.25 (m, 1.44H), 2.84 (m, 3H). $^{13}$C NMR (175 MHz, CD$_3$CN, 25° C.): δ 174.16, 173.82, 151.27, 148.41, 141.57, 134.71, 132.15, 131.80, 130.15, 127.42, 126.72, 125.52, 121.62, 119.55, 117.55 (t, $^1J$=259.0 Hz), 117.43 (t, $^1J_{CF}$=258.6 Hz), 45.08, 44.28, 40.09, 38.67, 37.74, 34.63. $^{19}$F NMR (376 MHz, CDCl$_3$, 25° C.): δ −82.6 (d, $^2J_{FH}$=73.4 Hz, 0.35F), −82.8 (d, $^2J_{FH}$=73.4 Hz, 2F). HRMS (ESI) m/z calcd for C$_{11}$H$_{13}$NO$_3$F2Cl [(M+H)$^+$], 280.0552, found, 280.0554.

2-(3-cyano-5-(Difluoromethoxy)-4-isobutoxyphenyl)-4-methylthiazole-5-carboxylic acid trifluoroacetic acid (5b)

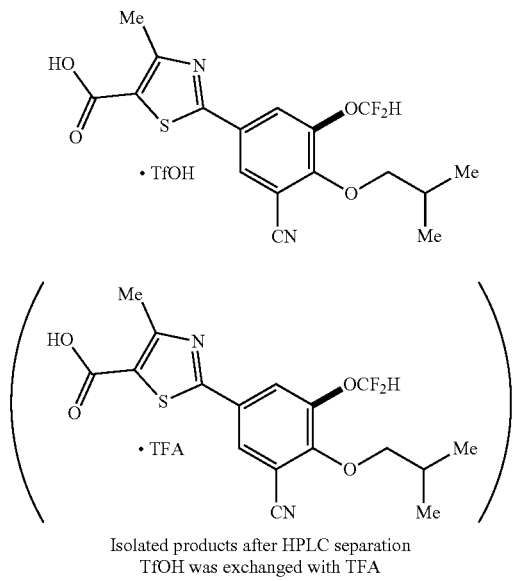

Isolated products after HPLC separation
TfOH was exchanged with TFA

Prepared according to the General Procedure B using Febuxostat® (63.3 mg, 0.200 mmol, 1.00 equiv) as the substrate with trifluoromethanesulfonic acid (30.0 mg, 17.8 µL, 0.200 mmol, 1.0 equiv). After 12 h, the reaction mixture (14.6 mg, 15% yield) was purified by HPLC to provide the title compound(s). Substrate Febuxostat® was also recovered ($t_R$=52.6 min, 54.4 mg, 63% yield) as the trifluoroacetic acid salt.

2-(3-cyano-5-(difluoromethoxy)-4-isobutoxyphenyl)-4-methylthiazole-5-carboxylic acid trifluoroacetic acid (5b') $t_R$=99.6 min, 45% (v/v) acetonitrile in water with 0.100% TFA. 1H NMR (700 MHz, CDCl$_3$, 25° C.): δ 8.03 (d, J=2.2 Hz, 1H), 8.00 (d, J=2.2 Hz, 1H), 6.62 (t, $^2J_{HF}$=73.0 Hz, 1H), 5.62 (br. s, 2H), 4.12 (d, J=6.3 Hz, 2H), 2.80 (s, 3H), 2.16 (m, 1H), 1.09 (s, 3H), 1.08 (s, 3H). 13C NMR (175 MHz, CDCl$_3$, ° C.): δ 167.34, 166.60, 163.28, 155.69, 143.96, 129.12, 128.75, 124.91, 122.28, 115.83 (t, $^1J_{CF}$=263.6 Hz), 115.00, 108.52, 82.04, 29.33, 19.00, 17.71. 19F NMR (376 MHz, CDCl$_3$, 25° C.): δ −81.3 (s, 3F). −86.8 (d, $^2J_{FH}$=73.0 Hz, 2F). HRMS (ESI) m/z calcd for C$_{17}$H$_{17}$N$_2$O$_4$F$_2$S [(M+H)$^+$], 383.0877, found, 383.0876.

1-(3-(Difluoromethoxy)-2,6-dimethylphenoxy)propan-2-amine (5c)

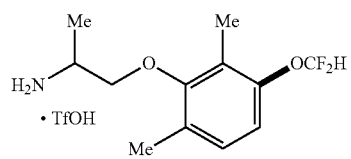

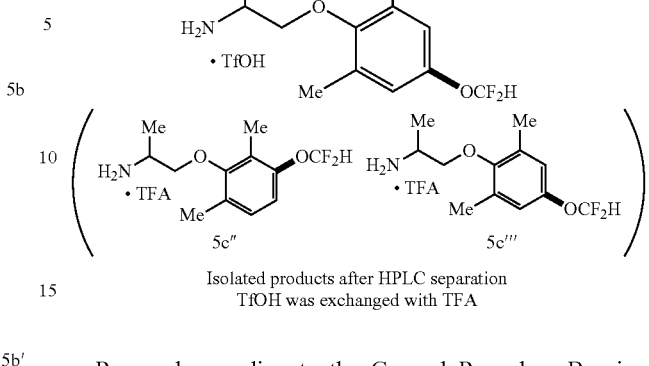

Isolated products after HPLC separation
TfOH was exchanged with TFA

Prepared according to the General Procedure B using Mexlietine® HCl (43.1 mg, 0.200 mmol, 1.00 equiv) as the substrate with trifluoromethanesulfonic acid (30.0 mg, 17.8 µL, 0.200 mmol, 1.0 equiv). After 12 h, the reaction mixture (22.3 mg, 33% yield) was purified by HPLC to provide the title compound(s). Substrate Mexlietine® HCl was also recovered ($t_R$=37.6 min, 33.9 mg, 58% yield) as the trifluoroacetic acid salt.

1-(3-(Difluoromethoxy)-2,6-dimethylphenoxy)propan-2-amine (5c) and 1-(4-(difluoromethoxy)-2,6-dimethylphenoxy)propan-2-amine (5c') to =116 min, 20V (v/v) acetonitrile in water with 0.1004 TFA. 1H NMR (700 MHz, CD$_3$CN, 25° C.): δ 7.63 (br. s, 3.37H), 7.09 (d, J=8.2 Hz, 1H), 6.90 (d, J=8.2 Hz, 1H), 6.86 (s, 0.33H), 6.71 (t, $^2J_{HF}$=74.6 Hz, 1.28H), 3.90 (m, 2H), 3.81 (m, 1.13H), 2.28 (s, 4.34H), 2.21 (s, 2.86H), 1.97 (m, 1.21H), 1.43 (m, 4.05H). 13C NMR (175 MHz, CDCl$_3$, 25° C.): δ 156.09, 152.67, 149.59, 148.29, 133.74, 130.24, 129.62, 129.33, 124.38, 120.37, 117.91 (t, $^1J_{CF}$=256.9 Hz), 117.55 (t, $^1J_{CF}$=256.7 Hz), 116.38, 72.71, 72.54, 49.40, 16.47, 16.24, 16.10, 15.12, 13.67, 9.86. 19F NMR (376 MHz, CDCl$_3$, 25° C.): δ −76.4 (s, 3F). -82.0 (d, $^2J_{FH}$=74.6 Hz, 2F), −82.7 (d, $^2J_{CF}$=74.6 Hz, 2F). HRMS (ESI) m/z calcd for C$_{12}$H$_{18}$NO$_2$F$_2$ [(M+H)$^+$], 246.1306, found, 246.1311.

(S)-6-Chloro-4-(cyclopropylethynyl)-8-(difluoromethoxy)-4-(trifluoromethyl)-1,4-dihydro-2H-benzo[d][1,3]oxazin-2-one (5d)

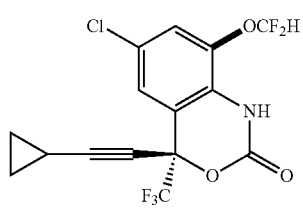

Prepared according to the General Procedure B using Efavirenz® (63.3 mg, 0.200 mmol, 1.00 equiv) as the substrate with potassium carbonate (27.6 mg, 0.200 mmol, 1.0 equiv). After 12 h, the reaction mixture (15.9 mg, 21% yield) was purified by HPLC to provide the title compound(s). Substrate Efavirenz® was also recovered ($t_R$=96.4 min, 31.7 mg, 50% yield).

(S)-6-Chloro-4-(cyclopropylethynyl)-8-(difluoromethoxy)-4-(trifluoromethyl)-1,4-dihydro-2H-benzo[d]

[1,3]oxazin-2-one (5d) $t_R$=146 min, 40i (v/v) acetonitrile in water. 1H NMR (700 MHz, CDCl$_3$, 25° C.): δ 8.17 (s, 1H), 7.39 (d, J=1.5 Hz, 1H), 7.30 (d, J=1.5 Hz, 1H), 6.62 (t, $J_{HF}$=71.4 Hz, 1H), 1.40 (m, 1H), 0.93 (m, 2H), 0.86 (m, 2H). $^{13}$C NMR (175 MHz, CDCl$_3$, 25° C.): δ 147.03, 136.32, 128.56, 126.69, 124.87, 122.64, 122.13 (q, $^1J_{CF}$=287.5 Hz), 116.57, 116.00 (t, $^1J_{CF}$=269.57 Hz), 96.40, 79.02 (q, $^2J_{CF}$=35.1 Hz), 65.92, 9.00, 8.98, −0.47. $^{19}$F NMR (376 MHz, CDCl$_3$, 25° C.): δ −80.8 (s, 3F). −82.2 (d, $^2J_{FH}$=71.4 Hz, 1F), −82.4 (d, $^2J_{FH}$=71.4 Hz, 1F). HRMS (ESI) m/z calcd for C$_{15}$H$_{10}$NO$_3$F$_5$Cl [(M+H)$^+$], 382.0269, found, 382.0265.

2-(2-Methyl-5-nitro-1H-imidazol-1-yl)ethyl 3-(difluoromethoxy)-4-methylbenzoate (5e)

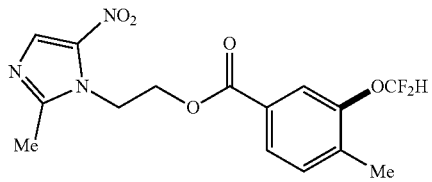

5e

Prepared according to the General Procedure B using 2-(2-methyl-5-nitro-1H-imidazol-1-yl)ethyl 4-methylbenzoate® (57.9 mg, 0.200 mmol, 1.00 equiv) as the substrate with potassium carbonate (27.6 mg, 0.200 mmol, 1.0 equiv). After 12 h, the reaction mixture (18.2 mg, 26% yield) was purified by HPLC to provide the title compound(s). Substrate 2-(2-methyl-5-nitro-1H-imidazol-1-yl)ethyl 4-methylbenzoate was also recovered ($t_R$=61.9 min, 30.5 mg, 53% yield).

2-(2-Methyl-5-nitro-1H-imidazol-1-yl)ethyl 3-(difluoromethoxy)-4-methylbenzoate (5e) $t_R$=117 min, 35% (v/v) acetonitrile in water. $^1$H NMR (700 MHz, CDCl$_3$, 25° C.): δ 7.97 (s, 1H), 7.67 (m, 1H), 7.61 (s, 1H), 7.30 (d, J=7.9 Hz, 1H), 6.57 (t, $^2J_{HF}$=73.4 Hz, 1H), 4.72 (t, J=5.1 Hz, 2H), 4.66 (t, J=5.1 Hz, 2H), 2.49 (s, 3H), 2.34 (s, 3H). $^{13}$C NMR (175 MHz, CDCl$_3$, 25° C.): δ 165.23, 150.92, 149.60, 138.72, 136.66, 133.43, 131.88, 128.23, 126.59, 119.71, 115.95 (t, $^1J_{CF}$=260.9 Hz), 63.15, 45.27, 16.71, 14.43. $^{19}$F NMR (376 MHz, CDCl$_3$, 25° C.): δ −82.6 (d, $^2J_{FH}$=73.4 Hz, 2F). HRMS (ESI) m/z calcd for C$_{15}$H$_{16}$N$_3$O$_5$F$_2$ [(M+H)$^+$], 356.1058, found, 356.1049.

(1R,2S,5R)-2-Isopropyl-5-methylcyclohexyl 4-bromo-5-(difluoromethoxy)thiophene-2-carboxylate (5f)

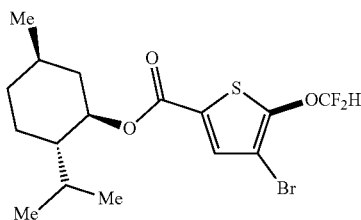

5f

Prepared according to the General Procedure B using (1R,2S,5R)-2-isopropyl-5-methylcyclohexyl 4-bromothiophene-2-carboxylate (69.1 mg, 0.200 mmol, 1.00 equiv) as the substrate with potassium carbonate (27.6 mg, 0.200 mmol, 1.0 equiv) (Zheng, W. et al. 2018). After 12 h, the reaction mixture (16.4 mg, 20S yield) was purified by HPLC to provide the title compound(s). Substrate (1R,2S,5R)-2-isopropyl-5-methylcyclohexyl 4-bromothiophene-2-carboxylate was also recovered ($t_R$=63.7 min, 36.9 mg, 53% yield).

(1R,2S,5R)-2-Isopropyl-5-methylcyclohexyl 4-bromo-5-(difluoromethoxy) thiophene-2-carboxylate (5f) $t_R$=80.0 min, 65% (v/v) acetonitrile in water. $^1$H NMR (700 MHz, CDCl$_3$, 25° C.): δ 7.55 (s, 1H), 6.54 (t, $^2J_{HF}$=71.9 Hz, 1H), 4.86 (m, 1H), 2.07 (m, 1H), 1.89 (m, 1H), 1.71 (m, 2H), 1.51 (m, 1H), 1.09 (m, 2H), 0.92 (d, J=7.4 Hz, 3H), 0.91 (J=7.4 Hz, 3H), 0.78 (d, J=7.0 Hz, 3H). $^{13}$C NMR (175 MHz, CDCl$_3$, 25° C.): δ 160.56, 150.87, 133.23, 127.07, 115.32 (t, $^1J_{CF}$=269.6 Hz), 101.91, 76.25, 47.23, 40.95, 34.28, 31.56, 26.65, 23.73, 22.12, 20.83, 16.64. $^{19}$F NMR (376 MHz, CDCl$_3$, 25° C.): δ −85.2 (d, $^2J_{FH}$=72.1 Hz, 2F). HRMS (ESI) m/z calcd for C$_{10}$H$_{11}$OF$_2$Br [(M+H)$^+$], 280.0552, found, 280.0554.

Trifluoromethoxylation Reaction Optimization

Scheme 15

Optimization of the Trifluoromethoxylation Reaction

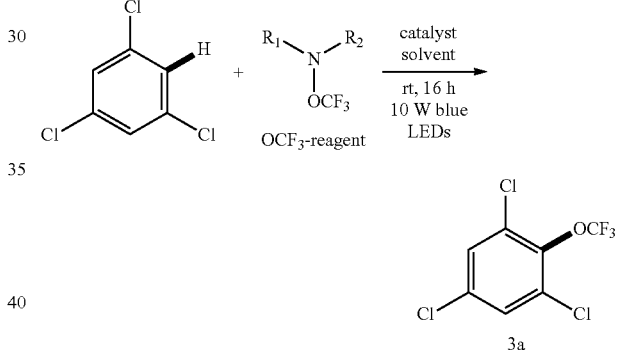

| Entry | Reagent (1 equiv) | Catalyst (1 mol %) | Solvent (0.200M) | Yield[b] 3a |
|---|---|---|---|---|
| 1 | TR1 | Ru(bpy)$_3$(PF$_6$)$_2$ | CH$_3$CN | 0% |
| 2 | TR2 | Ru(bpy)$_3$(PF$_6$)$_2$ | CH$_3$CN | 60% |
| 3 | 1b | Ru(bpy)$_3$(PF$_6$)$_2$ | CH$_3$CN | 70% |
| 4 | 1b | Ru(bpy)$_3$(PF$_6$)$_2$ | MeCN/CH$_2$Cl$_2$ (1:1) | 84% |
| 5[c] | 1b | Pu(bpy)$_3$(PF$_6$)$_2$ | MeCN/CH$_2$Cl$_2$ (1:1) | 51% |
| 6 | 1b | Ir(ppy)$_3$ | MeCN/CH$_2$Cl$_2$ (1:1) | 46% |
| 7 | 1b | Rhodamine-6G | MeCN/CH$_2$Cl$_2$ (1:1) | 51% |
| 8 | 1b | — | MeCN/CH$_2$Cl$_2$ (1:1) | <5% |
| 9[d] | 1b | Ru(bpy)$_3$(PF$_6$)$_2$ | MeCN/CH$_2$Cl$_2$ (1:1) | <5% |
| 10[e] | 1b | Ru(bpy)$_3$(PF$_6$)$_2$ | MeCN/CH$_2$Cl$_2$ (1:1) | 82% |

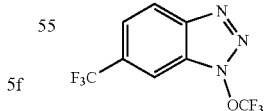

TR1

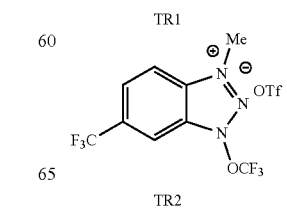

TR2

Scheme 15

Optimization of the Trifluoromethoxylation Reaction

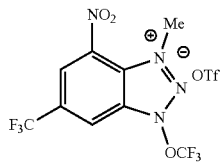
1b

[a] 10 equivalents of 1,3,5-trichlorobenzene was used.
[b] Yields were determined by $^{19}$F-NMR using PhCF$_3$ as an internal standard.
[c] 1 equivalent of 1,3,5-trichlorobenzene was used.
[d] Without light.
[e] Under air atmosphere.

Reagent Synthesis

4-Nitro-6-(trifluoromethyl)-1H-benzo[d][1,2,3]triazol-1-ol (S1b)

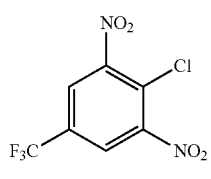 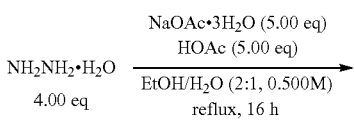

S1b

To a 500 mL round bottom flask charged with a magnetic stir bar, 2-chloro-1,3-dinitro-5-(trifluoromethyl)benzene (32.4 g, 120 mmol, 1.00 equiv), sodium acetate trihydrate (81.6 g, 600 mmol, 5.00 equiv) and acetic acid (34.4 mL, 600 mmol, 5.00 equiv) was added ethanol (160 mL) and water (80 mL, 0.500 M). After the reaction mixture was stirred for 10 min, hydrazine monohydate (23.4 mL, 480 mmol, 4.00 equiv) was added and the water condenser was installed. The resulting mixture was refluxed at 105° C. for 16 h and then cooled to room temperature, concentrated under vacuo and quenched with 500 mL 1 M HCl aqueous solution. The mixture was transferred to a 1 L separatory funnel and extracted with ethyl acetate (3×300 mL). The combined organic layers were sequentially washed with 1 M HCl aqueous solution (2×100 mL), water (2×100 mL), and brine (2×100 mL). The organic layer was then dried with magnesium sulfate, filtered, and concentrated in vacuo. The solid was further washed with dichloromethane (3×50 mL) to afford the title compound Sib as a yellow solid (25.9 g, 104 mmol, 87, yield). $^1$H NMR (400 MHz, DMSO-d6, 25° C.), δ 8.77 (s, 1H), 8.52 (s, 1H); $^{13}$C NMR (175 MHz, DMSO-d6, 25° C.), δ 138.1, 135.9, 130.2, 126.6 (q, J=34.4 Hz), 122.9 (q, J=273.1 Hz), 118.7, 116.5; $^{19}$F NMR (376 MHz, CDCl$_3$, 25° C.) δ −60.1 (s, 3F). HRMS (ESI) m/z calcd for C$_7$H$_4$N$_4$O$_3$F$_3$ [(M+H)$^+$], 249.0235, found, 249.0237.

4-Nitro-1-(trifluoromethoxy)-6-(trifluormethyl)-1H-benzo[d][1,2,3]triazole (S1b')

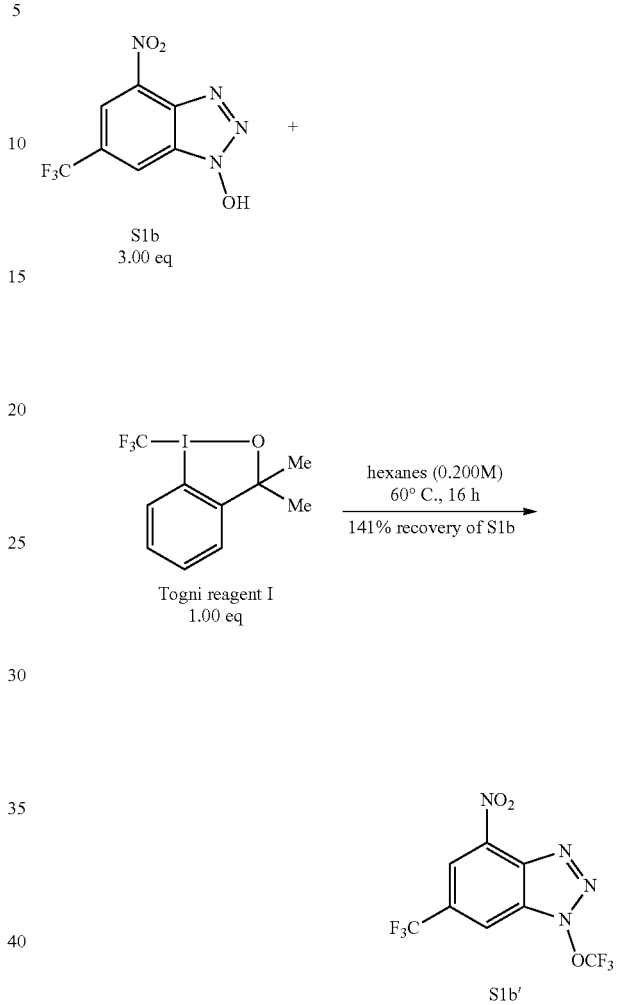

Under nitrogen atmosphere, to an oven-dried 100 mL round bottom flask charged with a magnetic stir bar was added 4-nitro-6-(trifluoromethyl)-1H-benzo[d][1,2,3]triazol-1-ol (Sib) (7.44 g, 30.0 mmol, 3.00 equiv) and Togni reagent I (3.32 g, 10.0 mmol, 1.00 equiv). Then, hexanes (50.0 mL, 0.200 M) was added. After the reaction mixture was stirred at 60° C. for 16 h, it was cooled to room temperature, concentrated in vacuo, then added dicholoromethane (100 mL). The mixture was filtered and solid was washed with dicholoromethane (3×50.0 mL) to recover starting material Sib (3.50 g, 14.1 mmol, 141 recovery). The filtrate was concentrated under vacuo and purified by flash column chromatography using 1-2% ethyl acetate in hexanes to afford the title compound S1b' as a yellow oil (1.16 g, 3.67 mmol, 37% yield). R$_f$=0.43 (EA:hexanes v/v=1:10); $^1$H NMR (400 MHz, CDCl$_3$, 25° C.), δ 8.60 (d, J=0.9 Hz, 1H), 8.31 (s, 1H); $^{13}$C NMR (175 MHz, CDCl$_3$, 25° C.), δ 139.7, 136.7, 132.5 (q, J=35.5 Hz), 130.6, 122.3 (q, J=273.6 Hz), 121.9 (q, J=275.4 Hz), 119.8 (q, J=3.2 Hz), 113.1 (q, J=4.2 Hz); $^{19}$F NMR (376 MHz, CDCl$_3$, 25° C.) δ −62.1 (s, 3F), −64.3 (s, 3F). HRMS (ESI) m/z calcd for C$_8$H$_3$N$_4$O$_3$F$_6$ [(M+H)$^+$], 317.0109, found, 317.0108.

3-Methyl-4-nitro-1-(trifluoromethoxy)-6-(trifluoromethyl)-1H-benzo[d][1,2,3]triazol-3-ium trifluoromethanesulfonate (1b)

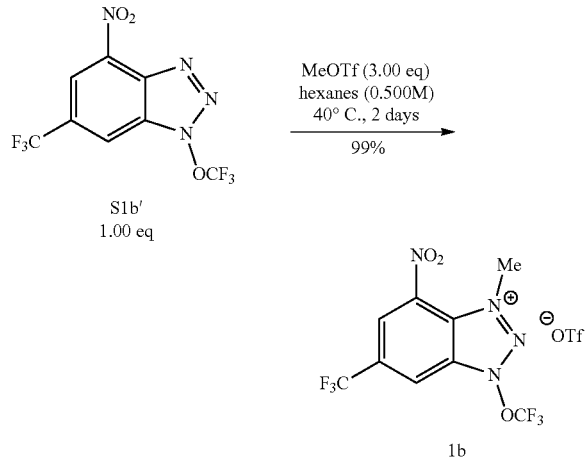

Under nitrogen atmosphere, to an oven-dried 100 mL round bottom flask charged with a magnetic stir bar was added 4-nitro-1-(trifluoromethoxy)-6-(trifluoromethyl)-1H-benzo[d][1,2,3]triazole (S1b') (1.16 g, 3.67 mmol, 1.00 equiv) was diluted in hexanes (7.34 mL, 0.500 M). Then methyl trifluoromethanesulfonate (1.20 mL, 11.0 mmol, 3.00 equiv) was added. After the reaction mixture was stirred at 40° C. for 48 h, it was cooled to room temperature, concentrated in vacuo, then added dicholoromethane (100 mL) and filtered. Solid was washed with dicholoromethane (3×50.0 mL) to obtain the title compound 1b as an off-white solid (1.76 g, 3.67 mmol, 99% yield). $^1$H NMR (400 MHz, DMSO-d6, 25° C.), δ 9.93 (s, 1H), 9.20 (d, J=1.1 Hz, 1H), 4.91 (s, 3H); $^{13}$C NMR (175 MHz, DMSO-d6, 25° C.), δ 137.5, 133.7, 133.0 (q, J=36.0 Hz), 129.7, 126.4 (q, J=3.5 Hz), 121.7 (q, J=274.4 Hz), 120.8 (q, J=279.9 Hz), 120.6 (q, J=322.6 Hz), 118.0 (q, J=4.8 Hz), 45.5; $^{19}$F NMR (376 MHz, DMSO-d6, 25° C.) δ −61.4 (s, 3F), −62.5 (s, 3F), −78.3 (s, 3F). HRMS (ESI) m/z calcd for $C_9H_5N_4O_3F_6$ [(M+H)$^+$], 331.0266, found, 331.0267.

1-(Trifluoromethoxy)-6-(trifluoromethyl)-1H-benzo[d][1,2,3]triazole (TR1)

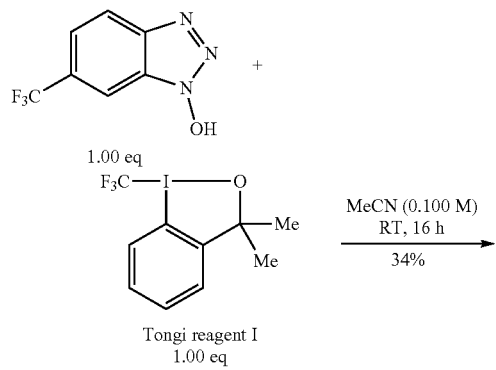

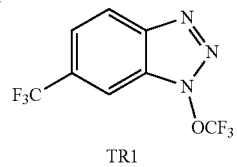

Under nitrogen atmosphere, to an oven-dried 100 mL round bottom flask charged with a magnetic stir bar was added 6-(trifluoromethyl)-1H-benzo[d][1,2,3]triazol-1-ol which was prepared following a reported procedure[10] (0.406 g, 2.00 mmol, 1.00 equiv) and Togni reagent I (0.664 g, 2.00 mmol, 1.00 equiv). Then, acetonitrile (20.0 mL, 0.100 M) was added. After the reaction mixture was stirred at room temperature for 16 h, it was concentrated in vacuo and purified by flash column chromatography using 1-2% ethyl acetate in hexanes to afford the title compound TR1 as a light yellow oil (0.184 g, 0.68 mmol, 34% yield, 94% NMR purity). $R_f$=0.48 (EA:hexanes v/v=1:10). The product can be further purified by HPLC on the Luna® PFP(2) preparative column (250×21.2 mm) using 45% acetonitrile in water (10 mL/min flow rate, $t_R$=105 min). $^1$H NMR (400 MHz, CDCl$_3$, 25° C.), δ 8.25 (d, J=8.8 Hz, 1H), 7.95 (s, 1H), 7.74 (dd, J=8.8 Hz, 1.2 Hz); $^{13}$C NMR (175 MHz, CDCl$_3$, 25° C.), δ 144.2, 132.3, 128.3, 123.4 (q, J=273.3 Hz), 122.7 (q, J=3.7 Hz), 122.0 (q, J=273.2 Hz), 122.2, 107.0 (q, J=5.1 Hz); $^{19}$F NMR (376 MHz, CDCl$_3$, 25° C.) δ −62.1 (s, 3F), −64.7 (s, 3F). HRMS (ESI) m/z calcd for $C_8H_4N_3OF_6$ [(M+H)$^+$], 272.0259, found, 272.0259.

3-Methyl-1-(trifluoromethoxy)-6-(trifluoromethyl)-1-benzo[d][1,2,3]triazol-3-ium trifluoromethanesulfonate (TR2)

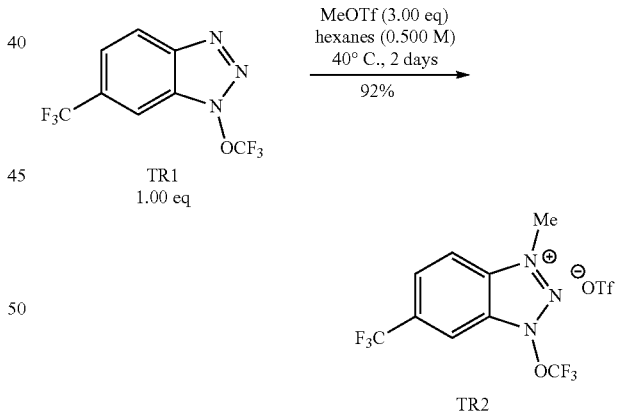

In a glovebox, to an oven-dried 20 mL vial charged with a magnetic stir bar was added 4-nitro-1-(trifluoromethoxy)-6-(trifluoromethyl)-1H-benzo[d][1,2,3]triazole (TR1) (0.136 g, 0.500 mmol, 1.00 equiv) was diluted in hexanes (1.00 mL, 0.500 M). Then methyl trifluoromethanesulfonate (0.164 mL, 1.50 mmol, 3.00 equiv) was added. After the reaction mixture was stirred at 40° C. for 48 h, it was cooled to room temperature, concentrated in vacuo, then added dicholoromethane (100 mL) and filtered. Solid was washed with dicholoromethane (3×5.00 mL) to obtain the title compound TR2 as an off-white solid (0.200 g, 0.460 mmol, 92% yield). $^1$H NMR (400 MHz, CD$_3$CN, 25° C.), δ 8.73 (s, 1H), 8.50 (d, J=9.2 Hz, 1H), 8.35 (dd, J=9.2 Hz, 1.0 Hz, 1H), 4.72 (s, 3H); $^{13}$C NMR (175 MHz, CD$_3$CN, 25° C.), δ 138.3, 136.2 (q, J=34.3 Hz), 131.9, 130.2, 123.6 (q, J=273.4 Hz), 122.4 (q, J=278.9 Hz), 122.0 (q, J=320.6 Hz), 118.0, 111.9 (q, J=4.6 Hz), 41.2; $^{19}$F NMR (376 MHz, CD$_3$CN, 25° C.) δ −63.8 (s, 3F), −64.5 (s, 3F), −80.0 (s, 3F). HRMS (ESI) m/z calcd for C$_9$H$_6$N$_3$OF$_6$ [(M+H)$^+$], 286.0415, found, 286.0419.

General Procedure A: Trifluoromethoxylation Using MeCN as Solvent.

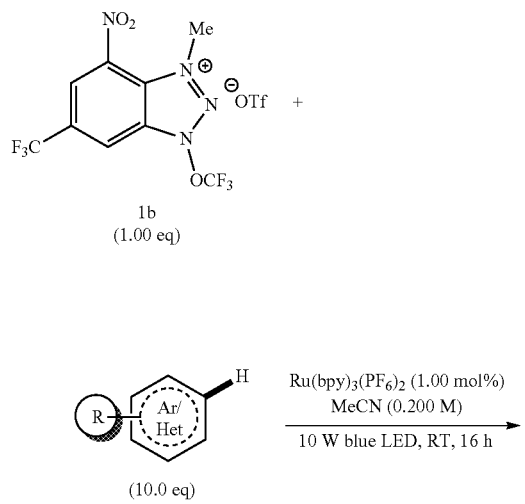

In a glovebox, to an oven-dried 20 mL screw cap vial was added 3-methyl-4-nitro-1-(trifluoromethoxy)-6-(trifluoromethyl)-1H-benzo[d][1,2,3]triazol-3-ium trifluoromethanesulfonate (1b) (98.0 mg, 0.200 mmol, 1.00 equiv), arene (2.00 mmol, 10.0 equiv) and Ru(bpy)$_3$(PF$_6$)$_2$, (1.72 mg, 2.00 µmol, 1.00 mol %). Then MeCN (1.00 mL, 0.200 M) and a magnetic stir bar were added. The vial was capped and taken out of the glovebox. The reaction mixture was then stirred and irradiated with 2 of 10 W LED (λ$_{max}$=447 nm) at room temperature. After 16 h, an internal standard PhCF$_3$ (24.6 µL, 0.200 mmol, 1.00 equiv) was added to the reaction vial, 0.200 mL of the resulting mixture was transferred to a 2 mL vial containing 0.500 mL of CDCl$_3$. After the yield was determined using $^{19}$F NMR, the NMR sample was combined with the rest of the reaction mixture and the solvent was removed in vacuo. The crude material was purified by HPLC under noted conditions. The fractions containing the desired product were combined and extracted with CDCl$_3$ (3×10.0 mL), dried with magnesium sulfate, and filtered unless otherwise noted. The filtrate was concentrated in vacuo to furnish the desired product of trifluoromethoxylation. For volatile compounds, after purification by HPLC, the desired product was extracted with 1 mL CDCl$_3$ and then directly characterized. The NMR peaks are referring to CH$_3$CN residue signal ($^1$H-NMR: δ 1.94, $^{13}$C-NMR: δ 118.26, 1.32).[2]

General Procedure B: Trifluoromethoxylation Using MeCN/DCM as Solvent.

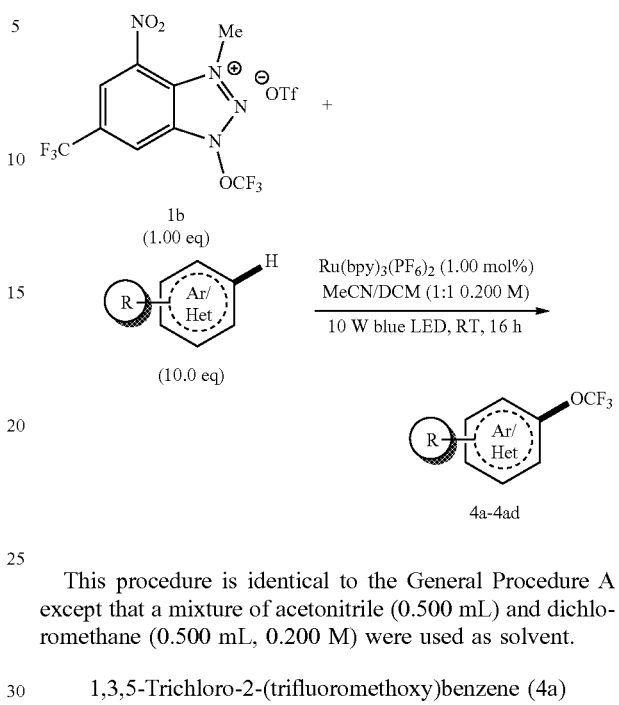

This procedure is identical to the General Procedure A except that a mixture of acetonitrile (0.500 mL) and dichloromethane (0.500 mL, 0.200 M) were used as solvent.

1,3,5-Trichloro-2-(trifluoromethoxy)benzene (4a)

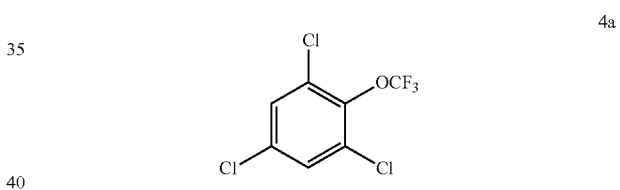

The reaction was performed according to the general procedure B using 1,3,5-trichloro-benzene (0.360 g, 2.00 mmol) as the substrate. After 16 h, the reaction mixture (80% yield by $^{19}$F NMR) was purified by HPLC on the Luna® PFP(2) preparative column (250×21.2 mm) using 65% v/v acetonitrile in water (10 mL/min flow rate, t$_R$=35 min) to provide the title compound. $^1$H NMR (400 MHz, CDCl$_3$, 25° C.) 7.4 (s, 2H); $^{13}$C NMR (175 MHz, CDCl$_3$, 25° C.) δ 141.3, 133.6, 131.2, 129.4, 120.7 (q, J=262.6 Hz); $^{19}$F NMR (376 MHz, CDCl$_3$, 25° C.) δ −56.9 (s, 3F). HRMS (EI): Calcd for: C$_7$H$_2$OF$_3$Cl$_3$$^+$ (M$^+$) 263.9124, found: 263.9125.

Fluoro(trifluoromethoxy)benzene (4b)

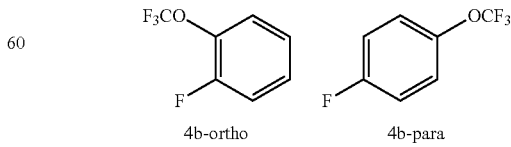

The reaction was performed according to the general procedure A using flourobenzene (0.192 g, 2.00 mmol) as the substrate. After 16 h, the reaction mixture (66% yield with o:m:p=1.8:1:1.4 by $^{19}$F NMR) was purified by HPLC on the Luna® PFP(2) preparative column (250×21.2 mm) using 65% v/v acetonitrile in water (12 mL/min flow rate, $t_R$=16.5 min) to provide a mixture of p- and o-regioisomers. $^1$H NMR (700 MHz, CDCl$_3$/CH$_3$CN, 25° C.), δ 7.16-7.12 (m), 7.06-7.00 (m), 6.94-6.91 (m); $^{13}$C NMR (175 MHz, CDCl$_3$, CH$_3$CN, 25° C.), δ 160.7 (d, J=245.4 Hz), 154.2 (d, J=250.5 Hz), 144.7, 136.0, 135.9, 128.70, 128.66, 124.9, 124.8, 122.9 (d, J=8.9 Hz), 120.3 (q, J=256.2 Hz), 120.2 (q, J=256.2 Hz); $^{19}$F NMR (470 MHz, CDCl$_3$/CH$_3$CN, 25° C.) δ −59.1 (s, 3F), −59.5 (d, J=4.9 Hz), −116.1 (m, 1F), −130.8 (m, 1F).

Chloro(trifluoromethoxy)benzene (4c)

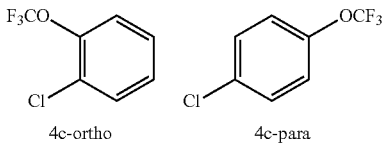

4c-ortho      4c-para

The reaction was performed according to the general procedure A using chlorobenzene (0.224 g, 2.00 mmol) as the substrate. After 16 h, the reaction mixture (73% yield with o:m:p=1.7:1:1.3 by $^{19}$F NMR) was purified by HPLC on the Luna® PFP(2) preparative column (250×21.2 mm) using 55% v/v acetonitrile in water (12 mL/min flow rate, $t_R$=40 min) to provide a mixture of m- and p-regioisomers.

1-Chloro-4-(trifluoromethoxy)benzene (4c-para): $^1$H NMR (400 MHz, CDCl$_3$/CH$_3$CN, 25° C.) δ 7.40-7.36 (m, 2H), 7.18-7.16 (m, 2H). $^{19}$F NMR (376 MHz, CDCl$_3$/CH$_3$CN, 25° C.) δ −58.5. The spectroscopic data is in agreement with the literature.[11]

1-Chloro-2-(trifluoromethoxy)benzene (4c-ortho): $t_R$=36 min. $^1$H NMR (400 MHz, CDCl$_3$/CH$_3$CN, 25° C.), δ 7.46 (d, J=7.4, 1H), 7.31-7.23 (m, 3H); $^{13}$C NMR (175 MHz, CDCl$_3$/CH$_3$CN, 25° C.), δ 144.7, 130.8, 128.1, 128.0, 126.8, 122.5, 120.2 (q, J=256.6 Hz); $^{19}$F NMR (376 MHz, CDCl$_3$/CH$_3$CN, 25° C.) δ −58.2 (s, 3F). HRMS (EI): Calcd for: C$_7$H$_4$OClF$_3$$^+$ (M$^+$) 195.9903, found: 195.9895.

Bromo(trifluoromethoxy)benzene (4d)

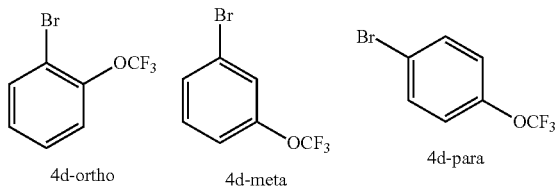 [SMILES: FC(F)(F)Oc1ccccc1Br ; FC(F)(F)Oc1cccc(Br)c1 ; FC(F)(F)Oc1ccc(Br)cc1]

4d-ortho    4d-meta    4d-para

The reaction was performed according to the general procedure A using bromobenzene (0.312 g, 2.00 mmol) as the substrate. After 16 h, the reaction mixture (54% yield with o:m:p=2.9:1:2.1 by $^{19}$F NMR) was purified by HPLC on the Luna® PFP(2) preparative column (250×21.2 mm) using 55% v/v acetonitrile in water (12 mL/min flow rate, $t_R$=38 min) to provide a mixture of m- and p-regioisomers.

Bromo-4-(trifluoromethoxy)benzene (4d-para): $^1$H NMR (500 MHz, CDCl$_3$/CH$_3$CN, 25° C.), δ 7.47 (m, 2H), 7.07 (m, 2H); $^{19}$F NMR (470 MHz, CDCl$_3$/CH$_3$CN, 25° C.) δ −58.5 (s, 3F). The spectroscopic data is in agreement with the literature.[11]

Bromo-3-(trifluoromethoxy)benzene (4d-meta): $^1$H NMR (500 MHz, CDCl$_3$/CH$_3$CN, 25° C.) δ 7.43-7.38 (m, 2H), 7.27-7.23 (m, 1H), 7.16-7.13 (m, 1H). $^{19}$F NMR (470 MHz, CDCl$_3$/CH$_3$CN, 25° C.) δ −58.3. The spectroscopic data is in agreement with the literature.[11]

Bromo-4-(trifluoromethoxy)benzene (4d-ortho): $t_R$=34 min. $^1$H NMR (400 MHz, CDCl$_3$, 25° C.), δ 7.59 (dd, J=8.0, 1.5, 1H), 7.32-7.26 (m, 2H), 7.13 (ddd, J=9.0, 8.9, 1.5 Hz, 1H); $^{13}$C NMR (175 MHz, CDCl$_3$, 25° C.), δ 145.9, 133.7, 128.6, 128.1, 122.3, 120.1 (q, J=256.5 Hz), 115.5; $^{19}$F NMR (470 MHz, CDCl$_3$, 25° C.) δ −58.2 (s, 3F). HRMS (EI): Calcd for: C$_7$H$_4$OF$_3$Br$^+$ (M$^+$) 239.9398, found: 239.9406.

1-Bromo-3,5-dichloro-(trifluoromethoxy)benzene (4e)

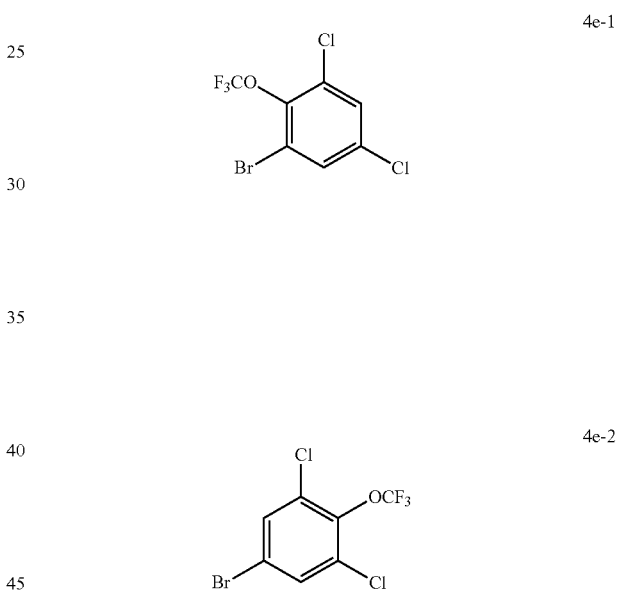

The reaction was performed according to the general procedure B using 1-bromo-3,5-dichlorobenzene (0.448 g, 2.00 mmol) as the substrate. After 16 h, the reaction mixture (68% yield with 4e-1:4e-2=1.8:1 by $^{19}$F NMR) was purified by HPLC on the Luna® PFP(2) preparative column (250× 21.2 mm) using 60G v/v acetonitrile in water (10 mL/min flow rate, $t_R$=53 min) to provide a mixture of regioisomers.

1-Bromo-3,5-dichloro-2-(trifluoromethoxy)benzene (4e-1): $^1$H NMR (400 MHz, CDCl$_3$, 25° C.), δ 7.57 (d, J=2.4 Hz, 1H), 7.45 (d, J=2.4 Hz, 1H); $^{19}$F NMR (376 MHz, CDCl$_3$, 25° C.) δ −55.5 (s, 3F).

5-Bromo-1,3-dichloro-2-(trifluoromethoxy)benzene (4e-2): $^1$H NMR (400 MHz, CDCl$_3$, 25° C.), δ 7.56 (s, 2H); $^{13}$C NMR (175 MHz, CDCl$_3$, 25° C.) (a mixture of 3e-1 and 3e-2), δ 142.5, 141.7, 133.8, 132.2, 132.1, 131.3, 130.8, 130.0, 120.6, 120.52 (q, J=262.5), 120.50 (q, J=262.7), 119.5. $^{19}$F NMR (376 MHz, CDCl$_3$, 25° C.) δ −56.2 (s, 3F). HRMS (EI): Calcd for: C$_7$H$_2$OF$_3$Cl$_2$Br$^+$ (M$^+$) 307.8618, found: 307.8623.

1-Chloro-2-(trifluoromethoxy)-4-(trifluoromethyl)benzene (4f)

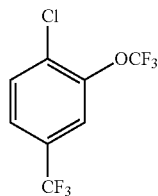

The reaction was performed according to the general procedure A using 1-chloro-4-(trifluoromethyl)benzene (0.360 g, 2.00 mmol) as the substrate. After 16 h, the reaction mixture (58% yield, by $^{19}$F NMR) was purified by HPLC on Luna® PFP(2) preparative column (250×21.2 mm) using 50% v/v acetonitrile in water (10.0 mL/min flow rate, $t_R$=110 min) to provide the title compound. $^1$H NMR (700 MHz, CDCl$_3$/CH$_3$CN, ° C.) δ 7.62 (d, J=8.2 Hz, 1H), 7.54 (s, 1H), 7.53 (d, J=8.2 Hz, 1H); $^{13}$C NMR (175 MHz, CDCl$_3$/CH$_3$CN, 25° C.): δ 145.4, 132.2, 131.8, 130.7 (q, J=34.2 Hz), 125.3 (q, J=3.9 Hz), 123.2 (q, J=273.2 Hz), 120.6 (q, J=260.6 Hz), 120.2. $^{19}$F NMR (376 MHz, CDCl$_3$, 25° C.) δ −58.7 (s, 3F), −63.4 (s, 3F).

3,5-Difluoro-(trifluoromethoxy)benzoic acid (4g)

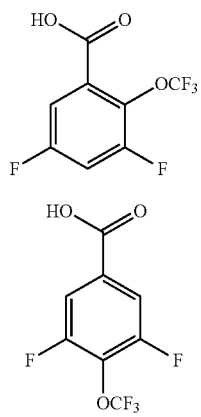

The reaction was performed according to the general procedure B using 3,5-difluorobenzoic acid (0.316 g, 2.00 mmol) as the substrate. After 16 h, the reaction mixture (70% yield with 4g-1:4g-2=3.4:1 by $^{19}$F NMR) was concentrated and added NaOH solution (1.00 M, 5 mL) dichloromethane (10 mL) and extracted with dichloromethane (3×10 mL). Then to the aqueous layer was added HCl solution (1.00 M, 20 mL) and extracted with ethyl acetate (5×20 mL), dried with MgSO$_4$ and concentrated. Then the mixture was purified by HPLC on the Luna® PFP(2) preparative column (250×21.2 mm) using 40% v/v acetonitrile in water (with 0.1% TFA) (12 mL/min flow rate) to provide the title compound(s). And 287 mg unreacted substrate (3,5-difluorobenzoic acid) (91 with respect to 3,5-difluorobenzoic acid) was recovered. ($t_R$=15.0 min).

3,5-difluoro-2-(trifluoromethoxy)benzoic acid (4g-1). 24.9 mg, 51% yield, $t_R$=31 min. $^1$H NMR (400 MHz, CDCl$_3$, 25° C.), δ 7.61-7.58 (m, 1H), 7.25-7.20 (m, 1H); $^{13}$C NMR (175 MHz, CDCl$_3$, 25° C.), δ 167.1, 160.1 (dd, J=252.5 Hz, 11.3 Hz), 156.2 (dd, J=257.4 Hz, 13.6 Hz), 133.0-132.9 (m), 127.6, 120.4 (q, J=260.8), 114.9-114.7 (m), 110.6-110.3 (m). $^{19}$F NMR (376 MHz, CDCl$_3$, 25° C.) δ −59.2 (d, J=9.5 Hz, 3F), −108.39--108.45 (m, 1F), −120.45--120.52 (m, 1F).

3,5-Difluoro-4-(trifluoromethoxy)benzoic acid (4g-2): 7.1 mg, 15% yield, $t_R$=47 min. $^1$H NMR (400 MHz, CDCl$_3$, 25° C.), δ 7.80-7.77 (m, 2H); $^{13}$C NMR (175 MHz, CDCl$_3$, 25° C.), δ 168.5, 156.0 (dd, J=257.5 Hz, 2.6 Hz), 130.1-129.9 (m), 129.5-129.4 (m), 120.5 (q, J=262.7 Hz), 114.8-114.7 (m), $^{19}$F NMR (376 MHz, CDCl$_3$, 25° C.) δ −59.8 (dd, J=8.2 Hz, 8.2 Hz, 3F), −122.46--122.54 (m, 2F). HRMS (ESI) m/z calcd for C$_7$H$_4$NOF$_2$S [(M−H)$^-$], 240.9924, found, 240.9924.

(Trifluoromethoxy)benzoic acid (4h)

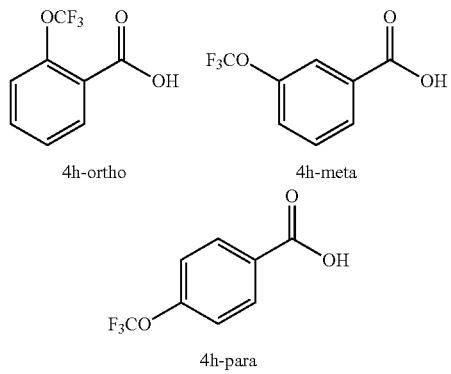

The reaction was performed according to the general procedure B using benzoic acid (0.412 g, 2.00 mmol) as the substrate. After 16 h, the reaction mixture (63% yield with o:m:p=1.8:2.4:1 by $^{19}$F NMR) was purified by HPLC on the Luna® PFP(2) preparative column (250×21.2 mm) using 50 v/v acetonitrile in water (contains 0.1z trifluoroacetic acid) (12 mL/min flow rate, $t_R$=52 min) to provide 3-(trifluoromethoxy)benzoic acid (4h-meta): $^1$H NMR (400 MHz, CDCl$_3$, 25° C.) δ 8.06 (d, J=7.9 Hz, 1H), 7.97 (s, 1H), 7.54 (dd, J=7.9 Hz, 7.9 Hz, 1H), 7.48 (d, J=7.9 Hz, 1H); $^{13}$C NMR (176 MHz, CDCl$_3$, 25° C.) δ 170.2, 149.4, 131.3, 130.3, 128.7, 126.5, 122.8, 120.5 (q, J=258.3 Hz); $^{19}$F NMR (376 MHz, CDCl$_3$, 25° C.) δ −58.3 (s, 3F). HRMS (ESI): Calcd for: C$_8$H$_4$O$_3$F$_3^-$ ([M−H]$^-$) 205.0113, found: 205.0114.

2-(Trifluoromethoxy)benzoic acid (4h-ortho): $T_R$=34 min. $^1$H NMR (500 MHz, CDCl$_3$, 25° C.) δ 8.11 (dd, J=7.8, 1.3 Hz, 1H), 7.63 (ddd, J=7.8, 7.8, 1.3 Hz, 1H), 7.43 (dd, J=7.8 Hz, 1H), 7.38 (d, J=7.8 Hz, 1H); $^{13}$C NMR (176 MHz, CDCl$_3$, 25° C.) δ 169.4, 148.7, 134.8, 133.1, 127.3, 123.9, 123.0, 120.5 (q, J=257.9 Hz); $^{19}$F NMR (376 MHz, CDCl$_3$, 25° C.) δ −58.1 (s, 3F). The spectroscopic data is in agreement with the literature.[12]

4-(Trifluoromethoxy)benzoic acid (4h-para): $T_R$=55 min. $^1$H NMR (500 MHz, CDCl$_3$, 25° C.) δ $^1$H NMR: δ=8.17 (dd, J=8.8, 3.1 Hz, 2H), 7.31 (d, J=8.8 Hz, 2H); $^{19}$F NMR (376 MHz, CDCl$_3$, 25° C.) δ −58.7 (s, 3F). The spectroscopic data is in agreement with the literature.[12]

(Trifluoromethoxy)phenylethanone (4i)

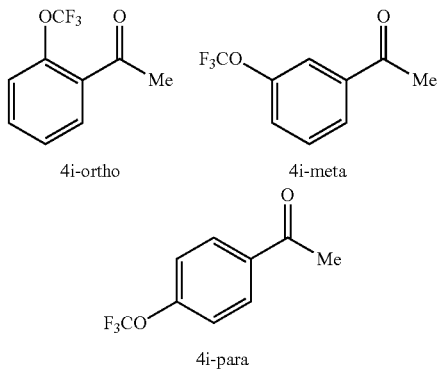

The reaction was performed according to the general procedure A using acetophenone (0.240 g, 2.00 mmol) as the substrate. After 16 h, the reaction mixture (73S yield with o:m:p=1.6:1.9:1 by $^{19}$F NMR) was purified by HPLC on the Luna® PFP(2) preparative column (250×21.2 mm) using 50% v/v acetonitrile in water (12 mL/min flow rate, $t_R$=43 min) to provide a mixture of o-, m-, and p-regioisomers.

1-(3-(Trifluoromethoxy)phenyl)ethanone (4i-meta): $^1$H NMR (500 MHz, CDCl$_3$/CH$_3$CN, 25° C.) δ 7.91 (d, J=7.7 Hz, 1H), 7.76 (s, 1H), 7.59 (t, J=7.9 Hz, 1H), 7.43 (d, J=8.2 Hz, 1H), 2.60 (s, 3H). $^{19}$F NMR (376 MHz, CDCl$_3$/CH$_3$CN, 25° C.) δ −57.9 (s, 3F). The spectroscopic data is in agreement with the literature.[13]

1-(4-(Trifluoromethoxy)phenyl)ethanone (4i-para): $^1$H NMR (500 MHz, CDCl$_3$/CH$_3$CN, 25° C.) δ 8.02-7.95 (m, 2H), 7.27 (d, J=8.0 Hz, 2H), 2.59 (s, 3H). $^{19}$F NMR (376 MHz, CDCl$_3$/CH$_3$CN, 25° C.) δ −57.7 (s, 3F). The spectroscopic data is in agreement with the literature.[13]

1-(2-(Trifluoromethoxy)phenyl)ethanone (4i-ortho): $T_R$=40 min. $^1$H NMR (700 MHz, CDCl$_3$/CH$_3$CN, 25° C.) δ 7.70 (dd, J=7.7, 1.7 Hz, 1H), 7.56 (ddd, J=8.3, 7.7, 1.7 Hz, 1H), 7.49 (ddd, J=7.7, 7.7, 1.1 Hz, 1H), 7.41 (ddd, J=8.3, 1.7, 1.1 Hz, 1H), 2.53 (s, 3H); $^{13}$C NMR (175 MHz, CDCl$_3$/CH$_3$CN, 25° C.) δ 199.2, 147.7, 134.8, 133.9, 131.6, 128.8, 122.9, 121.6 (q, J=257.3 Hz), 31.5; $^{19}$F NMR (376 MHz, CDCl$_3$/CH$_3$CN, 25° C.) δ −57.7 (s, 3F). HRMS (EI): Calcd for: C$_3$H$_7$O$_2$F$_3^+$ (M$^+$) 204.0398, found: 204.0400.

Methyl 3-(trifluoromethoxy)benzoate (4j)

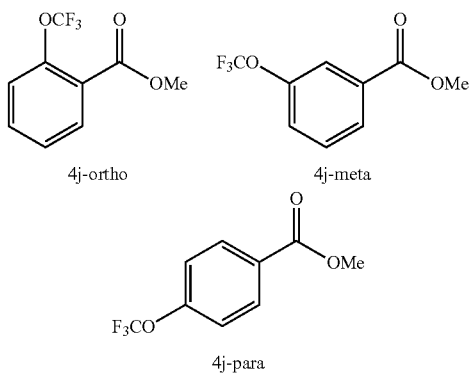

The reaction was performed according to the general procedure A using methyl benzoate (0.272 g, 2.00 mmol) as the substrate. After 16 h, the reaction mixture (75% yield with o:m:p=1.8:2.2:1 by $^{19}$F NMR) was purified by HPLC on the Luna® PFP(2) preparative column (250×21.2 mm) using 50 v/v acetonitrile in water (10 mL/min flow rate, $t_R$=42 min) to provide a mixture of m-, p-regioisomers.

Methyl 3-(trifluoromethoxy)benzoate (4j-meta): $^1$H NMR (500 MHz, CDCl$_3$, 25° C.), δ 7.98 (d, J=8.0 Hz, 1H), 7.89 (s, 1H), 7.48 (dd, J=8.0 Hz), 7.41 (d, J=8.0 Hz, 1H), 3.94 (s, 3H); $^{13}$C NMR (175 MHz, CDCl$_3$, ° C.), δ 165.9, 149.4, 132.4, 130.1, 128.1, 125.6, 122.3, 120.6 (q, J=258.0 Hz), 52.7; $^{19}$F NMR (376 MHz, CDCl$_3$, 25° C.) δ −58.5 (s, 3F). The spectroscopic data is in agreement with the literature.[14]

Methyl 4-(trifluoromethoxy)benzoate (4j-para): $^1$H NMR (500 MHz, CDCl$_3$, 25° C.) δ 8.10-8.08 (m, 2H), 7.26 (d, J=8.7 Hz, 2H), 3.92 (s, 3H). $^{13}$C NMR (175 MHz, CDCl$_3$, 25° C.) δ 166.1, 152.8, 131.8, 128.7, 120.5 (q, J=258.7 Hz), 120.6, 52.6. $^{19}$F NMR (376 MHz, CDCl$_3$, 25° C.) δ −58.2 (s, 3F). The spectroscopic data is in agreement with the literature.[13]

Methyl 2-(trifluoromethoxy)benzoate (4j-ortho): $T_R$=32 min. $^1$H NMR (400 MHz, CDCl$_3$, 25° C.), δ 7.98 (d, J=7.6 Hz, 1H), 7.56 (ddd, J=8.2, 7.6, 1.6 Hz, 1H), 7.38 (ddd, J=7.6 Hz, 7.6 Hz, 0.8 Hz, 1H), 7.33 (d, 8.2 Hz, 1H), 3.93 (s, 3H); $^{13}$C NMR (175 MHz, CDCl$_3$, 25° C.), δ 165.2, 147.8, 133.7, 132.2, 127.1, 125.1, 122.8, 120.5 (q, J=255.8 Hz), 52.6; $^{19}$F NMR (376 MHz, CDCl$_3$, 25° C.) δ −58.0 (s, 3F). HRMS (EI): Calcd for: C$_9$H$_7$O$_3$F$_3^+$ (M$^+$) 220.0347, found: 220.0348.

Dimethyl 5-methyl-(trifluoromethoxy)isophthalate (4k)

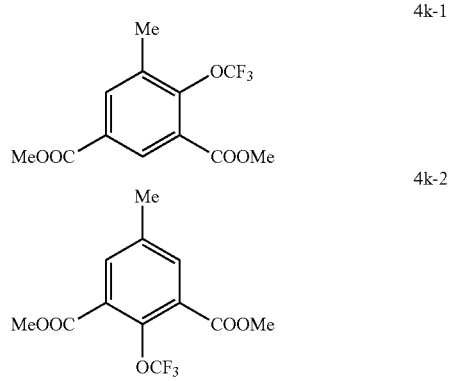

The reaction was performed according to the general procedure B using dimethyl 5-methylisophthalate (0.416 g, 2.00 mmol) as the substrate. After 16 h, the reaction mixture (63S yield with 4k-1:4k-2=2.2:1 by $^{19}$F NMR) was purified by HPLC on the Luna® PFP(2) preparative column (250× 21.2 mm) using 40 v/v acetonitrile in water (10 mL/min flow rate) to provide dimethyl 5-methyl-4-(trifluoromethoxy) isophthalate (4k-1). $t_R$=57.8 min. $^1$H NMR (400 MHz, CDCl$_3$, 25° C.), δ 8.38 (d, J=2.0 Hz, 1H), 8.11 (d, J=2.0 Hz, 1H), 3.94 (s, 6H), 2.43 (s, 3H); $^{13}$C NMR (175 MHz, CDCl$_3$, 25° C.), δ 165.4, 165.1, 148.9, 136.5, 134.4, 130.9, 129.1, 127.0, 120.6 (q, J=259.2), 52.79, 52.73, 16.7. $^{19}$F NMR (376 MHz, CDCl$_3$, 25° C.) δ −56.9 (s, 3F).

Dimethyl 5-methyl-2-(trifluoromethoxy)isophthalate (4k-2): $t_R$=69.3 min. $^1$H NMR (400 MHz, CDCl$_3$, 25° C.), δ 7.84

(s, 2H), 3.93 (s, 6H), 2.43 (s, 3H); $^{13}$C NMR (175 MHz, CDCl$_3$, 25° C.), δ 165.1, 143.1 (q, J=2.6 Hz), 137.7, 135.5, 127.3, 120.2 (q, J=258.1), 52.7, 20.7. $^{19}$F NMR (376 MHz, CDCl$_3$, 25° C.) δ −58.2 (s, 3F). HRMS (ESI) m/z calcd for C$_{12}$H$_{12}$O$_5$F$_3$ [(M+H)$^+$], 293.0637, found, 293.0635.

(Trifluoromethoxy)benzene (41)

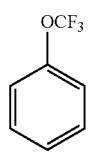

41

The reaction was performed according to the general procedure A using benzene (0.156 g, 2.00 mmol) as the substrate. After 16 h, the reaction mixture (63% yield by $^{19}$F NMR) was purified by HPLC on the Luna® PFP(2) preparative column (250×21.2 mm) using 65% v/v acetonitrile in water (12.0 mL/min flow rate, t$_R$=16.5 min) to provide the title compound. $^1$H NMR (400 MHz, CDCl$_3$/CH$_3$CN, 25° C.) δ 7.41 (t, J=7.8 Hz, 2H), 7.29 (dd, J=7.8, 7.8 Hz), 7.22 (d, J=7.8 Hz); $^{13}$C NMR (175 MHz, CDCl$_3$/CH$_3$CN, 25° C.) δ 149.4, 129.9, 126.9, 121.1, 120.6 (q, J=256.7 Hz); $^{19}$F NMR (376 MHz, CDCl$_3$/CH$_3$CN, 25° C.) δ −58.5 (s, 3F). The spectroscopic data is in agreement with the literature.[11]

1-Methyl-(trifluoromethoxy)benzene (4m)

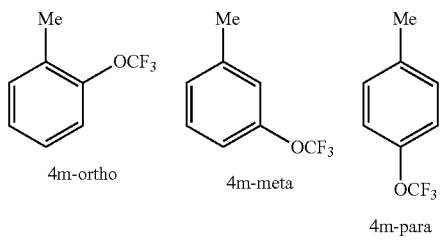 [SMILES: Cc1ccccc1OC(F)(F)F ; Cc1cccc(OC(F)(F)F)c1 ; Cc1ccc(OC(F)(F)F)cc1]

4m-ortho  4m-meta  4m-para

The reaction was performed according to the general procedure A using toluene (0.184 g, 2.00 mmol) as the substrate. After 16 h, the reaction mixture (54% yield with o:m:p=1.7:1:1.3 by $^{19}$F NMR) was purified by HPLC on the Luna® PFP(2) preparative column (250×21.2 mm) using 45% v/v acetonitrile in water (12 mL/min flow rate, t, =80.8 min) to provide a mixture of o-,m-,p-regioisomers.

1-Methyl-2-(trifluoromethoxy)benzene (4m-ortho): 1H NMR (400 MHz, CDCl$_3$/CH$_3$CN, 25° C.), δ 7.20 (m, 4H), 2.28 (s, 3H); $^{19}$F NMR (376 MHz, CDCl$_3$/CH$_3$CN, 25° C.) δ −57.8 (s, 3F). The spectroscopic data is in agreement with the literature[15].

1-Methyl-3-(trifluoromethoxy)benzene (4m-meta): $^1$H NMR (400 MHz, CDCl$_3$/CH$_3$CN, 25° C.) δ7.22 (m, 1H), 7.05 (m, 1H), 2.28 (s, 3H); $^{19}$F NMR (376 MHz, CDCl$_3$/CH$_3$CN, 25° C.) δ −58.1 (s, 3F). The spectroscopic data is in agreement with the literature[15].

1-Methyl-4-(trifluoromethoxy)benzene (4m-para): $^1$H NMR (400 MHz, CDCl$_3$/CH$_3$CN, 25° C.), δ 7.29 (m, 2H), 7.21 (m, 2H), 2.32 (s, 3H); $^{19}$F NMR (376 MHz, CDCl$_3$/CH$_3$CN, 25° C.) δ −58.3 (s, 3F). The spectroscopic data is in agreement with the literature[15].

1-(tert-Butyl)-(trifluoromethoxy)benzene (4n)

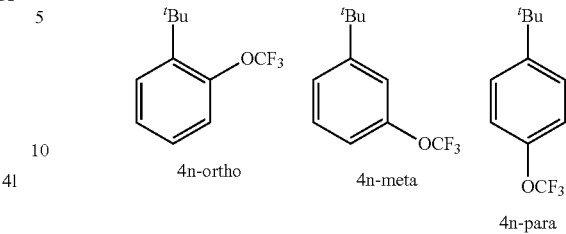

4n-ortho  4n-meta  4n-para

The reaction was performed according to the general procedure A using tert-butyl benzene (0.268 g, 2.00 mmol) as the substrate. After 16 h, the reaction mixture (61% yield with o:m:p=1:2.6:3.2 by $^{19}$F NMR) was purified by HPLC on the Luna® PFP (2) preparative column (250×21.2 mm) using 50G v/v acetonitrile in water (10 mL/min flow rate, t$_r$=120 min) to provide a mixture of o-,m-,p-regioisomers.

1-(tert-Butyl)-3-(trifluoromethoxy)benzene (4n-meta): $^1$H NMR (400 MHz, CDCl$_3$/CH$_3$CN, 25° C.) 57.31 (m, 2H), 7.20 (s, 1H), 7.03 (m, 1H), 1.32 (s, 9H). $^{19}$F NMR (376 MHz, CDCl$_3$/CH$_3$CN, 25° C.) δ −58.2 (s, 3F). The spectroscopic data is in agreement with the literature[16].

1-(tert-Butyl)-4-(trifluoromethoxy)benzene (4n-para): $^1$H NMR (400 MHz, CDCl$_3$/CH$_3$CN, 25° C.), δ 7.40 (m, 2H), 7.13 (m, 2H), 1.32 (s, 9H). $^{19}$F NMR (376 MHz, CDCl$_3$/CH$_3$CN, 25° C.) δ −58.0 (s, 3F). The spectroscopic data is in agreement with the literature[17].

4-(tert-Butyl)-(trifluoromethoxy)benzonitrile (4o)

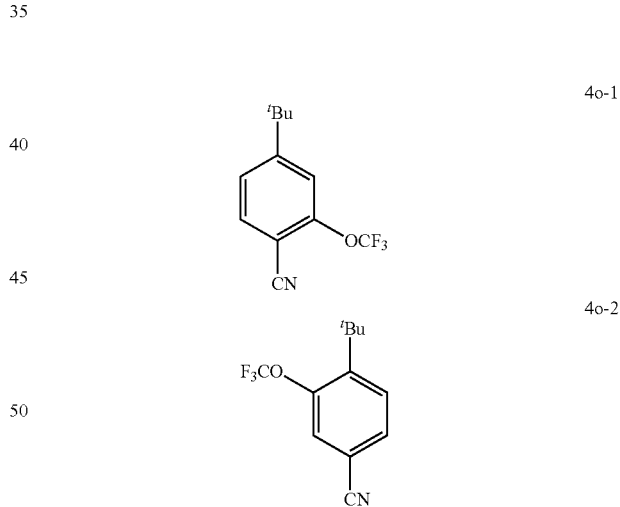

4o-1

4o-2

The reaction was performed according to the general procedure A using 4-(tert-butyl)benzonitrile (0.320 g, 2.00 mmol) as the substrate. After 16 h, the reaction mixture (56% yield with 4o-1:4o-2=13:1 by $^{19}$F NMR) was purified by HPLC on the Luna® PFP(2) preparative column (250× 21.2 mm) using 60G v/v acetonitrile in water (10 mL/min flow rate, t$_R$=61 min) to provide 4-(tert-butyl)-2-(trifluoromethoxy)benzonitrile (4o-1). 1H NMR (400 MHz, CDCl$_3$, 25° C.) δ 7.63 (d, J=8.2 Hz, 1H), 7.43 (dd, J=8.2, 1.5 Hz, 1H), 7.38 (dd, J=1.5 Hz, 1.5 Hz, 1H), 1.34 (s, 9H); =$^{13}$C NMR (175 MHz, CDCl$_3$, 25° C.), δ 159.6, 150.0, 133.7, 124.6, 120.4 (q, J=260.3 Hz), 119.0, 114.7, 104.4, 35.7, 30.9; $^{19}$F NMR (376 MHz, CDCl$_3$, 25° C.) δ −58.5 (s, 3F). HRMS (EI): Calcd for: C$_{12}$H$_{12}$OF$_3$N$^+$ (M$^+$) 243.0871, found: 243.0866.

Phenyl (trifluoromethoxy)phenyl carbonate (4p)

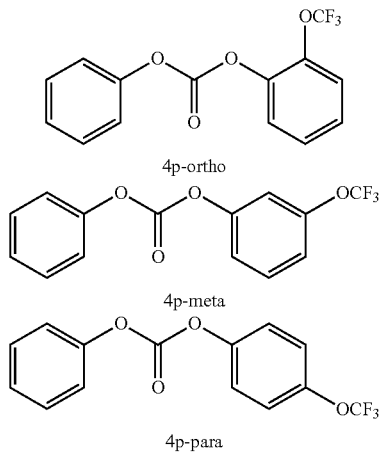

4p-ortho 4p-meta 4p-para

The reaction was performed according to the general procedure A using diphenyl carbonate (0.428 g, 2.00 mmol) as the substrate. After 16 h, the reaction mixture (84S yield with o:m:p=1.3:1:1.1 by $^{19}$F NMR) was purified by HPLC on the Luna® PFP (2) preparative column (250×21.2 mm) using 70% v/v acetonitrile in water (10.0 mL/min flow rate, $t_R$=27 min) to provide a mixture of m- and p-regioisomers.

Phenyl (3-(trifluoromethoxy)phenyl) carbonate (4p-meta): $^1$H NMR (700 MHz, CDCl$_3$, 25° C.) δ 7.46-7.42 (m, 2H), 7.34-7.25 (m, 5H), 7.22 (s, 1H), 7.16 (ddd, J=8.3, 1.0, 1.0 Hz, 1H); $^{19}$F NMR (376 MHz, CDCl$_3$, 25° C.) δ −58.0 (s, 3F).

Phenyl (4-(trifluoromethoxy)phenyl) carbonate (4p-para): 1H NMR (700 MHz, CDCl$_3$, 25° C.) δ 7.46-7.42 (m, 2H), 7.34-7.25 (m, 7H); $^{13}$C NMR (175 MHz, CDCl$_3$, 25° C.) (a mixture of 3-,4-regioisomers) δ 151.8, 151.6, 151.5, 150.9, 150.8, 149.6, 149.1, 146.9, 130.4, 129.7, 126.54, 126.50, 122.32, 122.25, 120.8, 120.41 (q, J=258.5 Hz), 120.36 (q, J=258.7 Hz), 119.4, 118.7, 114.4. $^{19}$F NMR (376 MHz, CDCl$_3$, 25° C.) δ −58.1 (s, 3F).

Phenyl (2-(trifluoromethoxy)phenyl) carbonate (4p-ortho): $t_R$=25 min. $^1$H NMR (400 MHz, CDCl$_3$, 25° C.) δ 7.33-7.41 (m, 2H), 7.40-7.37 (m, 2H), 7.36 (td, J=7.7, 1.8 Hz, 1H), 7.34-7.31 (m, 1H), 7.29 (dd, J=7.7 Hz, 7.7 Hz, 1H), 7.27-7.25 (m, 2H); $^{13}$C NMR (175 MHz, CDCl$_3$, ° C.) δ 151.4, 151.1, 142.9, 140.8 (d, J=2.9 Hz), 129.8, 127.9, 127.6, 126.6, 123.7, 122.5, 120.9, 120.6 (q, J=259.4 Hz); $^{19}$F NMR (376 MHz, CDCl$_3$, 25° C.) δ −58.6 (s, 3F). HRMS (EI): Calcd for: C$_{14}$H$_9$O$_4$F$_3^+$ (M$^+$) 298.0453, found: 298.0458.

1-(Phenylsulfonyl)-(trifluoromethoxy)benzene (4q)

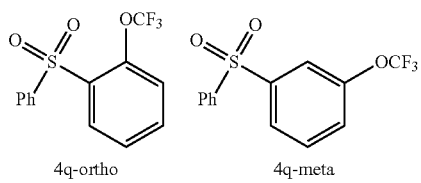

4q-ortho 4q-meta

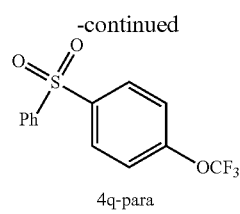

4q-para

The reaction was performed according to the general procedure B using sulfonyldibenzene (0.436 g, 2.00 mmol) as the substrate. After 16 h, the reaction mixture (71% yield with o:m:p=1:4.1:1.4 by $^{19}$F NMR) was purified by HPLC on the Luna® PFP(2) preparative column (250×21.2 mm) using 45% v/v acetonitrile in water (10.0 mL/min flow rate, $t_R$=87 min) to provide a mixture of m- and p-regioisomers.

1-(Phenylsulfonyl)-3-(trifluoromethoxy)benzene (4q-meta) $^1$H NMR (700 MHz, CDCl$_3$, 25° C.) δ 7.96-7.94 (m, 2H), 7.87 (d, J=7.9 Hz, 1H), 7.80 (s, 1H) 7.62-7.52 (m, 4H), 7.41 (d, J=8.2 Hz, 1H); $^{19}$F NMR (376 MHz, CDCl$_3$, 25° C.) δ −58.5 (s, 3F).

1-(Phenylsulfonyl)-4-(trifluoromethoxy)benzene (4q-para): $^1$H NMR (700 MHz, CDCl$_3$, 25° C.) δ 8.01-7.99 (m, 2H), 7.96-7.94 (m, 2H), 7.62-7.52 (m, 3H), 7.32 (d, J=8.3 Hz, 2H); $^{19}$F NMR (376 MHz, CDCl$_3$, 25° C.) δ −58.2 (s, 3F). $^{13}$C NMR (175 MHz, CDCl$_3$, 25° C.) (a mixture of m-, p-regioisomers) δ 152.7, 149.6, 143.3, 141.2, 140.9, 140.1, 133.8, 133.7, 131.1, 130.1, 129.65, 129.60, 127.97, 127.86, 126.1, 125.6, 121.2, 120.36 (q, J=259.2 Hz), 120.27 (q, J=262.3 Hz), 120.3. HRMS (ESI) m/z calcd for C$_{13}$H$_{10}$O$_3$F$_3$S [(M+H)$^+$], 303.0303, found, 303.0300.

Diphenyl(3-(trifluoromethoxy)phenyl)phosphine oxide (4r)

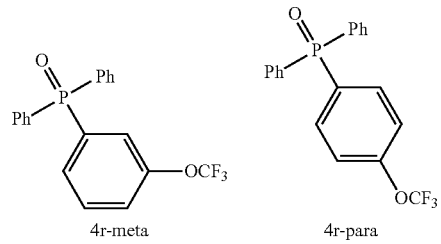 [SMILES: O=P(c1ccccc1)(c1ccccc1)c1cccc(OC(F)(F)F)c1 ; O=P(c1ccccc1)(c1ccccc1)c1ccc(OC(F)(F)F)cc1]

4r-meta 4r-para

The reaction was performed according to the general procedure A using triphenylphosphine oxide (0.556 g, 2.00 mmol) as the substrate. After 16 h, the reaction mixture (75% yield, m:p=2.4:1 by $^{19}$F NMR) was concentrated and performed flash chromatography using hexanes:ethyl acetate=5:1 to 2:1 v/v to obtain a crude product (R$_f$=0.23, hexanes:ethyl acetate=1:1 v/v) and 439 mg (79% with respect to triphenylphosphine oxide) unreacted triphenylphosphine oxide (R$_f$=0.14 ethyl hexanes:ethyl acetate=1:1 v/v) was recovered. The crude product was further purified by HPLC on Luna® PFP(2) preparative column (250×21.2 mm) using 50% v/v acetonitrile in water (10.0 mL/min flow rate, $t_R$=26 min) to provide the a mixture of m-, p-regioisomers (49.3 mg, 68% yield).

Diphenyl(3-(trifluoromethoxy)phenyl)phosphine oxide (4r-meta): $^1$H NMR (700 MHz, CDCl$_3$, 25° C.) δ 7.71 (dd, J=11.3, 8.7 Hz, 1H), 7.66 (dd, J=12.1, 7.1 Hz, 4H), 7.62-7.45 (m, 9H); $^{19}$F NMR (376 MHz, CDCl$_3$, 25° C.) δ −58.3 (s, 3F). $^{31}$P NMR (202 MHz, CDCl$_3$, 25° C.) δ −27.8 (s, 1P). The spectroscopic data is in agreement with the literature.[18]

Diphenyl(4-(trifluoromethoxy)phenyl)phosphine oxide (4r-para): $^1$H NMR (700 MHz, CDCl$_3$, 25° C.) δ 7.73-7.65 (m, 6H), 7.49-7.47 (m, 4H), 7.39 (d, J=8.4 Hz, 2H) 7.30 (d, J=8.4 Hz, 2H); $^{13}$C NMR. (175 MHz, CDCl$_3$, 25° C.): δ 152.1, 134.3 (d, J=11.3 Hz), 132.4 (d, J=2.5 Hz), 132.3 (d, J=10.2 Hz), 132.2 (d, J=99.2 Hz), 130.6, 128.8 (d, J=12.7 Hz), 120.7 (d, J=12.8 Hz), 120.5 (q, J=258.6 Hz). $^{19}$F NMR (376 MHz, CDCl$_3$, 25° C.) δ −58.1 (s, 3F). $^{31}$P NMR (202 MHz, CDCl$_3$, 25° C.) δ −28.0 (s, 1P). The spectroscopic data is in agreement with the literature.[19]

2,6-Dichloro-3-(trifluoromethoxy)pyridine (4s)

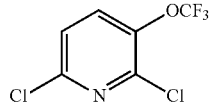

The reaction was performed according to the general procedure B using 2,6-dichloropyridine (0.362 g, 2.00 mmol) as the substrate. After 16 h, the reaction mixture (73% yield by $^{19}$F NMR) was purified by HPLC on the Gemini® 5 μm NX-C18 semi-preparative column (250×10 mm) using 50% v/v acetonitrile in water (3.5 mL/min flow rate, $t_R$=26 min) to provide the title compound. $^1$H NMR (400 MHz, CDCl$_3$, 25° C.) δ 7.6 (dd, J=8.4, 1.2 Hz, 1H), 7.3 (d, J=8.4 Hz, 1H); $^{13}$C NMR (175 MHz, CDCl$_3$, ° C.) δ 148.0, 144.3, 141.5, 133.0, 124.1, 120.5 (q, J=261.6 Hz); $^{19}$F NMR (376 MHz, CDCl$_3$, 25° C.) δ −58.9 (s, 3F). HRMS (EI): Calcd for: C$_6$H$_2$ONF$_3$Cl$_2$$^+$ (M$^+$) 230.9456, found: 230.9462.

2,4,6-Trichloro-3-(trifluoromethoxy)pyridine (4t)

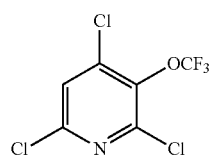

The reaction was performed according to the general procedure B using 2,4,6-trichloropyridine (0.362 g, 2.00 mmol) as the substrate. After 16 h, the reaction mixture (82% yield by $^{19}$F NMR) was purified by HPLC on the Gemini® 5 μm NX-C18 semi-preparative column (250×10 mm) using 604 v/v acetonitrile in water (3.5 mL/min flow rate, $t_R$=23 min) to provide the title compound. $^1$H NMR (400 MHz, CDCl$_3$, 25° C.) 7.4 (s, 1H); $^{13}$C NMR (175 MHz, CDCl$_3$, 25° C.) δ 148.4, 146.6, 142.3, 139.1, 125.3, 120.7 (q, J=264.1 Hz); $^{19}$F NMR (376 MHz, CDCl$_3$, 25° C.) δ −56.9 (s, 3F). HRMS (EI): Calcd for: C$_6$HONF$_3$Cl$_3$$^+$ (M$^+$) 264.9076, found: 264.9070.

Dimethyl 4-methoxy-3-(trifluoromethoxy)pyridine-2,6-dicarboxylate (4u)

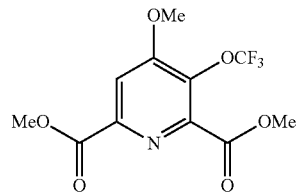

Dimethyl 4-methoxypyridine-2,6-dicarboxylate was prepared according to reported procedures (Pellegatti, L. et al. 2008; Zeng, T. et al. 2011). The reaction was performed according to the general procedure B using dimethyl 4-methoxypyridine-2,6-dicarboxylate (0.550 g, 2.00 mmol) as the substrate. After 16 h, the reaction mixture (78% yield by $^{19}$F NMR) was purified by HPLC on the Gemini® 5 μm NX-C18 semi-preparative column (250×10 mm) using 40% v/v acetonitrile in water (3.5 mL/min flow rate, $t_R$=19 min) to provide the title compound. $^1$H NMR (400 MHz, CDCl$_3$, 25° C.) δ 7.91 (s, 1H), 4.06 (s, 3H), 4.02 (s, 3H), 3.99 (s, 3H); $^{13}$C NMR (175 MHz, CDCl$_3$, 25° C.) δ 164.4, 163.4, 160.6, 147.8, 145.3, 136.5, 120.5 (q, J=260.6 Hz), 111.8, 57.2, 53.7, 53.4; $^{19}$F NMR (376 MHz, CDCl$_3$, 25° C.) δ −58.2 (s, 3F). HRMS (ESI): Calcd for: C$_{11}$H$_{11}$NO$_6$F$_3$$^+$ ([M+H]$^+$) 310.0538, found: 310.0530.

2,4-Dichloro-6-methyl-5-(trifluoromethoxy)pyrimidine (4v)

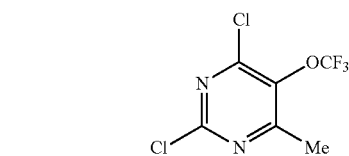

The reaction was performed according to the general procedure B using 2,4-dichloro-6-methylpyrimidine (0.324 g, 2.00 mmol) as the substrate. After 16 h, the reaction mixture (72% yield by $^{19}$F NMR) was purified by HPLC on the Gemini® 5 μm NX-C18 semi-preparative column (250× 10 mm) using 65% v/v acetonitrile in water (3.5 mL/min flow rate, to =25 min) to provide the title compound. $^1$H NMR (400 MHz, CDCl$_3$) δ 2.60 (s, 3H); $^{13}$C NMR (175 MHz, CDCl$_3$, 25° C.) δ 166.6, 157.1, 157.0, 139.3, 120.8 (q, J=264.3 Hz), 20.1; $^{19}$F NMR (376 MHz, CDCl$_3$, 25° C.) δ −57.5 (s, 3F). HRMS (EI): Calcd for: C$_6$H$_3$ON$_2$F$_3$Cl$_2$$^+$ (M$^+$) 245.9575, found: 245.9577.

4,6-Dichloro-2-methyl-5-(trifluoromethoxy)pyrimidine (4w)

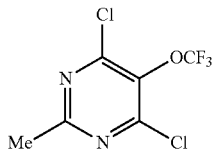

The reaction was performed according to the general procedure B using 4,6-dichloro-2-methylpyrimidine (0.324 g, 2.00 mmol) as the substrate. After 16 h, the reaction mixture (74% yield by $^{19}$F NMR) was purified by HPLC on the Gemini® 5 μm NX-C18 semi-preparative column (250× 10 mm) using 40% v/v acetonitrile in water (3.5 mL/min flow rate, $t_R$=19 min) to provide the title compound. $^1$H NMR (400 MHz, CDCl$_3$, 25° C.) δ 2.72 (s, 3H); $^{13}$C NMR (175 MHz, CDCl$_3$, 25° C.) δ 166.9, 156.1, 136.2, 120.7 (q, J=264.5 Hz), 25.4; $^{19}$F NMR (376 MHz, CDCl$_3$, 25° C.) δ −57.1 (s, 3F). HRMS (EI): Calcd for: $C_6H_3ON_2F3Cl_2^+$ (M$^+$) 245.9575, found: 245.9576.

2,4,6-Trichloro-5-(trifluoromethoxy)pyrimidine (4x)

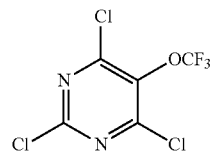

The reaction was performed according to the general procedure B using 2,4,6-trichloropyrimidine (0.364 g, 2.00 mmol) as the substrate. After 16 h, the reaction mixture (62% yield by $^{19}$F NMR) was purified by HPLC on Luna® PFP(2) preparative column (250×21.2 mm) using 45% v/v acetonitrile in water (10 mL/min flow rate, $t_R$=42 min) to provide the title compound. $^{13}$C NMR (175 MHz, CDCl$_3$, 25° C.) δ 158.0, 156.7, 137.8, 120.6 (q, J=265.7 Hz); $^{19}$F NMR (376 MHz, CDCl$_3$, 25° C.) δ −56.8 (s, 3F). HRMS (EI) m/z calcd for $C_5N_2OF_3Cl_3$[M$^+$], 265.9028, found, 265.9031.

3,4-Dibromo-2-(trifluoromethoxy)thiophene (4y)

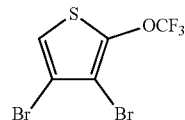

The reaction was performed according to the general procedure A using 3,4-dibromothiophene (0.480 g, 2.00 mmol) as the substrate. After 16 h, the reaction mixture (60% yield by $^{19}$F NMR) was purified by HPLC on Luna® PFP(2) preparative column (250×21.2 mm) using 40% v/v acetonitrile in water (10 mL/min flow rate, $t_R$=35.0 min). Fractions containing the desired product was combined and extracted with diethyl ether, dried with MgSO$_4$ and concentrated to provide the title compound (34.3 mg, 53% yield, calculated according to $^1$H NMR). $^1$H NMR (400 MHz, CDCl$_3$, 25° C.) δ 7.14 (s, 1H); $^{13}$C NMR (175 MHz, CDCl$_3$, 25° C.) δ 144.7, 120.2 (q, J=263.2 Hz), 117.2, 111.7, 107.5; $^{19}$F NMR (376 MHz, CDCl$_3$, ° C.) δ −59.9 (s, 3F). 441 mg unreacted substrate (3,4-dibromothiophene) was recovered ($t_A$=19 min, 92% recovery with respect to 3,4-dibromothiophene) from the reaction mixture. HRMS (EI) m/z calcd for $C_5HOF_3SBr_2$ [M$^+$], 323.8067, found, 323.8067.

4-Bromo-(trifluoromethoxy)thiophene-2-carbonitrile (4z)

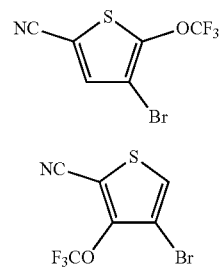

The reaction was performed according to the general procedure A using 4-bromothiophene-2-carbonitrile (0.374 g, 2.00 mmol) as the substrate. After 16 h, the reaction mixture (60S yield by $^{19}$F NMR, 4z-1:4z-2=7.7:1) was purified by HPLC on Luna® PFP(2) preparative column (250×21.2 mm) using 50 v/v acetonitrile in water (10 mL/min flow rate). Fractions containing products were combined and extracted with diethyl ether, dried with MgSO$_4$ and concentrated to provide title compounds. 325 mg (87% with respect to 4-bromothiophene-2-carbonitrile) unreacted substrate 4-bromothiophene-2-carbonitrile was recovered (t, =20.9 min).

4-Bromo-5-(trifluoromethoxy)thiophene-2-carbonitrile (4z-1). 25.9 mg, 48V yield calculated by $^1$H NMR, $t_R$=43.3 min. $^1$H NMR (400 MHz, CDCl$_3$, 25° C.) δ 7.43 (s, 1H); $^{13}$C NMR (175 MHz, CDCl$_3$, 25° C.) δ 148.6, 137.8, 120.0 (q, J=265.0 Hz), 112.2, 105.5, 104.3; $^{19}$F NMR (376 MHz, CDCl$_3$, 25° C.) δ −59.8 (s, 3F).

4-Bromo-2-(trifluoromethoxy)thiophene-2-carbonitrile (4z-2). $T_R$=28.9 min. $^1$H NMR (400 MHz, CDCl$_3$, 25° C.) δ 7.59 (s, 1H); $^{13}$C NMR (175 MHz, CDCl$_3$, 25° C.) δ 148.5, 129.0, 120.1 (q, J=263.5 Hz), 109.7, 107.7, 102.7; $^{19}$F NMR (376 MHz, CDCl$_3$, 25° C.) δ −58.0 (s, 3F). HRMS (EI) m/z calcd for $C_6HNOF_3SBr$ [M$^+$], 270.8914, found, 270.8916.

4-Bromo-(trifluoromethoxy)thiophene-2-carbaldehyde (4aa)

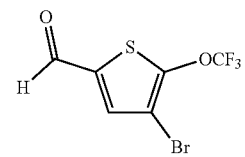

131

-continued

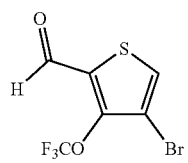
4aa-2

The reaction was performed according to the general procedure A using 4-bromothiophene-2-carbaldehyde (0.380 g, 2.00 mmol) as the substrate. After 16 h, the reaction mixture (48% yield by $^{19}$F NMR, 4aa-1:4aa-2=11:1) was purified by HPLC on Luna® PFP(2) preparative column (250×21.2 mm) using 45 v/v acetonitrile in water (10 mL/min flow rate, $t_R$=52 min) to provide 4-bromo-5-(trifluoromethoxy)thiophene-2-carbaldehyde (4aa-1). $^1$H NMR (400 MHz, CDCl$_3$, 25° C.) δ 9.80 (s, 1H), 7.58 (s, 1H); $^{13}$C NMR (175 MHz, CDCl$_3$, ° C.) δ 182.1, 152.3 (q, J=2.6 Hz), 136.8, 136.3, 120.1 (q, J=264.0), 104.5; $^{19}$F NMR (376 MHz, CDCl$_3$, 25° C.) δ −59.7 (s, 3F). HRMS (EI) m/z calcd for C$_6$H$_2$O$_2$F$_3$SBr [M$^+$], 273.8911, found, 273.8913.

4-Bromo-(trifluoromethoxy)thiophene-2-carboxylic acid (4ab)

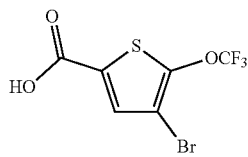
4ab-1

The reaction was performed according to the general procedure A using 4-bromothiophene-2-carboxylic acid (0.412 g, 2.00 mmol) as the substrate. After 16 h, the reaction mixture (52% yield by $^{19}$F NMR, 4ab-1:4ab-2=6.4:1) was concentrated and added NaOH solution (1.00 M, 5 mL) dichloromethane (10 mL) and extracted with dichloromethane (3×10 mL). Then to the aqueous layer was added HCl solution (1.00 M, 20 mL) and extracted with ethyl acetate (5×20 mL), dried with MgSO$_4$ and concentrated. Then the mixture was purified by HPLC on the Luna® PFP(2) preparative column (250×21.2 mm) using was purified by HPLC on Luna® PFP(2) preparative column (250×21.2 mm) using 35% v/v acetonitrile in water (with 0.1 TFA) 12 mL/min flow rate) to provide title compound(s). And 358 mg unreacted substrate (4-bromothiophene-2-carboxylic acid) (87 with respect to 4-bromothiophene-2-carboxylic acid) was recovered. ($t_R$=17.7 min). 4ab-2 was always mixed with inseparable impurities, so we failed to obtain the spectroscopically pure NMR spectra.

4-Bromo-5-(trifluoromethoxy)thiophene-2-carboxylic acid (4ab-1). 23.3 mg, 40% yield, $t_R$=48.7 min. $^1$H NMR (400 MHz, CDCl$_3$, 25° C.) δ 10.83 (br, 1H), 7.70 (s, 1H); $^{13}$C NMR (175 MHz, CDCl$_3$, 25° C.) δ 166.4, 150.5, 135.4, 126.4, 120.1 (q, J=263.8 Hz), 104.5; $^{19}$F NMR (376 MHz, CDCl$_3$, 25° C.) δ −60.2 (s, 3F). HRMS (EI) m/z calcd for C$_6$H$_2$O$_3$F$_3$SBr [M$^+$], 289.8860, found, 289.8863.

Ethyl (trifluoromethoxy)thiophene-2-carboxylate (4ac)

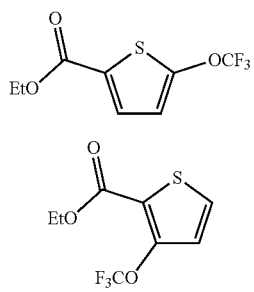
4ac-1

4ac-2

The reaction was performed according to the general procedure A using ethyl thiophene-2-carboxylate (0.312 g, 2.00 mmol) as the substrate. After 16 h, the reaction mixture (65% yield by $^{19}$F NMR, 4ac-1:4ac-2=1.5:1) was purified by HPLC on Luna® PFP(2) preparative column (250×21.2 mm) using 48S v/v acetonitrile in water (10 mL/min flow rate, $t_R$ 66.2 min) to provide ethyl 5-(trifluoromethoxy)thiophene-2-carboxylate (4ac-1). $^1$H NMR (700 MHz, CDCl$_3$, 25° C.) δ 7.56 (d, J=4.1 Hz, 1H), 6.79 (dd, J=4.1 Hz, 0.7 Hz, 1H), 4.34 (q, J=7.1 Hz, 2H), 1.36 (t, J=7.1 Hz, 3H); $^{13}$C NMR (175 MHz, CDCl$_3$, 25° C.) δ 161.6, 155.2 (q, J=2.6 Hz), 131.2, 127.7, 120.1 (q, J=260.4 Hz), 117.9, 61.7, 14.4; $^{19}$F NMR (376 MHz, CDCl$_3$, 25° C.) δ −60.8 (s, 3F).

Ethyl 3-(trifluoromethoxy)thiophene-2-carboxylate (4ac-2). $T_R$=46 min. $^1$H NMR (700 MHz, CDCl$_3$, 25° C.) δ 7.48 (d, J=5.5 Hz, 1H), 7.00 (dd, J=5.5 Hz, 1.4 Hz), 4.35 (q, J=7.1 Hz, 2H), 1.37 (t, J=7.1 Hz, 3H); $^{13}$C NMR (175 MHz, CDCl$_3$, 25° C.) δ 160.3, 147.1, 130.2, 122.0, 121.3, 120.2 (q, J=259.4), 61.6, 14.3. $^{19}$F NMR (376 MHz, CDCl$_3$, 25° C.) δ −59.1 (s, 3F). HRMS (EI) m/z calcd for C$_8$H$_7$O$_3$F$_3$S [M$^+$], 240.0068, found, 240.0069.

3-Methyl-5-(trifluoromethoxy)thiophene-2-carbonitrile (4ad)

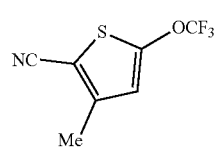
4ad

The reaction was performed according to the general procedure A using 3-methylthiophene-2-carbonitrile (0.246 g, 2.00 mmol) as the substrate. After 16 h, the reaction mixture (62% yield by $^{19}$F NMR) was purified by HPLC on Luna® PFP(2) preparative column (250×21.2 mm) using 45% v/v acetonitrile in water (10 mL/min flow rate, $t_R$=61.8 min) to provide the title compound. $^1$H NMR (400 MHz, CDCl$_3$, 25° C.) δ 6.67 (s, 1H), 2.42 (s, 3H); $^{13}$C NMR (175 MHz, CDCl$_3$, 25° C.) δ 153.9, 148.2, 120.0 (q, J=262.5 Hz), 119.3, 113.2, 100.2, 16.3; $^{19}$F NMR (376 MHz, CDCl$_3$, 25° C.) δ −60.4 (s, 3F). HRMS (EI) m/z calcd for C$_7$H$_4$NOF$_3$S [M$^+$], 206.9966, found, 206.9967.

4-Chloro-N-(propylcarbamoyl)-3-(trifluoromethoxy) benzenesulfonamide (6a)

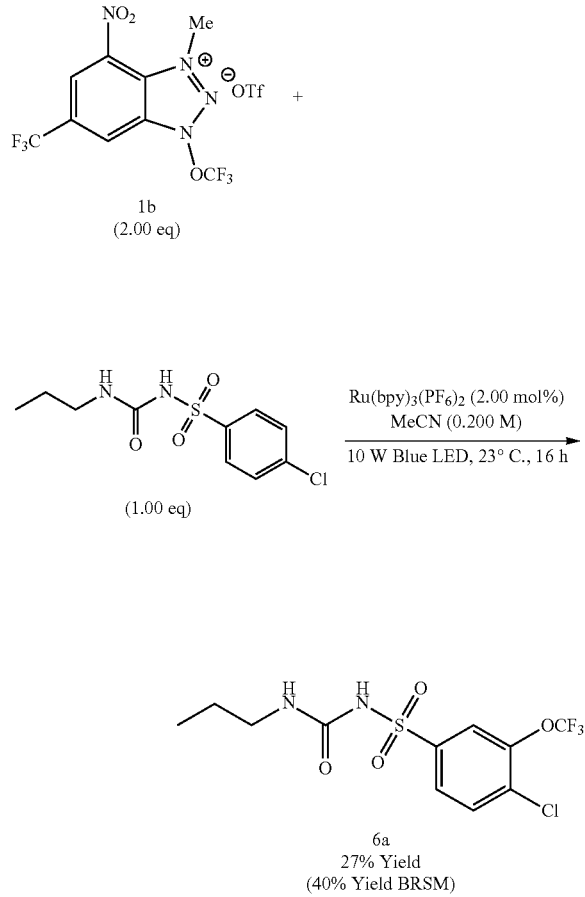

6a
27% Yield
(40% Yield BRSM)

In a glovebox, to an oven-dried 20 mL screw cap vial was added 3-methyl-4-nitro-1-(trifluoromethoxy)-6-(trifluoromethyl)-1H-benzo[d][1,2,3]triazol-3-ium trifluoromethanesulfonate (1b) (288 mg, 0.600 mmol, 2.00 equiv), 4-chloro-N-(propylcarbamoyl)benzenesulfonamide (83.1 mg, 0.300 mmol, 1.00 equiv) and Ru(bpy)$_3$(PF$_6$)$_2$, (5.16 mg, 6.00 µmol, 2.00 mol %). Then MeCN (1.50 mL) and a magnetic stir bar were added. The vial was capped and taken out of the glovebox. The reaction mixture was then stirred and irradiated with a 10 W LEDs ($\lambda_{max}$=447 nm) at 23° C. for 16 h. After that period, the crude material was then purified by HPLC on the Luna® PFP (2) preparative column (250×21.2 mm) using 35% v/v acetonitrile in water (10 mL/min flow rate, $t_R$=131.8 min) to afford 29.0 mg (27z yield) of the title compound. 27.0 mg unreacted substrate (4-chloro-N-(propylcarbamoyl)benzenesulfonamide) was recovered ($t_R$=31.5 min, 32% recovery) from the reaction mixture. $^1$H NMR (700 MHz, CDCl$_3$, 25° C.) δ 9.24 (s, 1H). 7.85 (s, 1H). 7.78 (dd. J=8.4 Hz. 1.9 Hz. 1H). 7.66 (d, J=8.4 Hz, 1H), 6.57 (s, 1H), 3.21 (m, 2H), 1.55-1.50 (m, 2H), 0.90 (t, J=7.4 Hz, 3H); $^{13}$C NMR (176 MHz, CDCl$_3$, 25° C.) δ 151.7, 145.6, 139.7, 133.9, 132.2, 126.1, 121.2, 120.4 (q, J=261.4 Hz), 42.3, 22.8, 11.2; $^{19}$F NMR (376 MHz, CDCl$_3$, 25° C.) δ −57.9 (s, 3F); HRMS (ESI) m/z calcd for C$_{11}$H$_{12}$ClF$_3$N$_2$O$_4$S [(M+H)$^+$], 361.0231, found, 361.0245.

(R)-(4-ammonio-3-(4-chloro-3-(trifluoromethoxy) phenyl)butanoyl)oxonium 2,2,2-trifluoroacetate (6b')

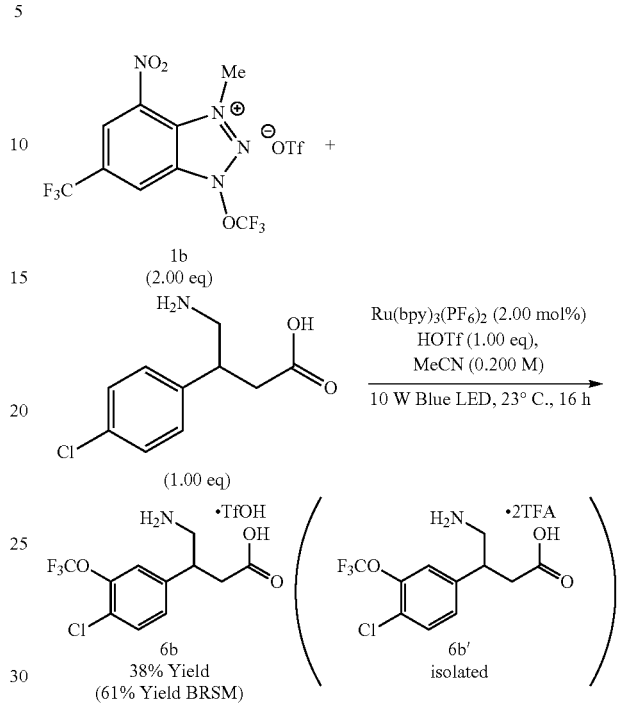

6b
38% Yield
(61% Yield BRSM)

6b'
isolated

In a glovebox, to an oven-dried 20 mL screw cap vial was added 3-methyl-4-nitro-1-(trifluoromethoxy)-6-(trifluoromethyl)-1H-benzo[d][1,2,3]triazol-3-ium trifluoromethanesulfonate (1b) (288 mg, 0.600 mmol, 2.00 equiv), (R)-4-amino-3-(4-chlorophenyl)butanoic acid (64.1 mg. 0.300 mmol, 1.00 equiv) and Ru(bpy)$_3$(PF$_6$)$_7$, (5.16 mg, 6.00 µmol, 2.00 mol %). Then MeCN (1.50 mL) and a magnetic stir bar were added. The vial was capped with a septum cap and taken out of the glovebox. Then added trifluoromethanesulfonic acid (26.5 µL, 0.300 mmol, 1.00 equiv). The reaction mixture was then stirred and irradiated with two of 10 W LEDs ($\lambda_{max}$=447 nm) at 23° C. for 16 h. After that period, the crude material was then diluted with water (50 mL) and dichloromethane (50 mL). Then extract with dichloromethane (10 mL×3) to get rid of most of the by-products and side-products. Then the aqueous layer was concentrated and purified by HPLC on the Luna® PFP(2) preparative column (250×21.2 mm) using pure water (0.1% TFA, 10 mL/min flow rate) 40 min then 20% v/v acetonitrile in water (0.1% TFA, 10 mL/min flow rate, to =67.1 min) to afford 60.0 mg (38G yield) of the title compound. 53.0 mg unreacted substrate ((R)-4-amino-3-(4-chlorophenyl)butanoic acid) di-TFA salt was recovered ($t_R$=27.7 min, 38% recovery) from the reaction mixture. $^1$H NMR (400 MHz, CD$_3$CN, 25° C.) δ 7.55 (d, J=8.3 Hz, 1H), 7.41 (s, 1H), 7.32 (dd, J=8.3 Hz, 1.5 Hz, 1H), 3.54-3.51 (m, 1H), 3.36-3.32 (m, 1H), 3.17-3.12 (m, 1H), 2.87-2.81 (m, 1H), 2.71-2.66 (m, 1H); $^{13}$C NMR (176 MHz, CD$_3$CN. 25° C.) δ 173.3, 161.0 (q, J=34.3 Hz), 146.0, 141.9, 132.4, 129.4, 127.1, 124.1, 121.5 (q, J=257.6 Hz), 117.8 (q, J=338.4 Hz), 45.0, 40.0, 38.6; $^{19}$F NMR (376 MHz, CD$_3$CN, 25° C.) δ −58.9 (s, 3F), −76.7 (s, 6F); HRMS (ESI) m/z calcd for C$_{11}$H$_{12}$NO$_3$ClF$_3$ [(M+H)$^+$], 290.1141, found, 290.1145.

2-(2-Methyl-5-nitro-1H-imidazol-1-yl)ethyl 4-methyl-3-(trifluoromethoxy)benzoate (6c)

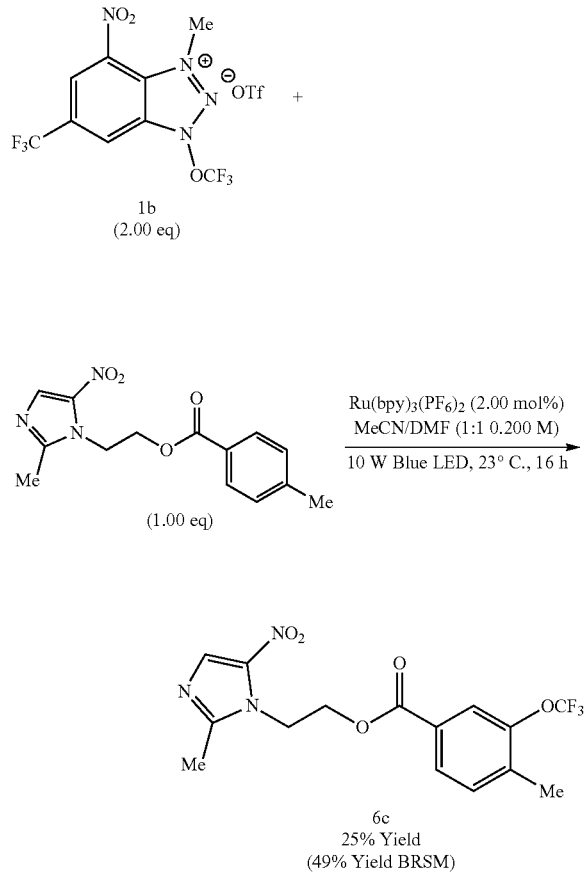

6c
25% Yield
(49% Yield BRSM)

In a glovebox, to an oven-dried 20 mL screw cap vial was added 3-methyl-4-nitro-1-(trifluoromethoxy)-6-(trifluoromethyl)-1H-benzo[d][1,2,3]triazol-3-ium trifluoromethanesulfonate (1b) (288 mg, 0.600 mmol, 2.00 equiv), 2-(2-methyl-5-nitro-1H-imidazol-1-yl)ethyl 4-methylbenzoate (prepared according to a reported procedure[8]) (86.7 mg. 0.300 mmol, 1.00 equiv) and Ru(bpy)$_3$ (PF$_6$)$_2$, (5.16 mg, 6.00 μmol, 2.00 mol %). Then MeCN (0.750 mL), DCM (0.750 mL, 0.200 M) and a magnetic stir bar were added. The vial was capped and taken out of the glovebox. The reaction mixture was then stirred and irradiated with two of 10 W LEDs ($\lambda_{max}$=447 nm) at 23° C. for 16 h. After that period, the crude material was then purified by HPLC on the Luna® PFP(2) preparative column (250×21.2 mm) using 45% v/v acetonitrile in water (10 mL/min flow rate, to =60 min) to afford 28.0 mg (25 yield) of the title compound. 42.0 mg unreacted 2-(2-methyl-5-nitro-1H-imidazol-1-yl)ethyl 4-methylbenzoate was recovered ($t_R$=24.6 min, 48% recovery) from the reaction mixture. $^1$H NMR (400 MHz, CDCl$_3$, 25° C.) δ 8.00 (s, 1H), 7.76-7.74 (m, 2H), 7.34 (d, J=8.3 Hz, 1H), 4.74-4.67 (m, 4H), 2.51 (s, 3H), 2.38 (s, 3H); $^{13}$C NMR (176 MHz, CDCl$_3$, ° C.) δ 165.0, 150.8, 147.9, 138.7, 137.7, 133.0, 132.1, 128.5, 128.0, 122.0, 120.7 (q, J=258.2 Hz), 63.2, 45.4, 16.7, 14.3; $^{19}$F NMR (376 MHz, CDCl$_3$, 25° C.) δ −58.1 (s, 3F); HRMS (ESI) m/z calcd for C$_{15}$H$_{15}$N$_3$O$_5$F$_3$ [(M+H)$^+$], 374.0964, found, 374.0964.

(1R,2S,5R)-2-isopropyl-5-methylcyclohexyl 4-bromo-5-(trifluoromethoxy) thiophene-2-carboxylate (6d)

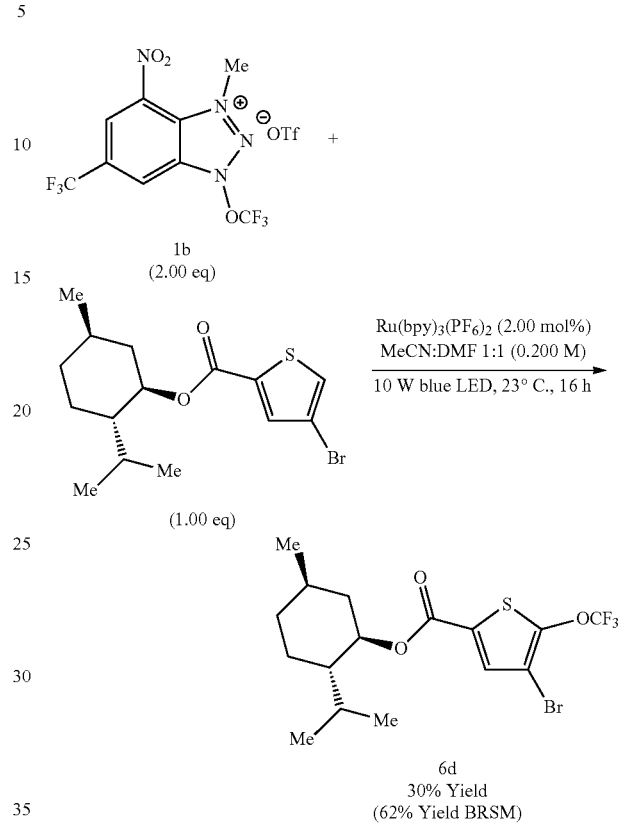

6d
30% Yield
(62% Yield BRSM)

In a glovebox, to an oven-dried 20 mL screw cap vial was added 3-methyl-4-nitro-1-(trifluoromethoxy)-6-(trifluoromethyl)-1H-benzo[d][1,2,3]triazol-3-ium trifluoromethanesulfonate (1b) (192 mg, 0.400 mmol, 2.00 equiv), (1R,2S, 5R)-2-isopropyl-5-methylcyclohexyl 4-bromothiophene-2-carboxylate (prepared according to a reported procedure[9]) (69.1 mg. 0.200 mmol, 1.00 equiv) and Ru(bpy)$_3$(PF$_6$)$_2$, (3.44 mg, 4.00 μmol, 2.00 mol %). Then MeCN (0.500 mL), DCM (0.500 mL, 0.200 M) and a magnetic stir bar were added. The vial was capped and taken out of the glovebox. The reaction mixture was then stirred and irradiated with two of 10 W LEDs ($\lambda_{max}$=447 nm) at 23° C. for 16 h. After that period, the reaction mixture was directly concentrated in vacuo and the residue was purified by preparative TLC, developing with DCM:Hexanes [1:1 (v/v)] to afford a mixture of (1R,2S,5R)-2-isopropyl-5-methylcyclohexyl 4-bromothiophene-2-carboxylate and 6d (R$_f$=0.61 DCM:Hexanes [1:1 (v/v)]). The crude material was then purified by HPLC on the Luna® PFP(2) preparative column (250×21.2 mm) using 70 acetonitrile in water (10.6 mL/min flow rate, $t_R$=59.4 min) to afford 26.0 mg (30G yield) of the title compound. 35.0 mg unreacted substrate ((1R,2S,5R)-2-isopropyl-5-methylcyclohexyl 4-bromothiophene-2-carboxylate) was recovered ($t_R$=41.1 min, 51% recovery) from the reaction mixture. $^1$H NMR (700 MHz, CDCl$_3$, 25° C.) δ 7.56 (s, 1H), 4.88 (m, 1H), 2.08 (d, J=12.0 Hz, 1H), 1.89 (m, 1H), 1.72 (m, 2H), 1.52 (m, 2H), 1.09 (m, 2H), 0.93 (d, J=7.7 Hz, 3H), 0.91 (d, J=7.7 Hz, 3H), 0.79 (d, J=7.0 Hz, 3H); $^{13}$C NMR (176 MHz, CDCl$_3$, 25° C.) δ 160.34, 148.88 (d, J=2.3 Hz), 133.12, 128.32, 120.14 (q, J=263.2 Hz), 103.95, 76.51, 47.22, 40.93, 34.27, 31.58, 26.67, 23.72, 22.12, 20.84, 16.63; $^{19}$F NMR (376 MHz, CDCl$_3$, 25° C.) δ −60.3 (s, 3F). HRMS (ESI): Calcd for: C$_{16}$H$_{20}$O$_3$F$_3$SBr$^+$ ([M+H]$^+$) 428.0269, found: 428.0265.

(3S,5S,8R,9S,10S,13S,14S)-10,13-Dimethyl-17-oxohexadecahydro-1H-cyclopenta[a]phenanthren-3-yl 4-bromo-5-(trifluoromethoxy)thiophene-2-carboxylate (6e)

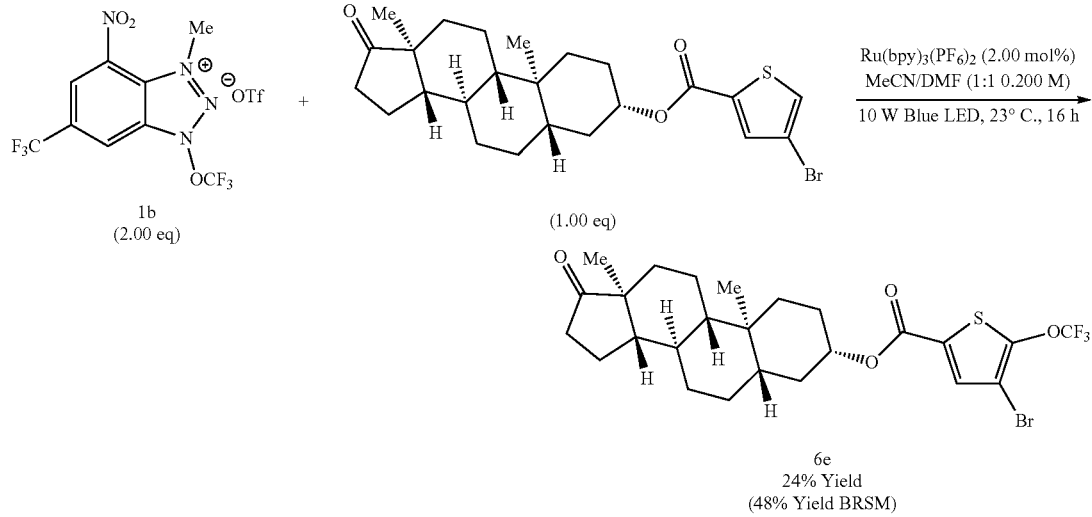

6e
24% Yield
(48% Yield BRSM)

In a glovebox, to an oven-dried 20 mL screw cap vial was added 3-methyl-4-nitro-1-(trifluoromethoxy)-6-(trifluoromethyl)-1H-benzo[d][1,2,3]triazol-3-ium trifluoromethanesulfonate (1b) (192 mg, 0.400 mmol, 2.00 equiv), (3S,5S,8R,9S,10S,13S,14S)-10,13-dimethyl-17-oxohexadecahydro-1H-cyclopenta[α]phenanthren-3-yl 4-bromothiophene-2-carboxylate (prepared according to a reported procedure—Zheng et al. 2018) 95.9 mg, 0.200 mmol, 1.00 equiv) and Ru(bpy)$_3$(PF$_6$)$_2$, (3.44 mg, 4.00 μmol, 2.00 mol %). Then MeCN (0.500 mL), DCM (0.500 mL, 0.200 M) and a magnetic stir bar were added. The vial was capped and taken out of the glovebox. The reaction mixture was then stirred and irradiated with two of 10 W LEDs ($\lambda_{max}$=447 nm) at 23° C. for 16 h. After that period, the reaction mixture was directly concentrated in vacuo and the residue was purified by preparative TLC, developing with DCM:DCE [1:1 (v/v)] ($R_f$=0.69 DCM:Hexanes [1:1 (v/v)]) to afford 24.0 mg (24% yield) of the title compound. 48.0 mg unreacted substrate ((3S,5S,8R,9S,10S,13S,14S)-10,13-dimethyl-17-oxohexadecahydro-1H-cyclopenta[α]phenanthren-3-yl 4-bromothiophene-2-carboxylate) was recovered ($R_f$=0.59 in DCM:DCE [1:1 (v/v)], 50S recovery) from the reaction mixture. $^1$H NMR (700 MHz, CDCl$_3$, 25° C.) δ 7.66 (s, 1H), 7.42 (s, 1H), 4.89 (m, 1H), 2.44 (m, 1H), 2.07 (m, 1H), 1.93 (m, 2H), 1.79 (m, 4H), 1.52 (m, 5H), 1.32 (m, 6H), 1.09 (m, 1H), 1.00 (m, 1H), 0.89 (s, 3H), 0.86 (s, 3H), 0.74 (m, 1H); $^{13}$C NMR (176 MHz, CDCl$_3$, 25° C.) δ 221.33, 160.23, 148.82, 133.17, 128.26, 120.10 (q, J=263.3 Hz), 103.85, 75.65, 54.37, 51.45, 47.89, 44.76, 36.75, 35.96, 35.76, 35.13, 33.98, 31.62, 30.89, 28.35, 27.49, 21.89, 20.60, 13.93, 12.37; $^{19}$F NMR (376 MHz, CDCl$_3$, 25° C.) δ −60.4 (s, 3F); HRMS (ESI): Calcd for: C$_{25}$H$_{30}$O$_4$NaSBr$^+$ ([M+Na]$^+$) 585.0898, found: 585.0883.

((3a,5aR,8aR,8b)-2,2,7,7-tetramethyltetrahydro-3aH-bis([1,3]dioxolo)[4,5-b:4',5'-d]pyran-3a-yl)methyl 4-bromo-5-(trifluoromethoxy) thiophene-2-carboxylate (6f)

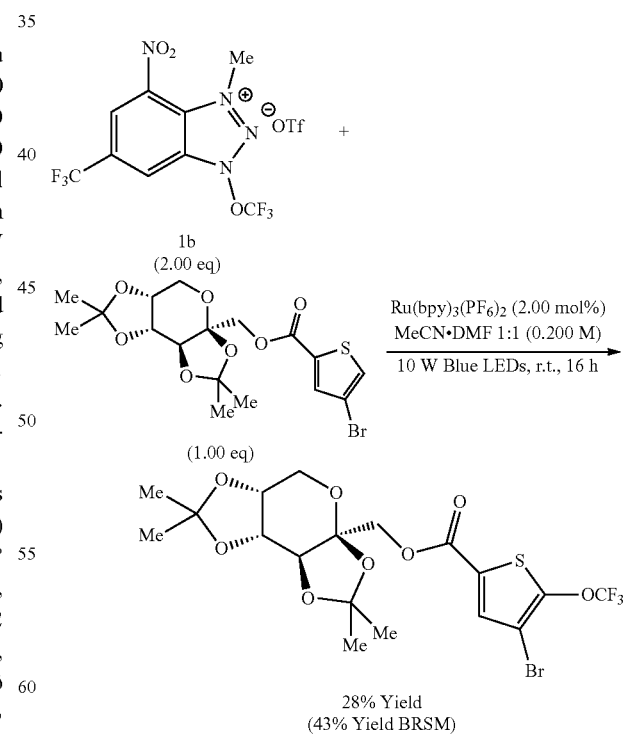

28% Yield
(43% Yield BRSM)

In a glovebox, to an oven-dried 20 mL screw cap vial was added 3-methyl-4-nitro-1-(trifluoromethoxy)-6-(trifluoromethyl)-1H-benzo[d][1,2,3]triazol-3-ium trifluoromethanesulfonate (1b) (192 mg, 0.400 mmol, 2.00 equiv), ((3aS, 5aR,8aR,8bS)-2,2,7,7-tetramethyltetrahydro-3aH-bis([1,3]dioxolo)[4,5-b:4',5'-d]pyran-3a-yl)methyl 4-bromothiophene-2-carboxylate (prepared according to a reported procedure) (89.6 mg. 0.200 mmol, 1.00 equiv) and Ru(bpy)$_3$(PF$_6$)$_2$, (3.44 mg, 4.00 μmol, 2.00 mol %). Then MeCN (0.500 mL) and DCM (0.500 mL, 0.200 M) and a magnetic stir bar were added. The vial was capped and taken out of the glovebox. The reaction mixture was then stirred and irradiated with two of 10 W LED ($\lambda_{max}$=447 nm) at room temperature. After 16 h, the crude material was purified by HPLC on the Luna® PFP(2) preparative column (250×21.2 mm) using 55% acetonitrile in water (10.0 mL/min flow rate, $t_R$=83.2 min) to provide 30.0 mg (28% yield) of the title compound. 30.0 mg unreacted substrate (((3aS,5aR,8aR,8bS)-2,2,7,7-tetramethyltetrahydro-3aH-bis([1,3]dioxolo)[4,5-b:4',5'-d]pyran-3a-yl)methyl 4-bromothiophene-2-carboxylate) was recovered ($t_R$=34.6 min, 33S recovery) from the reaction mixture. $^1$H NMR (400 MHz, CDCl$_3$, 25° C.) δ 7.63 (s, 1H), 4.65-4.61 (m, 2H), 4.38 (d, J=2.6 Hz, 1H), 4.29-4.24 (m, 2H), 3.94 (dd, J=13.0 Hz, 2.6 Hz, 1H), 3.77 (d, J—13.0 Hz, 1H), 1.55 (s, 3H), 1.47 (s, 3H), 1.39 (s, 3H), 1.35 (s, 3H); $^{13}$C NMR (175 MHz, CDCl$_3$, 25° C.) δ 160.0, 149.3, 134.0, 127.0 120.1 (q, J=263.5 Hz), 109.3, 109.2, 104.1, 101.4, 70.8, 70.6, 70.1, 66.1, 61.5, 26.6, 26.0, 25.6, 24.1; $^{19}$F NMR (376 MHz, CDCl$_3$, 25° C.) δ −60.1 (s, 3F). HRMS (ESI) Calcd for: C$_{18}$H$_{21}$O$_8$SBrF$_3^+$ ([M+H]$^+$) 533.0093, found: 533.0081.

Differential Scanning Calorimetry (DSC)

Differential Scanning Calorimeter (DSC) was performed to determine the temperature and heat flow associated with our material as a function of time and temperature. Reagents 1a and 1b are non-explosive.

Absorption and Emission Spectra

Figure 2:
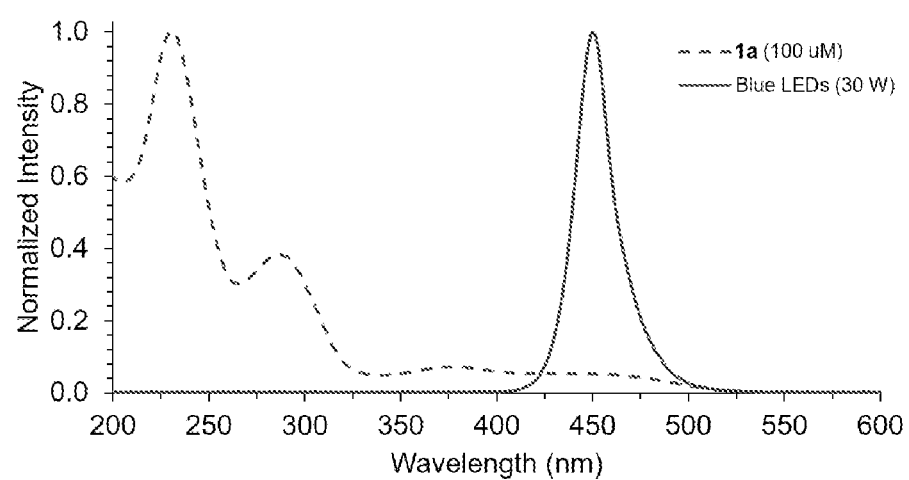
FIG. 2. Absorption spectrum of 1a ($\lambda_{max}$=230 nm) and emission spectrum of the 30 W blue LEDs ($\lambda_{max}$=450 nm).
Figure 3:
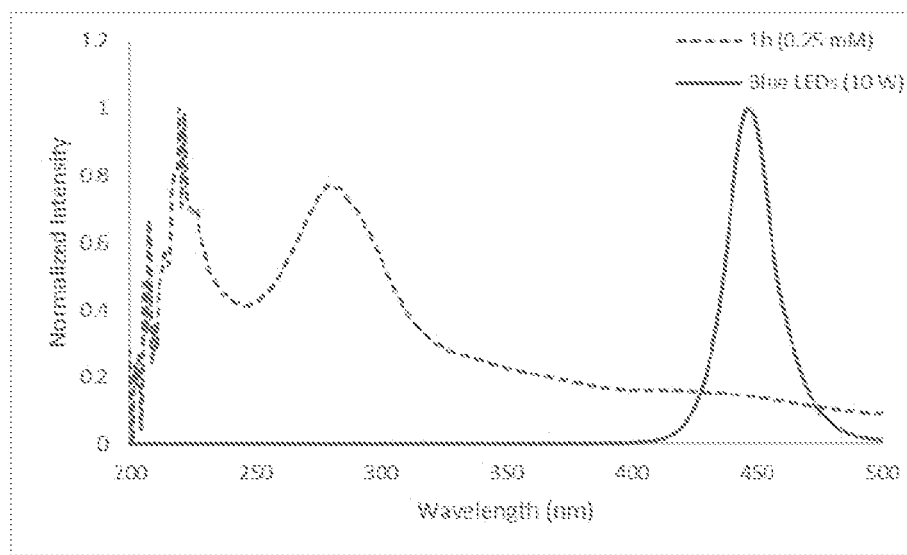
FIG. 3. Absorption spectrum of 1b ($\lambda_{max}$=280 nm) and emission spectrum of the 30 W blue LEDs ($\lambda_{max}$=447 nm).

Absorption of reagent 1a and emission spectrum of the 30 W blue LEDs (FIG. 2). Absorption of reagent 1b and emission of 10 W blue LED lights (FIG. 3).

Mechanistic Studies

Intermolecular Competitive Kinetic Isotope Effect

Difluoromethoxylation of Benzene and d$_6$-Benzene

We have performed deuterium kinetic isotope effect study using 5 equiv of benzene and 5 equiv of d$_6$-benzene in the presence of 1 equiv of reagent 1a (Scheme 16). The desired products Ph-OCF$_2$H and d$_5$-Ph-OCF$_2$H were obtained in 364 and 36% yields, respectively. This result rules out the possibility of H-atom abstraction/deprotonation as the rate-determining step.

Scheme 16.

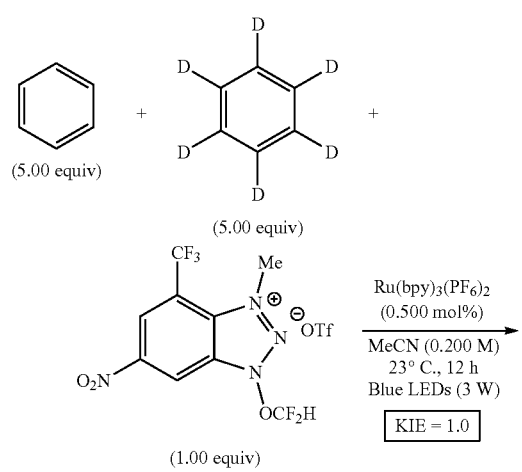

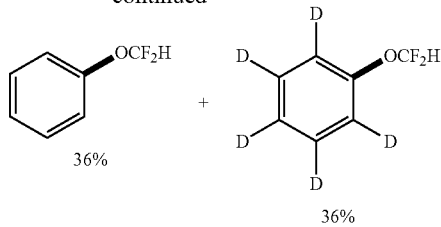

36%

36%

In a glovebox, to an oven-dried 20 mL screw cap vial was added 1-(difluoromethoxy)-3-methyl-6-nitro-4-(trifluoromethyl)-1H-benzo[d][1,2,3]triazol-3-ium trifluoromethanesulfonate (1a) (9.24 mg, 0.0200 mmol, 1.00 equiv), benzene (7.81 mg, 8.94 μL, 100 mmol, 5.00 equiv), hexadeuterobenzene (8.42 mg, 8.86 μL, 0.100 mmol, 5.00 equiv), Ru(bpy)$_3$(PF$_6$)$_2$, (0.0860 mg, 0.100 μmol, 0.500 mol %), and MeCN (0.100 mL, 0.200 M, with respect to 1a). To this solution was added a magnetic stir bar. Next, the reaction vial was capped and taken out of the glovebox. The reaction mixture was stirred at ambient temperature (23° C.) and irradiated with blue LEDs (3 W, $\lambda_{max}$=450 nm) which was placed 20.0 mm from the vial for 12 h. To determine the yield of the products, an internal standard, trifluorotoluene (PhCF$_3$) (1.46 mg, 1.23 μL, 0.0100 mmol, 0.500 equiv) was added to the vial. Then, the reaction mixture was diluted with 500 μL of CDCl$_3$ followed by $^{19}$F NMR.

Trifluoromethoxylation of Benzene and d$_6$-Benzene

We have performed deuterium kinetic isotope effect study using 5 equiv of benzene and 5 equiv of d$_6$-benzene in the presence of 1 equiv of reagent 1b (Scheme 17). The desired products Ph-OCF$_3$ and d$_5$-Ph-OCF$_3$ were obtained in 40.31 and 39.2% yields, respectively. This result rules out the possibility of H-atom abstraction/deprotonation as the rate-determining step.

Scheme 17.

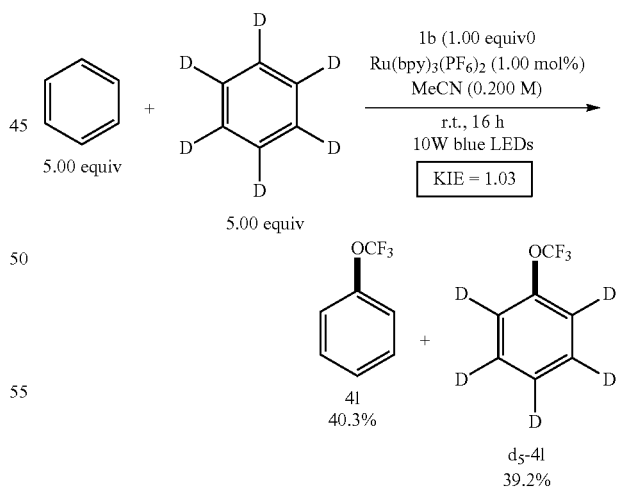

41
40.3% d$_5$-4l
39.2%

In a glovebox, to an oven-dried 4 mL screw cap vial was added 3-Methyl-4-nitro-1-(trifluoromethoxy)-6-(trifluoromethyl)-1H-benzo[d][1,2,3]triazol-3-ium trifluoromethanesulfonate (1b) (9.60 mg, 0.0200 mmol, 1.00 equiv), C$_6$H$_6$ (7.8 mg, 0.100 mmol, 5.00 equiv), C$_6$D$_6$ (8.4 mg, 0.100 mmol, 5.00 equiv), and Ru(bpy)$_3$(PF$_6$)$_2$, (0.172 mg, 0.200 μmol, 1.00 mol %). Then MeCN (0.100 mL, 0.200 M) and a magnetic stir bar were added. The reaction mixture were then stirred and irradiated with a 10 W LED (447 nm) at room temperature for 16 h. Then the mixture was added trifluorotoluene as an internal standard and $^{19}F$ NMR was taken to obtain the yields for $OCF_3$—$C_6H_5$ (40.3S) and for $OCF_3$—$C_6D_5$ (39.2).

Intermolecular Competition Experiment

We have performed competition reactions, and as expected, the electrophilic $OCF_2H$ and $OCF_3$ radicals react faster with electron-rich arenes (Schemes 18 and 19).

In a glovebox, to an oven-dried 20 mL screw cap vial was added 1-(difluoromethoxy)-3-methyl-6-nitro-4-(trifluoromethyl)-1H-benzo[d][1,2,3]triazol-3-ium trifluoromethanesulfonate (1a) (9.24 mg, 0.0200 mmol, 1.00 equiv), arene (0.100 mmol, 5.00 equiv), arene (0.100 mmol, 5.00 equiv), $Ru(bpy)_3(PF_6)_2$, (0.0860 mg, 0.100 μmol, 0.500 mol %), and MeCN (0.100 mL, 0.200 M, with respect to 1a). To this solution was added a magnetic stir bar. Next, the reaction vial was capped and taken out of the glovebox. The reaction mixture was stirred at ambient temperature (23° C.) and

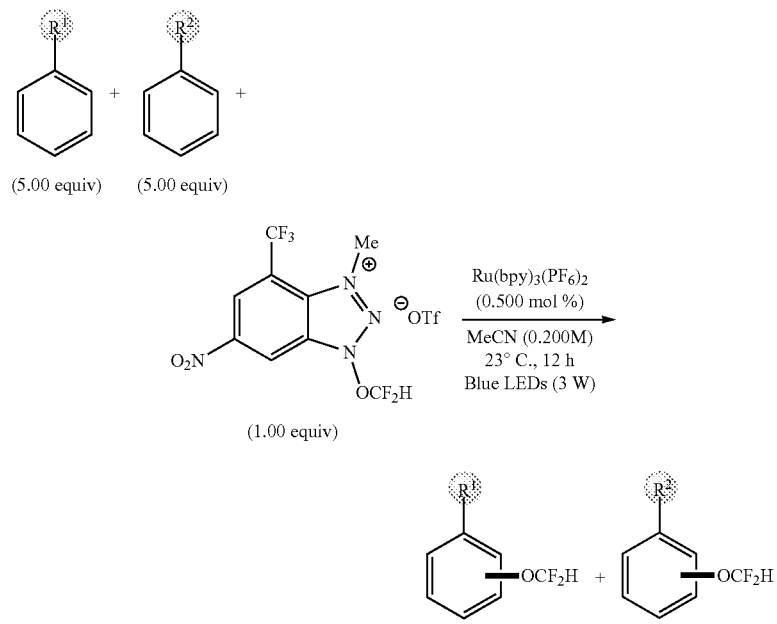

Scheme 18

Intermolecular competition experiment of difluoromethoxylation reactions irradiated with blue LEDs (3 W, $\lambda_{max}$=450 nm) which was placed 20.0 mm from the vial for 12 h. To determine the yield of the products, an internal standard, trifluorotoluene (PhCF$_3$) (1.46 mg, 1.23 μL, 0.0100 mmol, 0.500 equiv) was added to the vial. Then, the reaction mixture was diluted with 500 μL of CDCl$_3$ followed by $^{19}$F NMR.

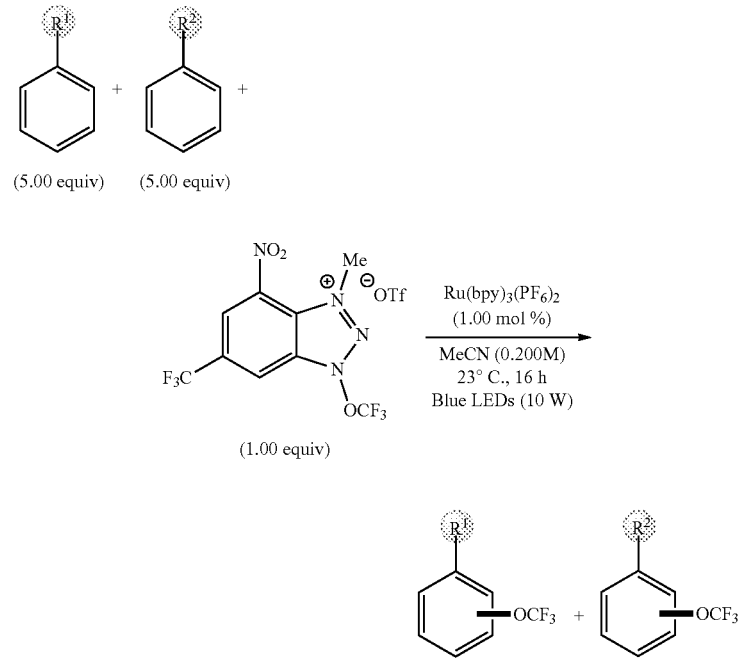

Scheme 19

Intermolecular competition experiment of trifluororoethoxylation reactions

In a glovebox, to an oven-dried 4 mL screw cap vial was added 3-Methyl-4-nitro-1-(trifluoromethoxy)-6-(trifluoromethyl)-1H-benzo[d][1,2,3]triazol-3-ium trifluoromethanesulfonate (1b) (9.60 mg, 0.0200 mmol, 1.00 equiv), arenes (0.100 mmol, 5.0 equiv), and Ru(bpy)$_3$(PF$_6$)$_2$, (0.172 mg, 0.200 μmol, 1.00 mol %). Then MeCN (0.100 mL, 0.200 M) and a magnetic stir bar were added. The reaction mixture were then stirred and irradiated with a 10 W LED (447 nm) at room temperature for 16 h. Then the mixture was added trifluorotoluene as an internal standard and $^{19}$F NMR was taken to obtain the yields.

Light/Dark Experiment

Figure 4A:
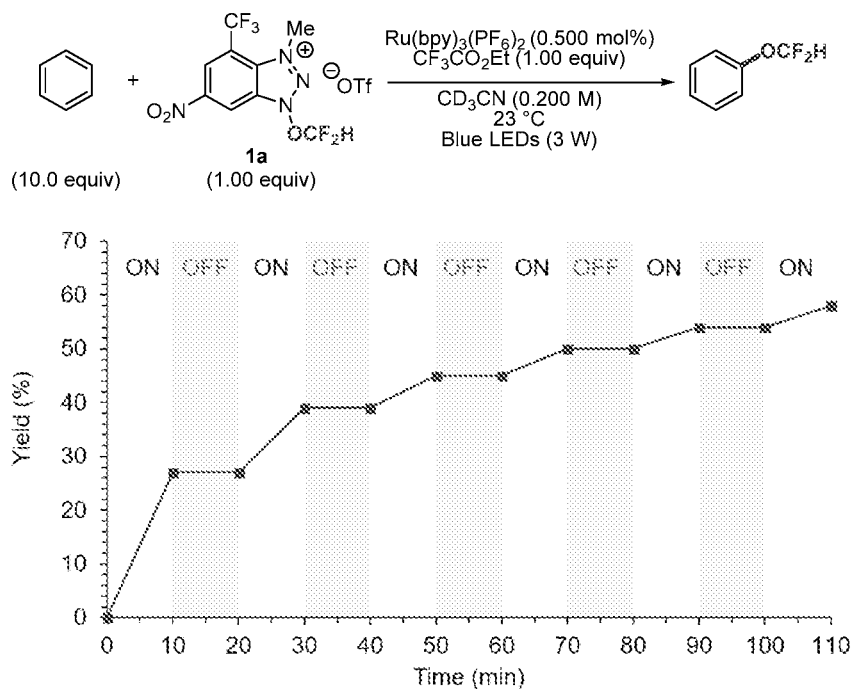
Figure 4B:
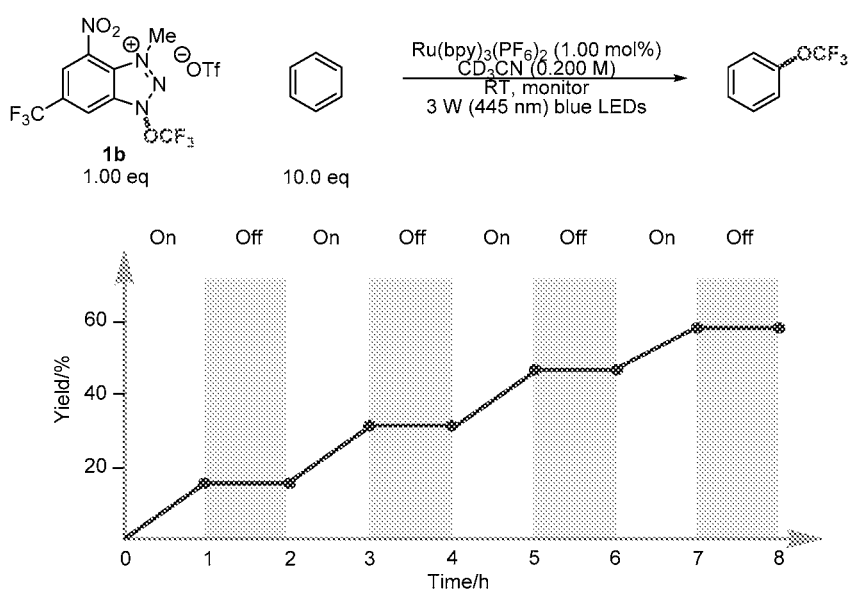
FIG. 4B. Light on-and-off experiments of trifluoromethoxylation reaction of benzene with 1b.

Based on the result of the reaction with the light on and off, it was observed that the transformation proceeded smoothly under light, but no further conversion was observed when the light is turned off. This result suggests a long-lived radical chain propagation is unlikely (FIGS. 4a and 4b).

Difluoromethoxylation reaction—In a glovebox, to an vacuum-dried screw cap NMR tube was added a solution of 1-(difluoromethoxy)-3-methyl-6-nitro-4-(trifluoromethyl)-1H-benzo[d][1,2,3]triazol-3-ium trifluoromethanesulfonate (1a) (46.2 mg, 0.100 mmol, 1.00 equiv), benzene (78.1 mg, 89.4 μL, 1.00 mmol, 10.0 equiv), ethyl trifluoroacetate (14.2 mg, 11.9 μL, 0.100 mmol, 10.0 equiv) (an internal standard, to determine the yield of the product), Ru(bpy)$_3$(PF$_6$)$_2$, (0.430 mg, 0.500 μmol, 0.500 mol %) in CD$_3$CN (0.500 mL, 0.200 M, with respect to 1a). Afterwards the NMR tube was capped and taken out of the glovebox. The reaction mixture was irradiated alternatively at ambient temperature (23° C.) with blue LEDs (3 W, $\lambda_{max}$=450 nm) which was placed 30.0 mm from the NMR tube and kept in the dark in 10 minutes intervals.

Trifluoromethoxylation reaction—In a glovebox, to an oven-dried 4 mL screw cap vial was added 3-Methyl-4-nitro-1-(trifluoromethoxy)-6-(trifluoromethyl)-1H-benzo[d][1,2,3]triazol-3-ium trifluoromethanesulfonate (1b) (48.0 mg, 0.100 mmol, 1.00 equiv), benzene (78.0 mg, 1.00 mmol, 10.0 equiv) and Ru(bpy)$_3$(PF$_6$)$_2$, (0.86 mg, 1.00 μmol, 1.00 mol %). Then MeCN (0.500 mL, 0.200 M) and internal standard ethyl 2,2,2-trifluoroacetate (14.2 mg, 0.1500 mmol, 1.00 equiv) was added. The reaction mixtures were then transferred into an NMR tube, capped and took out of glovebox. The NMR tube was irradiated with a 3 W LED (445 nm) at room temperature. After 1 hour, $^{19}$F NMR was taken for crude yield. Then the NMR tube was kept in dark for another hour, and $^{19}$F NMR was taken for crude yield. The process was repeated until all the crude yields were obtained.

DFT Calculations

All DFT calculations were performed with the Gaussian 09 (Frisch, M. et al. 2009) software package. Geometries were optimized using the M06-2X (Zhao, Y. et al. 2008) functional and the 6-31+G(d) basis set in gas phase. Single point energies were calculated using M06-2X and 6-311++G(d,p) and the SMD (Marenich, A. V. et al. 2009) solvation model in MeCN. Reported Gibbs free energies and enthalpies in solution include thermal corrections computed at 298 K. The experimental standard reduction potential (SRP) of Ru*(bpy)$_3^{2+}$ (−0.81 V vs. SCE in MeCN) (Bock, C. R. et al. 1975) was used in the computations of the reaction Gibbs free energies of the single electron transfer (SET) processes with the photoredox catalyst.

Scheme 20. Fragmentation energies of TR1 radical anion.

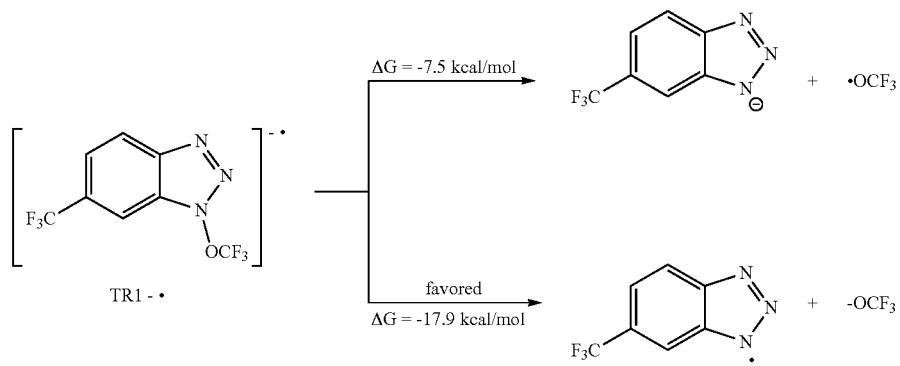

Scheme 21. Energies of photocatalytic difluoromethoxylation of benzene. All energies are in kcal/mol and are with respect to 1a and *Ru(bpy)$_3^{2+}$. The N—O bond distances in 1a and 1a′ are in Å. The Mulliken spin densities in 1a′ are provided.

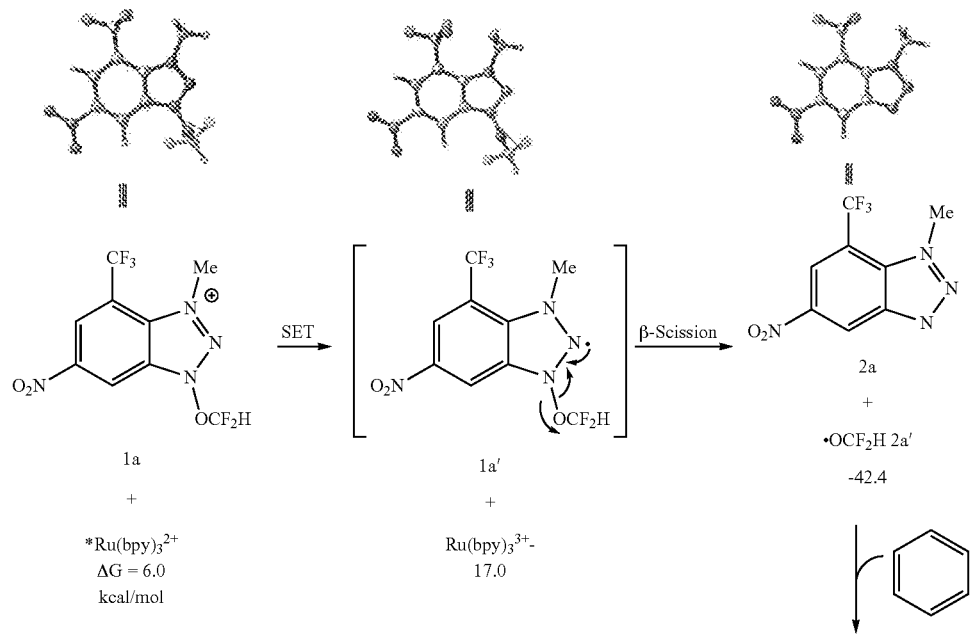

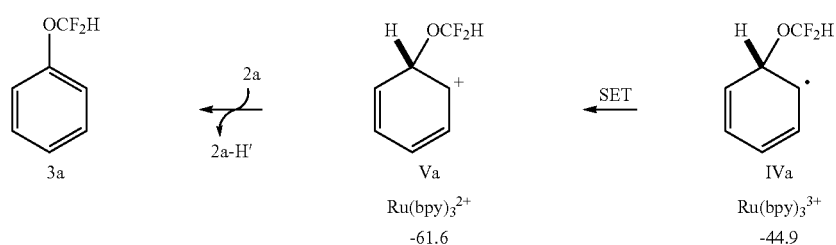

Scheme 22. Energies of photocatalytic trifluoromethoxylation of benzene. All energies are in kcal/mol and are with respect to 1b and *Ru(bpy)$_3^{2+}$. The N—O bond distances in 1b and 1b′ are in Å. The Mulliken spin densities in 1b′ are provided.

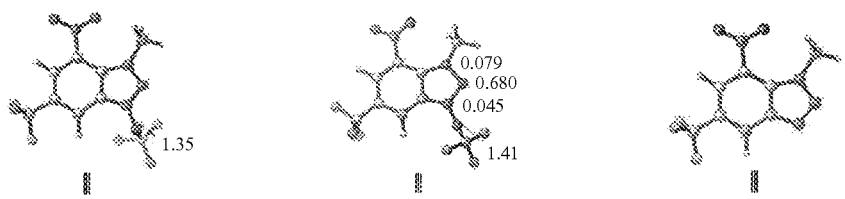

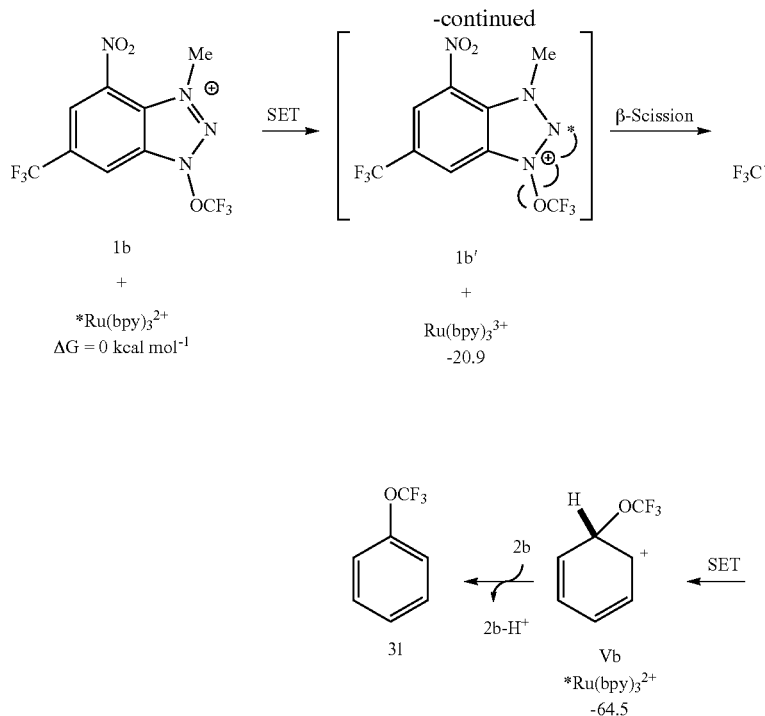

Example 3. Additional Substrates

An additional aspect of the invention provides substituted or unsubstituted arene and heteroarene analogs of the compounds of Examples 1 and 2 that are difluro- or trifluoromethoxylated using the reagents described herein.

Discussion

Only a handful of approaches have been reported for the synthesis of trifluoromethoxylated arenes over the last 60 years (Synthesis of trifluoromethoxylated (hetero)aromatic compounds: for reviews, see: Leroux, F. R. et al. 2008; Tlili, A. et al. 2016; Lee, K. N. et al. 2016; for a two-step chlorination/chlorine-fluorine exchange reaction of electron deficient anisoles, see: Yagupolskii, L. M. 1955; for deoxyfluorination of fluoroformates, see: Sheppard, W. A. et al. 1964; for electrophilic trifluoromethylation of phenols, see: Umemoto, T. 1996; Umemoto, T. et al. 2007; Stanek, K. et al. 2008; for nucleophilic trifluoromethoxylation of arenes, see: Nishida, M. et al. 1995; Kolomeitsev, A. A. et al. 2018; for radical trifluoromethoxylation of arenes, see: Venturini, F. et al. 2012).

Although recent reports of several powerful strategies such as silver-mediated synthesis of trifluoromethoxylated (hetero)arenes have advanced the state-of-the-art (A. Tlili, et al. 2016; Huang, C. et al. 2011; Liu, J. B. et al. 2015; Khotavivattana, T. et al. 2015; Zhang, Q. W. et al. 2016), a catalytic intermolecular C—H trifluoromethoxylation of (hetero)arenes remains elusive (Catalytic trifluoromethoxylation of alkenes, see: Chen, C. H. et al. 2015; Guo, S. et al. 2017; Chen, C. et al. 2018; Catalytic decarboxylative fluorination of aryloxydifluorocarboxylic acids, see: M. Zhou 2016; Catalytic allylic C—H trifluoromethoxylation, see: e) Qi, X, et al. 2017; Chen, C. et al. 2018). Such an approach is appealing because it precludes the need for the pre-functionalization of aromatic compounds. In addition, direct disconnection of the $OCF_3$ group could be envisioned anywhere onto the target and at any time of the synthesis, which would allow the late-stage trifluoromethoxylation of complex molecules.

Herein is described the design and development of redox-active reagents for the potential late-stage, direct difluoromethoxylation or trifluoromethoxylation of unactivated arenes and heteroarenes through a radical-mediated mechanism under visible light photocatalytic conditions at room temperature. It has been demonstrated the broad synthetic utility of these transformations through the addition of the $OCF_2H$ and $OCF_3$ radicals to a wide range of aromatic and heteroaromatic systems. Notably, the protocol is mild and operationally simple. It is applicable to late-stage functionalization of marketed drugs, and provides a useful tool in the discovery and development of new medicinal agents.

$OCF_3$-Reagent 1 (Example 1)

Seeking to establish C—H trifluoromethoxylation reactions, an easy and robust synthesis of a wide range of (hetero)aromatic hydroxylamides bearing the N—$OCF_3$ moiety was developed by our group, which undergoes thermally induced heterolytic cleavage of the N—$OCF_3$ bond to form a nitrenium-trifluoromethoxide ion pair (Hojczyk, K. N. et al. 2014; Feng, P. et al. 2016). Fast recombination of such an ion pair afford the products of intramolecular (hetero)aryl C—H trifluoromethoxylation. It was discovered herein that the photoexcitation of an appropriate N—$OCF_3$ compound could result in a homolytic cleavage of the N—$OCF_3$ bond (~50 kcal/mol) and the release of the $OCF_3$ radical, which is trapped intermolecularly by arenes to afford the products of trifluoromethoxylation. The successful development of a catalytic protocol utilizing redox-active catalysts and an unprecedented trifluoromethoxylating reagent for the direct intermolecular C—H trifluoromethoxylation of various (hetero)arenes at room temperature is described.

The first catalytic intermolecular C—H trifluoromethoxylation of (hetero)arenes employing redox-active catalysts and trifluoromethoxylating reagent 1 at ambient temperature was developed. The mild reaction conditions obviate the need for specialized reaction apparatus and tolerate a wide array of functional groups. Mechanistic studies showed that (i) photoexcitation of reagent 1 forms the ·OCF$_3$ and (ii) redox-active catalysts intervene in the radical coupling reaction of Ia and Ic to favor the formation of the desired product of trifluoromethoxylation.

OCF$_2$H-Reagent 1a and OCF$_3$-Reagent 1b (Example 2)

Seeking to establish C—H trifluoromethoxylation reactions, our group recently described an easy and robust synthesis of a wide range of (hetero)aromatic hydroxylamides bearing the N—OCF$_3$ moiety, which undergo thermally induced heterolytic cleavage of the N—OCF$_3$ bond to afford the products of intramolecular (hetero)aryl C—H trifluoromethoxylation via the formation of a nitrenium-trifluoromethoxide ion pair (Hojczyk, K. N. et al. 2016; Feng, P. et al. 2016). However, development of intermolecular trifluoromethoxylation using trifluoromethoxide is difficult due to its poor nucleophilicity (often requires a reactive electrophile) and intrinsic instability (readily decompose to form fluorophosgene and fluoride) (Seppelt. K. 1977; Kloeter, G. et al. 1979; Christe, K. O. et al. 2007). On the other hand, the OCF$_3$ radical is more reactive and less prone to decomposition (the formation of fluorine radical from the OCF$_3$ radical is energetically unfavorable, $\Delta G^\neq=35$ kcal/mol) than the OCF$_3$ anion (Francisco, J. S. et al. 1987. Thus, we questioned whether the photoexcitation of an appropriate N—OCF$_3$ compound could result in the homolytic cleavage of the N—OCF$_3$ bond (~50 kcal/mol) and the release of the OCF$_3$ radical, which might be trapped intermolecularly by aromatic compounds to afford the products of trifluoromethoxylation (Venturini, F. et al. 2012). M1 SI However, development of such a versatile trifluoromethoxylating reagent is challenging and should meet the following criteria. First, the absorption band of the trifluoromethoxylating reagents should fall in the ultraviolet A region (315 nm-400 nm) so that regular glass (borosilicate) vessels with UV cutoff at about 330 nm can be used for the reaction. In addition, employing a light source with wavelengths in that region will minimize excitation of other organic molecules and side reactions. Moreover, reagents that do not absorb strongly in the visible region will allow their preparation under ambient light without decomposition. Furthermore, the homolytic cleavage of the N—OCF$_3$ bond will also generate N-centered radicals, which might react with aromatic compounds and lead to undesired N-arylation side products. Therefore, the prevention of such a side reaction is crucial. Finally, for reagents bearing an aryl moiety, self-reaction or trifluoromethoxylation of the reagents needs to be avoided.

Methods for the synthesis of OCF$_2$H and OCF$_3$-containing aromatic and heteroaromatic compounds typically require the use of pre-functionalized or activated substrates and are limited in scope (Ni, C. et al. 2014; Tlili, A. et al. 2016). For example, OCF$_2$H analogues are commonly prepared through a reaction of phenols with a reactive difluorocarbene intermediate generated under strongly basic and/or elevated temperature conditions. On the other hand, the current state-of-the-art synthesis of OCF$_3$ analogues involves silver-mediated trifluoromethoxylation of aryl boronic acids and stannanes or trifluoromethylation of phenols (Shuang, C. et al. 2011; Liu, J. B. et al. 2015; Khotavivattana, T. et al. 2015; Zhang, Q. W. et al. 2016). These reactions have facilitated the site-selective synthesis of a broad array of OCF$_2$H and OCF$_3$ analogues without the reliance on pre-fluorinated building blocks. However, identification of the ideal position of the OCF$_2$H and OCF$_3$ substitution in a drug candidate still requires parallel and laborious multi-step syntheses from aryl precursors bearing activating or directing groups at various positions in an aromatic ring. A general catalytic process for direct installation of the OCF$_2$H and OCF$_3$ groups into aromatic and heteroaromatic systems remains a significant challenge in organic synthesis.

We questioned whether a radical-mediated aromatic substitution using the OCF$_2$H or OCF$_3$ radical would allow the direct introduction of the OCF$_2$H and OCF$_3$ group to a drug candidate generating multiple regioisomers in a single chemical operation. Such an approach is appealing because it obviates the need for redundant synthetic effort and the pre-functionalization of aromatic compounds. Moreover, the preparation and isolation of regioisomers would allow rapid assays of the biological activity of OCF$_2$H and OCF$_3$ analogues, a feature which would be particularly beneficial to modern drug discovery programs. Although a few methods for the generation of the OCF$_3$ radical using gaseous reagents under cryogenic or photolytic conditions are known (Rozen, S. 1996; von Ahsen, S. et al. 2004; Francesco, V. et al. 2013), experimental access to the OCF$_2$H radical has not been reported. Bench-stable, easily handled, and highly modular reagents that form the OCF$_2$H and OCF$_3$ radicals in a catalytic, selective, and controllable manner are very desirable.

Seeking to develop reagents that would be useful in this context, attention was focused on a class of compounds bearing the N—OR$_F$ moieties, N—OCF$_2$H or N—OCF$_3$. It was envisioned that the weak N—OR$_F$ bond, whose bond dissociation energy (BDE)≈60 kcal/mol, could be cleaved homolytically to release the OR$_F$ radical under mild conditions. We recently demonstrated the feasibility of photolysis of a photo-active OCF$_3$ reagent bearing the N—OCF$_3$ moiety using violet light ($\lambda_{max}$=402 nm) to stoichiometrically liberate the OCF$_3$ radical (Zheng, W. et al. 2018). Unfortunately, this photolytic process is limited to the formation of the OCF$_3$ radical, fails to generate the OCF$_3$ radical in a catalytic manner, and is complicated by the simultaneous formation of an undesired N-centered benzimidazole radical. Thus, it was proposed to develop redox-active reagents capable of accepting an electron from a catalyst (e.g., a photoredox catalyst) to form radical intermediates that fragment to release the OR$_F$ radical selectively. It was sought to exploit photoredox catalysis to mediate the formation the OR$_F$ radical because photoredox catalysts can efficiently engage in sequential single electron transfer (SET) events with organic compounds under mild reaction conditions for example at room temperature, after photoexcitation with visible light (400-700 nm) (Prier, C. K. et al. 2013).

The design of the disclosed redox-active reagents is based on the 1-hydroxybenzotriazole scaffold because these compounds, widely used in peptide synthesis, are inexpensive. Also, they can be easily prepared through a one-step condensation reaction of ortho-halonitrobenzene with hydrazine, which allows rapid exploration of the structure-reactivity relationship (SAR) of OR$_F$-reagents (Fu, J. et al. 2010). Furthermore, we have successfully established reaction protocols for the synthesis of a wide variety of 1-OCF$_3$/OCF$_2$H-benzotriazole compounds. More importantly, O-acylated 1-hydroxy-benzotriazoles are capable of accepting an electron to form the corresponding radical anion leading to the mesolytic cleavage of the N—O bond affording an O-centered radical (Cornella, J. et al. 2016).

However, reduction of neutral 1-OR$_F$-benzotriazole compounds is challenging due to their highly negative reduction potential [e.g., 1-OCF$_3$-6-CF$_3$-benzotriazole (TR1), $E_{1/2}^{red}$=-1.97 V versus saturated calomel electrode (SCE) in MeCN]. Even if the corresponding radical anions can be accessed, DFT calculations show that the mesolytic cleavage of the N—$OR_F$ bond would favour the formation of the N-centered benzotriazole radical rather than the $OR_F$ radical (Scheme 20) because of the electron withdrawing group (e.g., $CF_3$) on the O-atom (Zheng, W. et al. 2018; Alleb, L. J. et al. 2014). To address these challenges, we proposed that cationic N—$OR_F$ reagents such as 3-methylbenzotriazole derivative 1 would be better an electron acceptor and the resulting reduced neutral radical 1' would fragment to selectively liberate the $OR_F$ radical (Scheme 9). Indeed, after a series of reagent and reaction optimisations, we were able to identify two redox-active cationic reagents (1a and 1b) and photocatalytic conditions capable of direct C—H difluoromethoxylation or trifluoromethoxylation of arenes and hetereoarenes.

Figure 5:
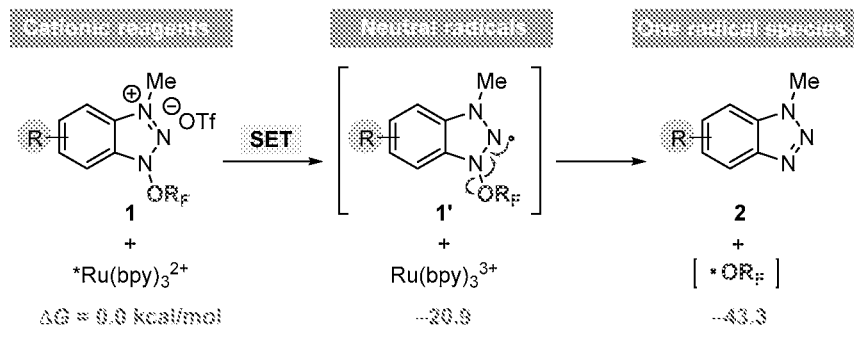
FIG. 5. Mechanistic hypothesis and energies for catalytic and selective formation of the $OR_F$ radical and polyfluoromethoxylation of arenes and heteroarenes. DFT calculations were performed at the M06-2X/6-311++G(d,p)/SMD (MeCN)//M06-2X/6-31+G(d) level of theory using reagent 1b and benzene as substrate. All energies are in kcal/mol and are with respect to II and 1b.
Figure 5:
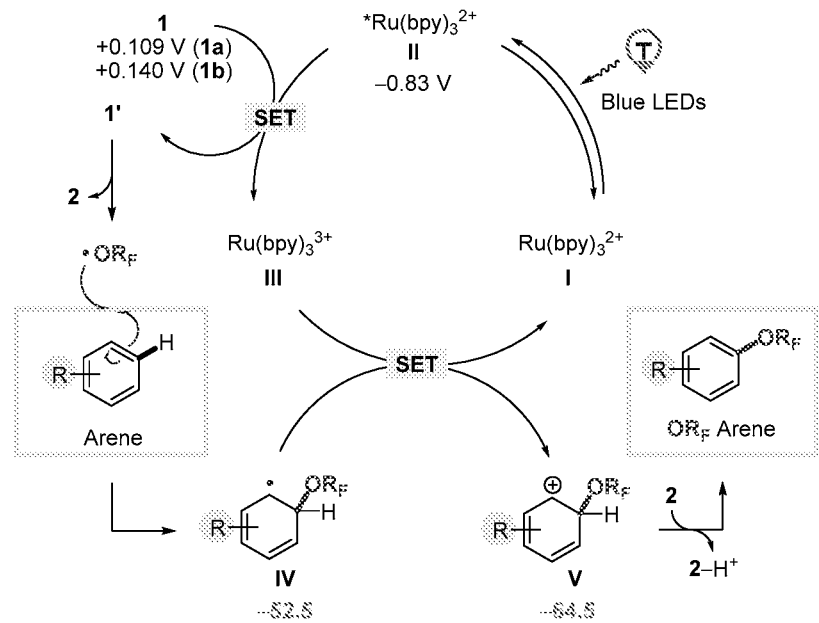
Figure 6A:
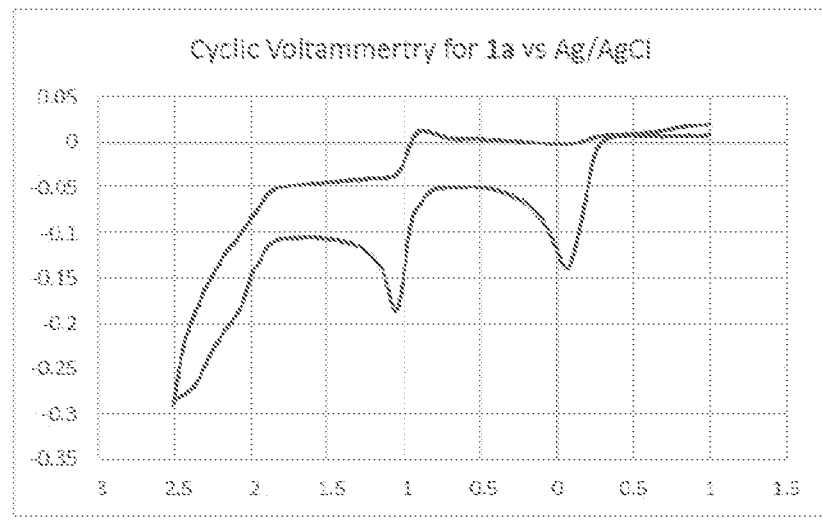
Figure 6B:
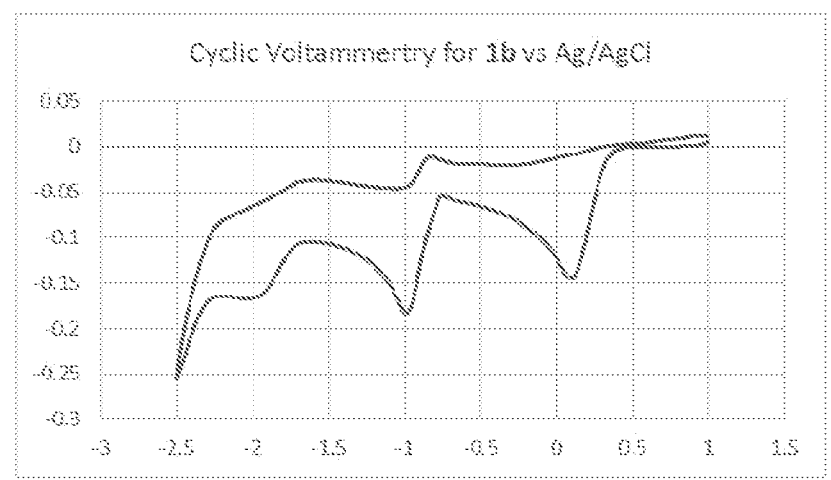
FIG. 6B. Cyclic Voltammetry of reagent 1b.

The photoredox catalytic cycle proposed in FIG. 5 serves as a working mechanistic model. Initial excitation of the Ru(bpy)$_3^{2+}$ photocatalyst (I, bpy=2,2'-bipyridine) produces the long-lived triplet-excited state of *Ru(bpy)$_3^{2+}$ (II, $t_{1/2}$=1.1 μs)$^{21}$. This catalyst (II) is sufficiently reducing ($E_{1/2}^{red}$=−0.81 V versus SCE in MeCN)$^{22}$ to undergo SET with the redox-active cationic reagent 1 ($E_p$ of 1a=0.109 V; $E_p$ of 1b=0.140 V, versus SCE in MeCN, FIGS. 6A and 6B) to generate Ru(bpy)$_{33}$ and neutral radical 1' that undergoes β-scission to liberate benzotriazole 2 and the ORF radical. The addition of this radical to an arene to form cyclohexadienyl radical IV is thermodynamically favourable, for example, when using reagent 1b and benzene as a substrate, ΔG=−10.3 kcal/mol (Scheme 22). Oxidation of IV by Ru(bpy)$_3^{3+}$ ($E_{1/2}^{red}$=+1.28 V, versus SCE in MeCN)$^{22}$ affords cyclohexadienyl cation V, which is deprotonated by benzotriazole to give the desired C—H polyfluoromethoxylated benzene.

The mechanistic hypothesis, described above for the photocatalytic polyfluoromethoxylation processes, is supported by DFT calculations, cyclic voltammetry, light on/off experiments, and deuterium kinetic isotope effect (KIE) studies. A key feature of our cationic redox-active reagents 1 is their susceptibility to single electron reduction to form neutral radicals (1') that undergo s-scission to selective liberate the $OR_F$ radical (FIG. 5). DFT calculations show that both of these steps are energetically favourable in the presence of photoredox catalysts (Schemes 21 and 22). Once the $OR_F$ radical is formed, the subsequent reactions, the addition of the $OR_F$ radical to an arene, oxidation of the resulting cyclohexadienyl radical by Ru(bpy)$_{33}$, and deprotonation are all exergonic. We have determined the reduction potential of reagents 1a and 1b, and these are in accord with the proposed reduction step using excited *Ru(bpy)$_3^{2+}$ (FIG. 2). Determination of the quantum yield and quenching constant via Stern-Volmer quenching studies proved to be challenging because both the Ru(bpy)$_3^{2+}$ sensitiser and reagents 1a and 1b absorb in the visible light region (Schemes 12 and 13). Nevertheless, light on/off experiments showed that the reaction halted when the irradiation stopped (FIGS. 4A and 4B). This indicates a long radical chain mechanism to be unlikely. Since the reaction is insensitive to oxygen (Scheme 14, entry 10), reagents 1a and 1b should quench excited Ru(bpy)$_3^{2+}$ faster than molecular oxygen and should have a quenching constant of at least 2.7×10$^9$ s$^{-1}$.$^{25}$ In addition, KIE studies using 5 equiv. of benzene and 5 equiv. of d-benzene in the presence of 1 equiv. of reagents 1a or 1b afforded the desired products Ph-$OR_F$ and d$_5$-Ph-$OR_F$ in a 1:1 ratio. This result excludes the possibility of H-atom abstraction/deprotonation as the rate-determining step.

Noteworthy is the unique ability to catalytically and selectively generate the ORF radical at ambient conditions allows studies of its properties and reactivity in organic solvents. Competition experiments using two electronically diverse arenes, methyl benzoate and toluene, revealed that both the OCF$_2$H and OCF$_3$ radicals reacted more favourably with electron-rich arenes, and this confirms their electrophilic character (Schemes 18 and 19).

In summary, cationic redox-active reagents and photocatalytic conditions have been developed that allow facile di- and trifluoromethoxylation of arenes and heteroarenes without the need for aryl ring pre-functionalization or pre-activation. These radical-based aromatic substitution processes provide rapid access to multiple regioisomers in a single synthetic operation, and this will facilitate molecular screening and SAR studies of $OR_F$ analogues. The synthetic utility of our strategy has been highlighted by the late-stage polyfluoromethoxylation of bio-relevant molecules at ambient temperature and pressure. Importantly, this report not only provides the first experimental access to and utilization of the OCF$_2$H radical but also establishes the first photocatalytic and selective formation of the $OR_F$ radicals. These protocols create a new reaction platform for the design and development of many polyfluoromethoxylation reactions of hydrocarbons and aid the discovery and synthesis of new pharmaceuticals.

REFERENCES

1. Allen, L. J. et al. N-Acyloxyphthalimides as nitrogen radical precursors in the visible light photocatalyzed room temperature C—H amination of arenes and heteroarenes. *J. Am. Chem. Soc.* 136, 5607-5610.
2. Abdel-Shafi, A. A. et al. Photosensitized generation of singlet oxygen from (substituted bipyridine) ruthenium (II) complexes. *Helv. Chim. Acta* 84, 2784-2795 (2001).
3. Bock, C. R. et al. Photochemistry of transition-metal complexes—mechanism and efficiency of energy-conversion by electron-transfer quenching. *J. Am. Chem. Soc.* 97, 2909-2911, (1975).
4. Castagnetti, E. & Schlosser, M. 2-, 3-, and 4-(Trifluoromethoxy)phenyllithiums: versatile intermediates offering access to a variety of new organofluorine compounds. *Eur. J. Org. Chem.,* 691-695, 2001).
5. Cernak, T. et al. The medicinal chemist's toolbox for late stage functionalization of drug-like molecules. *Chem. Soc. Rev.* 45, 546-576 (2016).
6. Chatalova-Sazepin, C. et al. Xenon difluoride mediated fluorodecarboxylations for the syntheses of di- and trifluoromethoxyarenes. *Org. Lett.* 18, 4570-4573, (2016).
7. Chen, C. H., Chen, P. H., Liu, G. S., J. Am. Chem. Soc. 2015, 137, 15648-15651.
8. Chen, C. et al. J. Am. Chem. Soc. 2018, 140, 1207-1210.
9. Christe, K. O. et al. *Angew. Chem. Int. Ed.* 2007, 46, 6155.
10. Cornella, J. et al. Practical Ni-catalyzed aryl-alkyl cross-coupling of secondary redox-active esters. *J. Am. Chem. Soc.* 138, 2174-2177, (2016).
11. Ellison, G. B. et al. Thermochemistry of the benzyl and allyl radicals and ions. *Int. J. Mass Spectrom. Ion Processes* 156, 109-131 (1996).
12. Federsel, D., Hermann, A., Chrisiten, D., Sander, S., Willner, H., & Oberhammer, H., *J. Mol. Struct.* 2001, 567, 127-136.
13. Feng, P. et al. Access to a new class of synthetic building blocks via trifluoromethoxylation of pyridines and pyrimidines. *Chem. Sci.* 7, 424-429, (2016).

14. Francesco, V., Sansotera, M. & Navarrini, W. Recent developments in the chemistry of organic perfluoro hypofluorites. *J. Fluorine Chem.* 155, 2-20, (2013).
15. Francisco, J. S.; Li, Z.; Williams, I. H., *Chem. Phys. Lett.* 1987, 140, 531.
16. Frisch, M. et al. Gaussian 09, Revision D. 01; Gaussian: Wallingford, Conn., USA, 2009.
17. Fu, J. et al. Discovery of 1H-benzo[d][1,2,3] triazol-1-yl 3,4,5-trimethoxybenzoate as a potential antiproliferative agent by inhibiting histone deacetylase. *Bioorg. Med. Chem.* 18, 8457-8462, (2010).
18. Fulmer, G. R. et al. NMR chemical shifts of trace impurities: Common laboratory solvents, organics, and gases in deuterated solvents relevant to the organometallic chemist. *Organometailics* 29, 2176-2179 (2010).
19. Guo, S. et al. *Nat. Chem.* 2017, 9, 546-551.
20. Guo, J. J. et al. Angew. Chem. Int. Ed. 2016, 55, 15319-15322; Angew. Chem. 2016, 128, 15545-15548.
21. Hansch, C. & Leo, A., Substituent Constants for Correlation Analysis in Chemistry and Biology, Wiley, New York, 1979.
22. Hojczyk, K. N. et al. Trifluoromethoxylation of arenes: Synthesis of ortho-trifluoromethoxylated aniline derivatives by $OCF_3$ migration. *Angew. Chem. Int. Ed.* 53, 14559-14563, (2014).
23. Huang, C., Liang, T., Harada, S., Lee, E. & Ritter, T. Silver-mediated trifluoromethoxylation of aryl stannanes and arylboronic acids. *J. Am. Chem. Soc.* 2011, 133, 13308-13310, (2011).
24. Huchet, Q. A. et al. Partially fluorinated alkoxy groups—Conformational adaptors to changing environments. *J. Fluorine Chem.* 198, 34-46, (2017).
25. Jamison, C. R., Overman, L. E., Acc. Chem. Res. 2016, 49, 1578-1586.
26. Jeschke, P. et al. Mini-Rev. Med. Chem. 2007, 7, 1027-1034.
27. Jia, K. F. et al. Angew. Chem. Int. Ed. 2017, 56, 2478-2481; Angew. Chem. 2017, 129, 2518-2521.
28. Jia, K. F. et al. J., Am. Chem. Soc. 2016, 138, 1514-1517.
29. Joshi-Pangu, A., Wang, C. Y. & Biscoe, M. R. Nickel-catalyzed Kumada cross-coupling reactions of tertiary alkylmagnesium halides and aryl bromides/triflates. *J. Am. Chem. Soc.* 133, 8478-8481 (2011).
30. Juris, A., Balzani, V., Belser, P. & von Zelewsky, A. Characterization of the excited state properties of some new photosensitizers of the ruthenium (polypyridine) family. *Helv. Chim. Acta* 64, 2175-2182, (1981).
31. Kanie, K. et al. A convenient synthesis of trifluoromethyl ethers by oxidative desulfurization-fluorination of dithio carbonates. *Bull. Chem. Soc. Jpn.* 73, 471-484, (2000).
32. Lee, K. N., Lee, J. W. & Ngai, M. Y., Synlett 2016, 27, 313-319; for a two-step chlorination/chlorine-fluorine exchange reaction of electron deficient anisoles.
33. Leowanawat, P.; Zhang, N.; Percec, V., *J. Org. Chem.* 2012, 77, 1018.
34. Leroux, F. R., Manteau, B., Vors, J. P., Pazenok, S. & Beilstein, J. Org. Chem. 2008, 4, 13.
35. Liu, J. B. et al. Silver-mediated oxidative trifluoromethylation of phenols: Direct synthesis of aryl trifluoromethyl ethers. *Angew. Chem. Int. Ed.* 54, 11839-11842, (2015).
36. Liang, T., Neumann, C. N. & Ritter, T. Introduction of fluorine and fluorine-containing functional groups. *Angew. Chem. Int. Ed.* 52, 8214-8264, (2013).
37. Khotavivattana, T. et al. F-18-Labeling of aryl-SCF3, —OCF3 and —OCHF2 with [F-18]fluoride. *Angew. Chem. Int. Ed.* 54, 9991-9995, (2015).
38. Kloeter, G.; Seppelt, K., *J. Am. Chem. Soc.* 1979, 101, 347.
39. Khotavivattana, T. et al. F-18-Labeling of aryl-$SCF_3$, —$OCF_3$ and —$OCHF_2$ with [F-18]fluoride. *Angew. Chem. Int. Ed.* 54, 9991-9995, (2015).
40. Kolomeutsev, A. A., Vorobyev, M., Gillandt, H., Tetrahedron Lett. 2008, 49, 449-454; for radical trifluoromethoxylation of arenes.
41. Marenich, A. V., Cramer, C. J. & Truhlar, D. G. Universal solvation model based on solute electron density and on a continuum model of the solvent defined by the bulk dielectric constant and atomic surface tensions. *J. Phys. Chem. B* 113, 6378-6396, (2009).
42. Mcclinton, M. A. & Mcclinton, D. A., Tetrahedron 1992, 48, 6555-6666.
43. Muller, K., Faeh, C. & Diederich, F. Fluorine in pharmaceuticals: Looking beyond intuition. *Science* 317, 1881-1886, (2007).
44. Murai, K.; Fukushima, S.; Nakamura, A.; Shimura, M.; Fujioka, H., Tetrahedron 2011, 67, 4862.
45. Niahida, M., Vij, A., Kirchmeier, R. L. & Shreeve, J. M., Inorg. Chem. 1995, 34, 6085-6092.
46. Ni, C. & Hu, J. Recent advances in the synthetic application of difluorocarbene. *Synthesis* 46, 842-863, (2014).
47. Ojima, I. *Fluorine in Medicinal Chemistry and Chemical Biology*. (Blackwell Publishing Ltd, 2009).
48. Pellegatti, L.; Zhang, J.; Drahos, B.; Villette, S.; Suzenet, F.; Guillaumet, G.; Petoud, S.; Tóth, E., *Pyridine-based lanthanide complexes: towards bimodal agents operating as near infrared luminescent and MRI reporters. Chem. Commun.* 60, 6591-6593, (2008).
49. Prier, C. K., Rankic, D. A. & MacMillan, D. W. C. Visible light photoredox catalysis with transition metal complexes: Applications in organic synthesis. *Chem. Rev.* 113, 5322-5363, (2013).
50. Purser, S., Moore, P. R., Swallow, S. & Gouverneur, V. Fluorine in medicinal chemistry. *Chem. Soc. Rev.* 37, 320-330, (2008).
51. Qi, X., Chen, P., Liu, G., Angew. Chem. Int. Ed. 2017, 56, 9517-9521; Angew. Chem. 2017, 129, 9645-9649.
52. Rozen, S. Selective fluorinations by reagents containing the OF group. *Chem. Rev.* 96, 1717-1736, (1996).
53. Salar, U. et al. Biology-oriented drug synthesis (BIODS): In vitro β-glucuronidase inhibitory and in silico studies on 2-(2-methyl-5-nitro-1H-imidazol-1-yl) ethyl aryl carboxylate derivatives. *Eur. J. Med. Chem.* 125, 1289-1299 (2017).
54. Seppelt, K., *Angew. Chem. Int. Ed.* 1977, 16, 322.
55. Sheppard, W. A., *Org. Chem.* 1964, 29, 1-11; for electrophilic trifluoromethylation of phenols.
56. Skarda, V. et al. Luminescent metal complexes. Part 3. Electrochemical potentials of ground and excited states of ring-substituted 2,2'-bipyridyl and 1,10-phenanthroline tris-complexes of ruthenium. *J. Chem. Soc. Perkin Trans.* 2, 1309-1311 (1984).
57. Stanek, K., Koller, R., Togni, A., J. Org. Chem. 2008, 73, 7678-7685.
58. Still, W. C., Kahn, M. & Mitra, A. Rapid chromatographic technique for preparative separations with moderate Resolution. J. Org. Chem. 43, 2923-2925 (1978).
59. Takeda, K., Tsuboyama, K., Yamaguchi, K. & Ogura, H. 1,1'-Bis[6-(trifluoromethyl)benzotriazolyl] oxalate (BTBO): a new reactive coupling reagent for the synthesis of dipeptides, esters, and thioesters. *J. Org. Chem.* 50, 273-275 (1985).

60. Tlili, A., Toulgoat, F. & Billard, T. Synthetic approaches to trifluoromethoxy-substituted compounds. *Angew. Chem. Int. Ed.* 55, 11726-11735, (2016).
61. Tlili, A., Toulgoat, F. & Billard, T., *Angew. Chem. Int. Ed.* 2016, 55, 11726-11735; Angew. Chem. 2016, 128, 11900-11909.
62. Umemoto, T., Chem. Rev. 1996, 96, 1757-1777.
63. Umemoto, T., Adachi, K., Ishihara, S., J. Org. Chem. 2007, 72, 6905-6917.
64. Venturini F., Navarrini, W., Famulari, A., Sansotera, M., Dardani, P., Tortelli, T., J. Fluorine Chem. 2012, 140, 43-48.
65. von Ahsen, S., Willner, H. & Arguello, G. A. Fluorocarbon oxy and peroxy radicals. *J. Fluorine Chem.* 125, 1057-1070, (2004).
66. Wang, C. Y., Harms, K., Meggers, E., Angew. Chem. Int. Ed. 2016, 55, 13495-13498; Angew. Chem. 2016, 128, 13693-13696.
67. Xu, J. et al. Copper-catalyzed P-arylation via direct coupling of diaryliodonium salts with phosphorus nucleophiles at room temperature. *J. Org. Chem.* 78, 8176-8183, (2013).
68. Yagupolskii, L. M., Dokl. Akad. Nauk SSSR 1955, 105, 100-102; for deoxyfluorination of fluoroformates.
69. Yang, J., Jiang, M., Jin, Y., Yang, H. & Fu, H. Visible-Light photoredox difluoromethylation of phenols and thiophenols with commercially available difluorobromoacetic acid. *Org. Lett.* 19, 2758-2761 (2017).
70. Yayla, H. G., Wang, H. J., Tarantino, K. T., Orbe, H. S., Knowles, R. R. J., Am. Chem. Soc. 2016, 138, 10794-10797.
71. Zafrani, Y., Sod-Moriah, G. & Segall, Y. Diethyl bromodifluoromethylphosphonate: a highly efficient and environmentally benign difluorocarbene precursor. *Tetrahedron* 65, 5278-5283 (2009).
72. Zeng, T.; Yang, L.; Hudson, R.; Song, G.; Moores, A. R.; Li, C. J., Fe3O4 nanoparticle-supported copper(I) pybox catalyst: Magnetically recoverable catalyst for enantioselective direct-addition of terminal alkynes to imines. *Org. Lett.* 13, (2011).
73. Zheng, W., Morales-Rivera, C. A., Lee, J. W., Liu, P. & Ngai, M. Y. Catalytic C—H trifluoromethoxylation of arenes and heteroarenes. *Angew. Chem. Int. Ed.*, (2018) and supporting online material.
74. Zhang, D. Y., Yu, C. B., Wang, M. C., Gao, K. & Zhou, Y. G. A new electronically deficient atropisomeric diphosphine ligand (S)—CF 3O-BiPhep and its application in asymmetric hydrogenation. *Tetrahedron Lett.* 53, 2556-2559, (2012).
75. Zhang, J., Li, Y., Zhang, F. Y., Hu, C. C., Chen, Y. Y., Angew. Chem. Int. Ed. 2016, 55, 1872-1875; Angew. Chem. 2016, 128, 1904-1907.
76. Zhao, Y. & Truhlar, D. G. The M06 suite of density functionals for main group thermochemistry, thermochemical kinetics, noncovalent interactions, excited states, and transition elements: two new functionals and systematic testing of four M06-class functionals and 12 other functionals. *Theor. Chem. Acc.* 120, 215-241, (2008).
77. Zhang, Q. W. et al. Fluorodecarboxylation for the synthesis of trifluoromethyl aryl ethers. *Angew. Chem. Int. Ed.* 55, 9758-9762, (2016).
78. Zheng, W., Morales-Rivera, C. A., Lee, J. W., Liu, P. & Ngai, M. Y. Catalytic C—H trifluoromethoxylation of arenes and heteroarenes. *Angew. Chem. Int. Ed.*, (2018).
79. Zhou, M., Ni, C. F., He, Z. B. & Hu, J. B. O-Trifluoromethylation of phenols: Access to aryl trifluoromethyl ethers by O-carboxydifluoromethylation and decarboxylative fluorination. *Org. Lett.* 18, 3754-3757, (2016).

What is claimed is:

1. A compound having the structure:

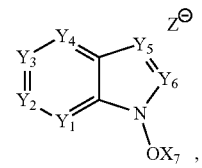

$Y_1$ is N or C—$X_1$, $Y_2$ is N or C—$X_2$, $Y_3$ is N or C—$X_3$, $Y_4$ is N or C—$X_4$ and $Y_6$ is N or C—$X_6$,
  wherein $X_1$, $X_2$, $X_3$, $X_4$, and $X_6$ are each, independently, —H, halogen, —$CF_3$, —$NO_2$, —$SO_2Me$, —CN, —$OCF_3$, —$OCF_2H$, -(alkyl), -(alkenyl), -(alkynyl), -(aryl), -(heteroaryl), —C(O)—$R_1$, —C(O)—$OR_1$, —C(O)—$SR_1$, —$OR_1$, —$SR_1$, —$NR_1R_2$, or —C(O)—$NR_1R_2$,
    wherein $R_1$ and $R_2$ are each, independently, —H, -(alkyl), -(alkenyl), -(alkynyl), -(aryl), -(heteroaryl), —C(O)—$R_3$, —C(O)—$OR_3$, —C(O)—$NR_4R_5$, —C(O)—$SR_3$, —C(S)—$R_3$, —C(S)—$OR_3$, —C(S)—$NR_4R_5$, —C(S)—$SR_3$, —C($NR_5$)—$R_3$, —C($NR_5$)—$OR_3$, —C($NR_6$)—$NR_4R_5$ or —C($NR_6$)—$SR_3$,
      wherein $R_3$, $R_4$, $R_5$ and $R_6$ are each, independently, —H, -(alkyl), -(alkenyl), -(alkynyl), -(aryl) or -(heteroaryl);
$Y_5$ is N or $N^+$—$X_5$,
  wherein $X_5$ is —H, -alkyl, —C(O)-alkyl, —C(O)-aryl, —C(O)—heteroaryl, —C(O)—O-alkyl or —C(O)—O-aryl;
$X_7$ is $CF_3$, $CF_2H$, $CFH_2$, perfluoroalkyl or polyfluoroalkyl; and
Z is OTf, $BF_4$, B(aryl)$_4$, $SbF_6$, $PF_6$, halogen, —OS(O)$_2$O$R_7$, —OS(O)$_2$—$R_7$, $ClO_4$ or —OP(O)(O$R_8$)(O$R_9$),
  wherein $R_7$, $R_8$, and $R_9$ are each, independently, —H, -(alkyl), -(aryl), -(heteroaryl);
wherein when $Y_6$ is N, then $Y_5$ is $N^+$—$X_5$ and $Z^-$ is present, or wherein
when $Y_6$ is C—$X_6$, then $Y_5$ is N and $Z^-$ is absent.

2. The compound of claim 1, wherein
i) $Y_1$ is N or C—$X_1$, $Y_2$ is N or C—$X_2$, $Y_3$ is N or C—$X_3$ and $Y_3$ is N or C—$X_3$ and $Y_4$ is N or C—$X_4$,
  wherein $X_1$, $X_2$, $X_3$, $X_4$ are each, independently, —H, halogen, —$CF_3$, —$NO_2$, —$SO_2Me$, —CN, —$OCF_3$, —$OCF_2H$;
$Y_5$ is N or $N^+$—$X_5$,
  wherein $X_5$ is alkyl;
$Y_6$ is N or C—$X_6$,
  wherein $X_6$ is substituted aryl or substituted heteroaryl;
$X_7$ is $CF_3$ or $CF_2H$; and
Z is OTf, $BF_4$, B(aryl)$_4$, $SbF_6$, $PF_6$, halogen, —OS(O)$_2$O$R_7$, —OS(O)$_2$—$R_7$, $ClO_4$ or —OP(O)(O$R_8$)(O$R_9$),
  wherein $R_7$, $R_8$, and $R_9$ are each, independently, —H, -(alkyl), -(aryl), -(heteroaryl);
wherein when $Y_6$ is N, then $Y_5$ is $N^+$—$X_5$ and $Z^-$ is present, and when $Y_6$ is C—$X_6$, then $Y_5$ is N and $Z^-$ is absent;

or ii)
$Y_1$ is N or C—$X_1$, $Y_2$ is N or C—$X_2$, $Y_3$ is N or C—$X_3$ and $Y_4$ is N or C—$X_4$, wherein $X_1$, $X_2$, $X_3$ and $X_4$ are each, independently, —H, —Cl, —Br, —F, —$CF_3$, —$NO_2$ or —$SO_2Me$ $Y_5$ is N or $N^+$—$X_5$,
  wherein $X_5$ is alkyl;

$Y_6$ is N or C—$X_6$,
  wherein $X_6$ is substituted aryl;

$X_7$ is $CF_3$ or $CF_2H$; and

Z is OTf, $BF_4$, B(aryl)$_4$, $SbF_6$, $PF_6$, halogen, —OS(O)$_2$OR$_7$, —OS(O)$_2$—R$_7$, $ClO_4$ or —OP(O)(OR$_8$)(OR$_9$), wherein R$_7$, R$_8$, and R$_9$ are each, independently, —H, -(alkyl), -(aryl), -(heteroaryl);

wherein when $Y_6$ is N, then $Y_5$ is $N^+$—$X_5$ and $Z^-$ is present, and when $Y_6$ is C—$X_6$, then $Y_5$ is N and $Z^-$ is absent.

3. The compound of claim 1, wherein
i) $Y_2$ is C—$X_2$,
  wherein $X_2$, is halogen, —$CF_3$, —$NO_2$, —$SO_2Me$, —CN, —$OCF_3$ or —$OCF_2H$;
or
ii)
$Y_2$ is C—$X_2$, and
$Y_4$ is C—$X_4$
  wherein $X_2$ and $K_4$ are each, independently, halogen, —$CF_3$, —$NO_2$, —$SO_2Me$, —CN, —$OCF_3$ or —$OCF_2H$;
or
iii) at least two of $Y_1$, $Y_2$, $Y_3$ and $Y_4$ are other than C—H.

4. The compound of claim 1, wherein Z is OTf.

5. The compound of claim 1, having the structure:

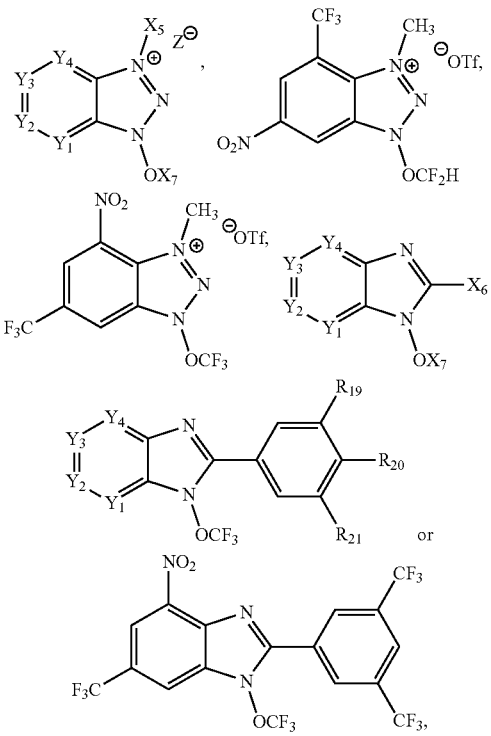

wherein
$Y_2$ is C—$X_2$; and
$Y_4$ is C—$X_4$, wherein $X_2$ and $X_4$ are each, independently, halogen, —$CF_3$, —$NO_2$, —$SO_2Me$, —CN, —$OCF_3$ or —$OCF_2H$;

or having the structure:

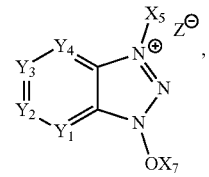

wherein $X_7$ is —$CF_2H$ or —$CF_3$.

6. A process for preparing the compound of claim 5 having the structure:

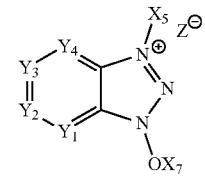

wherein $X_5$ is alkyl and $X_7$ is —$CF_2H$, comprising (a) reacting the compound having the structure:

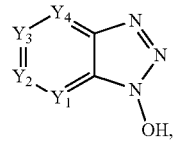

with a difluoromethylating agent in a first suitable solvent,
  wherein the difluormethylating agent is diethyl (bromodifluoromethyl)phosphonate;
under conditions sufficient to produce the compound having the structure:

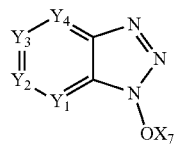

wherein $X_7$ is —$CF_2H$; and (b) reacting the product of step (a) with an alkylating agent bearing a Z group in a second suitable solvent under conditions sufficient to produce the compound.

7. The process of claim 6 for preparing the compound having the structure:

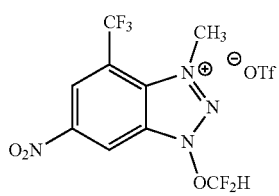

comprising
(a) reacting the compound having the structure:

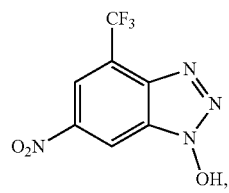 [SMILES: O=[N+]([O-])c1cc(C(F)(F)F)c2nnn(O)c2c1]

with a difluoromethylating agent in a first suitable solvent, wherein the difluormethylating agent is diethyl (bromodifluoromethyl)phosphonate;
under conditions sufficient to produce the compound having the structure:

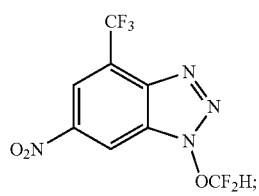

(b) reacting the product of step (a) with a methylating agent bearing a triflate group in a second suitable solvent under conditions sufficient to produce the compound.

8. A process for preparing the compound of claim 5 having the structure:

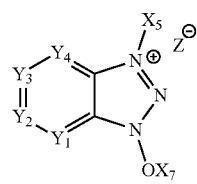

wherein $X_5$ is alkyl and $X_7$ is —CF$_3$, comprising
(a) reacting the compound having the structure:

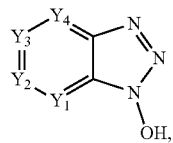

with a trifluoromethylating agent in a first suitable solvent, wherein the trifluormethylating agent is Togni reagent I or Togni reagent II,
under conditions sufficient to produce the compound having the structure:

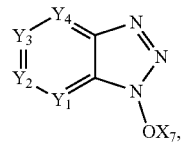

wherein $X_7$ is —CF$_3$;
(b) reacting the product of step (a) with an alkylating agent bearing a triflate group in a second suitable solvent under conditions sufficient to produce the compound.

9. The process of claim 8 for preparing the compound having the structure:

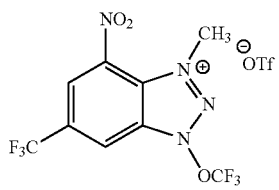

comprising
(a) reacting the compound having the structure:

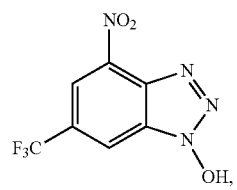 [SMILES: O=[N+]([O-])c1cc(C(F)(F)F)cc2c1nnn2O]

with a trifluoromethylating agent in a first suitable solvent, wherein the trifluormethylating agent is Togni reagent I or Togni reagent II,
under conditions sufficient to produce the compound having the structure:

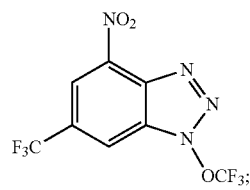

(b) reacting the product of step (a) with a methylating agent bearing a triflate group in a second suitable solvent under conditions sufficient to produce the compound.

10. A process of fluoromethoxylating an arene or heteroarene, or an aryl or heteroaryl group of an aryl or heteroaryl containing compound, wherein at least one carbon of the arene or heteroarene, or aryl or heteroaryl group, is unsubstituted, comprising reacting the arene or heteroarene, or aryl or heteroaryl group, with the compound of claim 1 under conditions sufficient to thereby produce the fluoromethoxylated arene or heteroarene, or aryl or heteroaryl group, wherein the arene or heteroarene is a phenyl, pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene or quinolone.

11. The process of claim 10, wherein the reaction occurs in the presence of a metal catalyst;
or
wherein the reaction occurs in the presence of a Ruthenium catalyst or Iridium catalyst;
or
wherein the reaction occurs under irradiation with visible light.

12. The process of claim 10 for producing a fluoromethoxylated compound having the structure:

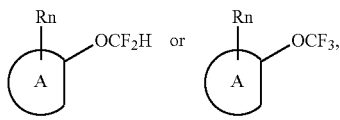

wherein
A is an aryl or heteroaryl; and
R is —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$H, —CO$_2$-(alkyl), —CO$_2$-(alkenyl), —CO$_2$-(alkynyl) —CO$_2$-(aryl), —C(—CO$_2$-(heteroaryl), —C(O)NH-(alkyl), —C(O)NH-(alkenyl), —C(O)NH-(alkynyl), —C(O)NH-(aryl), —C(O)NH-(heteroaryl), —C(O)N(alkyl)$_2$, —OH, —OAc, —C(O)-(alkyl), —C(O)-(alkenyl), —C(O)-(alkynyl), —C(O)-(aryl), —C(O)-(heteroaryl), —OCO$_2$-(alkyl), —OCO$_2$-(alkenyl), —OCO$_2$-(alkynyl), —OCO$_2$-(aryl), —OCO$_2$-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl) or —S-(heteroaryl); and
n is 0-7,
comprising (a) reacting a compound having the structure:

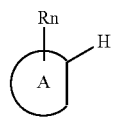

with the compound of claim 8 under conditions sufficient to thereby produce the fluoromethoxylated compound.

13. The process of claim 12 for producing a difluoromethoxylated compound having the structure:

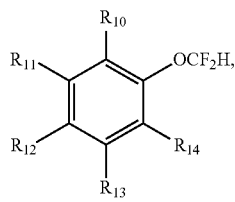

wherein
R$_{10}$, R$_{11}$, R$_{12}$, R$_{13}$ and R$_{14}$ are each, independently, —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$H, —CO$_2$-(alkyl), —CO$_2$-(alkenyl), —CO$_2$-(alkynyl) —CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —C(O)-(alkyl), —C(O)-(alkenyl), —C(O)-(alkynyl), —C(O)-(aryl), —C(O)-(heteroaryl), —OCO$_2$-(alkyl), —OCO$_2$-(alkenyl), —OCO$_2$-(alkynyl), —OCO$_2$-(aryl), —OCO$_2$-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl) or —S-(heteroaryl),
comprising (a) reacting a compound having the structure:

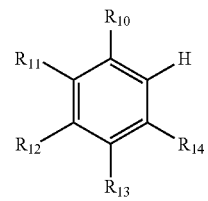

with the compound of claim 8 under conditions sufficient to thereby produce the difluoromethoxylated compound, or
for producing a difluoromethoxylated compound having the structure:

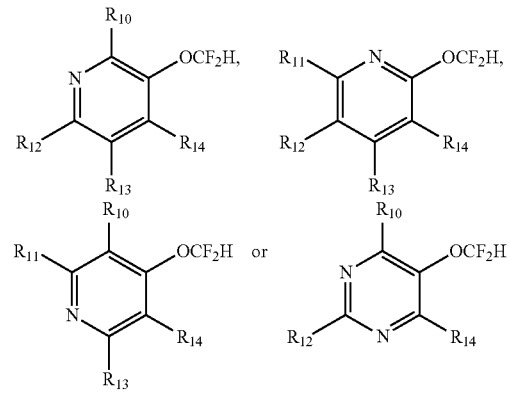

wherein
R$_{10}$, R$_{11}$, R$_{12}$, R$_{13}$ and R$_{14}$ are each, independently, —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), -φ$_2$H, —CO$_2$-(alkyl), —CO$_2$-(alkenyl), —CO$_2$-(alkynyl) —CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —C(O)-(alkyl), —C(O)-(alkenyl), —C(O)-(alkynyl), —C(O)-(aryl), —C(O)-(heteroaryl), —OCO$_2$-(alkyl), —OCO$_2$-(alkenyl), —OCO$_2$-(alkynyl), —OCO$_2$-(aryl), —OCO$_2$-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl) or —S-(heteroaryl), comprising (a) reacting a compound having the structure:

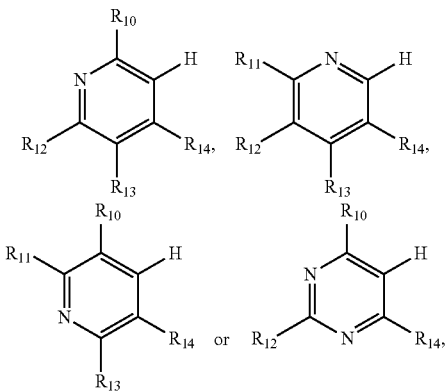

with the compound of claim 8 under conditions sufficient to thereby produce the difluoromethoxylated compound, or for producing a difluoromethoxylated compound having the structure:

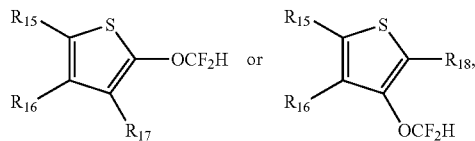

wherein $R_{15}$, $R_{16}$, $R_{17}$ and $R_{18}$ are each, independently, —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$H, —CO$_2$-(alkyl), —CO$_2$-(alkenyl), —CO$_2$-(alkynyl) —CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —C(O)-(alkyl), —C(O)-(alkenyl), —C(O)-(alkynyl), —C(O)-(aryl), —C(O)-(heteroaryl), —OCO$_2$-(alkyl), —OCO$_2$-(alkenyl), —OCO$_2$-(alkynyl), —OCO$_2$-(aryl), —OCO$_2$-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl) or —S-(heteroaryl), comprising (a) reacting a compound having the structure:

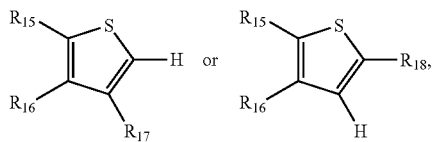

with the compound of claim 8 under conditions sufficient to thereby produce the difluoromethoxylated compound.

14. The process of claim 12 for producing a trifluoromethoxylated compound having the structure:

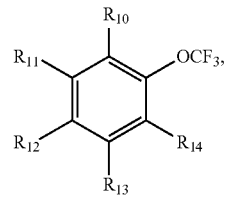

wherein $R_{10}$, $R_{11}$, $R_{12}$, $R_{13}$ and $R_{14}$ are each, independently, —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$H, —CO$_2$-(alkyl), —CO$_2$-(alkenyl), —CO$_2$-(alkynyl) —CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —C(O)-(alkyl), —C(O)-(alkenyl), —C(O)-(alkynyl), —C(O)-(aryl), —C(O)-(heteroaryl), —OCO$_2$-(alkyl), —OCO$_2$-(alkenyl), —OCO$_2$-(alkynyl), —OCO$_2$-(aryl), —OCO$_2$-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl) or —S-(heteroaryl), comprising (a) reacting a compound having the structure:

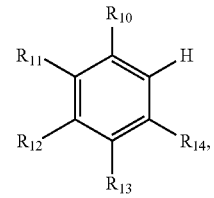

with the compound of claim 8 under conditions sufficient to thereby produce the trifluoromethoxylated compound, or for producing a trifluoromethoxylated compound having the structure:

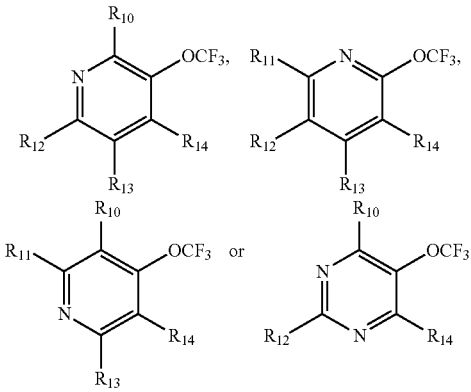

wherein $R_{10}$, $R_{11}$, $R_{12}$, $R_{13}$ and $R_{14}$ are each, independently, —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH- (heteroaryl), —CO₂H, —CO₂-(alkyl), —CO₂-(alkenyl), —CO₂-(alkynyl) —CO₂-(aryl), —C(—CO₂-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)₂, —OH, —OAc, —C(O)-(alkyl), —C(O)-(alkenyl), —C(O)-(alkynyl), —C(O)-(aryl), —C(O)-(heteroaryl), —OCO₂-(alkyl), —OCO₂-(alkenyl), —OCO₂-(alkynyl), —OCO₂-(aryl), —OCO₂-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl) or —S-(heteroaryl), comprising (a) reacting a compound having the structure:

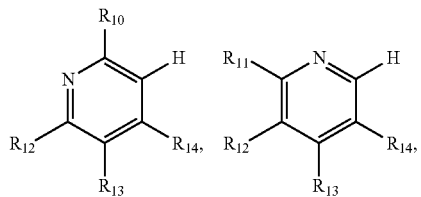

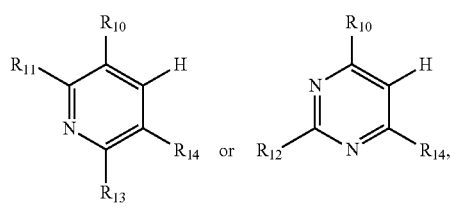

with the compound of claim 8 under conditions sufficient to thereby produce the trifluoromethoxylated compound, or for producing a trifluoromethoxylated compound having the structure:

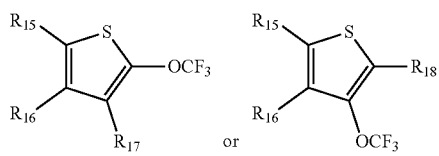

wherein $R_{15}$, $R_{16}$, $R_{17}$ and $R_{18}$ are each, independently, —H, halogen, —CN, —CF₃, —OCF₃, -(alkyl), -(alkenyl), -(alkynyl), -(aryl), -(heteroaryl), —NH₂, —NH-(alkyl), —NH-(alkenyl), —NH-(alkynyl) —NH-(aryl), —NH-(heteroaryl), —CO₂H, —CO₂-(alkyl), —CO₂-(alkenyl), —CO₂-(alkynyl) —CO₂-(aryl), —C(—CO₂-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)₂, —OH, —OAc, —C(O)-(alkyl), —C(O)-(alkenyl), —C(O)-(alkynyl), —C(O)-(aryl), —C(O)-(heteroaryl), —OCO₂-(alkyl), —OCO₂-(alkenyl), —OCO₂-(alkynyl), —OCO₂-(aryl), —OCO₂-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl) or —S-(heteroaryl), comprising (a) reacting a compound having the structure:

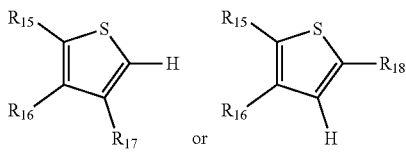

with the compound of claim 8 under conditions sufficient to thereby produce the trifluoromethoxylated compound.

15. The compound of claim 5, wherein $X_7$ is —OCF₃ and/or wherein $X_6$ is

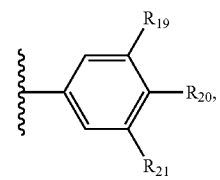

wherein $R_{19}$, $R_{20}$ and $R_{21}$ are each, independently, —H, —Cl, —Br, —F, —CF₃, —NO₂ or —SO₂Me.

16. The process of preparing the compound of claim 5, comprising reacting the compound having the structure:

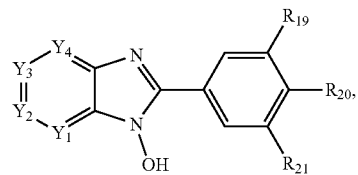

with a trifluoromethylating agent in a suitable solvent under conditions sufficient to thereby produce the compound, wherein the trifluormethylating agent is Togni reagent I or Togni reagent II.

17. A process of trifluoromethoxylating an arene or heteroarene, wherein at least one carbon of the arene or heteroarene is unsubstituted, or the aryl or heteroaryl group of an aryl or heteroaryl containing compound, wherein at least one carbon of the aryl or heteroaryl is unsubstituted, comprising reacting the arene, heteroarene, aryl or heteroaryl with the compound of claim 8 under conditions sufficient to thereby produce the trifluoromethoxylated arene, heteroarene, aryl or heteroaryl, wherein the arene or heteroarene is a phenyl, pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene or quinolone.

18. The process for producing a trifluoromethoxylated compound having the structure:

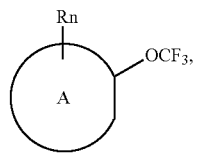

wherein
A is an aryl or heteroaryl; and
R is —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$H, —CO$_2$-(alkyl), —CO$_2$-(alkenyl), —CO$_2$-(alkynyl) —CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —C(O)-(alkyl), —C(O)-(alkenyl), —C(O)-(alkynyl), —C(O)-(aryl), —C(O)-(heteroaryl), —OCO$_2$-(alkyl), —OCO$_2$-(alkenyl), —OCO$_2$-(alkynyl), —OCO$_2$-(aryl), —OCO$_2$-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl) or —S-(heteroaryl); and n is 0-7, comprising (a) reacting a compound having the structure:

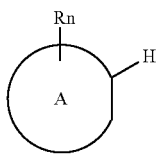

with the compound of claim 8 under conditions sufficient to thereby produce the trifluoromethoxylated compound;

or wherein

A is an aryl or heteroaryl,
wherein the aryl or heteroaryl is a phenyl, pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene or quinolone; and R is —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$H, —CO$_2$-(alkyl), —CO$_2$-(alkenyl), —CO$_2$-(alkynyl) —CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —C(O)-(alkyl), —C(O)-(alkenyl), —C(O)-(alkynyl), —C(O)-(aryl), —C(O)-(heteroaryl), —OCO$_2$-(alkyl), —OCO$_2$-(alkenyl), —OCO$_2$-(alkynyl), —OCO$_2$-(aryl), —OCO$_2$-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl) or —S-(heteroaryl), wherein the aryl or heteroaryl is a phenyl, pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene or quinolone; and n is 0-7, comprising (a) reacting a compound having the structure:

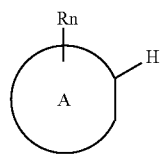

with the compound of claim 8 under conditions sufficient to thereby produce the trifluoromethoxylated compound.

19. A product or composition produced by the process of, or by the process comprising the process of claim 6.

20. A kit comprising the compound of claim 1 in a container and instructions for use of the compound.

* * * * *